(12) United States Patent
Mullen et al.

(10) Patent No.: US 12,076,240 B2
(45) Date of Patent: Sep. 3, 2024

(54) DEVICES AND METHODS FOR DELIVERY AND DEPLOYMENT OF BALLOON EXPANDABLE TRANSCATHETER VALVES

(71) Applicant: Medtronic, Inc., Minneapolis, MN (US)

(72) Inventors: Conleth Mullen, Galway (IE); Marc A. Anderson, Galway (IE); Micheal Fallon, Roscommon (IE)

(73) Assignee: Medtronic, Inc., Minneapolis, MN (US)

( * ) Notice: Subject to any disclaimer, the term of this patent is extended or adjusted under 35 U.S.C. 154(b) by 217 days.

(21) Appl. No.: 17/406,618

(22) Filed: Aug. 19, 2021

(65) Prior Publication Data

US 2022/0054264 A1 Feb. 24, 2022

Related U.S. Application Data

(60) Provisional application No. 63/234,882, filed on Aug. 19, 2021, provisional application No. 63/230,295, filed on Aug. 6, 2021, provisional application No. 63/123,801, filed on Dec. 10, 2020, provisional application No. 63/069,396, filed on Aug. 24, 2020, provisional application No. 63/069,417, filed on Aug. 24, 2020, provisional application No. 63/069,428, filed on Aug. 24, 2020, provisional application No.
(Continued)

(51) Int. Cl.
*A61F 2/24* (2006.01)
*A61M 25/10* (2013.01)
*A61F 2/958* (2013.01)
*A61M 25/00* (2006.01)

(52) U.S. Cl.
CPC ....... *A61F 2/2433* (2013.01); *A61M 25/1027* (2013.01); *A61F 2/2436* (2013.01); *A61F 2/2439* (2013.01); *A61F 2/958* (2013.01); *A61F 2002/9583* (2013.01); *A61F 2002/9586* (2013.01); *A61M 2025/0006* (2013.01); *A61M 2025/1004* (2013.01); *A61M 2025/1056* (2013.01); *A61M 2025/1061* (2013.01)

(58) Field of Classification Search
CPC .... A61F 2/2433; A61F 2/2436; A61F 2/2439; A61F 2002/9583; A61F 2002/9586; A61F 2/958; A61M 25/1009; A61B 2017/22065; A61B 2017/3486; A61B 2018/00285
USPC ....................................................... 623/2.11
See application file for complete search history.

(56) References Cited

U.S. PATENT DOCUMENTS 5,968,069 A 10/1999 Dusbabek et al.
6,264,683 B1 7/2001 Stack et al.
6,395,008 B1 * 5/2002 Ellis ................. A61F 2/958
606/108

(Continued)

OTHER PUBLICATIONS

Written Opinion and International Search Report issued Nov. 9, 2021 in International Appl. No. PCT/US2021/046823.

*Primary Examiner* — Shaun L David
*Assistant Examiner* — Mitchell Brian Hoag
(74) *Attorney, Agent, or Firm* — Medler Ferro Woodhouse & Mills PLLC

(57) ABSTRACT

Balloon catheters for delivery of prosthetic hear valves is provided. The balloon catheters are configured to deploy a prosthetic heart valve through inflation. The balloon catheters are further configured with one or more retention bumpers to reduce or prevent migration of the prosthetic heart valve during delivery. Balloon catheters described
(Continued)

herein are configured with substantially incompressible retention bumpers that promote longitudinal inflation fluid flow.

22 Claims, 96 Drawing Sheets

Related U.S. Application Data

63/069,409, filed on Aug. 24, 2020, provisional application No. 63/069,401, filed on Aug. 24, 2020.

(56) References Cited

U.S. PATENT DOCUMENTS

| | | | |
|---|---|---|---|
| 6,464,718 B1 | 10/2002 | Miller et al. | |
| 6,702,802 B1 | 3/2004 | Hancock et al. | |
| 8,795,346 B2 | 8/2014 | Alkhatib | |
| 9,352,133 B2* | 5/2016 | Godin | A61M 25/1006 |
| 9,795,477 B2 | 10/2017 | Tran et al. | |
| 11,123,209 B2* | 9/2021 | Alonso | A61F 2/90 |
| 2003/0135256 A1 | 7/2003 | Gallagher et al. | |
| 2004/0102791 A1* | 5/2004 | Murray, III | A61F 2/958 |
| | | | 623/1.11 |
| 2004/0267280 A1 | 12/2004 | Nishide et al. | |
| 2006/0009832 A1 | 1/2006 | Fisher | |
| 2006/0253185 A1* | 11/2006 | Beasley | A61F 2/958 |
| | | | 623/1.11 |
| 2007/0005092 A1* | 1/2007 | Godin | A61M 25/1006 |
| | | | 604/96.01 |
| 2008/0119922 A1* | 5/2008 | Alkhatib | A61F 2/958 |
| | | | 623/1.11 |
| 2011/0077731 A1* | 3/2011 | Lee | A61F 2/966 |
| | | | 623/1.11 |
| 2013/0030519 A1* | 1/2013 | Tran | A61F 2/958 |
| | | | 623/2.11 |
| 2014/0257457 A1* | 9/2014 | Glazier | A61F 2/2433 |
| | | | 623/1.11 |
| 2014/0257471 A1* | 9/2014 | Peterson | A61F 2/95 |
| | | | 623/2.11 |
| 2014/0330359 A1* | 11/2014 | Ramzipoor | A61F 2/958 |
| | | | 623/1.11 |
| 2015/0216691 A1* | 8/2015 | Chuter | A61F 2/958 |
| | | | 623/1.11 |
| 2017/0100270 A1* | 4/2017 | Cottone | A61F 2/958 |

* cited by examiner

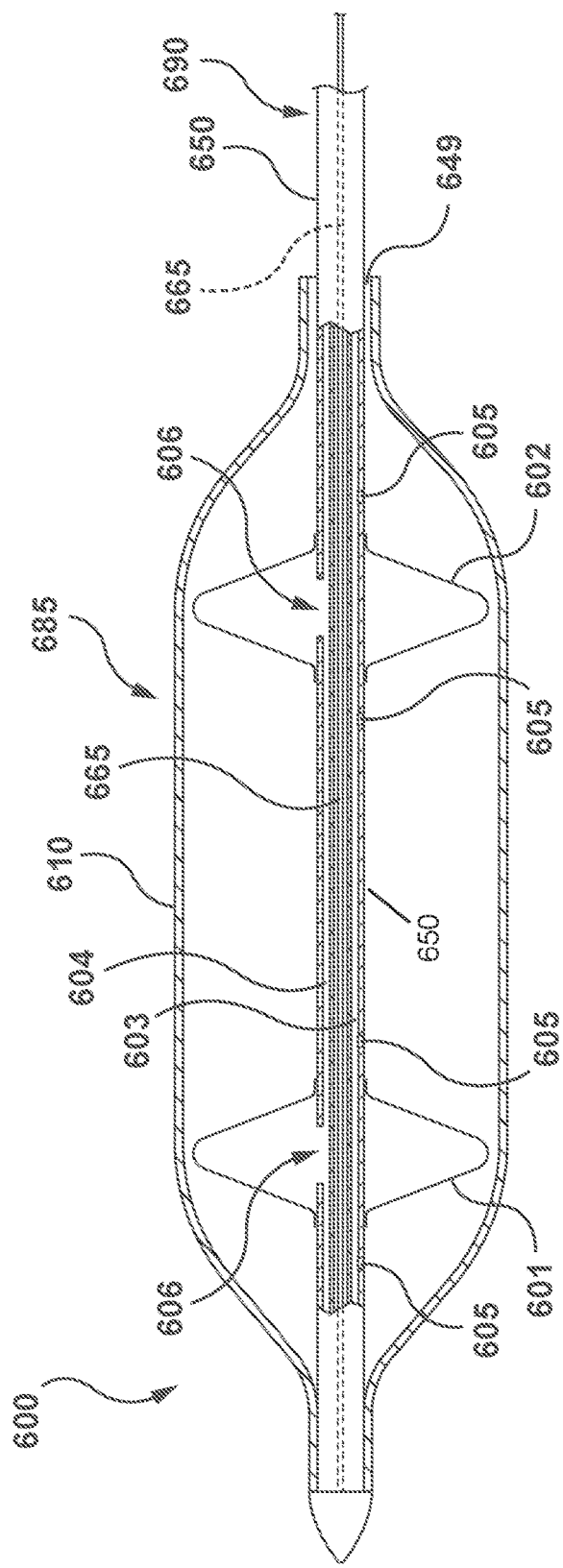
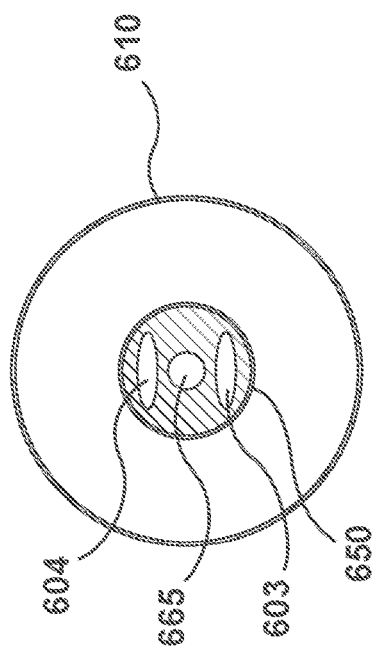
FIG. 6B
FIG. 6C

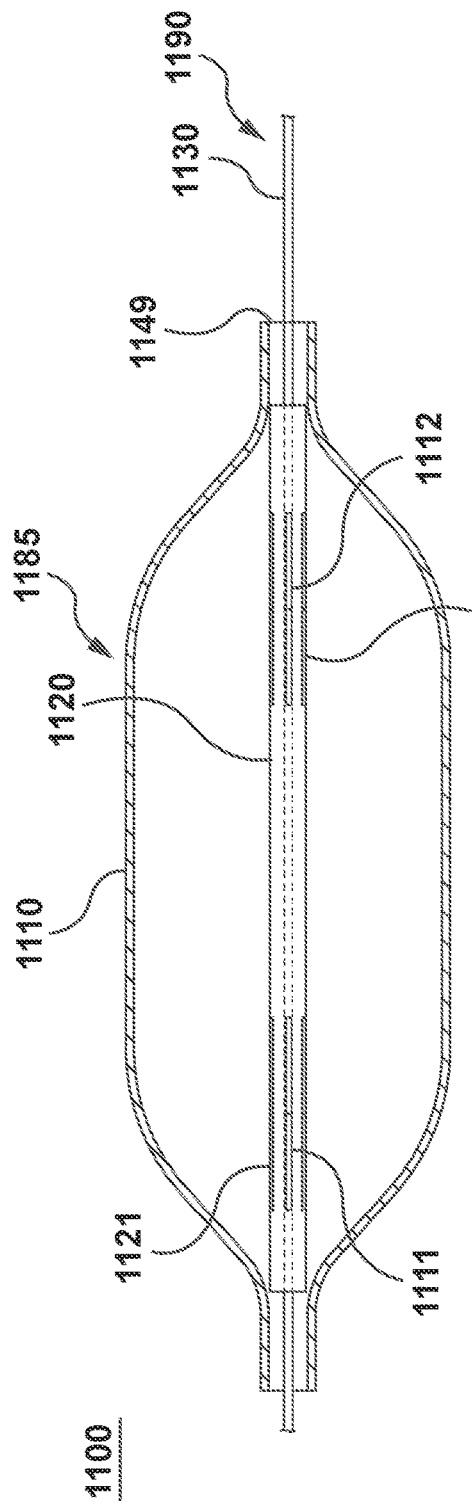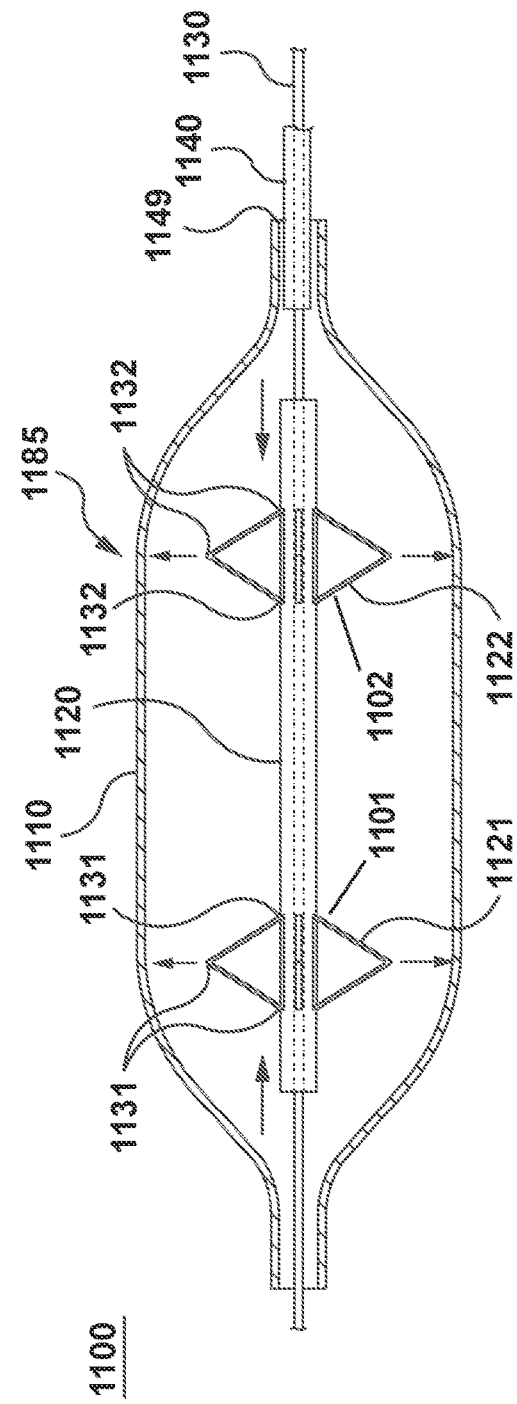
FIG. 11A
FIG. 11B

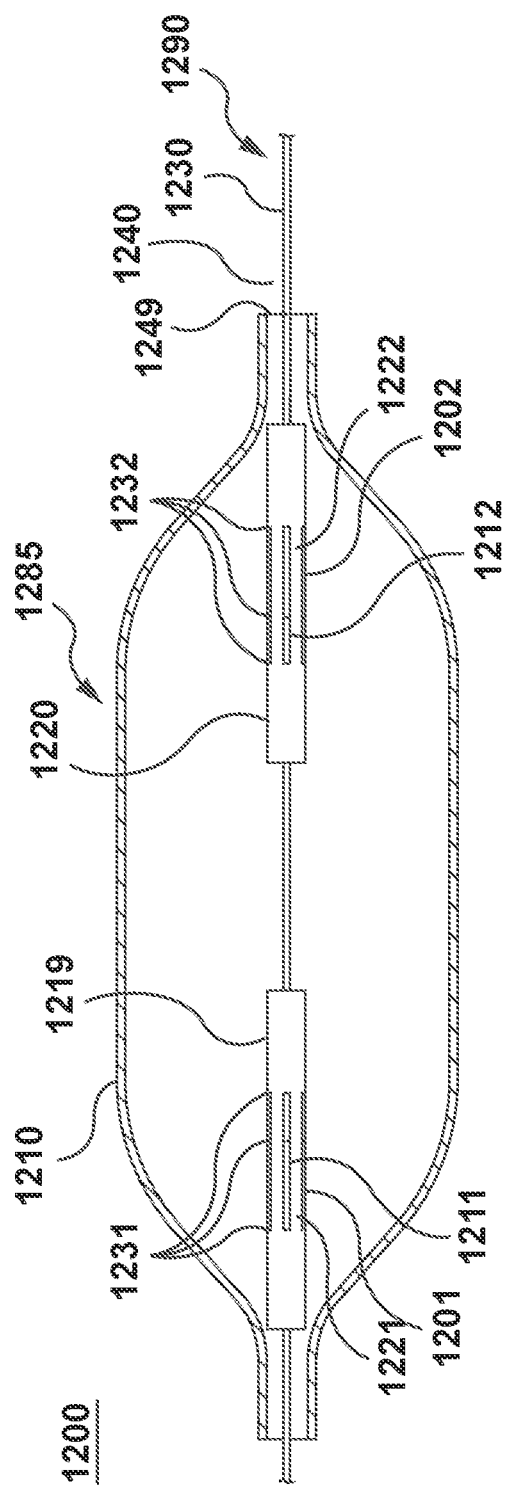
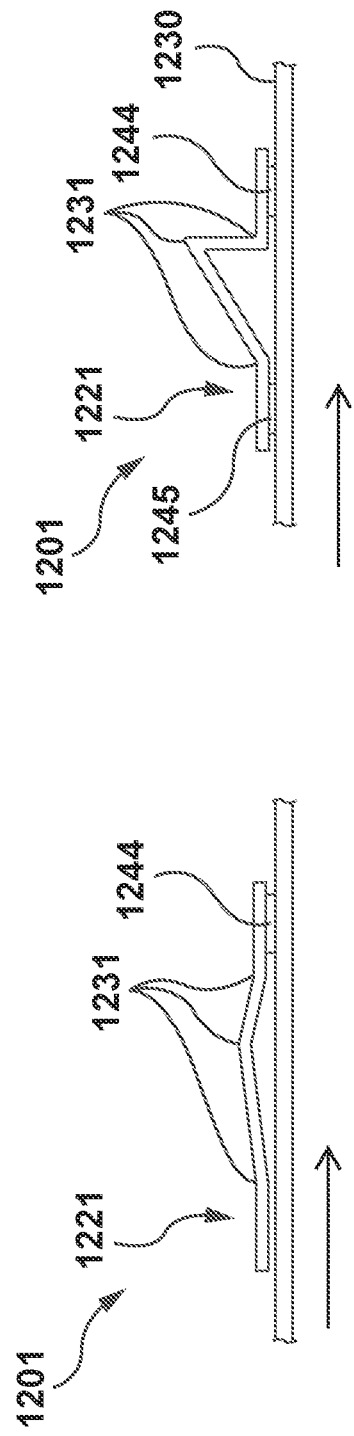
FIG. 12A
FIG. 12B
FIG. 12C

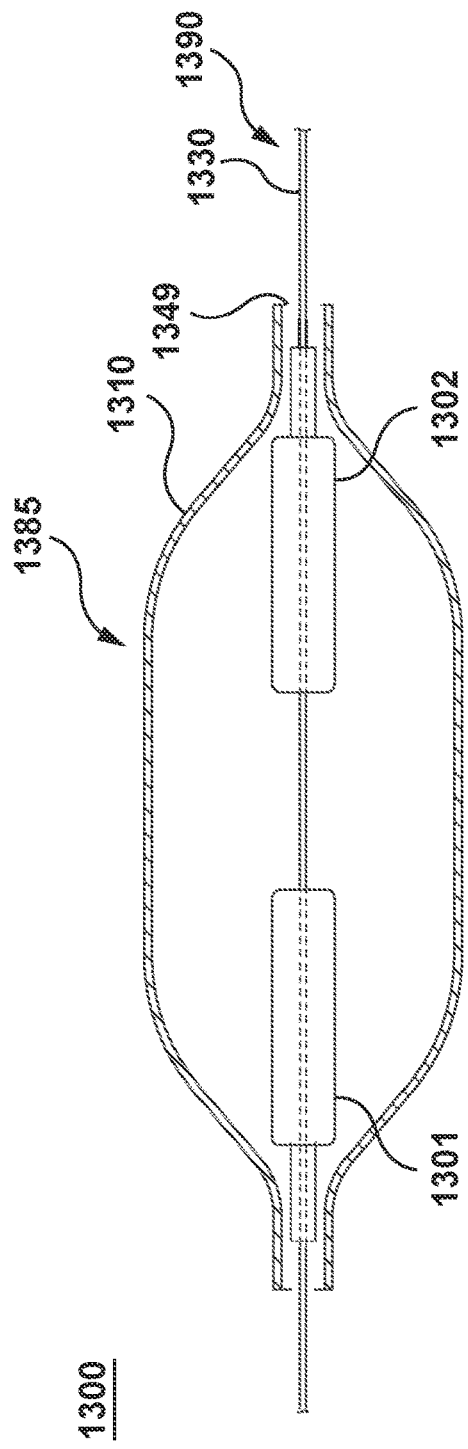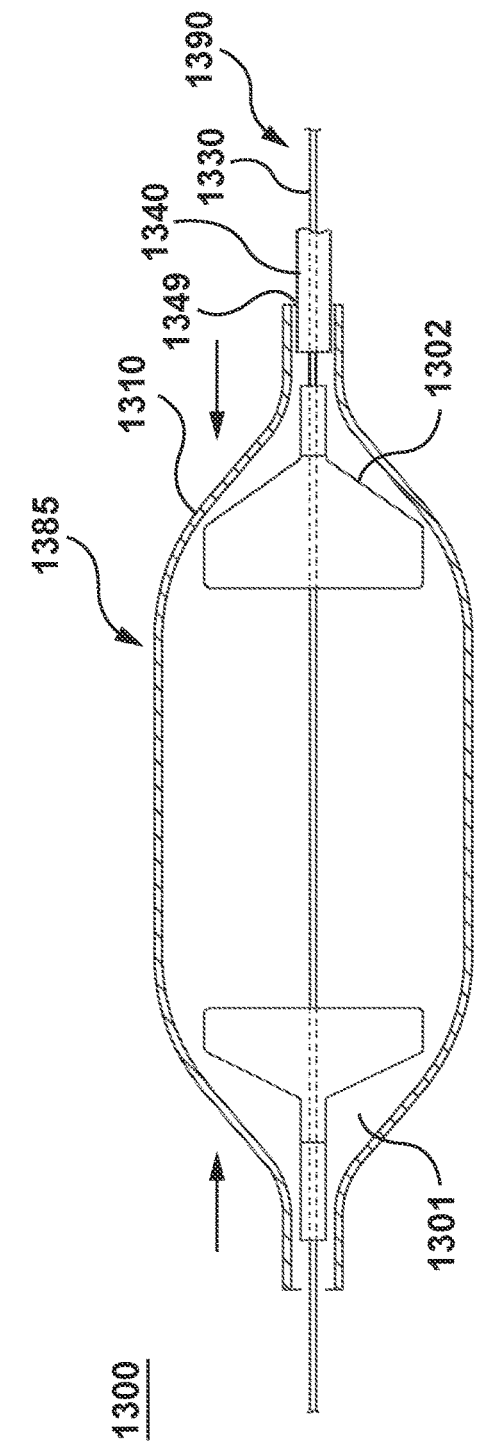
FIG. 13A
FIG. 13B

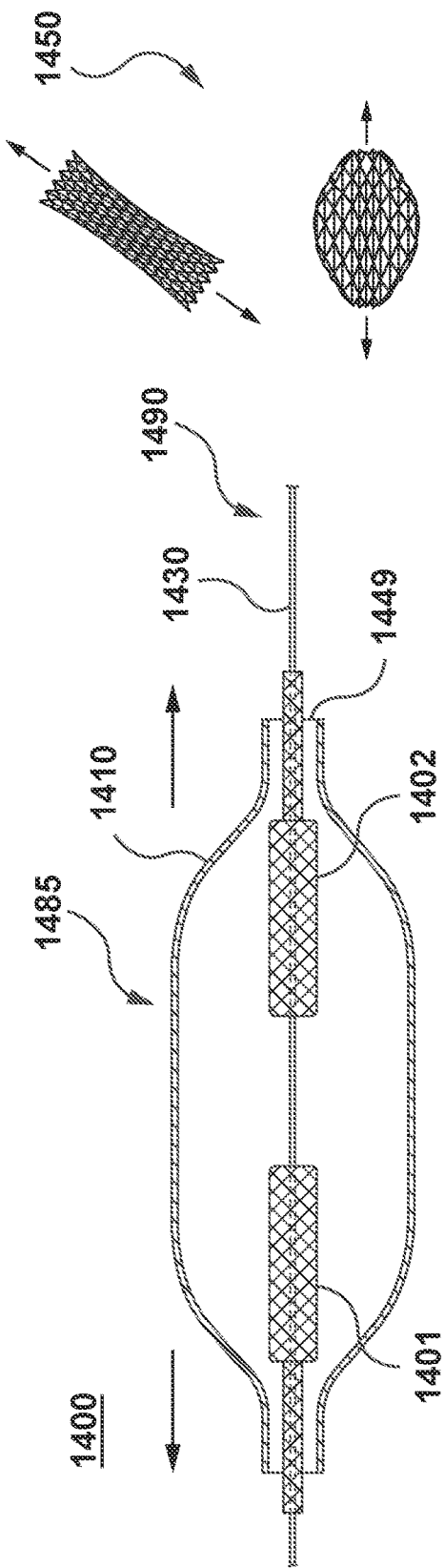
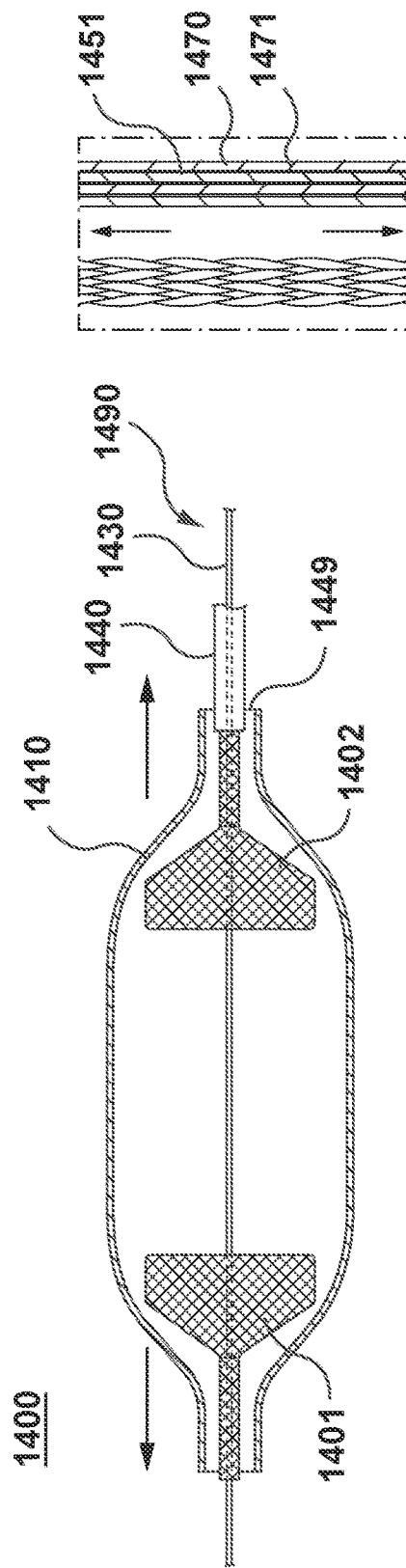
FIG. 14A
FIG. 14B
FIG. 14C
FIG. 14D

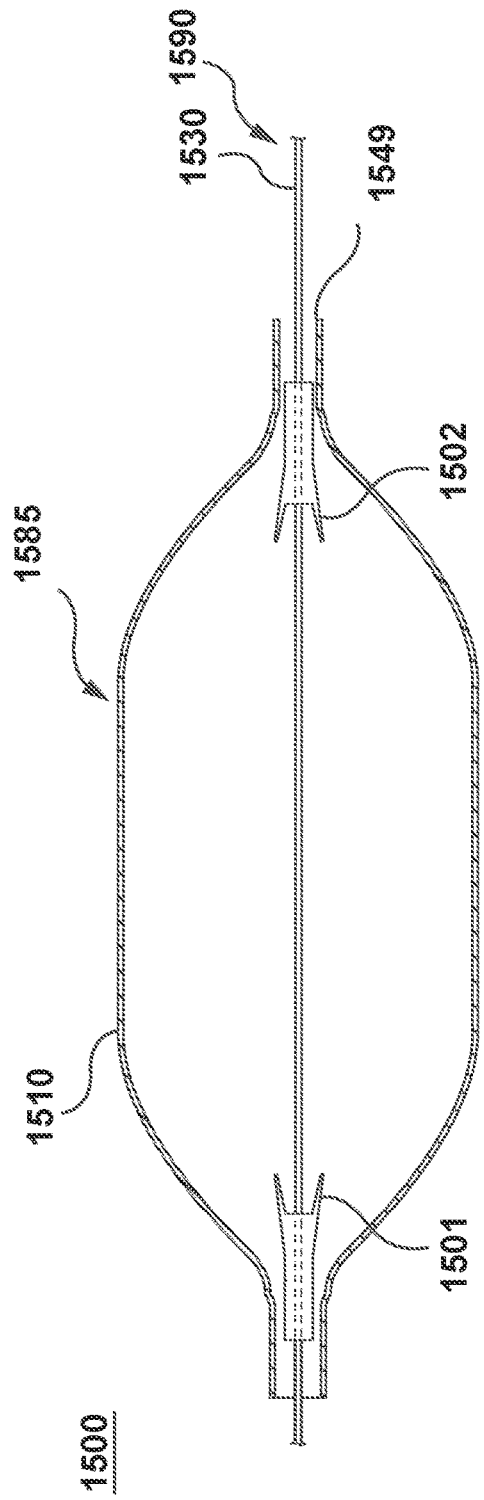
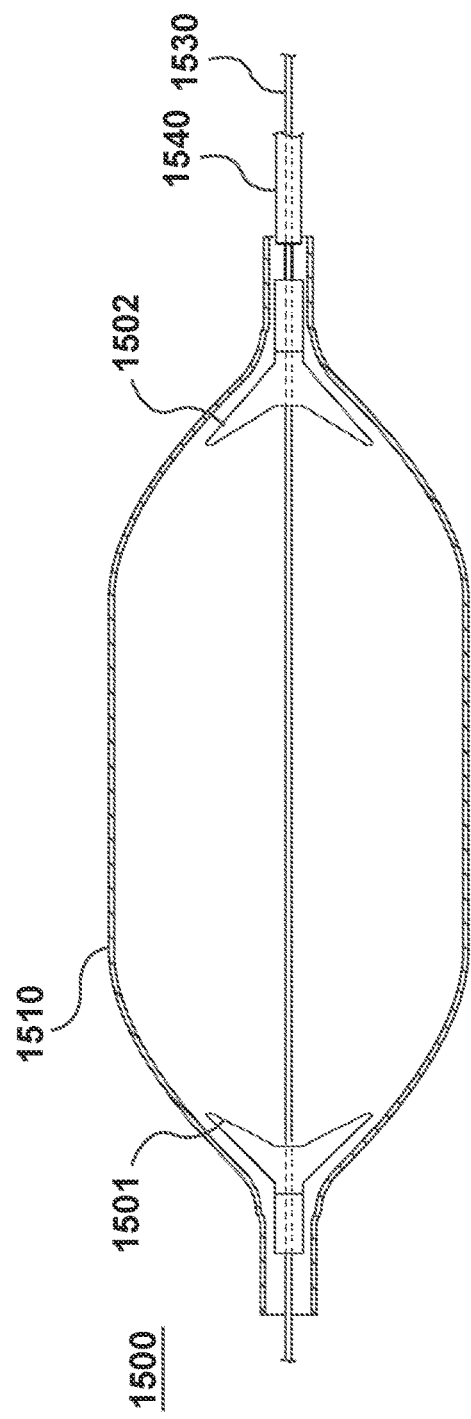

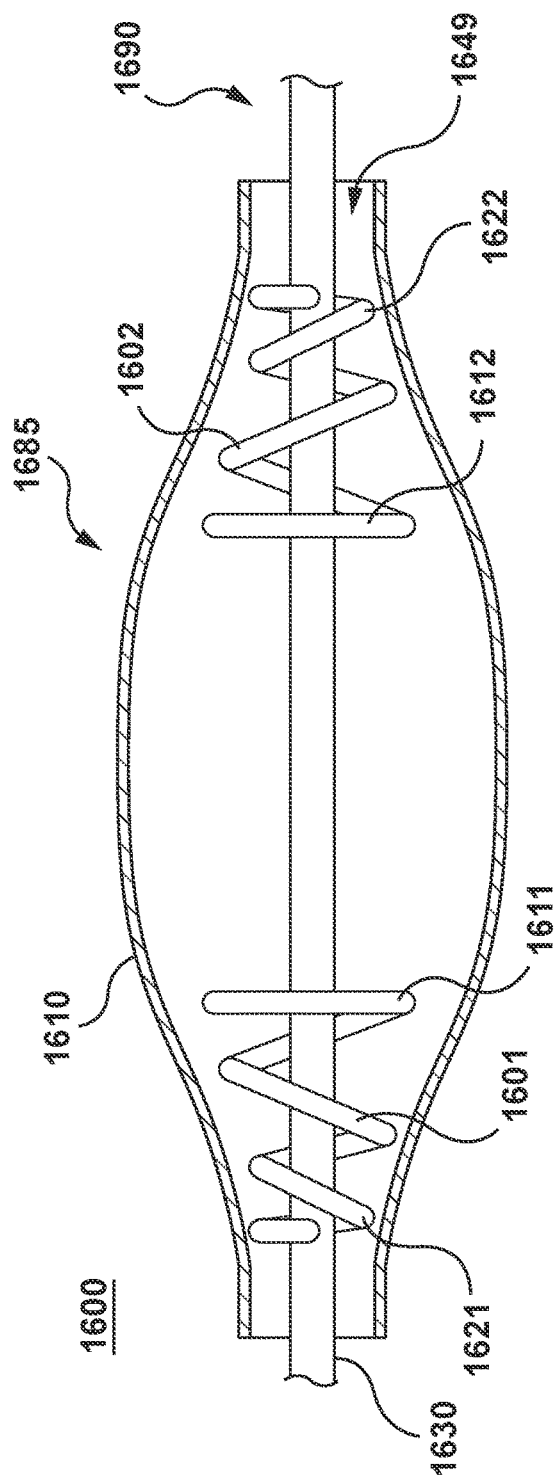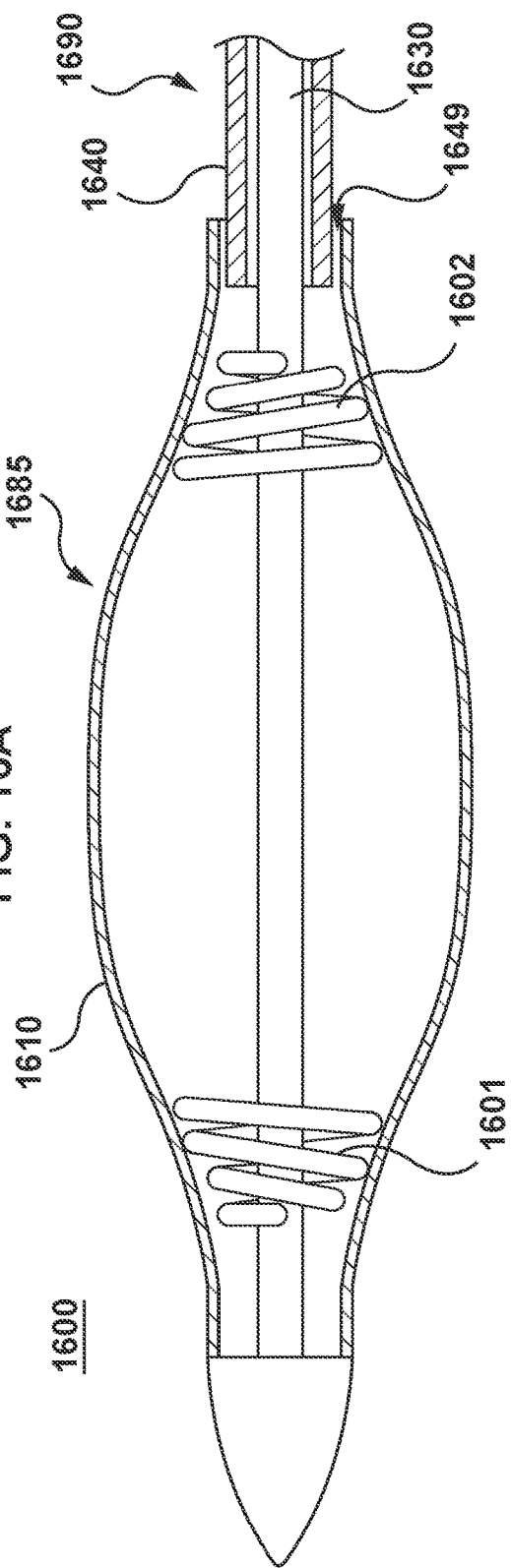

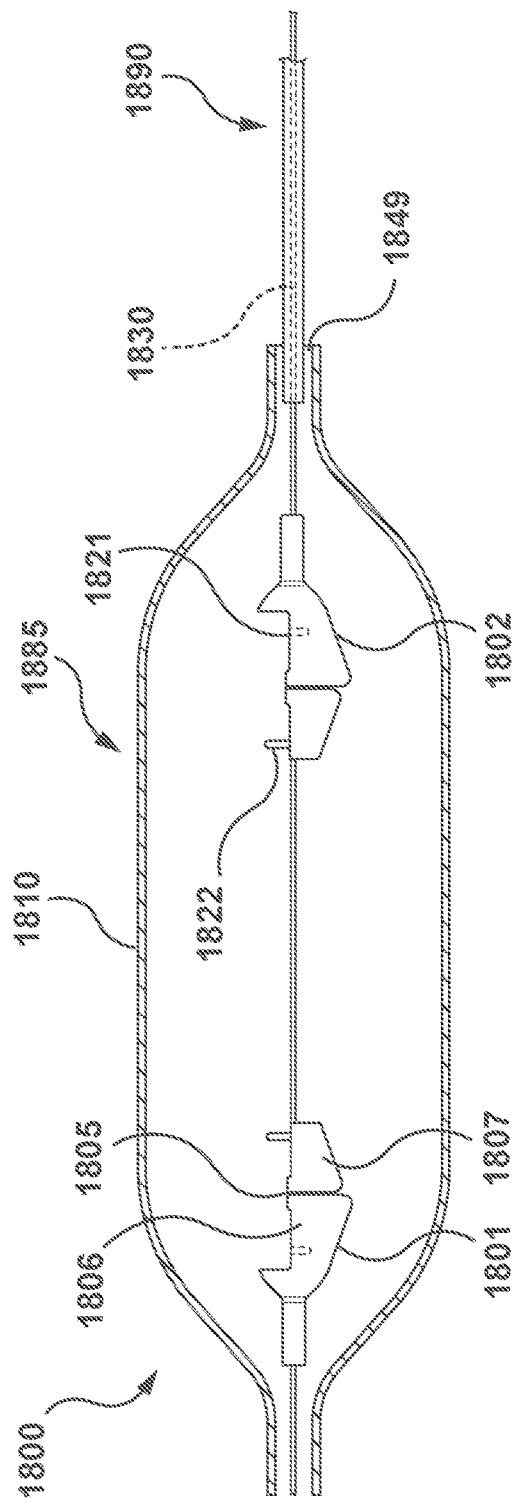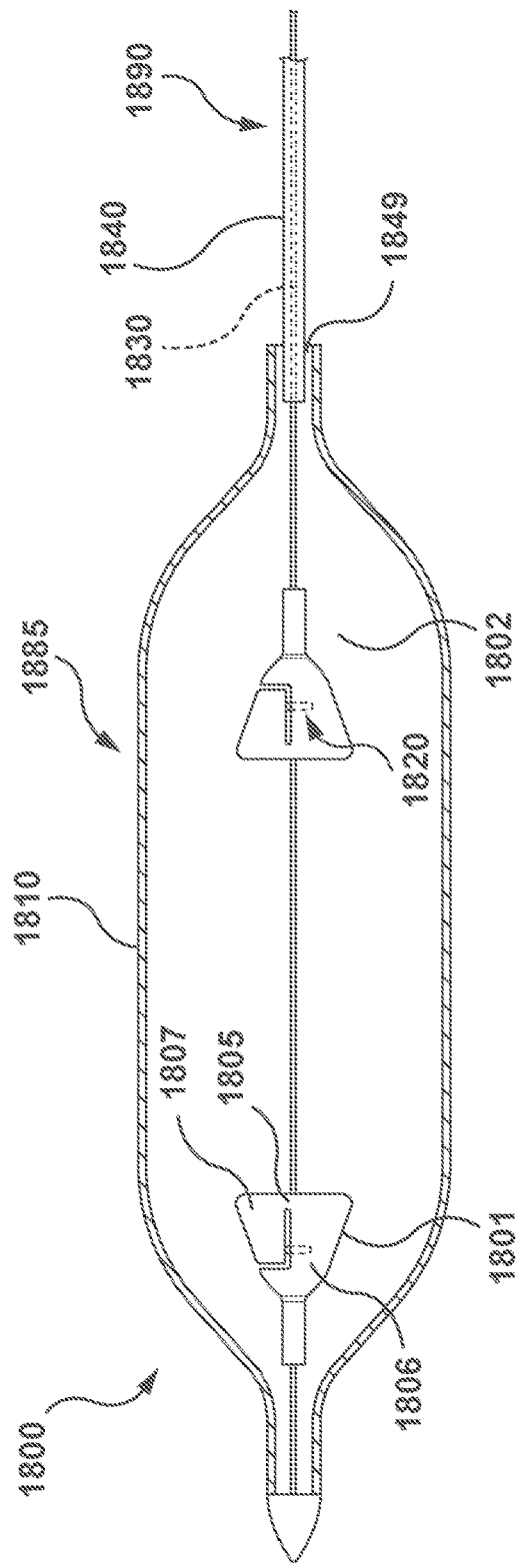

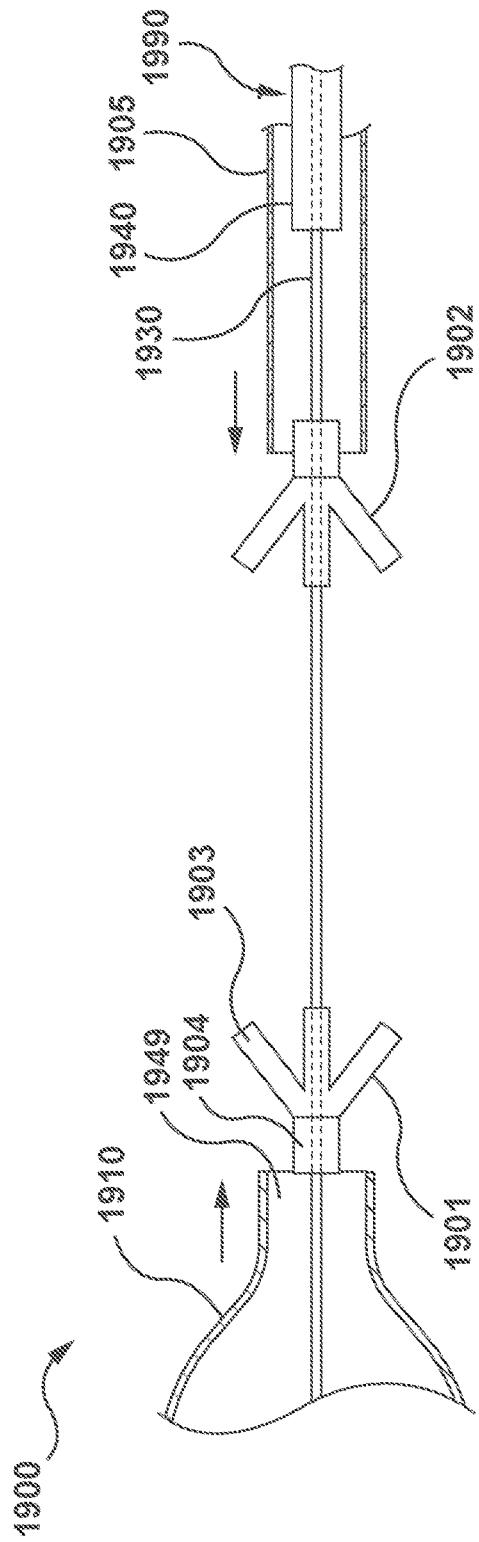
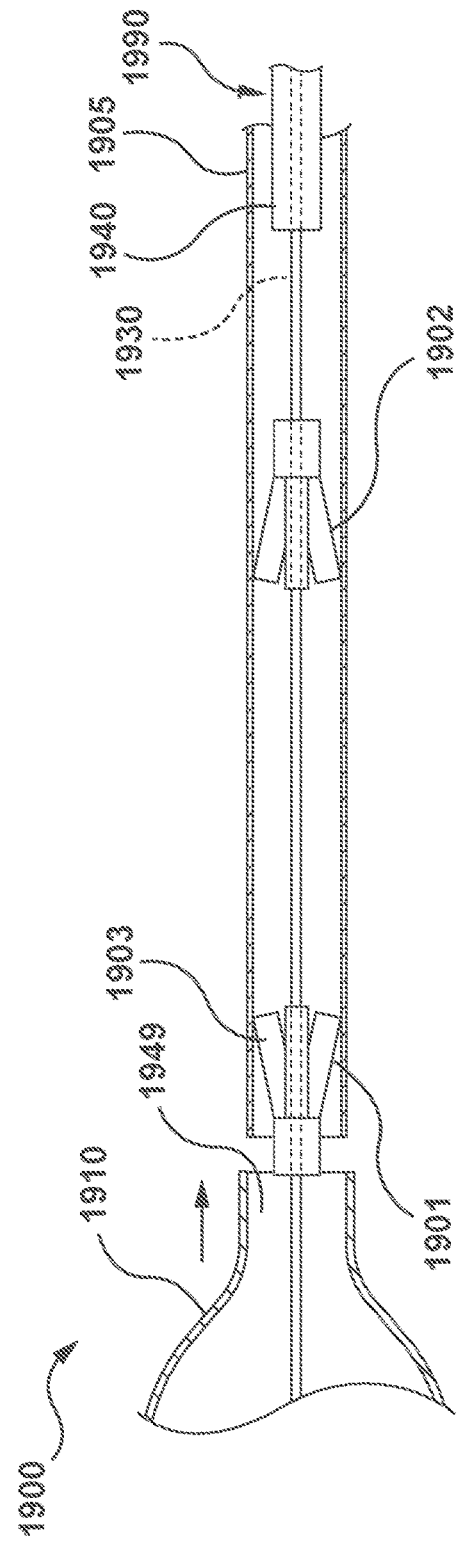
FIG. 19A
FIG. 19B

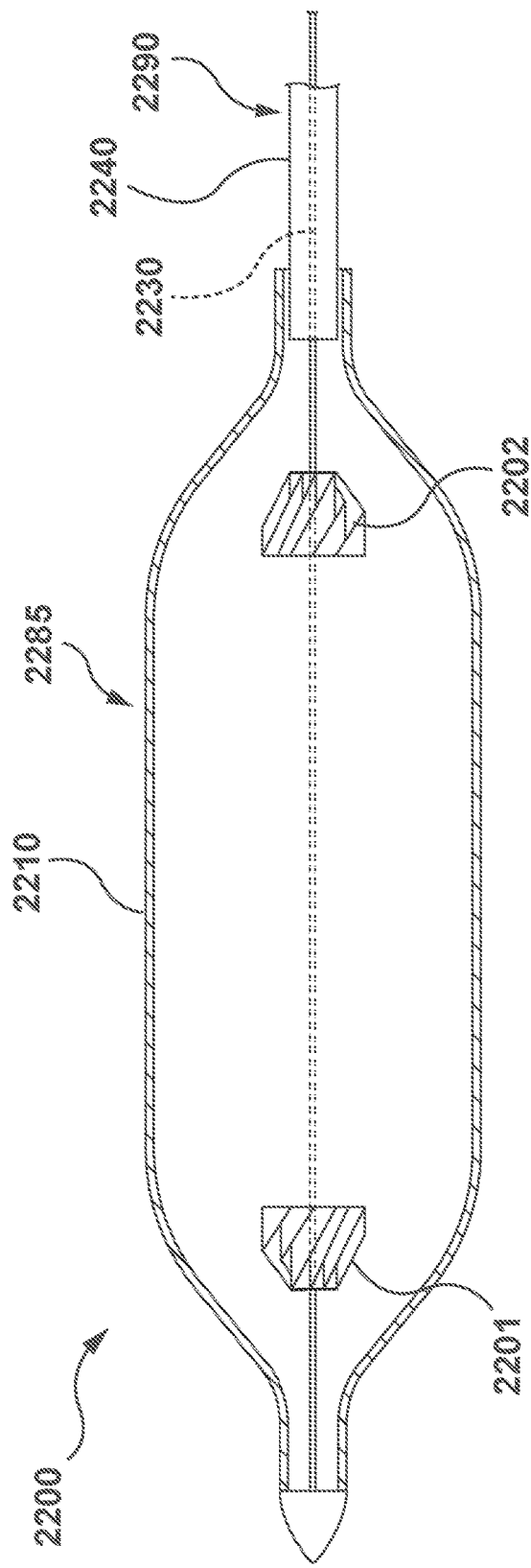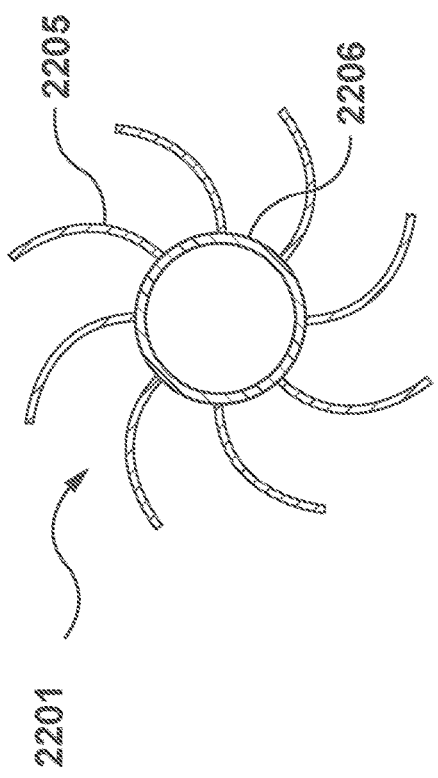
FIG. 22C
FIG. 22D

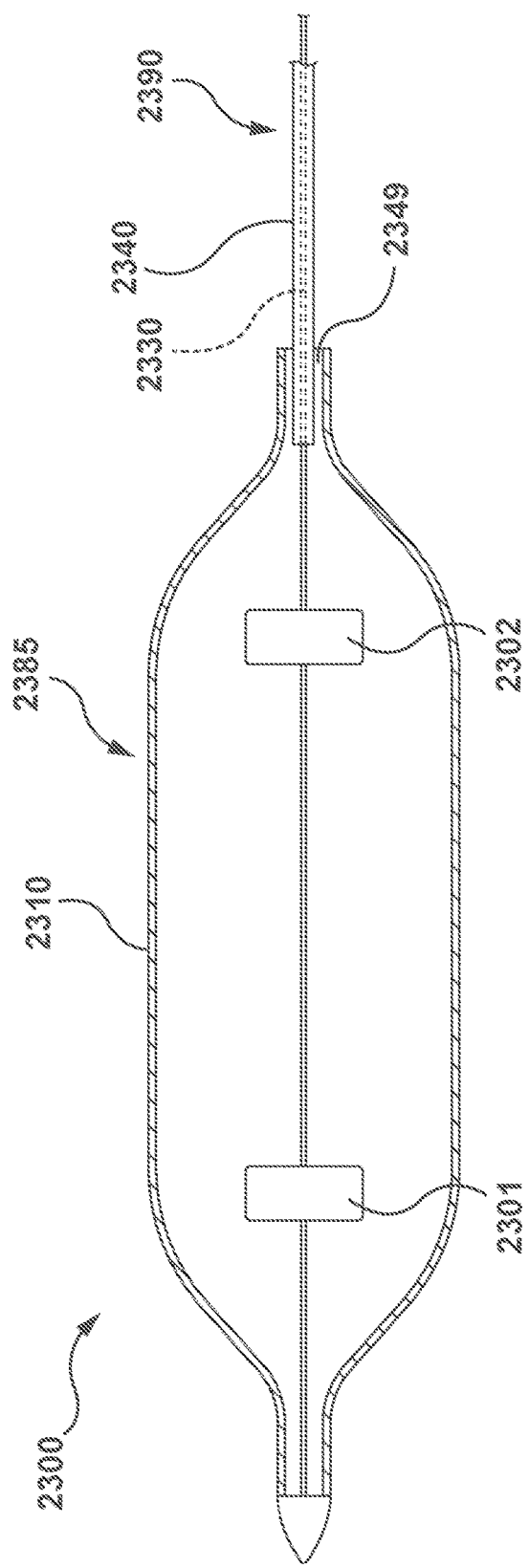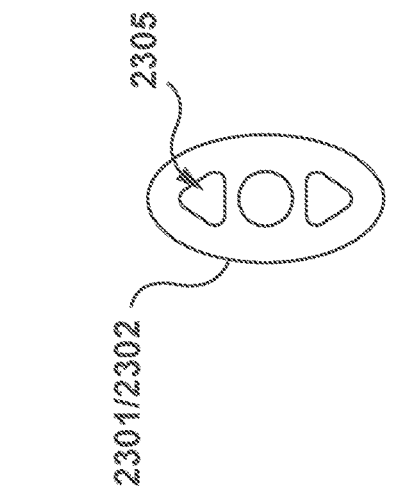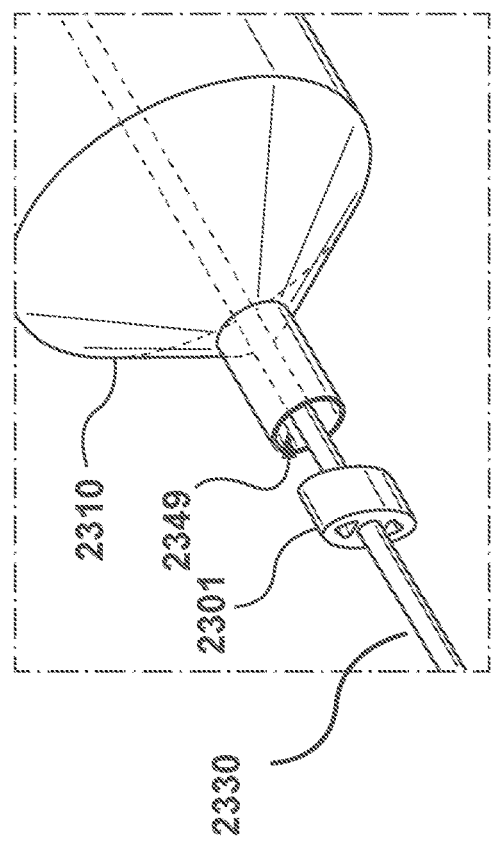
FIG. 23A
FIG. 23C
FIG. 23B

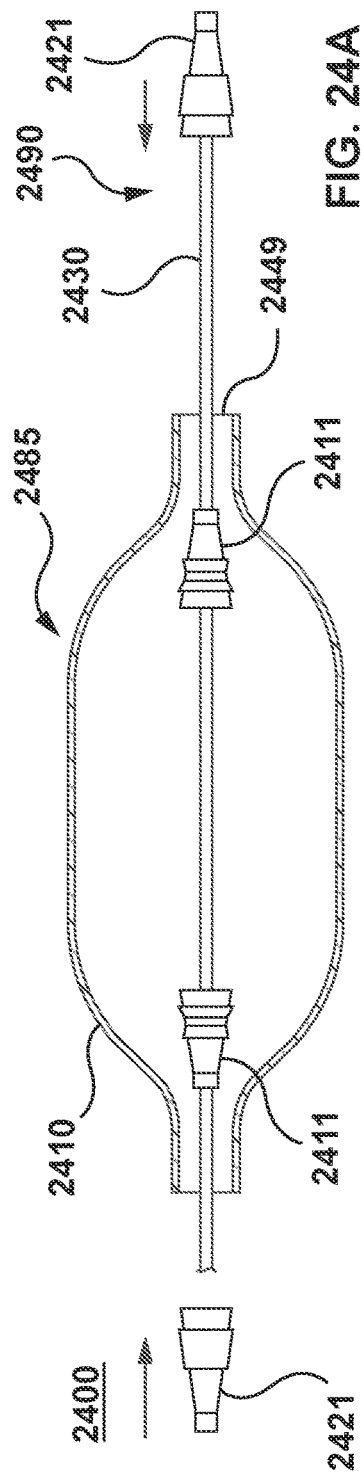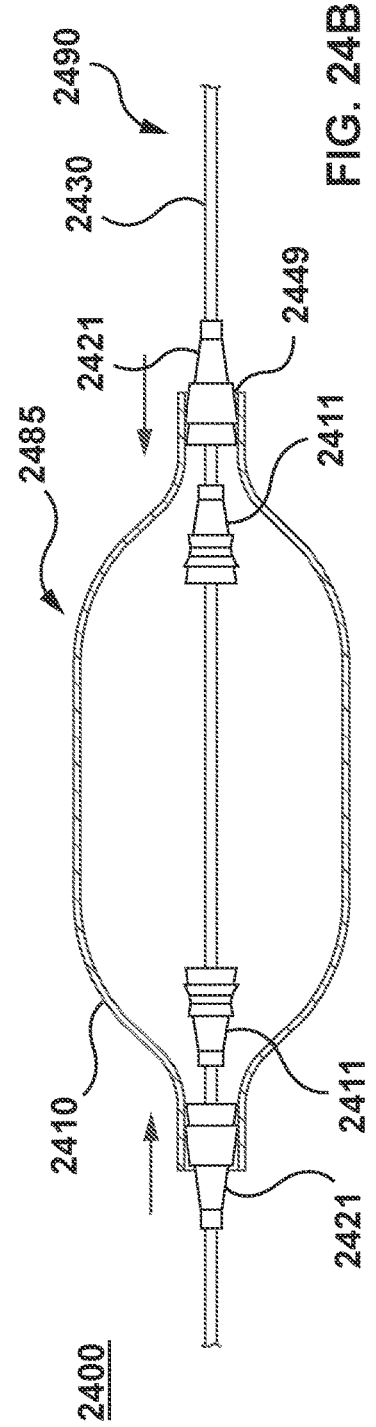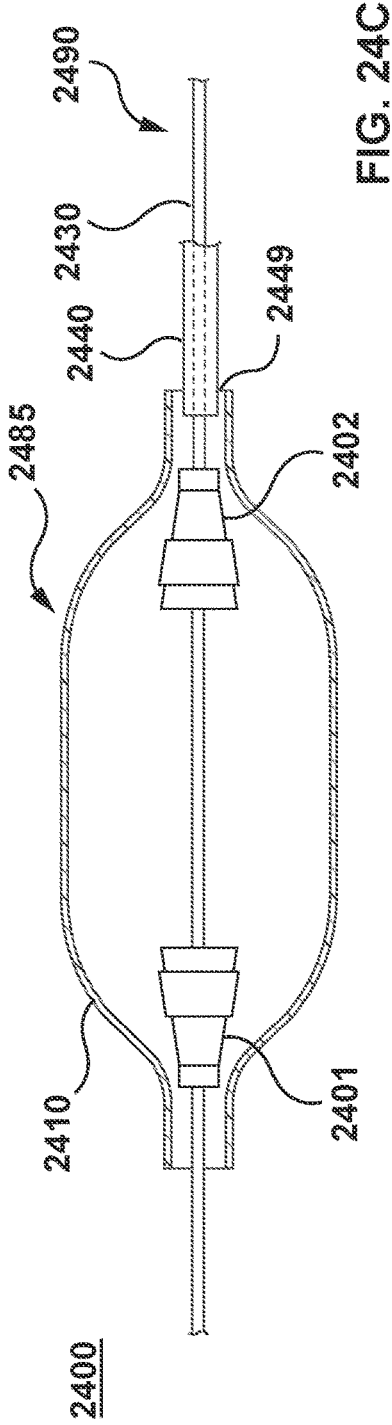

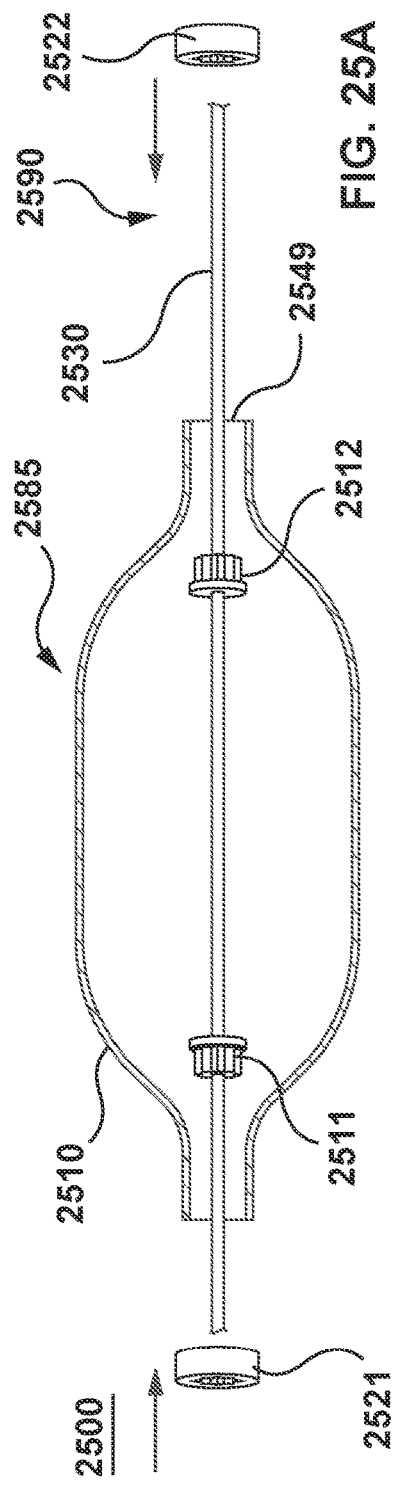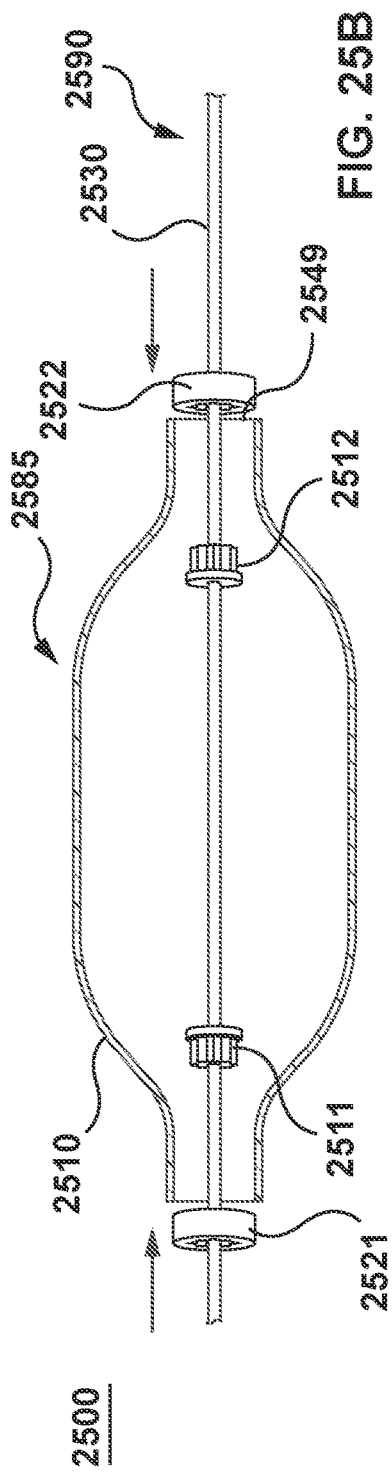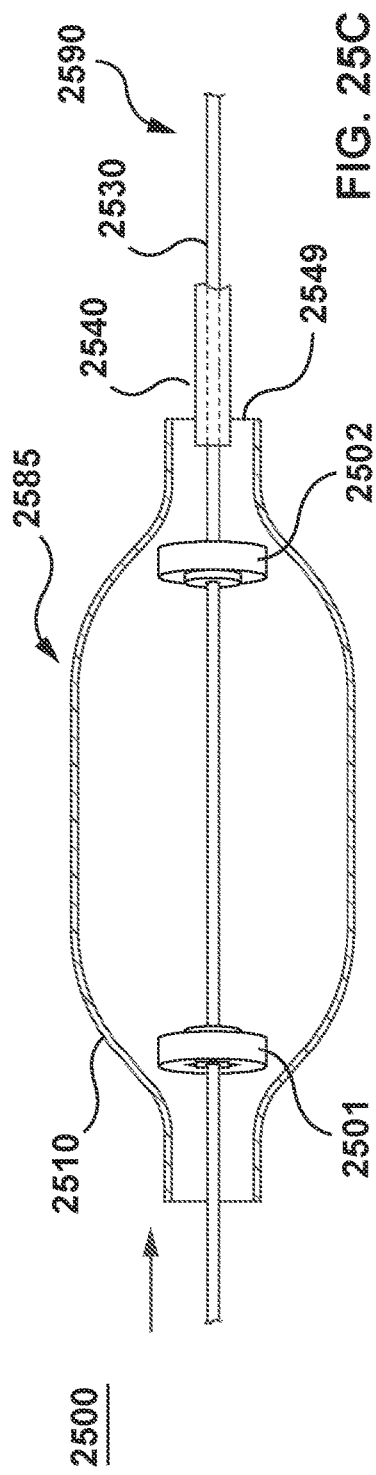

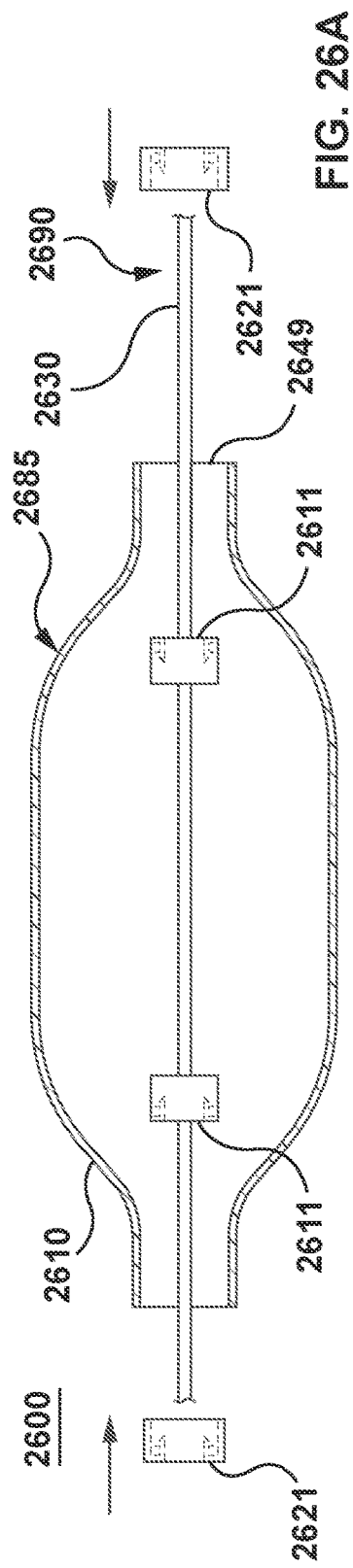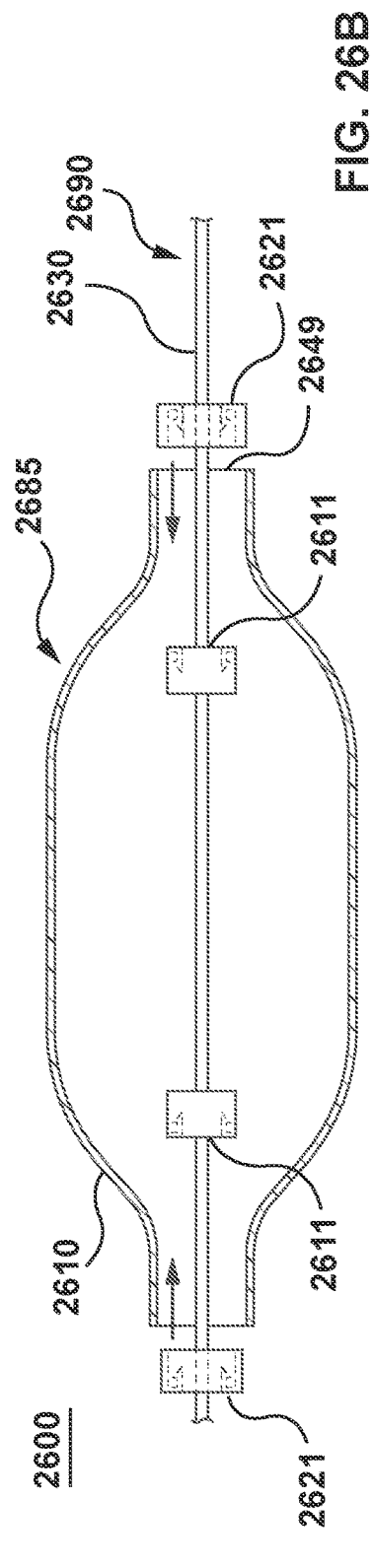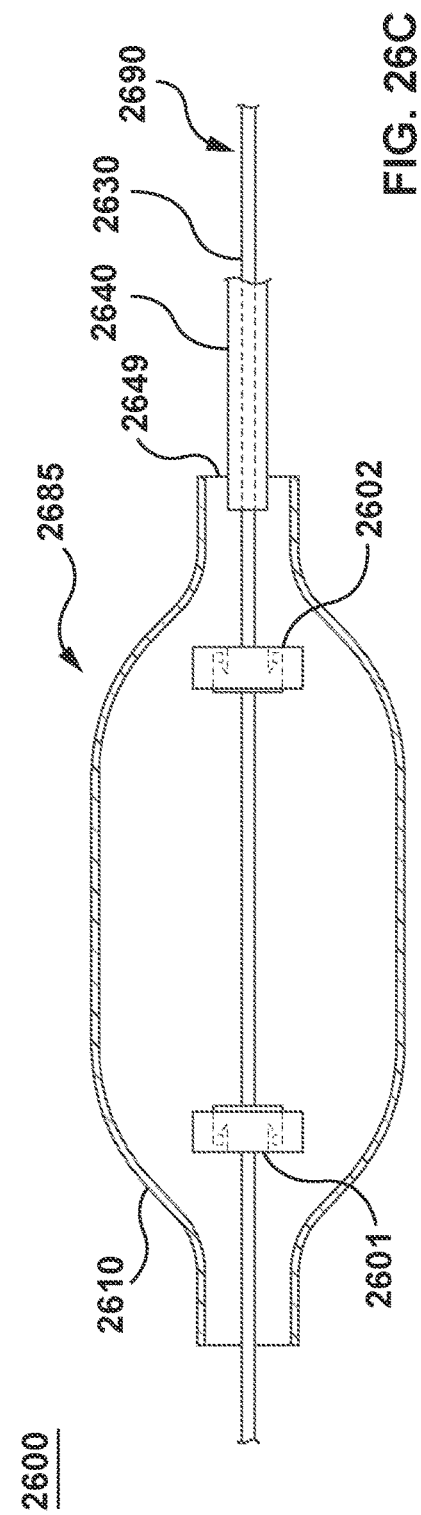

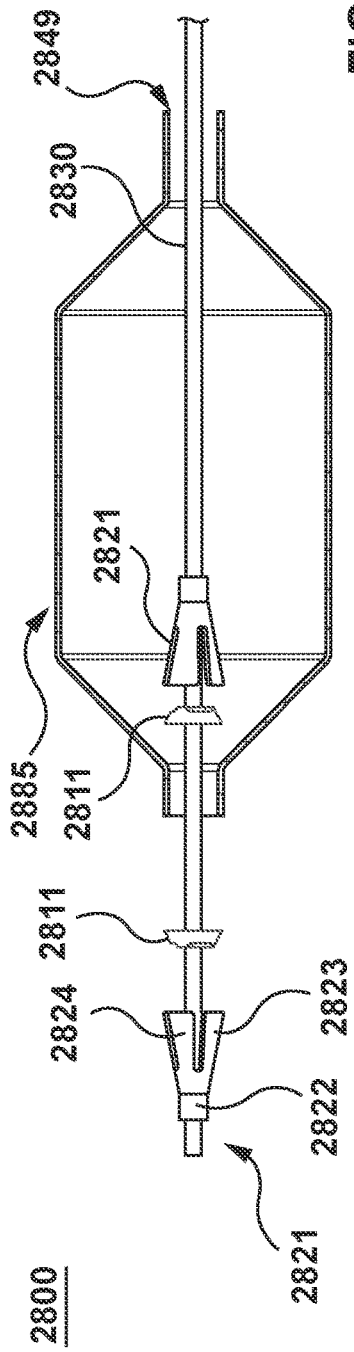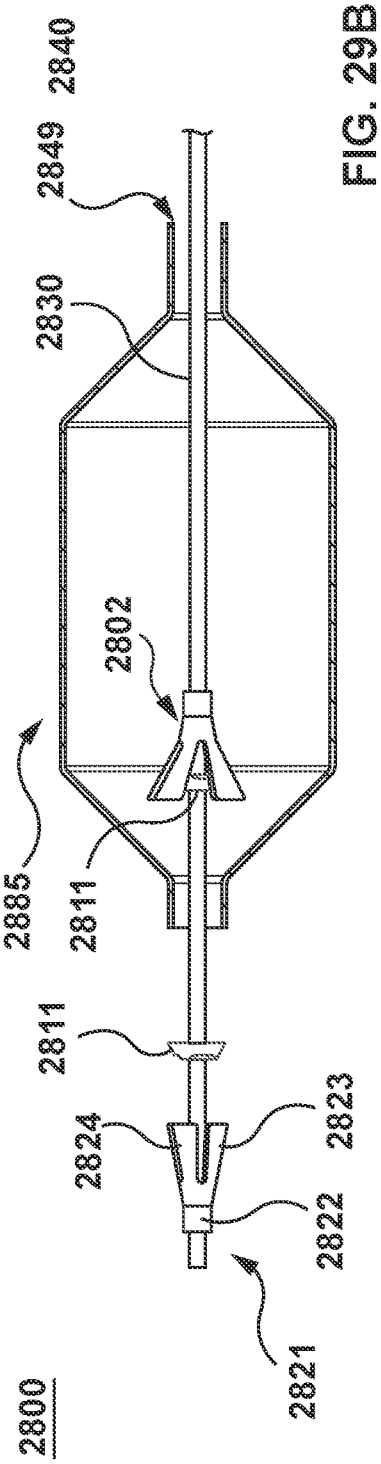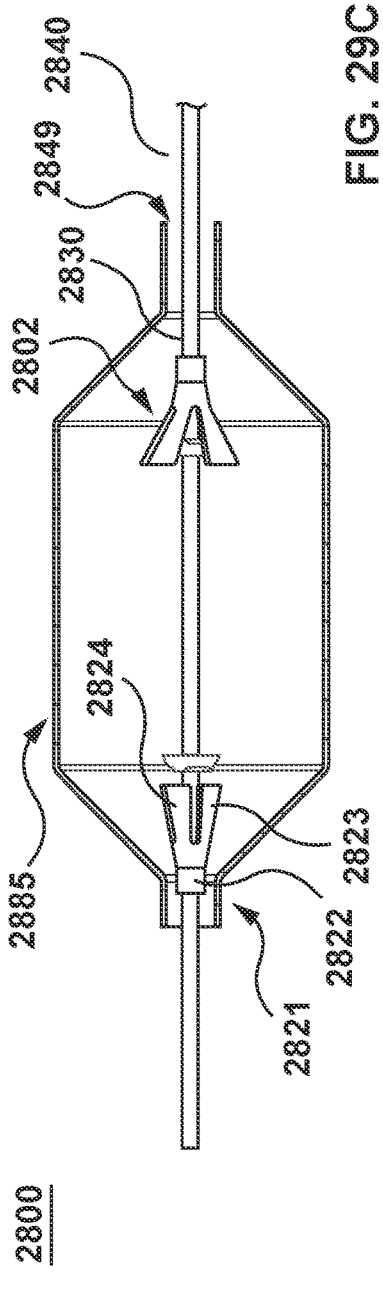

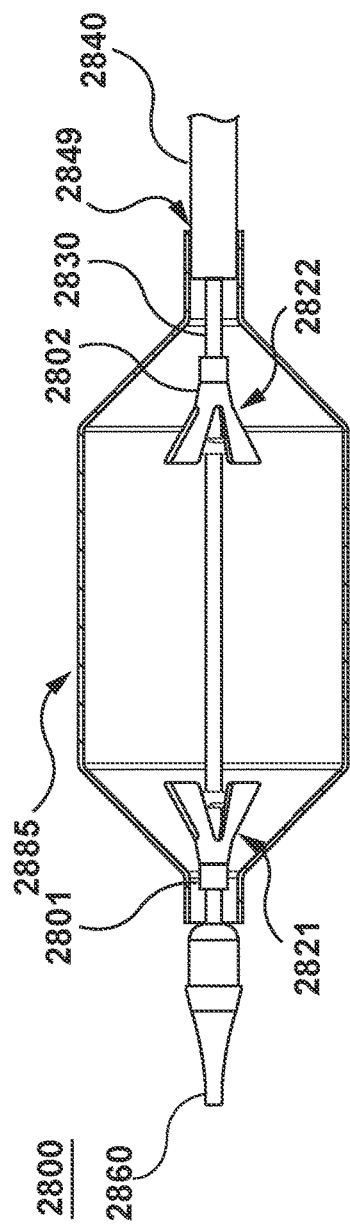
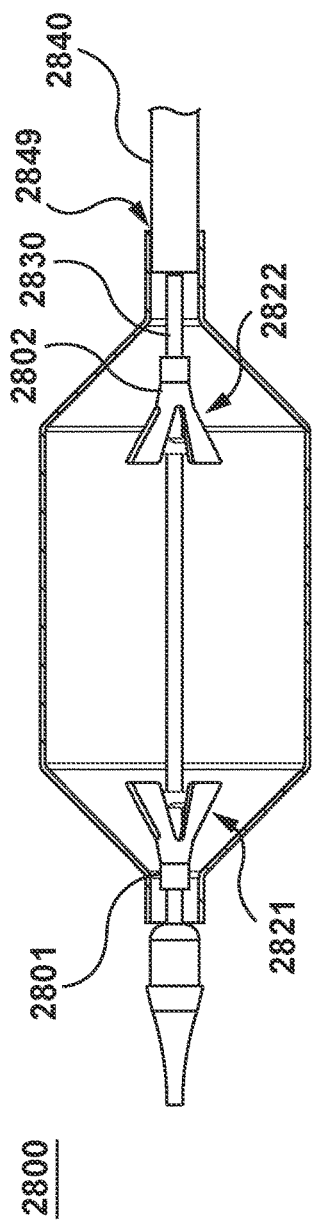
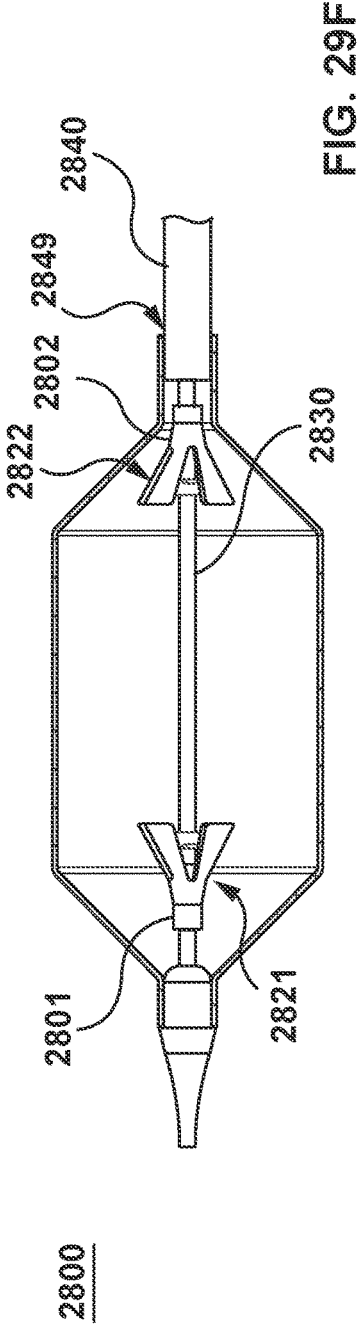
FIG. 29D
FIG. 29E
FIG. 29F

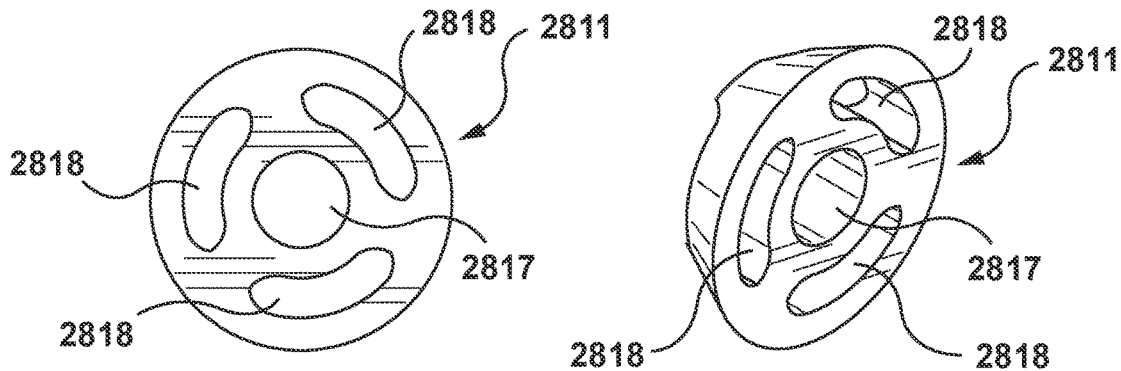
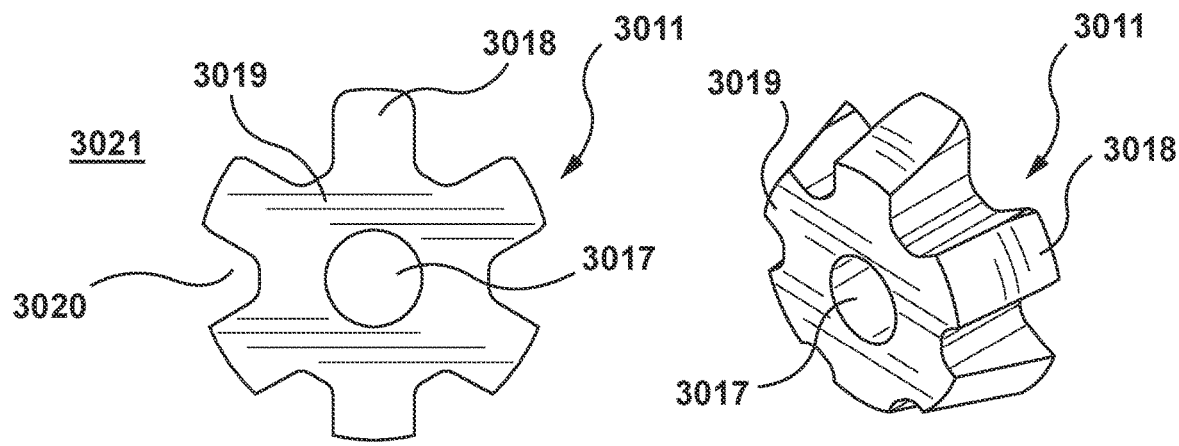
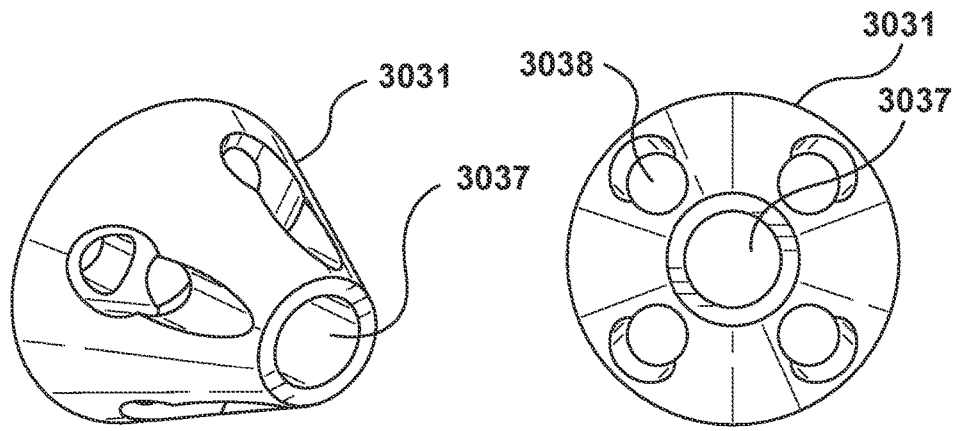
FIG. 30A    FIG. 30B
FIG. 30C    FIG. 30D
FIG. 30E    FIG. 30F

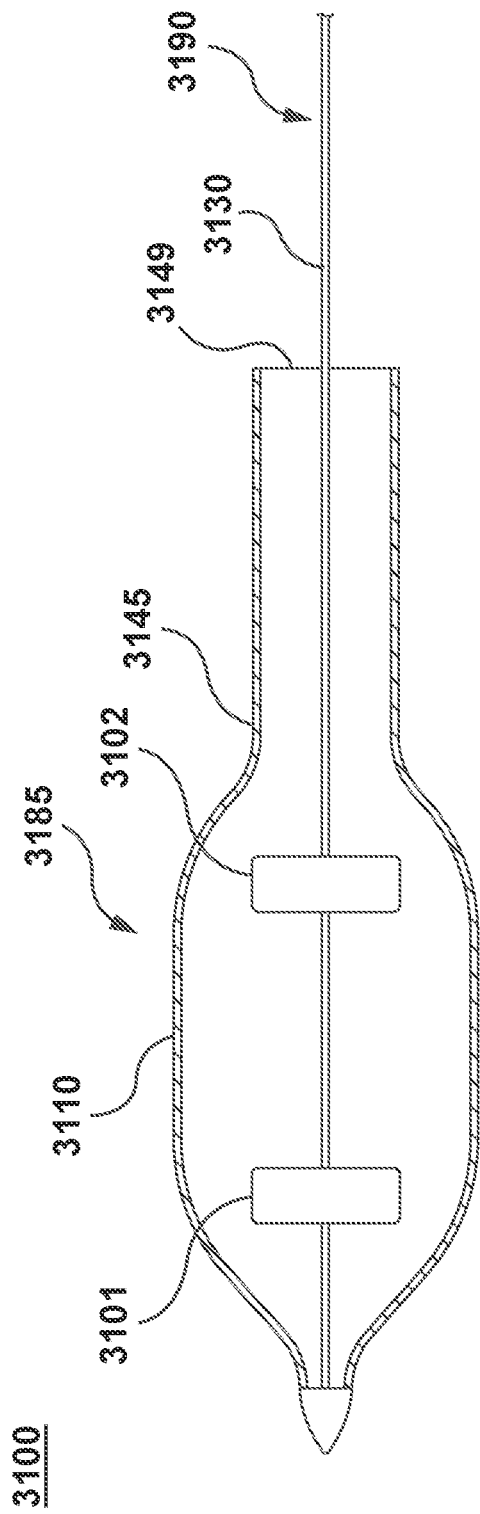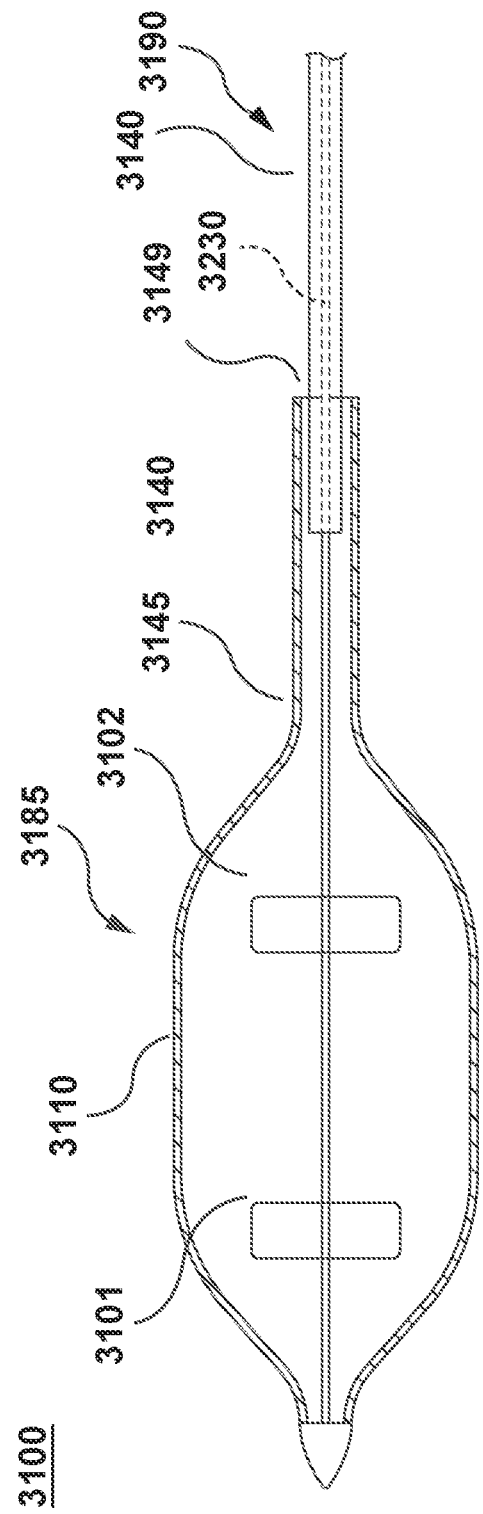

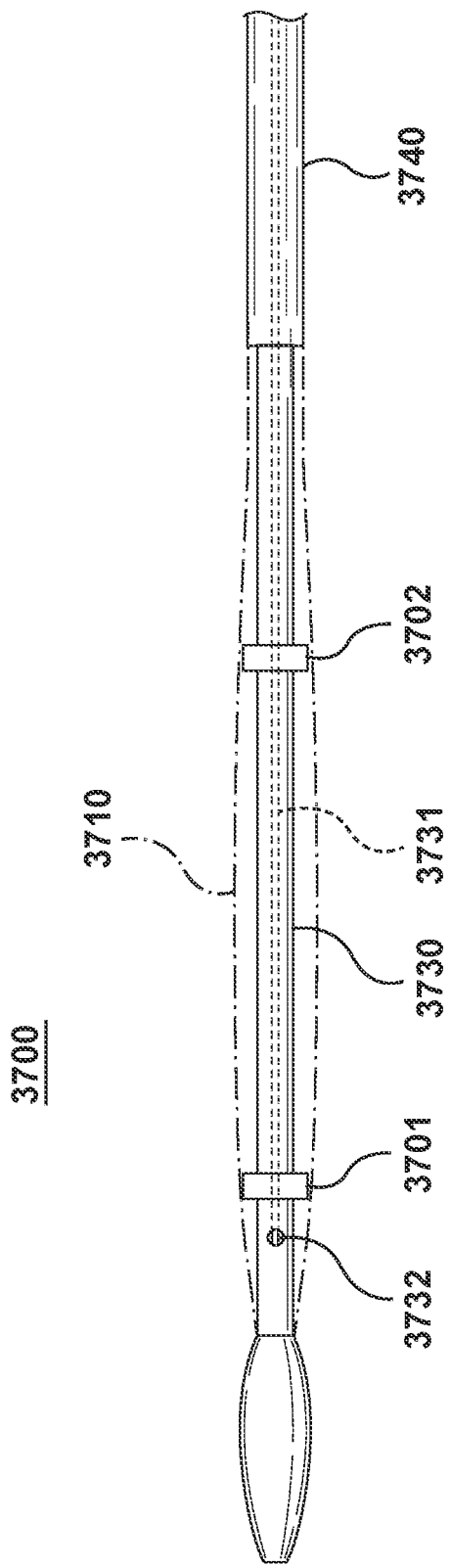
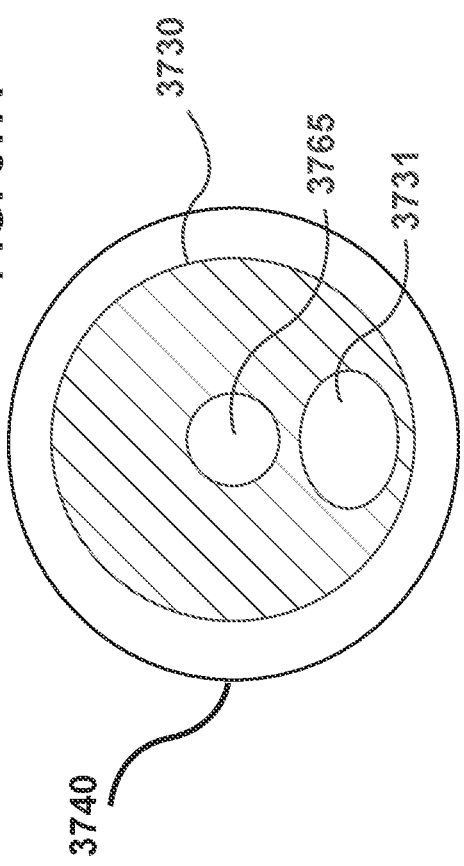
FIG. 37A
FIG. 37B

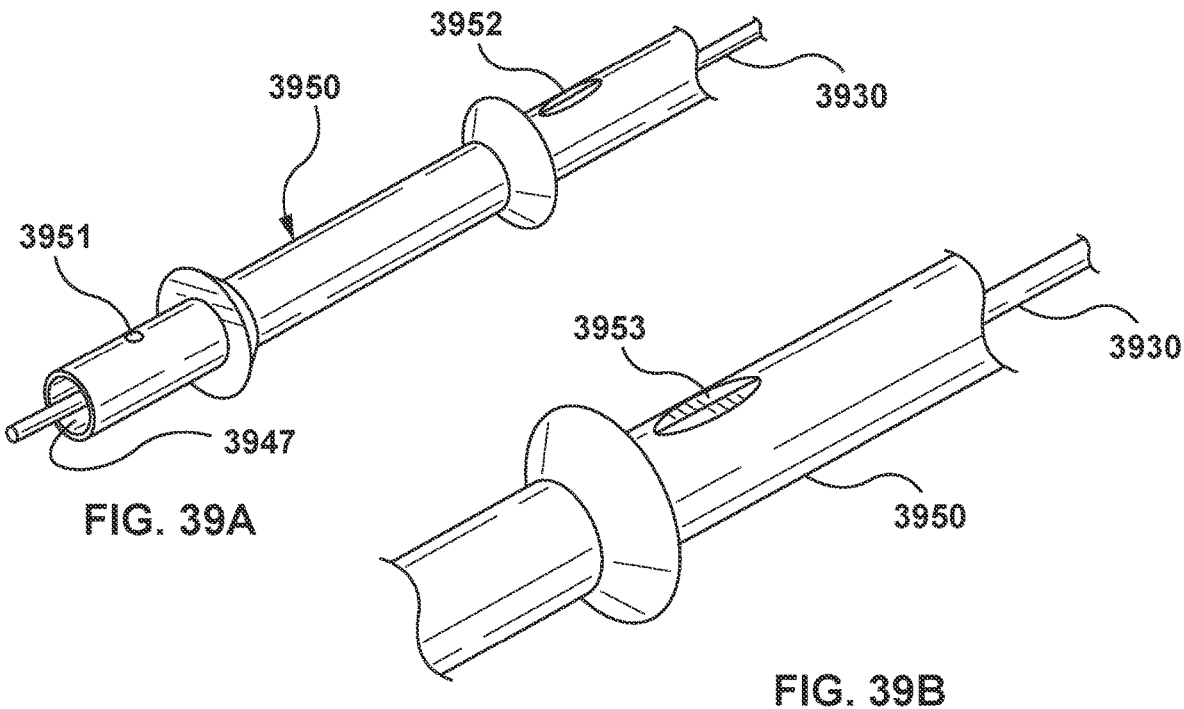
FIG. 39A
FIG. 39B
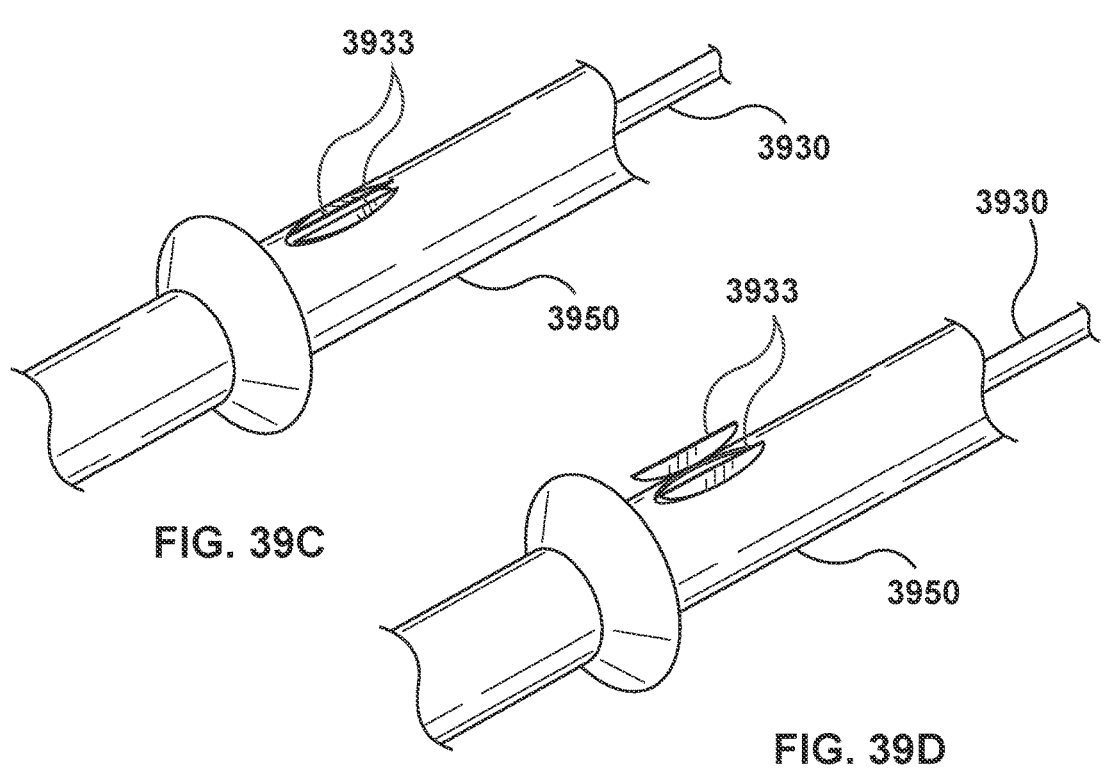
FIG. 39C
FIG. 39D

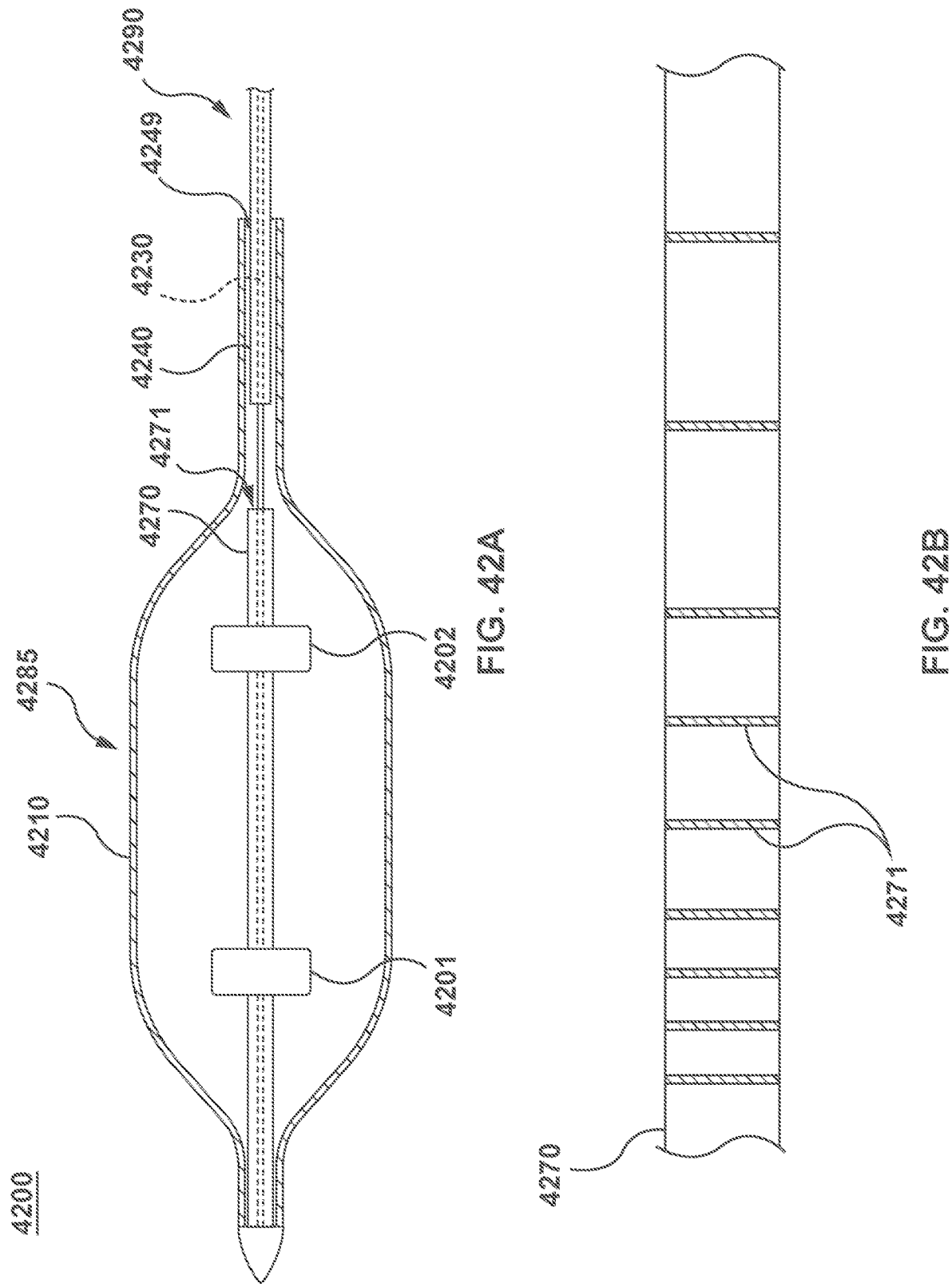

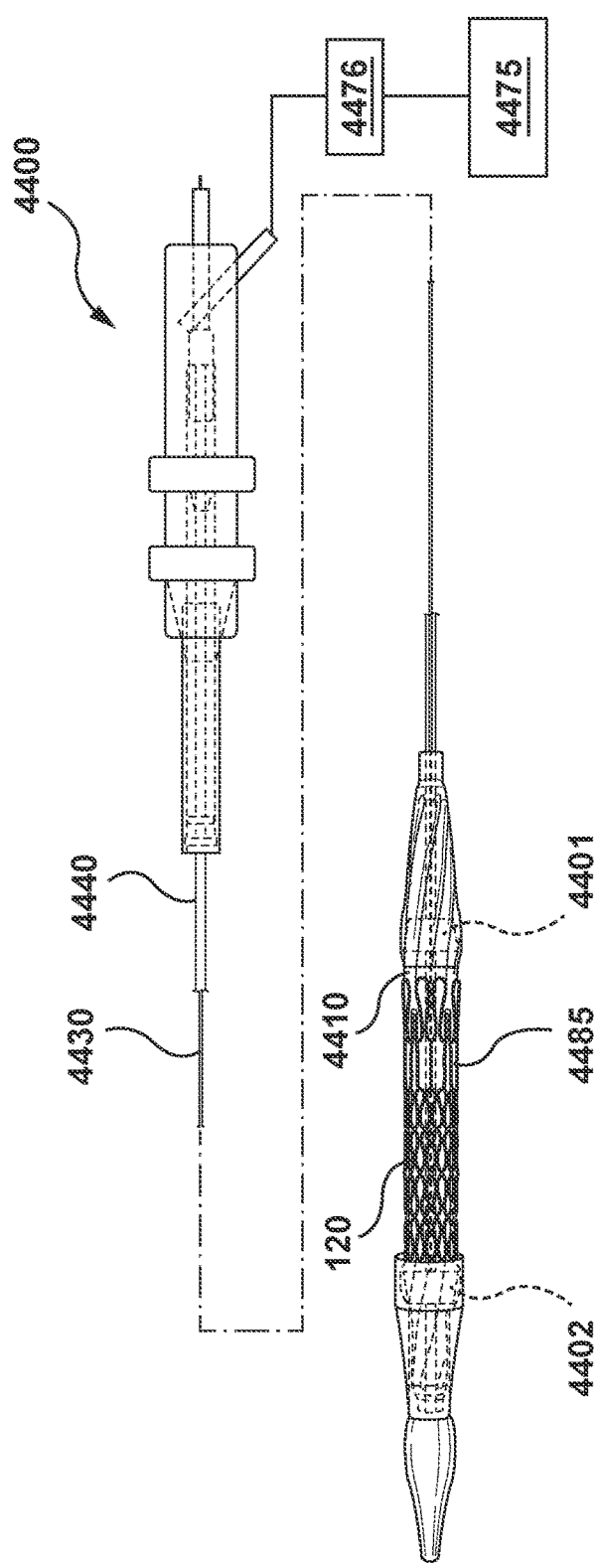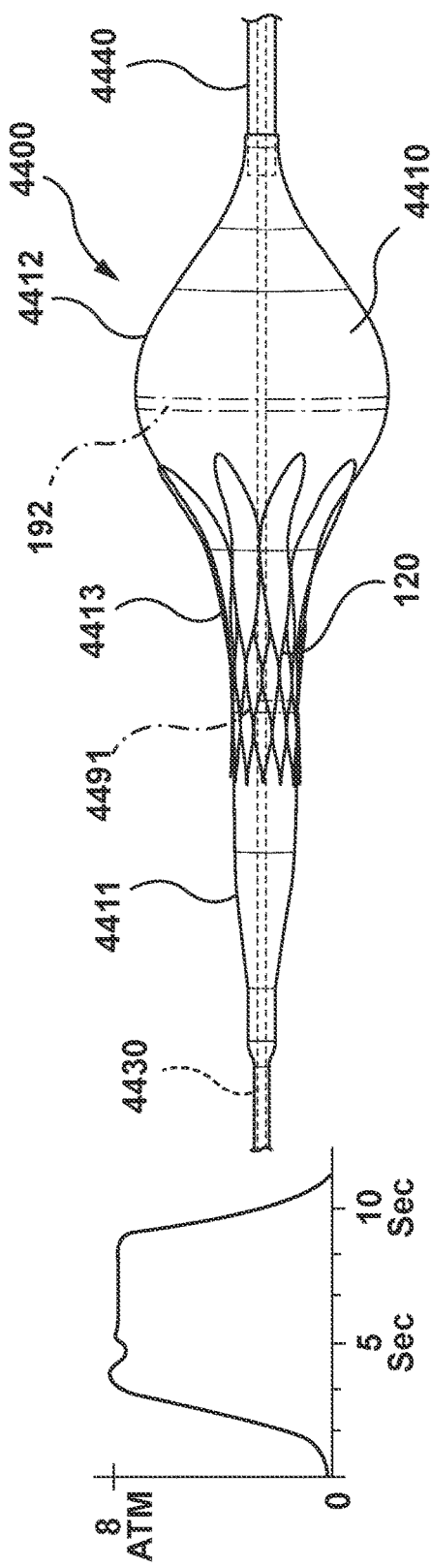
FIG. 44A
FIG. 44B
FIG. 44C

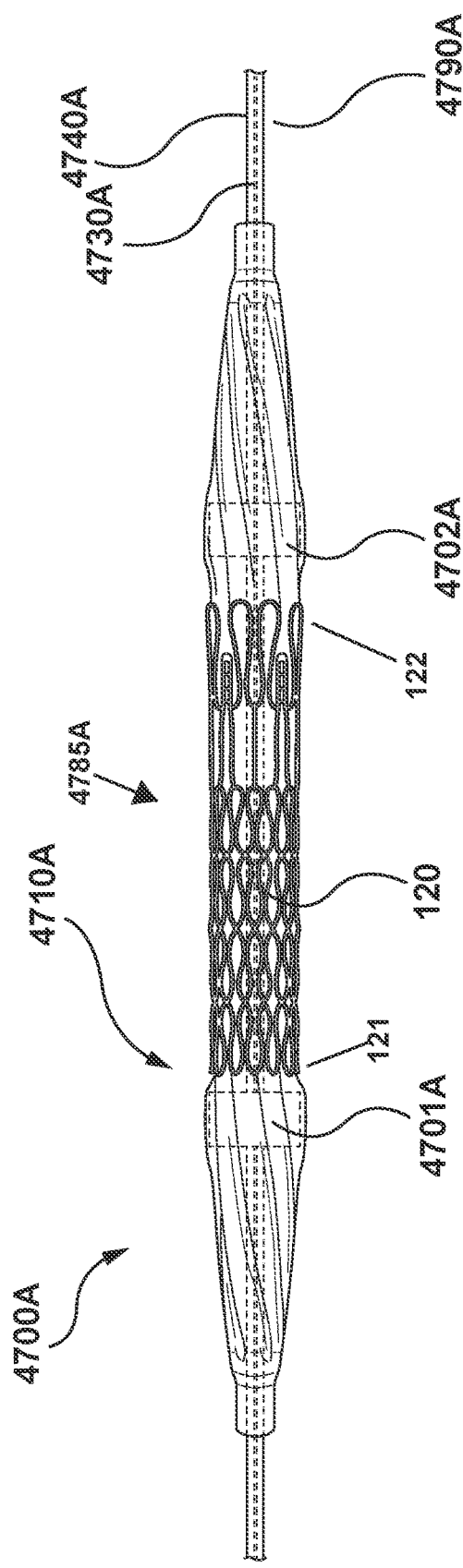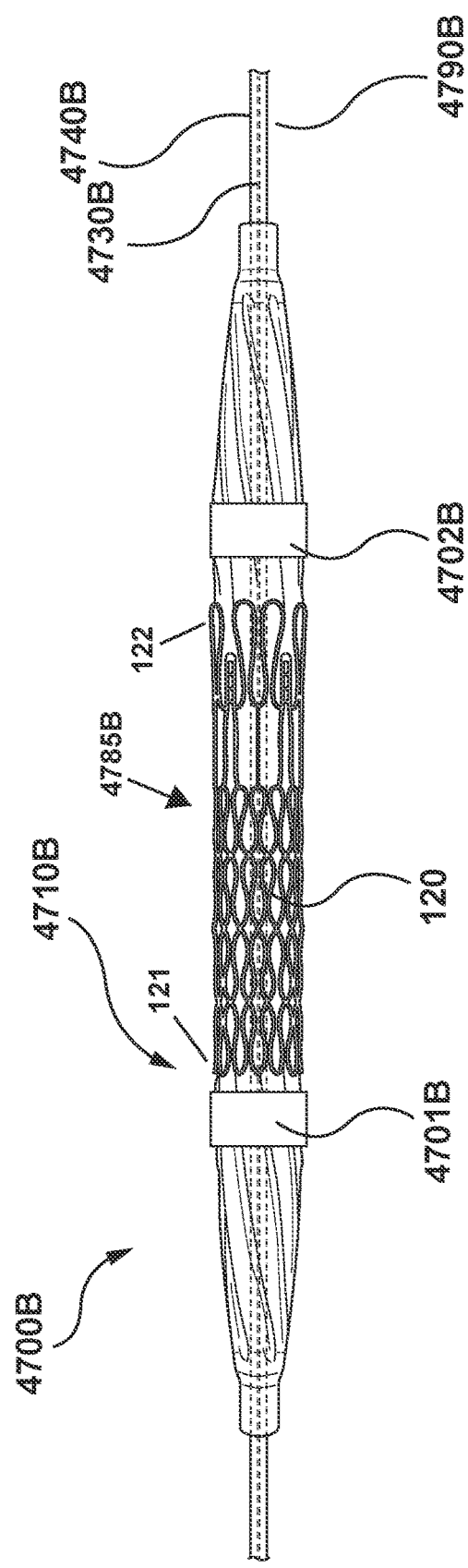
FIG. 47A
FIG. 47B

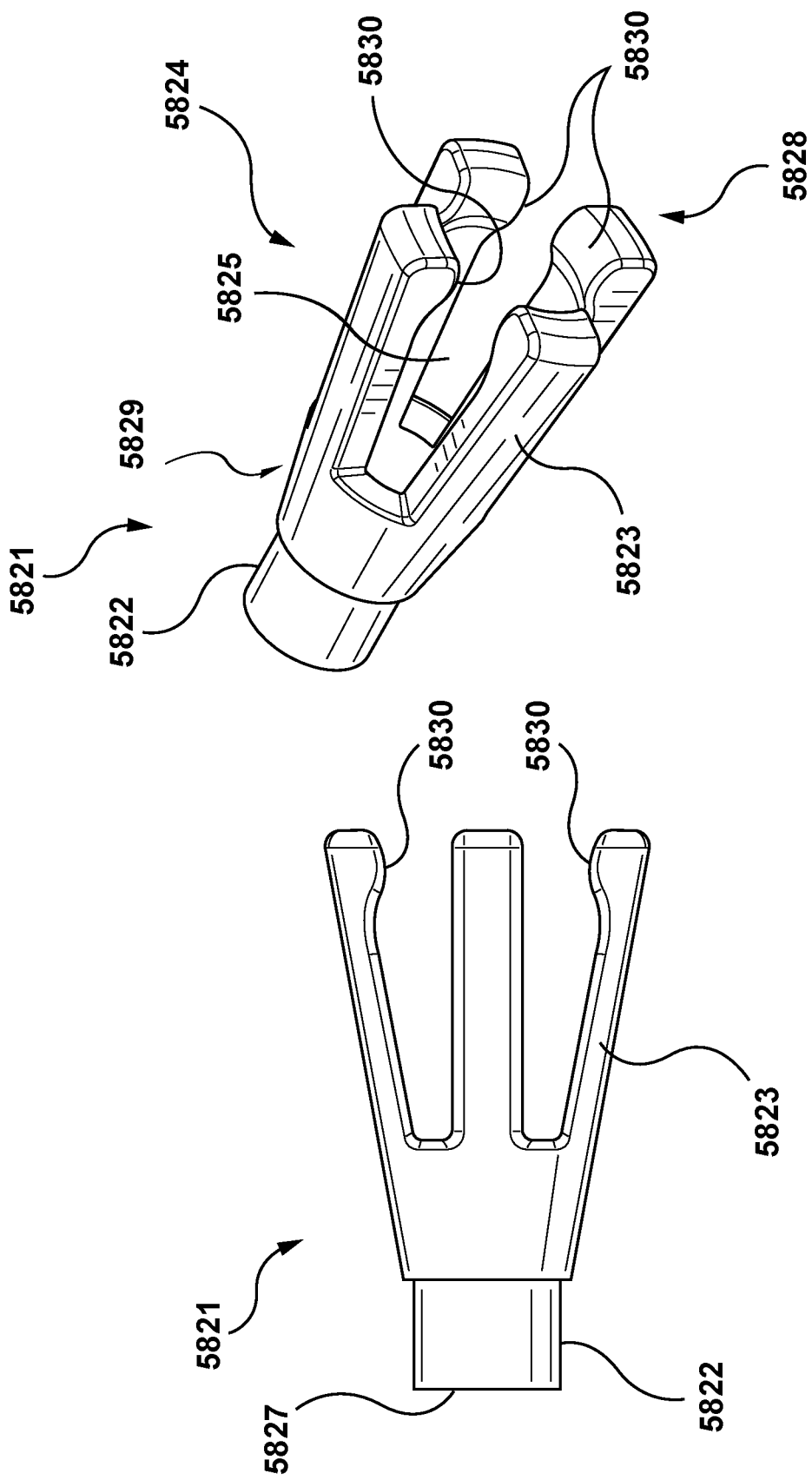

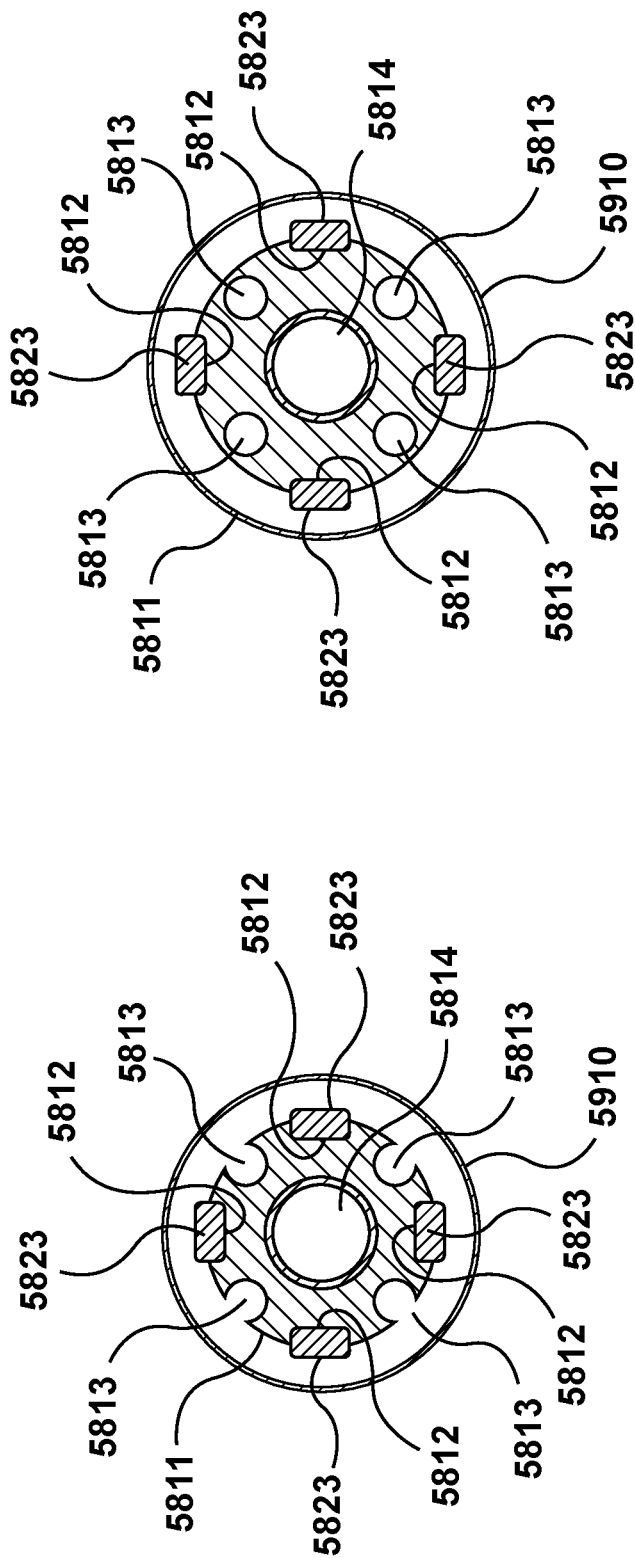

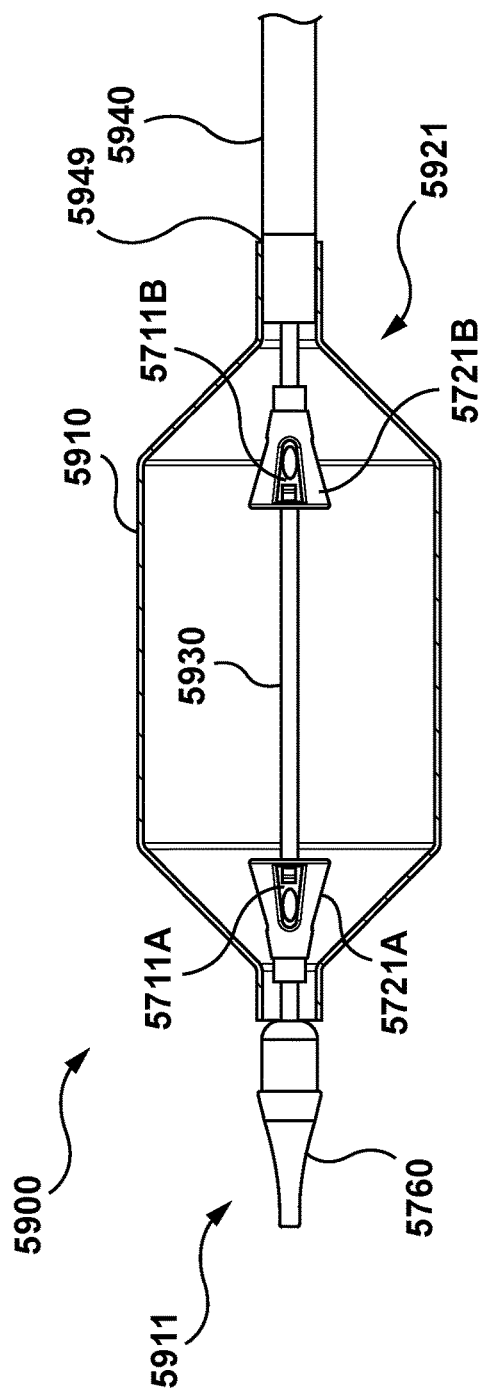
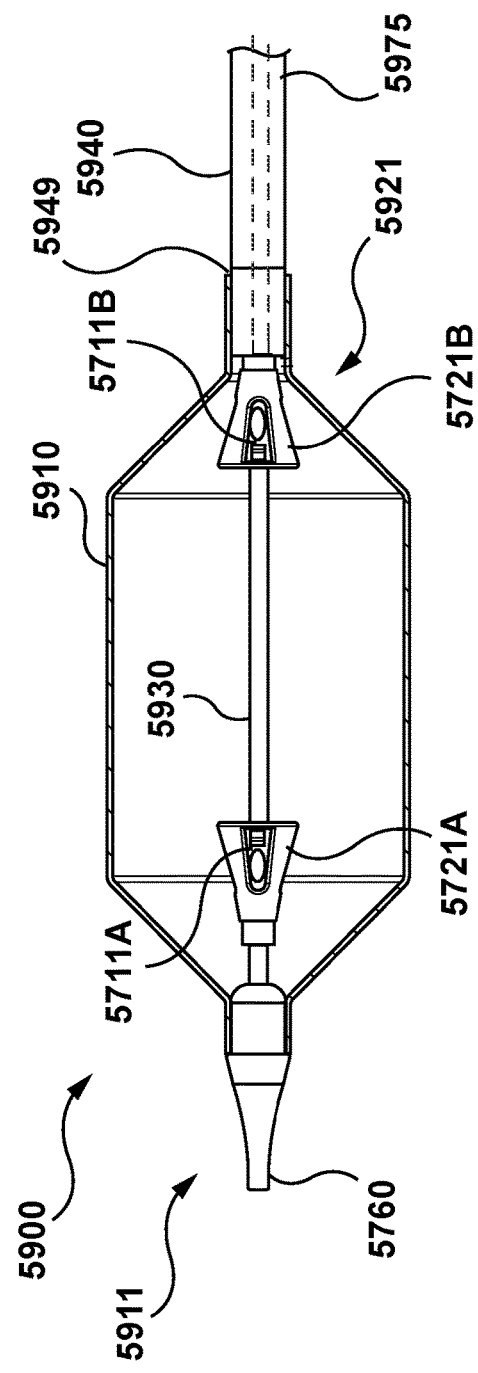
FIG. 59E
FIG. 59F

DEVICES AND METHODS FOR DELIVERY AND DEPLOYMENT OF BALLOON EXPANDABLE TRANSCATHETER VALVES

RELATED MATTERS

This application claims the benefit of prior U.S. Application No. 63/234,882, filed on Aug. 21, 2019, prior U.S. Application No. 63/230,295, filed on Aug. 6, 2021, prior U.S. Application No. 63/123,801, filed on Dec. 10, 2010, prior U.S. Application No. 63/069,428, filed on Aug. 24, 2020, prior U.S. Application No. 63/069,428, filed on Aug. 24, 2020, prior U.S. Application No. 63/069,417, filed on Aug. 24, 2020, prior U.S. Application No. 63/069,409, filed on Aug. 24, 2020, prior U.S. Application No. 63/069,401, filed on Aug. 24, 2020, prior U.S. Application No. 63/069,396, filed on Aug. 24, 2020, the entire contents of each of which are incorporated by reference herein.

TECHNICAL FIELD

The present invention is related to systems and methods for transcatheter valve delivery and deployment. In particular, the present invention is related to balloon catheter devices configured for prosthetic heart valve retention during delivery and deployment of prosthetic heart valves.

BACKGROUND

Transcatheter valve technology provides a minimally invasive means of implanting prosthetic heart valves. The prosthetic heart valve is loaded onto a delivery system that is able to access and navigate the vasculature to the intended implant location and implant the prosthetic heart valve. One approach for a transcatheter valve system is to use a balloon catheter for the delivery system and a prosthetic heart valve incorporating a balloon expandable frame. After reaching the delivery site, the balloon is inflated to expand the prosthetic heart valve into a deployment configuration. After deployment, the balloon is deflated and the balloon catheter is removed.

In some balloon catheters, transcatheter balloon expandable prosthetic heart valves are crimped onto the balloon of the balloon catheter. The balloon of the balloon catheter is processed such that the balloon is pleated then folded prior to crimping the prosthetic heart valve onto the balloon. The prosthetic heart valve is delivered to the treatment site and then deployed by inflating the balloon which thereby radially expands the prosthetic heart valve. During delivery procedures, such as gaining vessel access, tracking the balloon catheter through the patient anatomy, crossing the native valve, and advancing the balloon catheter past a distal end of an introducer catheter, forces on the prosthetic heart valve may lead to migration of the prosthetic heart valve on the balloon catheter. Movement of the prosthetic heart valve may lead to an inaccurate deployment position, a prosthetic heart valve that does not fully deploy, and other complications.

Challenges impacting valve retention include the minimum crimp diameter of the prosthetic heart valve, varying contact material and shape between the crimped prosthetic heart valve and the folded balloon, and high forces exerted on the crimped prosthetic heart valve during delivery and deployment procedures. The minimum crimp diameter of the prosthetic heart valve is typically larger than the minimum diameter of the folded balloon. This size mismatch limits contact between the balloon and the prosthetic heart valve and therefore reduces friction forces between the prosthetic heart valve and the balloon. Likewise, the size mismatch limits opportunities for a mechanical lock between the prosthetic heart valve and the balloon (i.e., valve imprinting into balloon during crimp). Along the length of the crimped prosthetic heart valve, the contact material can change between the metal scaffold and tissue and the tissue giving different friction coefficients and amount of compliance. Further, in the balloon catheter, the crimped prosthetic heart valve typically is the component having the largest diameter. This leads to the prosthetic heart valve being subject to the largest forces during delivery through an introducer.

Additionally, after reaching the delivery site, the balloon is inflated to expand the prosthetic heart valve into a deployment configuration. After deployment, the balloon is deflated and the delivery catheter is removed. A problem that may be encountered in the use of some balloon catheter delivery devices is that of prosthetic heart valve migration during deployment. As the balloon is inflated, the valve may migrate proximally or distally from an original position on the catheter, making accurate positioning more difficult. This migration may be caused by asymmetric balloon inflation.

Devices and methods disclosed herein address the issue of prosthetic heart valve migration during delivery and deployment.

SUMMARY

Embodiments hereof relate generally to balloon catheters for prosthetic heart valves, and, more specifically, to balloon catheters for prosthetic heart valve delivery and deployment. Balloon catheters consistent with embodiments hereof are configured to reduce or prevent valve migration during delivery and deployment procedures.

Embodiments hereof are directed to a balloon catheter for delivering a prosthetic heart valve to a deployment site. The balloon catheter includes an inner shaft defining a guidewire lumen; an outer shaft surrounding the inner shaft defining an inflation lumen between the outer shaft and the inner shaft; a distal portion at a distal end of the outer shaft; a balloon disposed at the distal portion such that fluid delivered to the balloon via the inflation lumen causes the balloon to inflate; a plurality of retention bumpers secured to the inner shaft and configurable in a first radially collapsed size and a second radially expanded size, the plurality of retention bumpers including a first retention bumper disposed at a proximal side of the distal portion and a second retention bumper disposed at a distal side of the distal portion.

Additional embodiments hereof are directed to a method of assembling a balloon catheter for delivering a prosthetic heart valve to a deployment site. The method comprises securing a plurality of retention bumpers to an inner shaft defining a guidewire lumen; positioning a balloon over the retention bumpers by inserting the retention bumpers and inner shaft into a balloon opening; processing the balloon to reduce a size of the balloon opening; securing an outer shaft to surround the inner shaft and define an inflation lumen between the outer shaft and the inner shaft; securing the balloon opening to the outer shaft such that fluid delivered to the balloon via the inflation lumen causes the balloon to inflate; and securing a crimped prosthetic heart valve over the balloon.

Additional embodiments hereof are directed to a balloon catheter for transvascular delivery of a prosthetic heart valve crimped to the balloon catheter. The balloon catheter includes an inner shaft defining a guidewire lumen; at least one of an inflation lumen disposed within a wall of the inner shaft; an outer shaft surrounding the inner shaft defining an inflation lumen between the outer shaft and the inner shaft; a distal portion at a distal end of the outer shaft; a balloon disposed at the distal portion such that fluid delivered to the balloon via the inflation lumen causes the balloon to inflate; a plurality of retention bumpers secured to the inner shaft and configured to prevent axial migration of the prosthetic heart valve crimped to the distal portion when the prosthetic heart valve is subject to force.

Embodiments hereof are directed to a balloon catheter for delivering a prosthetic heart valve to a deployment site. The balloon catheter includes an inner shaft defining a guidewire lumen; an outer shaft surrounding the inner shaft defining an inflation lumen between the outer shaft and the inner shaft; a distal portion at a distal end of the outer shaft; a balloon disposed at the distal portion such that fluid delivered to the balloon via the inflation lumen causes the balloon to inflate; a proximal multipart retention bumper secured to the inner shaft inside the balloon and configurable in an interlocked configuration and a non-interlocked configuration, the proximal multipart retention bumper including a proximal inner wedge and a proximal outer bumper; and a distal multipart retention bumper secured to the inner shaft inside the balloon and configurable in an interlocked configuration and a non-interlocked configuration, the distal multipart retention bumper including a distal inner wedge and a distal outer bumper.

Additional embodiments hereof are directed to a method of assembling a balloon catheter for delivering a prosthetic heart valve to a deployment site. The method includes disposing a proximal inner wedge and a distal inner wedge over an inner shaft of the balloon catheter at a distal portion of the inner shaft; securing a proximal outer bumper and a distal outer bumper to the inner shaft of the balloon catheter at the distal portion of the inner shaft; securing a proximal opening of a balloon to a distal end of an outer shaft of the balloon catheter; positioning a balloon of the balloon catheter over the proximal inner wedge and the proximal outer bumper by passing the proximal inner wedge and the proximal outer bumper into the balloon via a distal opening of the balloon; interlocking the proximal inner wedge and the proximal outer bumper to form a proximal multipart retention bumper; positioning that balloon over the distal inner wedge and the distal outer bumper by passing the distal inner wedge and the distal outer bumper into the balloon via a distal opening of the balloon; interlocking the distal inner wedge and the distal outer bumper to form a distal multipart retention bumper; and securing the balloon to a distal tip of the balloon catheter.

Additional embodiments hereof are directed to a method of assembling a balloon catheter for delivering a prosthetic heart valve to a deployment site. The method comprises securing a proximal retention bumper and a distal retention bumper to an inner shaft defining a guidewire lumen; positioning a balloon over the proximal retention bumper and the distal retention bumper by inserting the proximal retention bumper and the distal retention bumper and inner shaft into a balloon opening; processing the balloon to reduce a size of the balloon opening; securing an outer shaft to surround the inner shaft and define an inflation lumen between the outer shaft and the inner shaft; securing the balloon opening to the outer shaft such that fluid delivered to the balloon via the inflation lumen causes the balloon to inflate; and securing a crimped prosthetic heart valve over the balloon.

Additional embodiments hereof are directed to a balloon catheter for deploying a prosthetic heart valve through balloon inflation. The balloon catheter includes an inner shaft defining a guidewire lumen; an outer shaft surrounding the inner shaft defining an inflation lumen between the outer shaft and the inner shaft; a distal portion at a distal end of the outer shaft; a balloon disposed at the distal portion such that fluid delivered to the balloon via the inflation lumen causes the balloon to inflate; and a distal first retention bumper secured to the inner shaft, the distal first retention bumper including a spoked first portion including a first hub and first spokes defining first flow passages therebetween and a first tapered portion including first tapered spokes aligning with the first spokes.

Further embodiments provided herein include a method of assembling a balloon catheter for deploying a prosthetic heart valve through balloon inflation. The method includes securing a distal retention bumper to an inner shaft defining a guidewire lumen; positioning a balloon over the distal retention bumper by inserting the distal retention bumper and inner shaft into a balloon opening; securing an outer shaft to surround the inner shaft and define an inflation lumen between the outer shaft and the inner shaft; securing the balloon opening to the outer shaft such that fluid delivered to the balloon via the inflation lumen causes the balloon to inflate; and securing a crimped prosthetic heart valve over the balloon.

BRIEF DESCRIPTION OF THE DRAWINGS

The accompanying figures, which are incorporated herein, form part of the specification and illustrate embodiments of a prosthesis delivery system. Together with the description, the figures further explain the principles of and enable a person skilled in the relevant art(s) to make and use the balloon catheters described herein. The drawings are provided to illustrate various features of the embodiments described herein and are not necessarily drawn to scale. In the drawings, like reference numbers indicate identical or functionally similar elements.

FIGS. 6A-6C illustrate inflatable retention bumpers according to embodiments hereof.

FIGS. 11A-11B illustrate axial force expandable retention bumpers according to embodiments hereof.

FIGS. 12A-12E illustrate axial force expandable retention bumpers according to embodiments hereof.

FIGS. 13A-13B illustrate axial force expandable retention bumpers according to embodiments hereof.

FIGS. 14A-14D illustrate tension expandable retention bumpers according to embodiments hereof.

FIGS. 15A and 15B illustrate settable retention bumpers according to embodiments hereof.

FIGS. 16A-16G illustrate spring retention bumpers according to embodiments hereof.

FIGS. 18A and 18B illustrate foldable retention bumpers according to embodiments hereof.

FIGS. 19A-19D illustrate collapsible retention bumpers according to embodiments hereof.

FIGS. 22A-22D illustrate collapsible retention bumpers according to embodiments hereof.

FIGS. 23A-23C illustrate elongated retention bumpers according to embodiments hereof.

FIGS. 24A-24F illustrate multipart retention bumpers according to embodiments hereof.

FIGS. 25A-25E illustrate multipart retention bumpers according to embodiments hereof.

FIGS. 26A-26E illustrate multipart retention bumpers according to embodiments hereof.

FIGS. 29A-29F illustrate stages of an assembly process for a balloon catheter employing multipart retention bumpers.

FIGS. 30A-30F illustrate several different configurations for first inner parts of multipart retention bumpers.

FIGS. 31A and 31B illustrate a balloon catheter configured for balloon processing during assembly.

FIGS. 37A and 37B illustrate a balloon catheter having a protected balloon inflation lumen.

FIGS. 39A-39D illustrate a valved balloon inflation shaft.

FIGS. 42A and 42B illustrate a balloon catheter including a ported flow guide and retention bumpers.

FIGS. 44A-44E illustrate a pressure control system for a balloon catheter.

FIGS. 47A and 47B illustrate a balloon catheter employing retention bumpers as valve retention devices according to embodiments hereof.

FIGS. 58A-H illustrate multipart retention bumpers consistent with embodiments hereof.

FIGS. 59A-F illustrate aspects of assembly of a balloon catheter employing multipart retention bumpers consistent with embodiments hereof.

DETAILED DESCRIPTION OF THE INVENTION

Specific embodiments of the present invention are now described with reference to the figures. Unless otherwise indicated, for the balloon catheters discussed herein, the terms "distal" and "proximal" are used in the following description with respect to a position or direction relative to the treating clinician or operator. "Distal" and "distally" are positions distant from or in a direction away from the clinician, and "proximal" and "proximally" are positions near or in a direction toward the clinician. As used herein, the term "proximal force" refers to a force in the proximal direction and the term "distal force" refers to a force in the distal direction.

The following detailed description is merely illustrative in nature and is not intended to limit the invention or the application and uses of the invention. Although the description of the invention is in the context of balloon catheter enabled delivery and deployment of prosthetic heart valves, aspects of the invention may also be used in any other context that is useful. As an example, the description of the invention is in the context of delivery and deployment of heart valve prostheses. As used herein, "prosthesis" or "prostheses" may include any prosthesis including a balloon expandable structure. Modifications can be made to the embodiments described herein without departing from the spirit and scope of the present invention. Therefore, the following detailed description is not meant to be limiting. Furthermore, there is no intention to be bound by any expressed or implied theory presented in the preceding technical field, background, summary, or the following detailed description.

Figure 1:
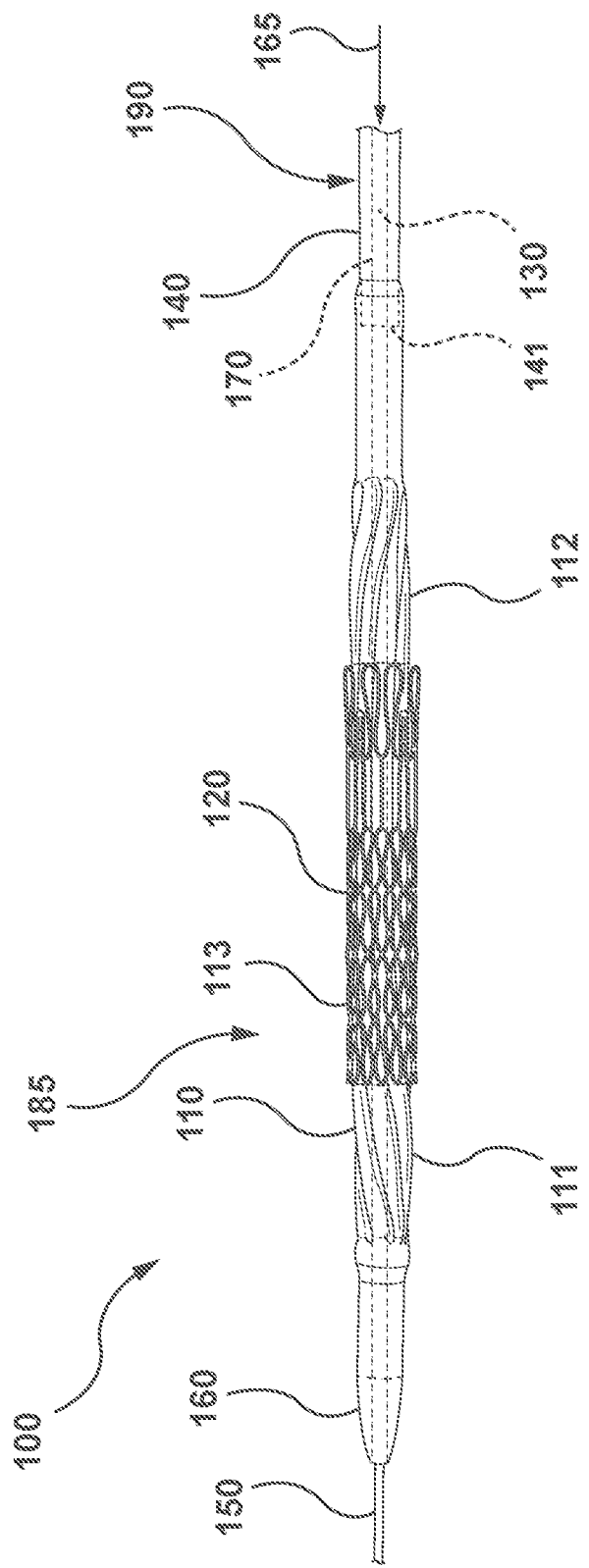
FIG. 1 illustrates a balloon catheter for prosthetic heart valve delivery and deployment.

FIG. 1 illustrates a balloon catheter 100 for prosthetic heart valve delivery and deployment. The balloon catheter 100 includes a balloon 110, a prosthetic heart valve 120, an outer shaft 140, and an inner shaft 130. The inner shaft 130 defines a guidewire lumen 165 such that the balloon catheter 100 may be slidably disposed and tracked over a guidewire 150. The outer shaft 140 defines an annular balloon inflation lumen 170 disposed between the inner shaft 130 and the outer shaft 140. The balloon 110 is disposed on the balloon catheter 100 at a distal portion 185 and includes a distal balloon portion 111, a proximal balloon portion 112, and a central balloon portion 113. The distal portion 185 is located at a distal end of the outer shaft 140. Proximal to the distal portion 185 is a proximal portion 190 of the balloon catheter 100, which includes the outer shaft 140 and proximal portions of the inner shaft 130. The proximal balloon portion 112 is disposed over the outer shaft 140. The outer shaft 140 may be tapered or stepped to a smaller diameter to accommodate the balloon 110. The distal balloon portion 111 may be retained by the distal tip 160 of the balloon catheter 100 or it may be attached to a portion of the inner shaft 130 proximal of the distal tip 160. Both the inner shaft 130 and the outer shaft 140 extend proximally and terminate in a handle or housing (not shown) of the balloon catheter 100.

The outer shaft 140 extends into the interior of the balloon 110 and terminates therein at an open distal end, while the inner shaft 130, defining the guidewire lumen 165, extends to the distal tip 160 and terminates therein. This arrangement permits the balloon inflation lumen 170 to carry fluid pumped from the handle of the balloon catheter 100 into the interior of the balloon 110. The release of fluid to the interior of the balloon 110 causes the balloon 110 to inflate, an action that is employed to expand a prosthetic heart valve frame and deploy the prosthetic heart valve 120.

The prosthetic heart valve 120 has a minimum size in a collapsed state beyond which it cannot be collapsed or compressed any further. The frame of the prosthetic heart valve 120 permits only a certain amount of compression. In some balloon catheters 100, this minimum size may not be small enough to create a large amount of contact between the balloon 110 and the prosthetic heart valve 120. In other embodiments, the frame of the prosthetic heart valve 120 may be configured for tighter crimping. Tighter crimping, however, may cause the crimped balloon 110 to interfere with fluid flowing into the balloon for inflation, leading to irregularities in deployment. These limitations on compression of the prosthetic heart valve 120 may thus prevent the prosthetic heart valve 120 from being crimped tightly onto the balloon 110. A looser crimping of the prosthetic heart valve 120 can result in a less secure fitting and a potential for migration of the prosthetic heart valve 120 when subject to proximal or distal forces during delivery.

Figure 2A:
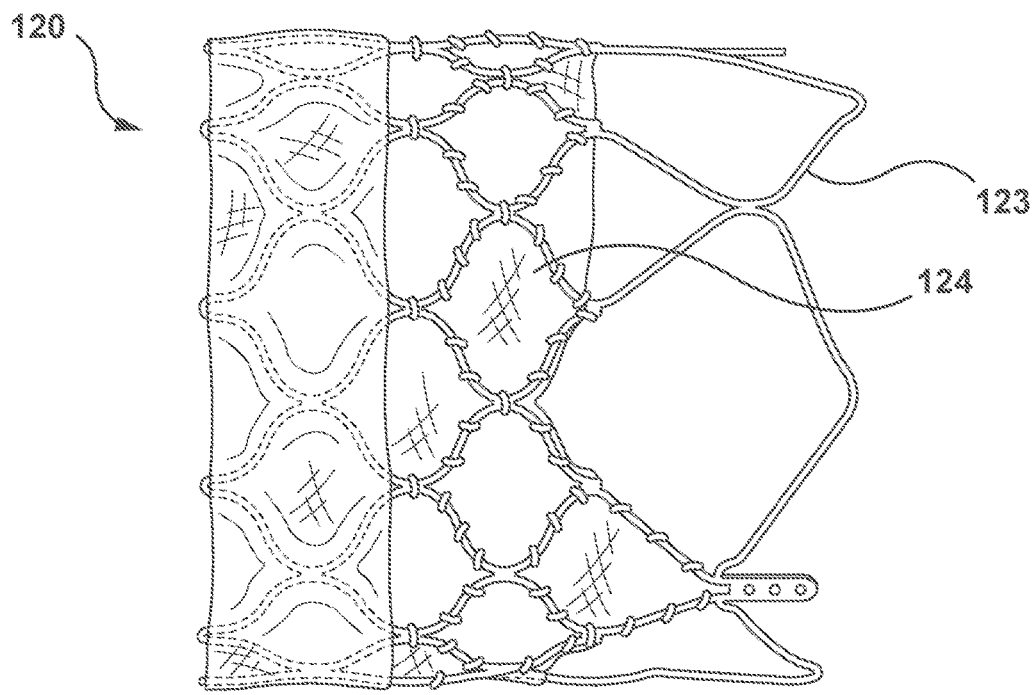
FIGS. 2A and 2B illustrate a prosthetic heart valve in expanded and compressed configurations.
Figure 2B:
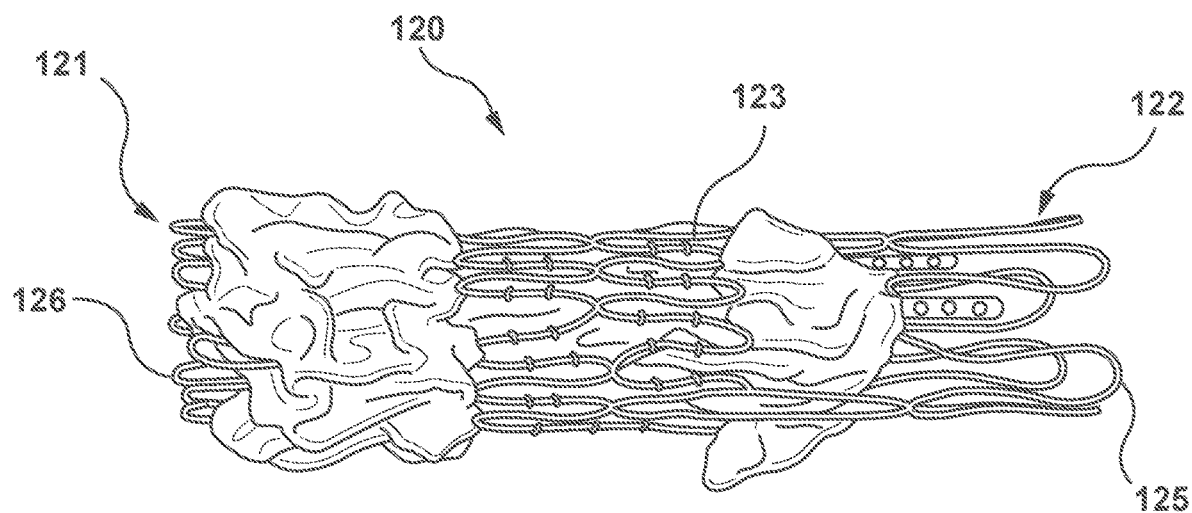

FIGS. 2A and 2B illustrate an example the prosthetic heart valve 120 in expanded and collapsed configurations. The prosthetic heart valve 120 includes a balloon expandable frame 123 and prosthetic valve tissue 124. In a pre-deployment state, the prosthetic heart valve 120 has a proximal end 122 and a distal end 121, which refer to the orientation of the prosthetic heart valve 120 as loaded onto the balloon catheter 100. In the embodiment shown, the distal end 121 is an inflow end of the prosthetic heart valve 120 and the proximal end 122 is an outflow end of the prosthetic heart valve 120. The frame 123 includes a plurality of crowns 125 at the proximal end 122 and a plurality of crowns 126 at the distal end 121. The crowns 125 are bends or turns in the frame structure. The prosthetic heart valve 120 may be non-symmetrical, having different expandable frame 123 geometry and prosthetic valve tissue 124 construction at the proximal end 122 and the distal end 121. Other prosthetic heart valves may differ in design, having expandable frames that differ in structure and construction and prosthetic valve elements that also differ. Accordingly, different prosthetic heart valves may react differently under balloon expansion deployment, due to variations in structural characteristics, such as radial stiffness. Because different prosthetic heart valves react differently to expansion and compression, embodiments hereof are designed to prevent migration of prosthetic heart valves regardless of their structure and construction.

Figure 3:
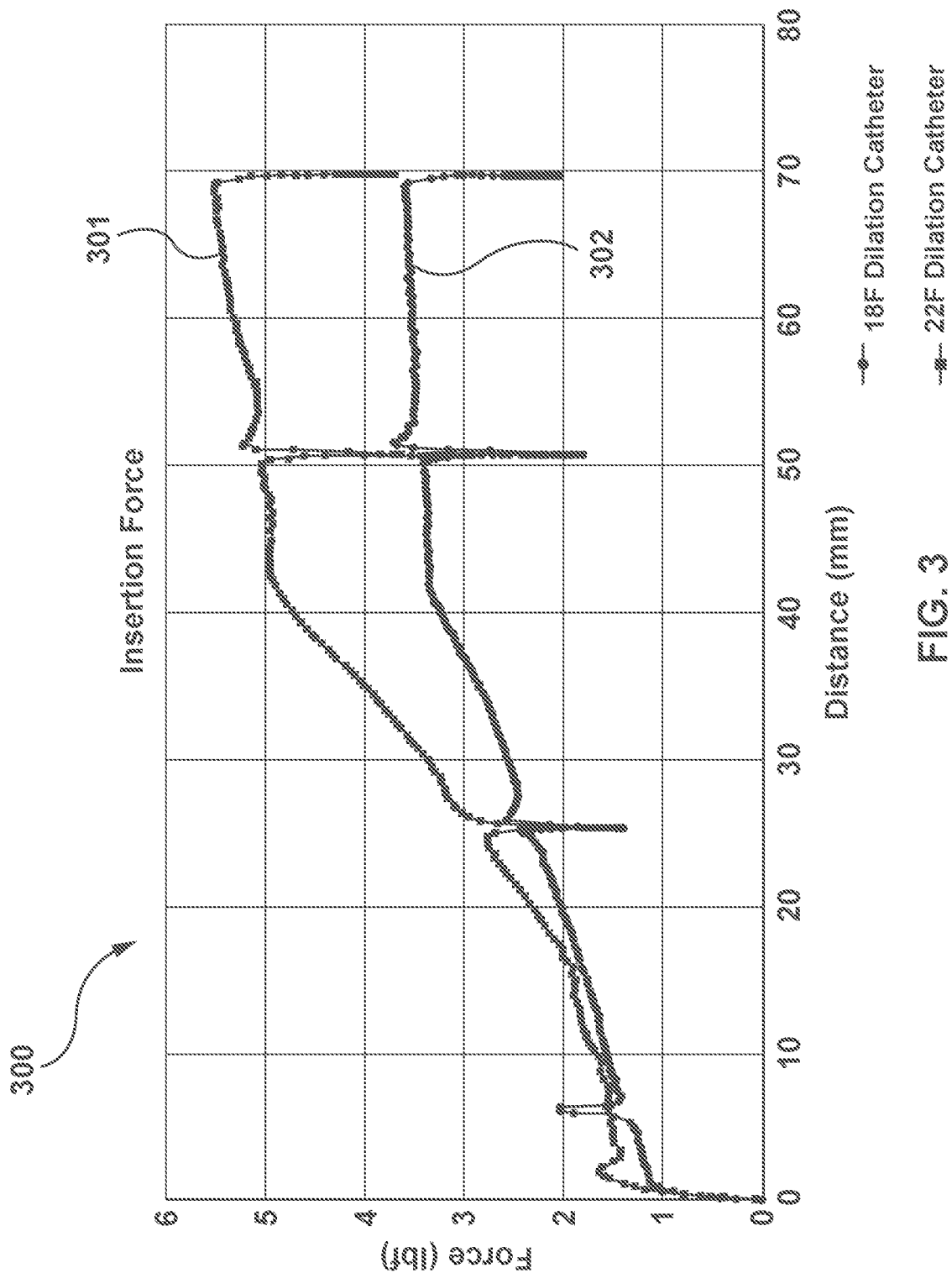
FIG. 3 is a graph illustrating forces on a balloon dilation catheter in various size introducers.

FIG. 3 illustrates a graph of forces associated with the passage of devices through introducers of different sizes. Chart 300 illustrates forces measured during insertion of a 22 French balloon dilation catheter and an 18 French balloon dilation catheter into a 22 French introducer manufactured by Cook Medical®. Plot 301 shows that the introduction of a 22 French balloon dilation catheter into a 22 French Cook Medical® introducer required up to 5.5 lbf while plot 302 shows that the introduction of an 18 French balloon dilation catheter into a 22 French Cook Medical® introducer required up to 3.5 lbf. Balloon catheters for delivery of prosthetic heart valves typically have a profile between 18 F and 22 F. Accordingly, the chart 300, although it shows the forces on balloon dilation catheters, provides an indication of the types of forces that a balloon catheter for prosthetic heart valve delivery is likely to be subject to. When using a balloon catheter without a sheath, the prosthetic heart valve contacts the interior wall of the introducer. Therefore, the prosthetic heart valve is subject to a significant amount of the force shown in chart 300 during delivery. This force may be large enough to cause the prosthetic heart valve to migrate on the balloon catheter during delivery.

Balloon catheters consistent with embodiments hereof are configured to deliver and deploy, through the use of an inflatable balloon, transcatheter balloon expandable prosthetic heart valves (referred to herein as "prosthetic heart valves"). Balloon catheters consistent with embodiments hereof include one or more valve retention devices configured to prevent or reduce valve migration during delivery and deployment. Balloon catheters including valve retention devices and methods of their use consistent with embodiments hereof are described below with respect to FIGS. 4-45.

Figure 4A:
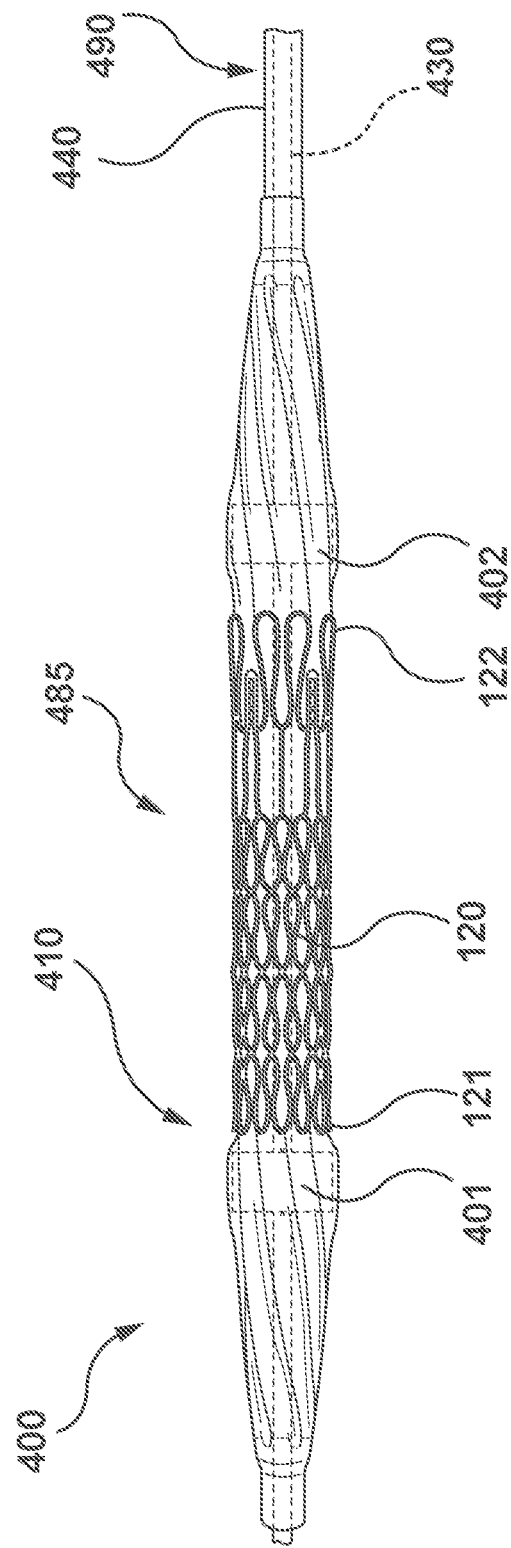
FIGS. 4A and 4B illustrate a balloon catheter employing retention bumpers as valve retention devices according to embodiments hereof.

FIG. 4A illustrates a balloon catheter 400 employing retention bumpers as valve retention devices according to embodiments hereof. Retention bumpers 401, 402 act as valve retention devices to maintain the position of a prosthetic heart valve such as the prosthetic heart valve 120 mounted on the balloon catheter 400. Balloon catheter 400 further includes a balloon 410, an inner shaft 430, and an outer shaft 440. The balloon catheter 400 further includes a distal portion 485 and a proximal portion 490. Also illustrated in FIG. 4A is the prosthetic heart valve 120 crimped onto the balloon 410. The retention bumpers 401, 402 are disposed in the distal portion 485 of the balloon catheter 400 beneath or within the balloon 410. A portion of the balloon 410 between the retention bumpers 401, 402 is configured to have a prosthetic valve crimped thereon. The retention bumpers 401, 402 are attached to the inner shaft 430. In further embodiments, retention bumpers 401, 402 may be secured via alternative means.

The retention bumpers 401, 402 function to maintain an axial position of the prosthetic heart valve 120. The retention bumpers 401, 402 are positioned adjacent to the prosthetic heart valve 120 so as to maintain an axial position, i.e., prevent or reduce axial migration, through contact. In particular, as shown in FIG. 4A, the retention bumper 402 is positioned adjacent the proximal end 122 of the prosthetic heart valve 120 and the retention bumper 401 is positioned adjacent the distal end 121 of the prosthetic heart valve 120. When subject to proximal or distal forces, the prosthetic heart valve 120 presses up against the portion of the balloon 410 raised by the retention bumpers 401, 402, which arrests the movement of the prosthetic heart valve 120.

The retention bumpers 401, 402 may also function to reduce forces acting on the prosthetic heart valve 120. The retention bumpers may be sized such that they (or the balloon 410 covering them) extend further radially outward than the prosthetic heart valve 120. Thus, the features of the balloon catheter 400 having the largest diameter are the retention bumpers 401, 402 and not the prosthetic heart valve 120. When inserted into an introducer, the retention bumpers 401, 402 therefore are the portion of the balloon catheter 400 that contacts the introducer wall, thereby preventing the wall of the introducer from contacting the prosthetic heart valve 120 and thereby reducing the amount of force acting on the prosthetic heart valve 120 from the inner walls of the introducer.

Figure 4B:
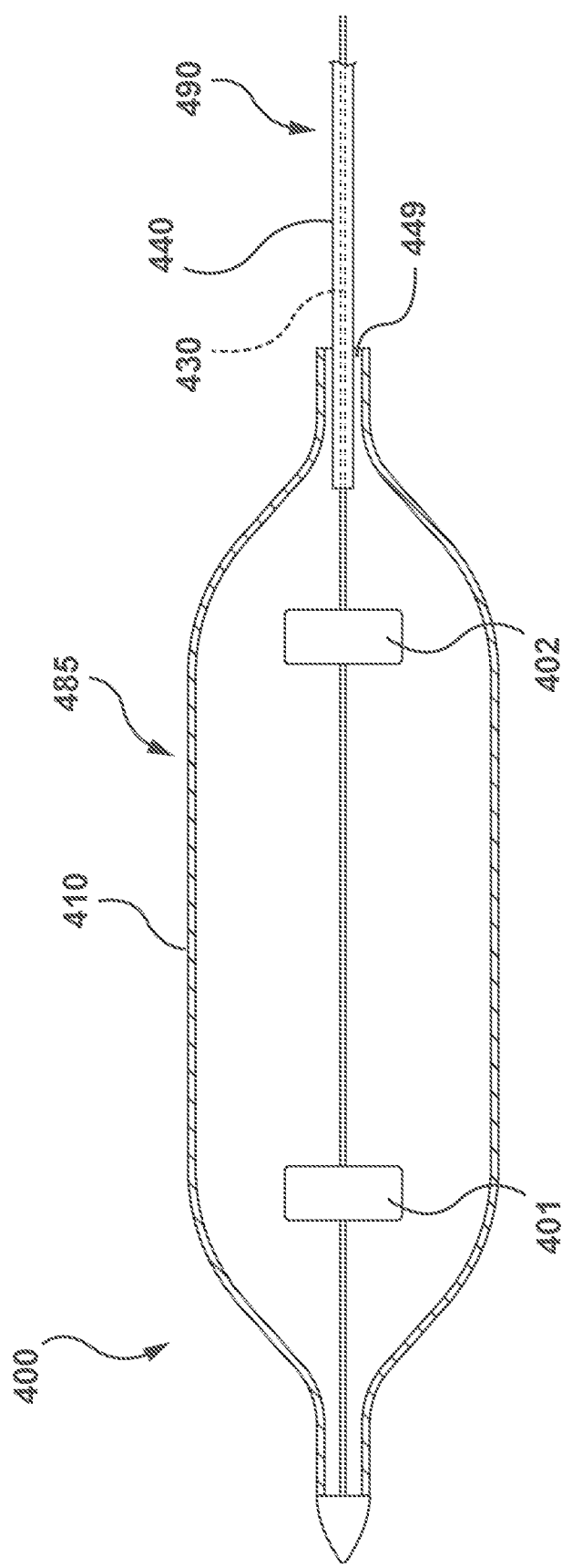

FIG. 4B illustrates assembly of the balloon catheter 400 employing retention bumpers as valve retention devices according to embodiments hereof. The retention bumpers 401/402 are disposed on the inner shaft 430, inside of the balloon 410. The balloon 410 has a balloon opening 449 at its proximal end, its distal end, or both. The balloon opening 449 has a diameter of approximately 0.2 inches. In further embodiments, the balloon opening 449 may have a diameter of anywhere between approximately 0.1 inches and 0.25 inches. The retention bumpers 401/402 each have an outer diameter of approximately 0.3 inches. In further embodiments, the retention bumpers 401/402 may each have a diameter of anywhere between approximately 0.25 inches and 0.35 inches. The retention bumpers 401/402 have outer diameters larger than the diameter of the balloon opening 449. Due to this imbalance in size, assembly of a balloon catheter 400 with solid and/or rigid retention bumpers 401/402 may be challenging.

In embodiments, as described below with respect to FIGS. 5-44, retention bumpers and balloons are constructed to mitigate challenges associated with the size discrepancy between outer bumper diameter and balloon opening diameter. Embodiments described herein include retention bumpers having collapsible and expandable characteristics as well as catheters having novel assembly and processing steps. All retention bumpers described herein may be employed to prevent prosthetic heart valve migration during delivery and deployment and to facilitate balloon catheter assembly, as described above. The embodiments illustrated in FIGS. 5-44 may include all features of the balloon catheter 400, whether stated or not. All features of the embodiments described herein may be suitably combined with features of other embodiments.

Retention bumpers described herein may be illustrated or described with respect to a specific profile. For example, FIGS. 4A and 4B show generally cylindrical retention bumpers that are generally rectangular in profile. Unless explicitly stated otherwise, bumper profiles illustrated or described with respect to a specific embodiment are non-limiting examples only, and any suitable bumper profile may be employed with any embodiments described herein. Suitable bumper profiles include tapered profiles, spherical profiles, cylindrical profiles, and others.

In embodiments, any or all of the retention bumpers described herein may include radiopaque markers to assist during prosthetic heart valve delivery. In embodiments, any or all of the retention bumpers described herein may be manufactured and assembled by any suitable manufacturing process or technique.

Figure 5A:
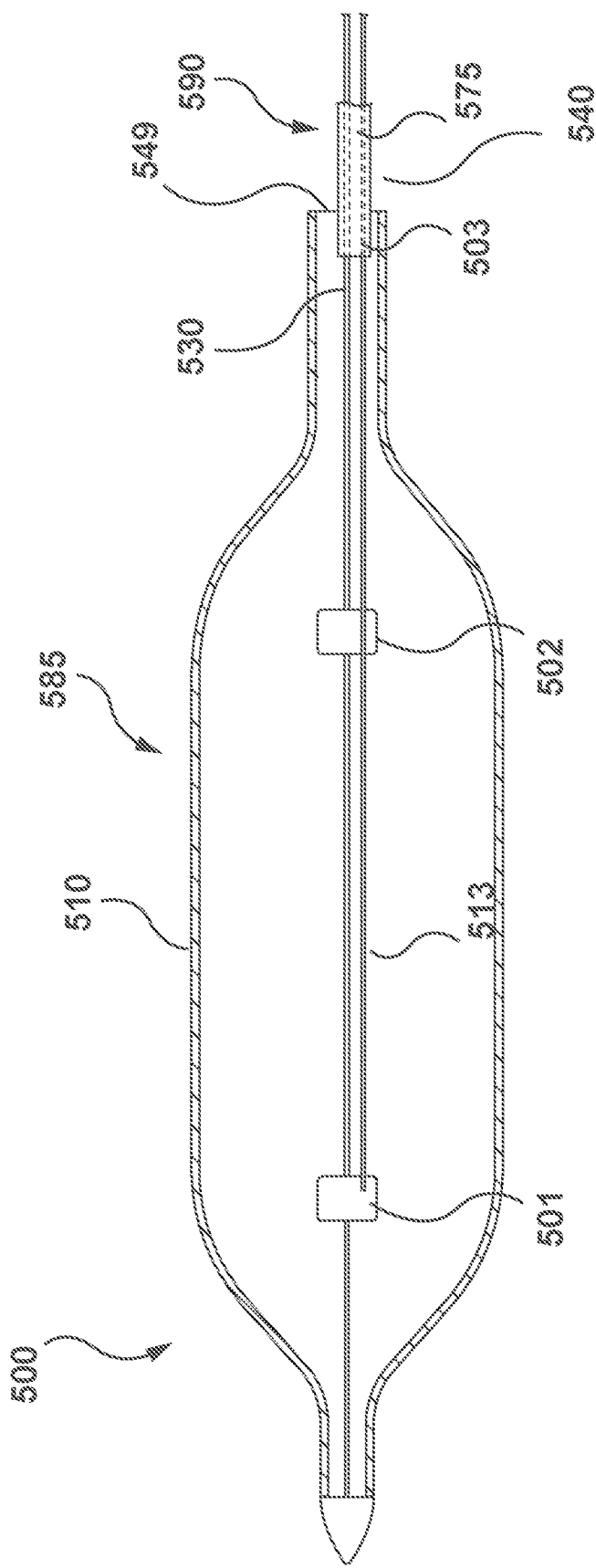
FIGS. 5A-5B illustrate inflatable retention bumpers according to embodiments hereof.
Figure 5B:
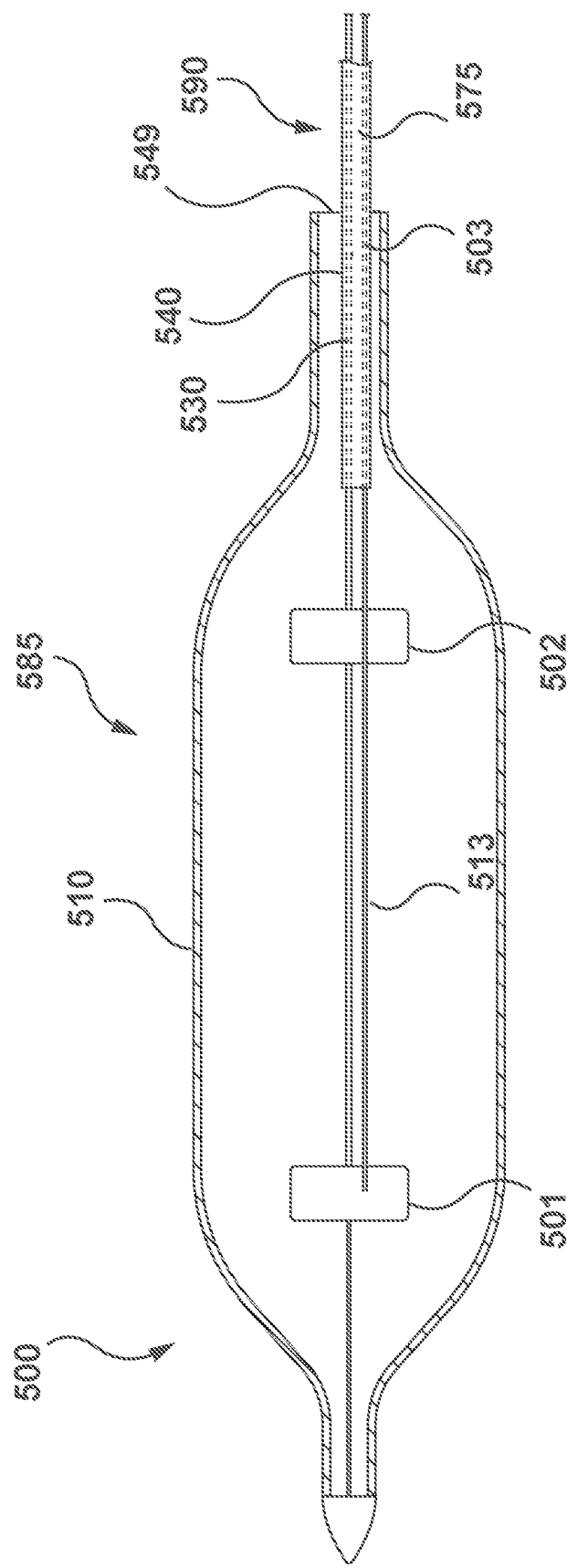

FIGS. 5A-5B illustrate inflatable retention bumpers according to embodiments hereof. Balloon catheter 500 includes at least a balloon 510, an inner shaft 530, and an outer shaft 540. Balloon catheter 500 is configured for delivering a prosthetic heart valve (not pictured) and may include any or all features and aspects of balloon catheter 400. Balloon catheter 500 further includes a distal portion 585, within which the balloon 510 is disposed, and a proximal portion 590. A portion of the balloon 510 between the inflatable retention bumpers 501, 502 is configured to have a prosthetic valve crimped thereon. Balloon inflation fluid is supplied to the balloon 510 via a balloon inflation lumen 575. Balloon inflation fluid may include, for example, saline, air, and/or contrast media.

Also, in the distal portion 585 are disposed the inflatable retention bumpers 501 and 502. The inflatable retention bumpers 501 and 502 are configured for expanding and collapsing via inflation pressure. Inflation pressure is provided by a bumper inflation lumen 503. The bumper inflation lumen 503 may be provided as an additional, off-center, lumen inside of outer shaft 540, as illustrated in FIG. 5A. Distal to the outer shaft 540, the bumper inflation lumen 503 may be defined by a bumper inflation shaft 513. In further embodiments, the bumper inflation shaft 513 may be disposed within the outer shaft 540 as an additional catheter shaft. For example, the bumper inflation shaft 513 may be disposed concentrically around the inner shaft 530, creating two annular lumens between the inner shaft 530 and the outer shaft 540. Between the two annular spaces, one may act as the bumper inflation lumen 503 to carry bumper inflation fluid to the inflatable retention bumpers 501 and 502 and the other may act as the balloon inflation lumen 575 to carry balloon inflation fluid to the balloon 510. The inflatable retention bumpers 501 and 502 include one or more hollow containers or sacs that, when expanded through inflation, expand to full size. The inflatable retention bumpers 501 and 502 have a first radially unexpanded size and a second radially expanded size. The first radially unexpanded size of the inflatable retention bumpers 501 and 502 is illustrated in FIG. 5A and is small enough to enter the balloon 510 through the balloon opening 549, which may have a diameter of approximately 0.2 inches. In further embodiments, the balloon opening 549 may have a diameter between 0.1 and 0.25 inches. The second radially expanded size of the inflatable retention bumpers 501 and 502 is large enough to provide valve retention during a delivery operation. For example, the second radially expanded size, illustrated in FIG. 5B, may be approximately 0.3 inches. In further embodiments, the second radially expanded size of the bumpers may have a diameter between 0.25 and 0.35 inches. The inflatable retention bumpers 501 and 502 may be expanded via the bumper inflation lumen 503, which is configured to deliver a bumper inflation fluid, such as air, saline, resin, contrast media, and/or glue, to the inflatable retention bumpers. The bumper inflation fluid may be delivered by any suitable means, including pumps, syringes, etc. Resin and/or glue may set inside the inflatable retention bumpers 501 and 502, causing them to retain their shape at the second radially expanded size.

In a process of assembling the balloon catheter 500, the inflatable retention bumpers 501 and 502 are positioned within the balloon 510 while at the first radially unexpanded size. The inflatable retention bumpers 501 and 502 are secured to the inner shaft 530 and the balloon 510 is secured to the outer shaft 540 at the proximal end of the balloon 510 and to the inner shaft 530 or the distal tip at the distal end of the balloon 510. The balloon 510 is then folded and a prosthetic heart valve is crimped onto the balloon catheter 500 between the inflatable retention bumpers 501 and 502. At any point during assembly after the inflatable retention bumpers 501 and 502 are positioned within the balloon, they may be radially expanded to the second radially expanded size (or to a size intermediate between the first radially unexpanded size and the second radially expanded size) through inflation via the bumper inflation lumen 503. For example, the inflatable retention bumpers 501 and 502 may be expanded after positioning within the balloon 510, after being secured to the outer shaft 540 and the inner shaft 530, after the balloon 510 is folded, and/or after the prosthetic heart valve is crimped onto the balloon 510. In embodiments, the inflatable retention bumpers 501 and 502 may be radially expanded during an assembly process and then collapsed for packaging. The inflatable retention bumpers 501 and 502 may then be radially expanded again prior to a delivery operation.

Figure 6A:
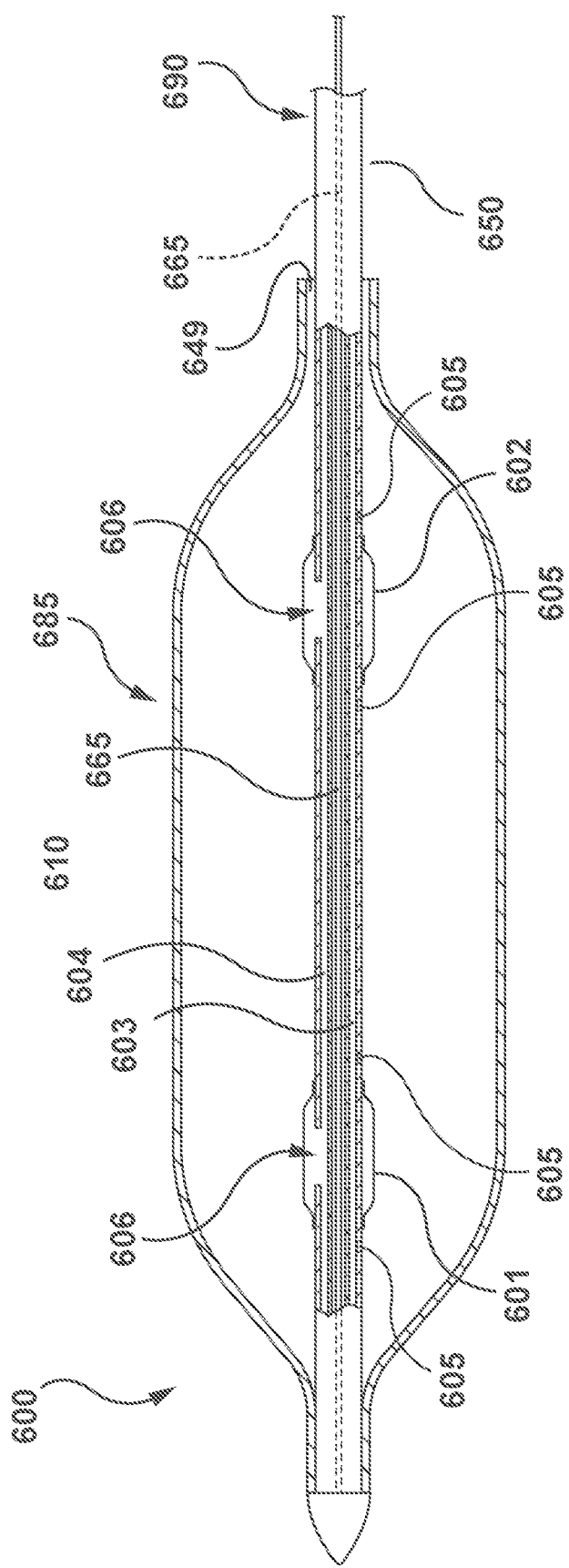

FIGS. 6A-6C illustrate inflatable retention bumpers according to embodiments hereof. A balloon catheter 600 includes at least a balloon 610 and an inflation shaft 650. In this embodiment, the inflation shaft 650 defines the guidewire lumen 665 and balloon inflation lumen 603 defined by an inner shaft and an outer shaft in other embodiments, as well as an additional bumper inflation lumen 604. Balloon catheter 600 further includes a distal portion 685, within which the balloon 610 is disposed, and a proximal portion 690. The balloon catheter 600 is configured for delivering a prosthetic heart valve (not pictured) and may include any or all features and aspects of the balloon catheter 400. A portion of the balloon 610 is configured to have a prosthetic valve crimped thereon. The balloon catheter 600 further includes inflatable retention bumpers 601 and 602 disposed on the inflation shaft 650 within a distal portion 685 of the balloon catheter 600.

The inflation shaft 650 is configured with a bumper inflation lumen 604, a balloon inflation lumen 603, and a guidewire lumen 665. The inflation shaft 650 further includes bumper inflation ports 606 and balloon inflation ports 605. The bumper inflation ports 606 are holes or skives in the wall of the inflation shaft 650 that expose the bumper inflation lumen 604 to the interior of the inflatable retention bumpers 601 and 602. The balloon inflation ports 605 are holes or skives in the wall of the inflation shaft 650 that expose the balloon inflation lumen 603 to the interior of the balloon 610.

The inflatable retention bumpers 601 and 602 are configured for expanding and collapsing via inflation pressure provided via the bumper inflation lumen 604 and through the bumper inflation ports 606. The inflatable retention bumpers 601 and 602 include one or more hollow containers or sacs that, when expanded through inflation, radially expand to full size. The inflatable retention bumpers 601 and 602 may include a flexible material that stretches or expands when the inflatable retention bumpers 601 and 602 are inflated. The inflatable retention bumpers 601 and 602 may include a flexible material that does not significantly stretch when inflated. In such an embodiment, the inflatable retention bumpers 601 and 602 may be configured as empty bags or balloons and may be filled with an inflation fluid delivered by the bumper inflation lumen 604 when inflated.

The inflatable retention bumpers 601 and 602 have a first radially unexpanded size and a second radially expanded size. The first radially unexpanded size of the inflatable retention bumpers 601 and 602 is illustrated in FIG. 6A and is small enough to enter the balloon 610 through the balloon opening 649, which may have a diameter of approximately 0.2 inches. In further embodiments, the balloon opening 649 may have a diameter between 0.1 and 0.25 inches. The second radially expanded size of the inflatable retention bumpers 601 and 602 is large enough to provide valve retention during a delivery operation. For example, the second radially expanded size, illustrated in FIG. 6B, may be approximately 0.3 inches. In further embodiments, the second radially expanded size of the inflatable retention bumpers 601 and 602 may have a diameter between 0.25 and 0.35 inches. The inflatable retention bumpers 601 and 602 may be expanded via the bumper inflation lumen 604, which is configured to deliver an inflation fluid, such as air, saline, contrast media, resin, and/or glue, to the inflatable retention bumpers 601 and 602.

In a process of assembling the balloon catheter 600, the inflatable retention bumpers 601 and 602 are secured to the inflation shaft 650 and positioned within the balloon 610 while at the first radially unexpanded size. The balloon 610 is secured to the outer shaft 640. The balloon 610 is then folded and a prosthetic heart valve is crimped onto the balloon catheter 600 between the inflatable retention bumpers 601 and 602. At any point during assembly after the inflatable retention bumpers 601 and 602 are positioned within the balloon 610, they may be expanded to the second radially expanded size (or to a size intermediate between the first radially unexpanded size and the second radially expanded size) through bumper inflation fluid pressure supplied via the bumper inflation lumen 604. For example, the inflatable retention bumpers 601 and 602 may be expanded (or partially expanded) after being secured to the inflation shaft 650, after positioning within the balloon 610, after the balloon 610 is folded, and/or after the prosthetic heart valve is crimped onto the balloon 610. In embodiments, the inflatable retention bumpers 601 and 602 may be expanded during an assembly process and then collapsed for packaging. The inflatable retention bumpers 601 and 602 may then be expanded again prior to a delivery operation and maintained in an inflated state through the use of valves. In embodiment involving resin and/or glue, the resin and/or glue is permitted to set after bumper inflation. During a delivery operation, the balloon inflation lumen 603 may be used to provide a balloon inflation fluid to inflate the balloon 610 via the balloon inflation ports 605. The pressure source for inflation of the balloon 610 and the inflatable retention bumpers 601 and 602 may be a syringe, pump, or any other suitable means for providing pressure to cause the balloon inflation fluid to flow through the inflation shaft 650 to the balloon 610 and the inflatable retention bumpers 601 and 602. In the embodiment of FIGS. 6A-6C, the inflation shaft 650 carries inflation fluid for both the balloon 610 and the inflatable retention bumpers 601 and 602. In embodiments, the diameter of the inflation shaft 650 may be large enough to appropriately support the balloon 610 and no additional shafts are provided around the inflation shaft 650. In additional embodiments, an outer shaft may be optionally included to support the balloon 610 and a smaller diameter inflation shaft 650 may be disposed within the outer shaft.

Figure 7B:
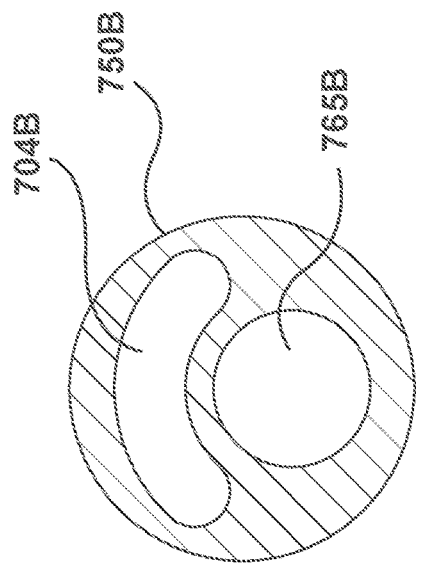
FIGS. 7A-7C illustrate inflation shafts for balloon catheters according to embodiments hereof.
Figure 7A:
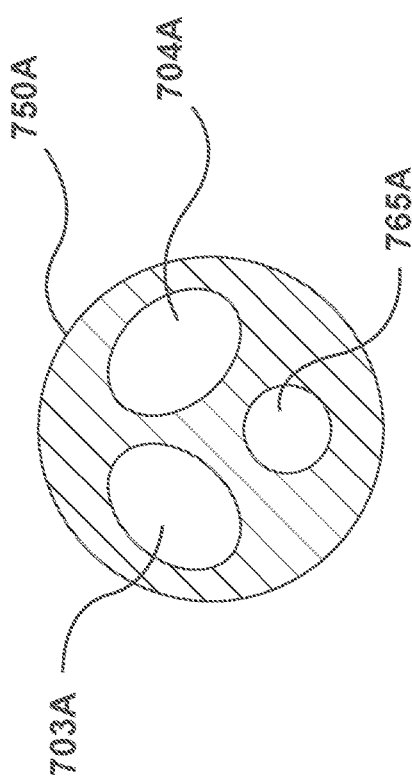
Figure 7C:
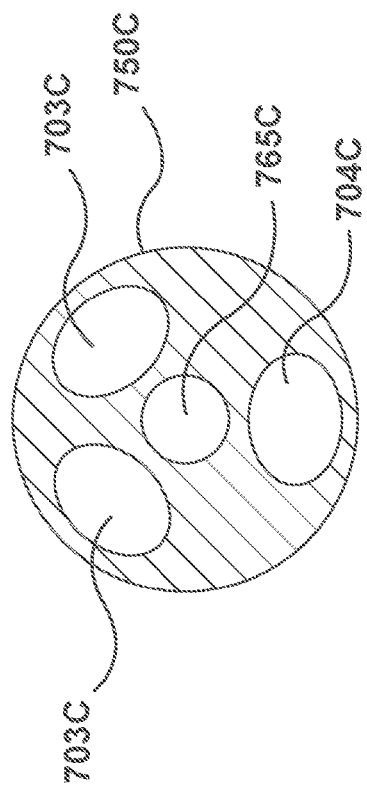

FIGS. 7A-7C illustrate additional lumen/shaft arrangements consistent with different inflatable retention bumper embodiments disclosed herein. The embodiments of FIGS. 7A-7C are consistent and compatible with the above-described inflatable retention bumpers, as described below. In embodiments, the various inflation lumens of FIGS. 7A-7C may be configured to provide any of the bumper and balloon inflation fluids as described herein.

FIG. 7A illustrates an inflation shaft 750A providing a guidewire lumen 765A, a balloon inflation lumen 703A, and a bumper inflation lumen 704A. The inflation shaft 750A includes bumper inflation ports (not shown) configured to provide fluid communication between the bumper inflation lumen 704A and the interior of inflatable retention bumpers according to any of the embodiments described herein, e.g., inflatable retention bumpers 501/502 and 601/602. The inflation shaft 750A further includes balloon inflation ports (not shown) configured to provide fluid communication between the balloon inflation lumen 703A and the interior of an inflatable valve deploying balloon.

FIG. 7B illustrates an inflation shaft 750B providing a guidewire lumen 765B and a bumper inflation lumen 704B. The inflation shaft 750B includes bumper inflation ports (not shown) configured to provide fluid communication between the bumper inflation lumen 704B and the interior of inflatable retention bumpers according to any of the embodiments described herein, e.g., inflatable retention bumpers 501/502 and 601/602. In balloon catheters employing the inflation shaft 750B, the associated balloon may be inflated via balloon inflation fluid supplied through an annular inflation lumen disposed between an outer shaft and the inflation shaft 750B, as disclosed with respect to FIGS. 4A and 4B.

FIG. 7C illustrates an inflation shaft 750C providing a guidewire lumen 765C, a plurality of balloon inflation lumens 703C, and a bumper inflation lumen 704C. The inflation shaft 750C includes bumper inflation ports (not shown) configured to provide fluid communication between the bumper inflation lumen 704C and the interior of inflatable retention bumpers according to any of the embodiments described herein, e.g., inflatable retention bumpers 501/502 and 601/602. The inflation shaft 750C further includes balloon inflation ports (not shown) configured to provide fluid communication between the balloon inflation lumens 703C and the interior of an inflatable valve deploying balloon. The multiple balloon inflation lumens 703C, e.g., two, three, four or more lumens, each have one or more balloon inflation ports communicating with the interior of the balloon. The one or more balloon inflation ports of each balloon inflation lumen 703C are disposed to provide inflation pressure to different portions of the valve delivery balloon. For example, a first balloon inflation lumen 703C may have a distally located balloon inflation port to provide inflation pressure to a distal portion of the valve delivery balloon while a second balloon inflation lumen 703C has a proximally located balloon inflation port to provide inflation pressure to a proximal portion of the valve delivery balloon.

Figure 8A:
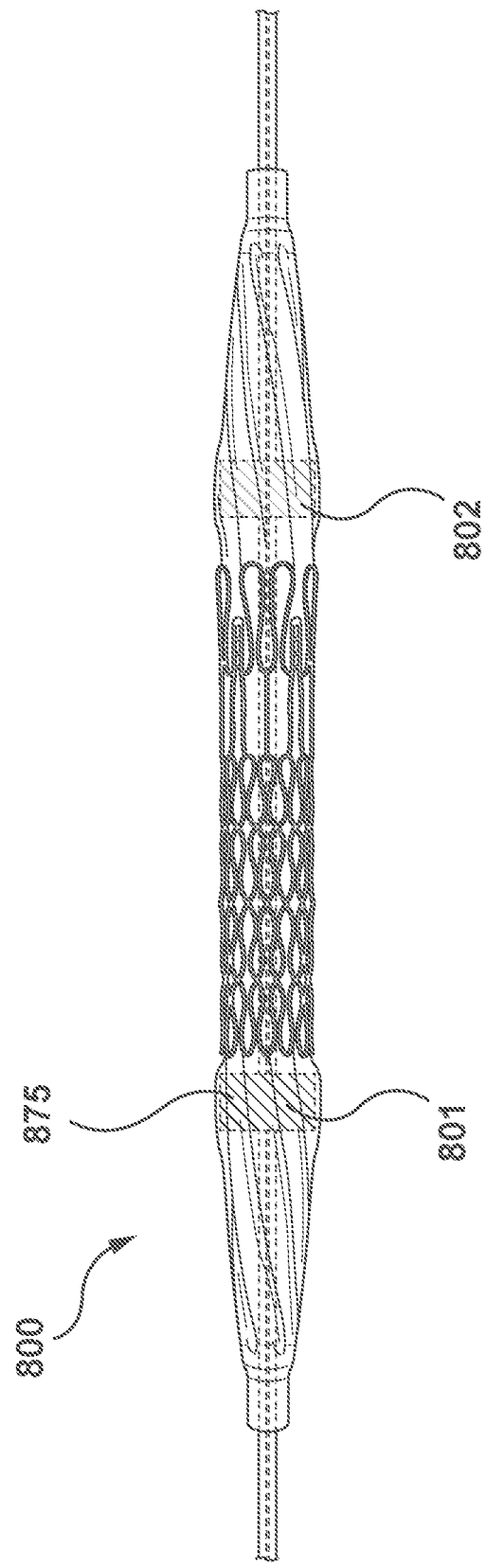
FIGS. 8A and 8B illustrate a balloon catheter having inflatable retention bumpers according to embodiments hereof.
Figure 8B:
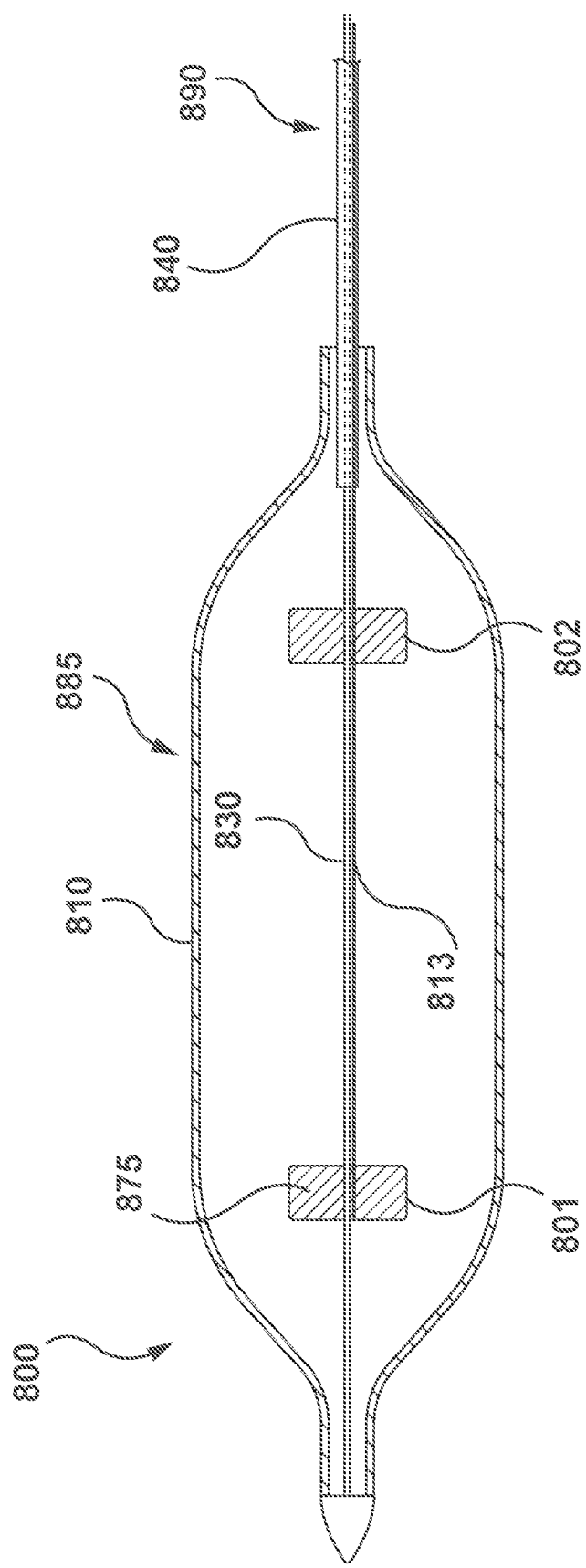

FIGS. 8A and 8B illustrate a balloon catheter 800 consistent with embodiments hereof. The balloon catheter 800 may include any or all of the features of the embodiments described with respect to FIGS. 4-7. The balloon catheter 800 includes at least a balloon 810, an inflation shaft 830, and outer shaft 840. The balloon catheter 800 further includes a distal portion 885, within which the balloon 810 is disposed, and a proximal portion 890. The balloon catheter 800 is configured for delivering a prosthetic heart valve (not pictured) and may include any or all features and aspects of the balloon catheter 400. A portion of the balloon 810 is configured to have a prosthetic valve crimped thereon.

In the balloon catheter 800, the inflatable retention bumpers 801 and 802 (which may be similar to inflatable retention bumpers 501/502 and 601/602) are inflated with a hardenable material 875 via an inflation shaft 813. The hardenable material 875 may include glue, resin, or any other hardenable material. The hardenable material may be configured to harden after inflating the inflation retention bumpers 801 and 802, for example, due to contact with air, UV curing, epoxy curing, thermal setting, chemical/gas setting, or any other suitable mechanism. After inflation and hardening, the inflatable retention bumpers 801 and 802 may serve as solid retention bumpers as described above with respect to FIGS. 4A and 4B. The inflatable retention bumpers 801 and 802 may be expanded and solidified during a manufacturing and assembly process of the balloon catheter 800 and/or prior to a valve delivery operation. The inflatable retention bumpers 801 and 802 may be employed with the balloon catheters 500 and 600 and/or with the inflation shafts 750A, 750B, and 750C.

FIGS. 9A-14D illustrate axial force and tension expandable retention bumpers according to embodiments hereof. Expandable retention bumpers consistent with the embodiments of FIGS. 9A-14D may be expanded by tension or inward force provided axially.

Figure 9A:
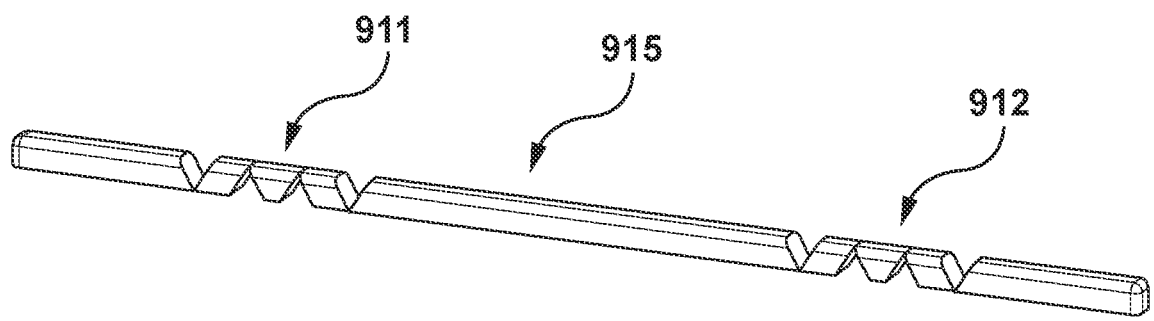
FIGS. 9A-9E illustrate axial force expandable retention bumpers according to embodiments hereof.
Figure 9B:
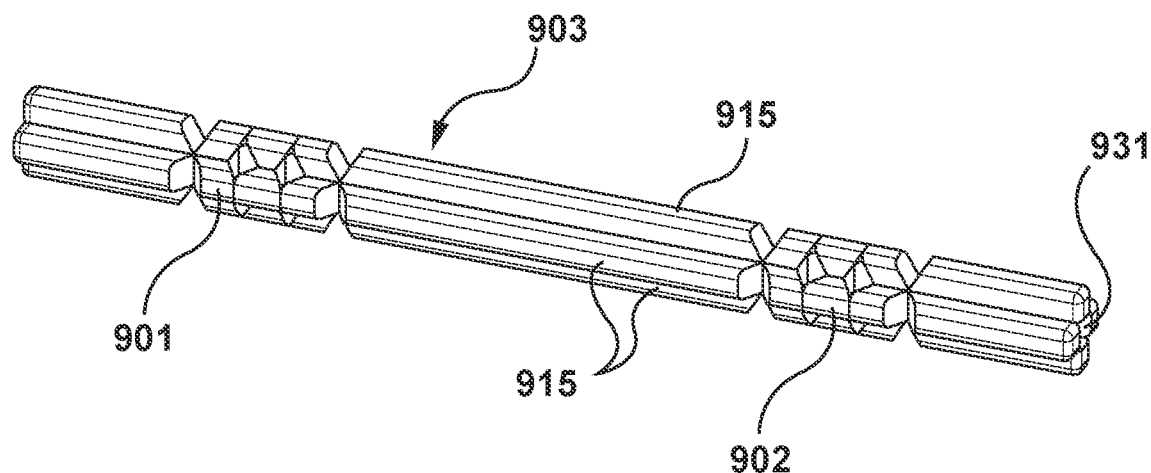
Figure 9C:
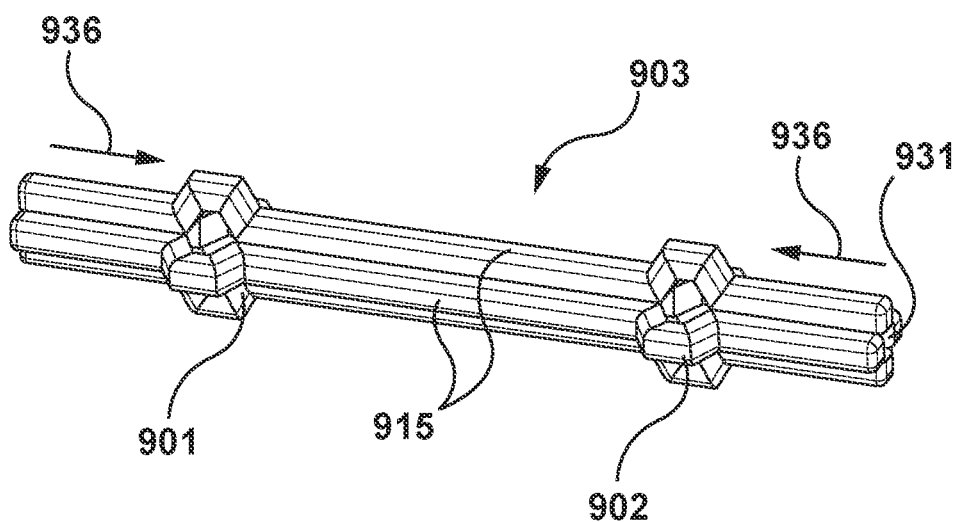
Figure 9D:
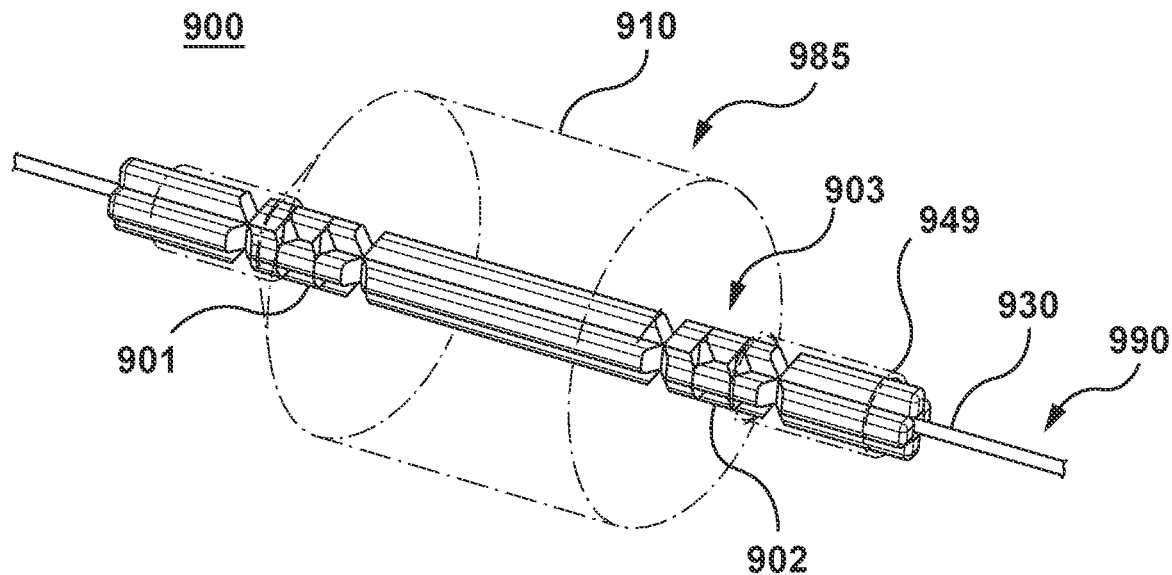
Figure 9E:
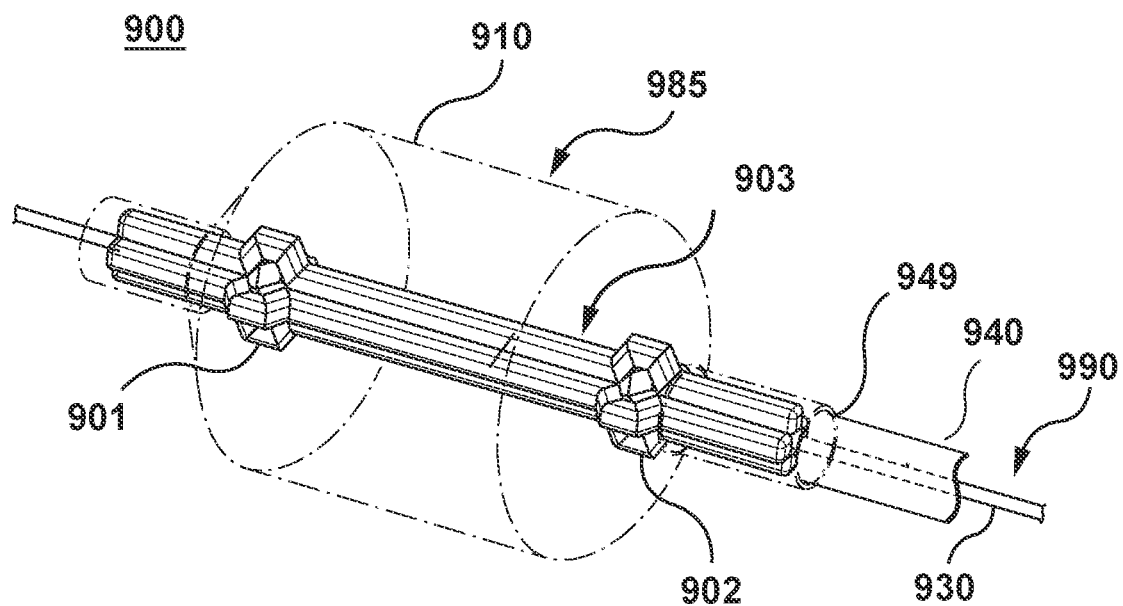

FIGS. 9A-9E illustrate axial force expandable retention bumpers 901 and 902. The axial force expandable retention bumpers 901 and 902 are configured for expanding under inward axial force. Inward axial force refers to force direct in an axial direct inward towards the center of the retention bumpers. A balloon catheter 900, as shown in FIGS. 9D and 9E, includes at least a balloon 910, an inner shaft 930, and an outer shaft 940. The balloon catheter 900 is configured for delivering a prosthetic heart valve (not pictured) and may include any or all features and aspects of the balloon catheter 400. The balloon catheter 900 further includes a distal portion 985, within which the balloon 910 is disposed, and a proximal portion 990.

As shown in FIG. 9E, in the distal portion 985 are disposed the axial force expandable retention bumpers 901 and 902. The axial force expandable retention bumpers 901 and 902 are formed from one or more folding structures 915, illustrated in FIG. 9A. A folding structure 915 is a length of material having a solid cross-section. Suitable materials may include, for example, rigid polymers (e.g., Grilamid), alloyed steels, stainless steel, titanium alloys (tube or wire), aluminum, and/or any other stiff biocompatible material. In an embodiment, a nylon 12 polymer may be selected for the folding structure. Each folding structure 915 includes a first expansion portion 911 and a second expansion portion 912. The expansion portions 911 and 912 are configured such that an inward axial force applied along the long axis of the folding structure 915 causes folding at the expansion portions 911 and 912. Folding at the expansion portions 911 and 912 causes the expansion portions 911 and 912 to project outward from the folding structure 915. Each of the expansion portions 911 and 912 includes one or more cuts, slits, and/or hinges (such as living hinges) to facilitate the projection under inward axial force. When the folding structure 915 is subject to inward axial force, the expansion portions 911 and 912 bend according to the cut, slits, and hinges to form a projection. A plurality of folding structures 915 may be grouped together and arranged radially, thereby forming an axial force expandable bumper structure 903 an inner hollow 931 at the center of the group, as shown in FIG. 9B. The inner hollow 931 is an empty space between the plurality of folding structures 915 and is configured to permit the folding structures 915 to be arranged around the inner shaft 930 of the balloon catheter 900. Inward axial force on the plurality of folding structures 915, as shown by the arrows 936 of FIG. 9C, causes the expansion portions 911 and 912 of each to project, thereby forming the axial force expandable retention bumpers 901 and 902, as illustrated in FIG. 9C and FIG. 9E.

The axial force expandable retention bumpers 901 and 902 have a first radially unexpanded size and a second radially expanded size. The first radially unexpanded size of the axial force expandable retention bumpers 901 and 902 is illustrated in FIG. 9B and is small enough to enter the balloon 910 through the balloon opening 949 (as illustrated in FIG. 9D), which may have a diameter of approximately 0.2 inches. In further embodiments, the balloon opening 949 may have a diameter between 0.1 and 0.25 inches. The second radially expanded size of the axial force expandable retention bumpers 901 and 902, as illustrated in FIG. 9E, is large enough to provide valve retention during a delivery operation. For example, the second radially expanded size, also illustrated in FIG. 9C, may be approximately 0.3 inches in diameter. In further embodiments, the second radially expanded size of the bumpers may have a diameter between 0.25 and 0.35 inches. The axial force expandable retention bumpers 901 and 902 may be expanded via inward axial force applied during an assembly process.

In a process of assembling balloon catheter 900, the axial force expandable retention bumpers 901 and 902 may be positioned within the balloon 910 while at the first radially unexpanded size. The axial force expandable retention bumpers 901 and 902 may then be expanded from the first radially unexpanded size to the second radially expanded size by applying compressive force to the opposite ends of the folding structures 915. Appropriate compressive force may be applied during assembly via any suitable means. For example, one or more inward axial force tools including tubular structures may be disposed over the inner shaft to apply compressive force to both ends of the axial force expandable bumper structure 903. The inward axial force tools may have an outer diameter smaller than the balloon opening 949 of the balloon and may therefore be inserted into the balloon during the axial force process. In embodiments, the axial force expandable retention bumpers 901 and 902 may have a natural state of radial expansion, due, for example, to a spring mechanism (e.g., thin nitinol wire/strip) within the axial force expandable retention bumpers 901 and 902 applying the compressive force permanently. On assembly, a tensile force may be applied to radially collapse the bumpers and allow assembly within the balloon. On correct positioning of the radially unexpanded bumpers within the balloon, the tensile force is released and the inward axial force is reinstated by the spring mechanism. Other methods of applying a compressive force include but are not limited to the use of stainless steel mandrels, custom tools to conform to the profile and application of the force, and temporary structures initially attached to either end of the folding structures 915 that may be detached on full radial expansion of the bumpers and may then be removed from the assembly.

After expansion, the folding structure 915 is secured to the inner shaft 930 and the balloon 910 is secured to the outer shaft 940. The folding structures 915 may be secured to the inner shaft 930 by adhesives, crimps, clamps, or any other appropriate means. For example, adhesive may be applied to secure the folding structures 915 via a syringe inserted through the balloon opening 949 and/or the open distal end of the balloon 910. The balloon 910 may then be folded and a prosthetic heart valve crimped onto the balloon catheter 900 between the axial force expandable retention bumpers 901 and 902. In further embodiments, the axial force expandable retention bumpers 901 and 902 are expanded to the second radially expanded size (or to a size intermediate between the first radially unexpanded size and the second radially expanded size) through inward axial force at any other time during assembly of the balloon catheter 900. For example, the axial force expandable retention bumpers 901 and 902 may be radially expanded after positioning within the balloon 910, after being partially secured to the inner shaft 930, after the balloon 910 is folded, and/or after the prosthetic heart valve is crimped to the balloon 910.

During use, inflation fluid is delivered to the balloon via a lumen between the outer shaft 940 and the inner shaft 930. In embodiments, portions of the axial force expandable bumper structure 903 may be disposed within an opening of the balloon 910. Inflation fluid delivered to the balloon 910 via the outer shaft 940 may flow around the axial force expandable bumper structure 903 and through gaps in the axial force expandable bumper structure 903 within the balloon opening 949. In further embodiments, the axial force expandable bumper structure 903 may be disposed within the balloon 910 such that inflation fluid flow from the outer shaft 940 into the balloon 910 is not substantially impeded.

Figure 10A:
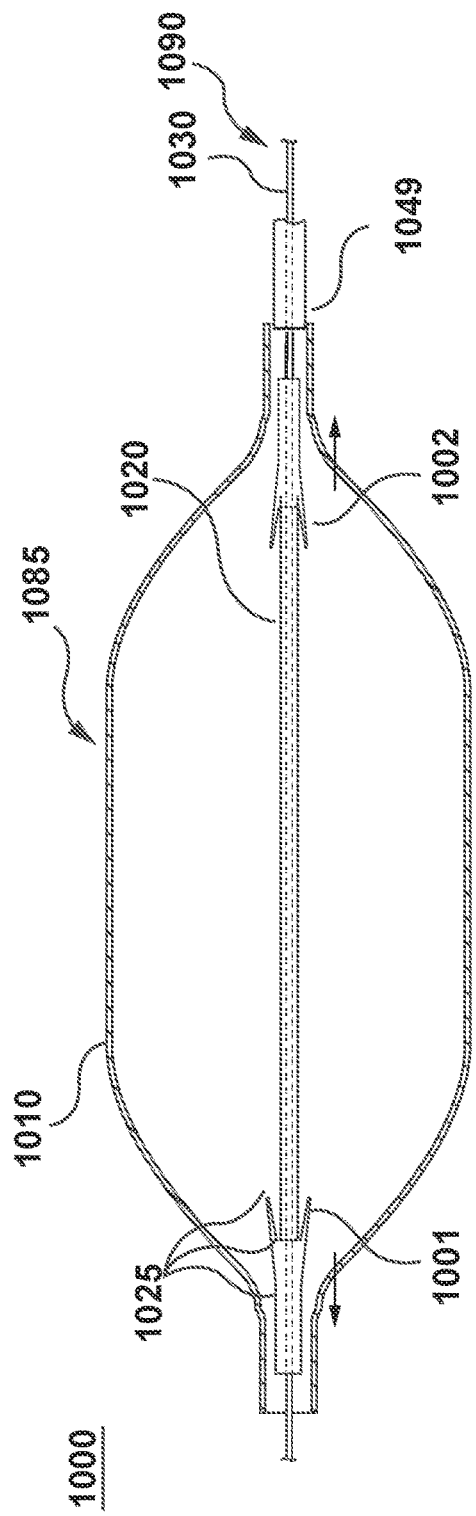
FIGS. 10A-10B illustrate tension expandable retention bumpers according to embodiments hereof.
Figure 10B:
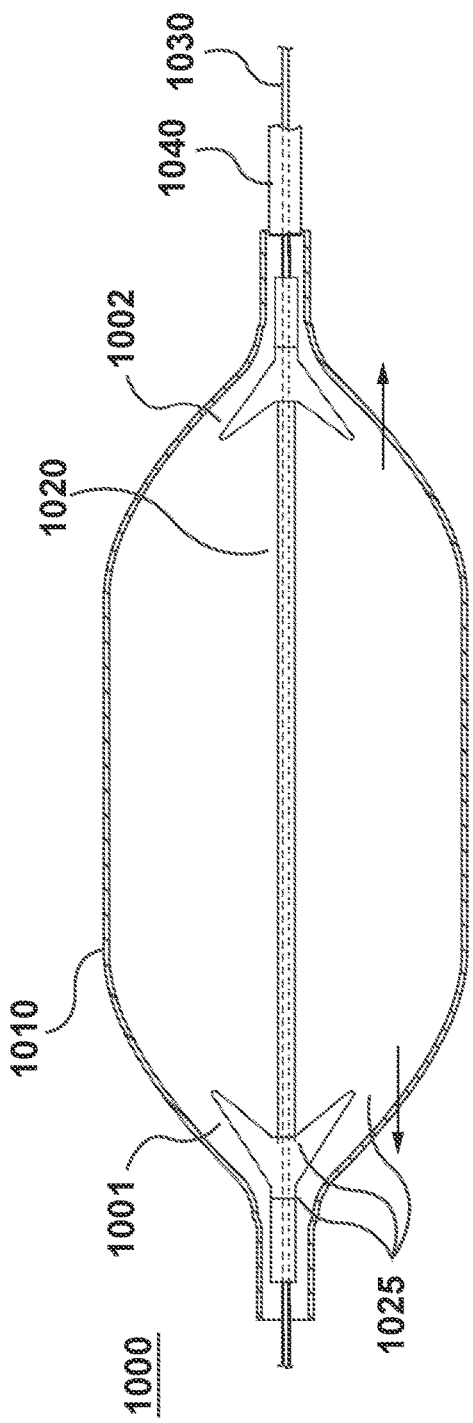
Figure 12D:
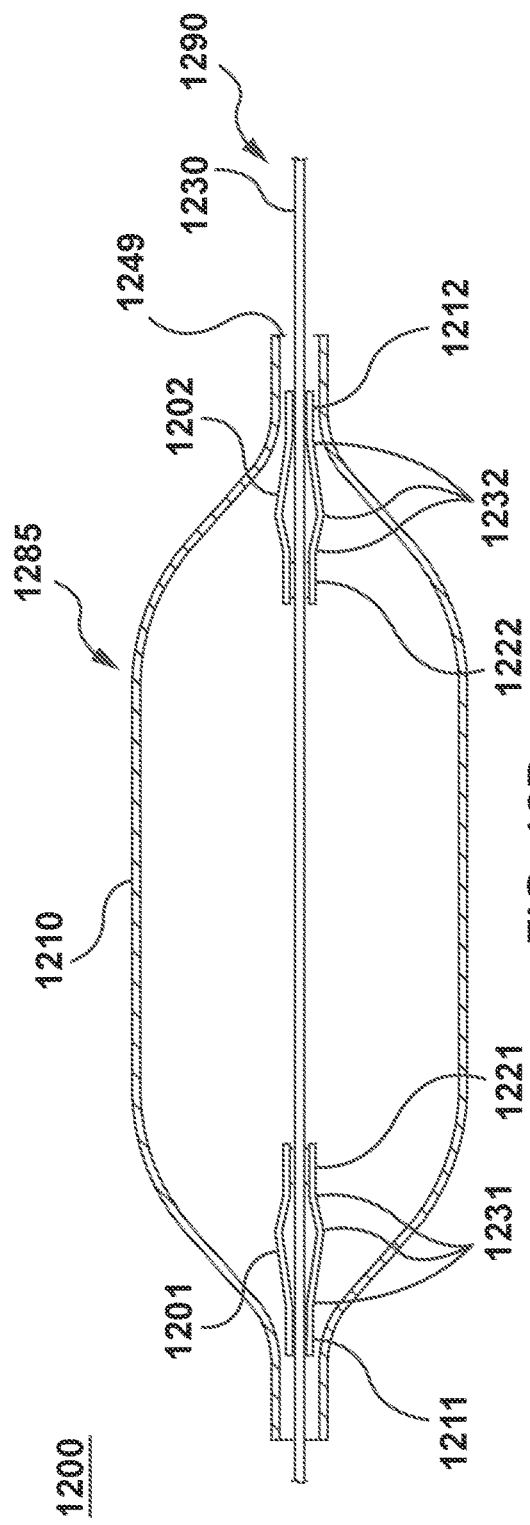
Figure 12E:
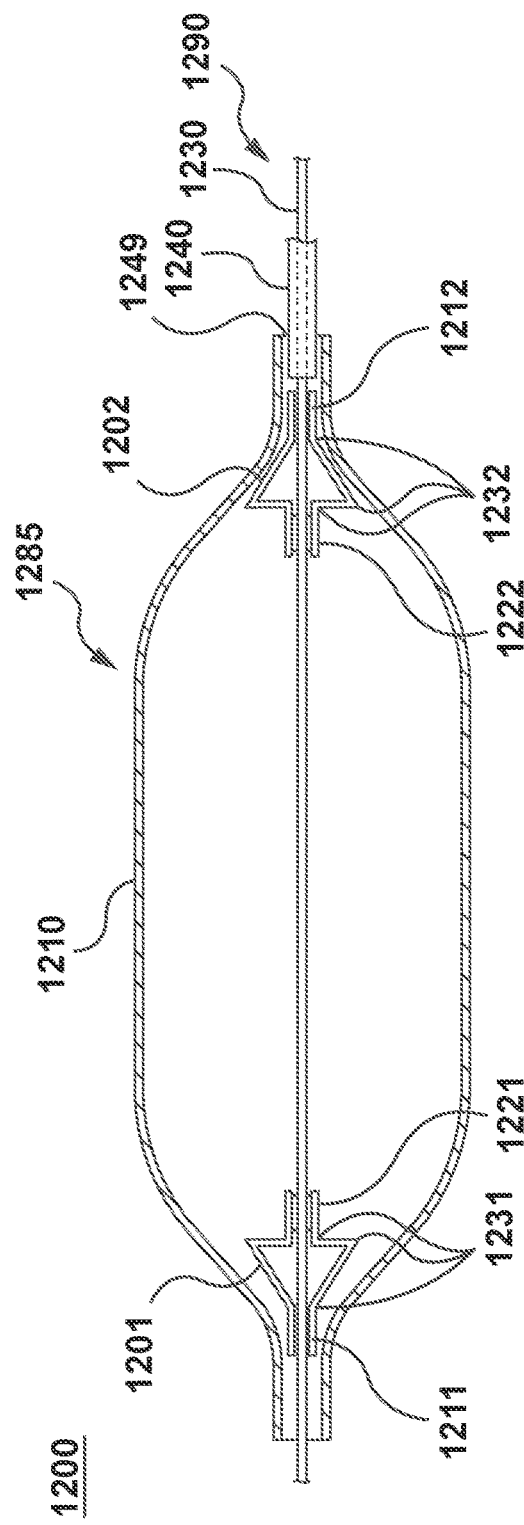

FIGS. 10A and 10B illustrate tension expandable retention bumpers according to embodiments hereof. The tension expandable retention bumpers 1001 and 1002 are configured for expanding under tension and may be employed with a balloon catheter 1000. The balloon catheter 1000 includes at least a balloon 1010, an inner shaft 1030, and an outer shaft 1040. The balloon catheter 1000 is configured for delivering a prosthetic heart valve (not pictured) and may include any or all features and aspects of the balloon catheter 400. The balloon catheter 1000 further includes a distal portion 1085, within which the balloon 1010 is disposed, and a proximal portion 1090.

Also, in the distal portion 1085 are disposed the tension expandable retention bumpers 1001 and 1002. The tension expandable retention bumpers 1001 and 1002 are formed from an expanding structure 1020, illustrated in FIG. 10A. The expanding structure 1020 is a tubular length of material having a lumen in the center to accommodate disposition over the inner shaft 1030 having the tension expandable retention bumpers 1001 and 1002 located at the proximal and distal ends thereof. Suitable materials may include, for example, rigid polymers (e.g., Grilamid), alloyed steels, stainless steel, titanium alloys (tube or wire), aluminum, and/or any other stiff biocompatible material. In an embodiment, a nylon 12 polymer may be selected for the folding structure. The expanding structure 1020 includes the tension expandable retention bumpers 1001 and 1002, positioned at each end of the expanding structure 1020. Each tension expandable retention bumper 1001 and 1002 is approximately radially symmetric and includes one or more hinges 1025 at which the tension expandable retention bumpers 1001 and 1002 are configured to flex or bend. When subjected to tensile force applied to the expanding structure 1020, the material of the tension expandable retention bumpers 1001 and 1002 flexes at the hinges 1025, causing the tension expandable retention bumpers 1001 and 1002 to change shape and expand radially.

The tension expandable retention bumpers 1001 and 1002 have a first radially unexpanded size and a second radially expanded size. The first radially unexpanded size of the tension expandable retention bumpers 1001 and 1002 is illustrated in FIG. 10A and is small enough to enter the balloon 1010 through the balloon opening 1049, which may have a diameter of approximately 0.2 inches. In further embodiments, the balloon opening 1049 may have a diameter between 0.1 and 0.25 inches. The second radially expanded size of the tension expandable retention bumpers 1001 and 1002, as illustrated in FIG. 10B, is large enough to provide valve retention during a delivery operation. For example, the second radially expanded size, may be approximately 0.3 inches in diameter. In further embodiments, the second radially expanded size of the bumpers may have a diameter between 0.25 and 0.35 inches. The tension expandable retention bumpers 1001 and 1002 may be expanded via tension forces applied during an assembly process. Appropriate tension force may be applied during assembly via any suitable means. For example, one or more tools may be employed to grasp either end the expanding structure 1020 to provide the tension force. In embodiments, the tension expandable retention bumpers 1001 and 1002 may have a natural state of radial expansion, due, for example, to a spring mechanism (e.g., thin nitinol wire/strip) within the tension expandable retention bumpers 1001 and 1002 applying the tensile force permanently. On assembly, an inward axial force may be applied to radially collapse the bumpers and allow assembly within the balloon. On correct positioning of the radially unexpanded bumpers within the balloon, the inward axial force is released and the tensile force is reinstated by the spring mechanism. Other methods of applying a tensile force include but are not limited to the use of stainless steel mandrels, custom tools to conform to the profile and application of the force, and temporary structures initially attached to either end of the expanding structure 1020 that may be detached on full radial expansion of the bumpers and may then be removed from the assembly.

In a process of assembling balloon catheter 1000, the tension expandable retention bumpers 1001 and 1002 are positioned within the balloon 1010 while at the first radially unexpanded size. The tension expandable retention bumpers 1001 and 1002 are then expanded to the second radially expanded size (or to a size intermediate between the first radially unexpanded size and the second radially expanded size) through tension. After expansion, the tension expandable retention bumpers 1001 and 1002 are secured to the inner shaft 1030 and the balloon 1010 is secured to the outer shaft 1040. Securement may be achieved through the use of adhesives, crimps or other securing means applied to the ends of the expanding structure 1020. Such securement may be achieved via tools inserted through the open distal end of the balloon 1010 and/or the opening of the balloon 1010. In further embodiments, securement may be achieved through laser bonding or welding, e.g., laser bonding or welding the expanding structure 1020 to the inner shaft 1030 through the balloon 1010 via laser transmission welding to prevent balloon damage. In further embodiments, securement may be achieved via induction welding, mechanical fixtures, and/or a male/female fitting between the expanding structure 1020 and the inner shaft 1030. The balloon 1010 may then be secured to the outer shaft 1040 and folded. A prosthetic heart valve is then crimped to balloon catheter 1000 between the tension expandable retention bumpers 1001 and 1002. In further embodiments, the tension expandable retention bumpers 1001 and 1002 may be partially secured prior to expansion.

During use, inflation fluid is delivered to the balloon via a lumen between the outer shaft 1040 and the inner shaft 1030. In embodiments, portions of the expanding structure 1020 may be disposed within a neck of the balloon 1010. Inflation fluid delivered to the balloon 1010 via the outer shaft 1040 may flow around the expanding structure 1020 within the neck of the balloon 1010. In embodiments, the expanding structure 1020 defines a lumen between the expanding structure 1020 and the inner shaft 1030 and is provided with inflation ports (not shown), within the neck of the balloon 1010 and/or along the length of the expanding structure 1020 between the tension expandable retention bumpers 1001 and 1002. In such embodiments, the expanding structure 1020 inflation fluid is delivered to the balloon at least partially through the expanding structure 1020. In further embodiments, the expanding structure 1020 may be disposed within the balloon 1010 such that inflation fluid flow from the outer shaft 1040 into the balloon 1010 is not substantially impeded.

FIGS. 11A and 11B illustrate axial force expandable retention bumpers 1101 and 1102 according to embodiments hereof. The axial force expandable retention bumpers 1101 and 1102 are configured for expanding under inward axial force and may be employed with a balloon catheter 1100. The balloon catheter 1100 includes at least a balloon 1110, an inner shaft 1130, and an outer shaft 1140. The balloon catheter 1100 is configured for delivering a prosthetic heart valve (not pictured) and may include any or all features and aspects of balloon catheter 400. The balloon catheter 1100 further includes a distal portion 1185, within which the balloon 1110 is disposed, and a proximal portion 1190.

The axial force expandable retention bumpers 1101 and 1102 are configured to expand from a first radially unexpanded size (illustrated in FIG. 11A) to a second radially expanded size (illustrated in FIG. 11B) when subject to inward axial force. As discussed with respect to axial force expandable retention bumpers 901 and 902, the first radially unexpanded size has a narrow enough diameter to fit into a balloon opening 1149 of the balloon 1110, e.g., between approximately 0.1 inches and 0.25 inches, while the second radially expanded size has a great enough diameter to secure the prosthetic heart valve during a delivery operation, e.g., between approximately 0.25 inches and 0.35 inches. Assembly and use of the axial force expandable retention bumpers 1101 and 1102 is similar to that of axial force expandable retention bumpers 901 and 902, but the mechanism of expansion is different.

The axial force expandable retention bumpers 1101 and 1102 are disposed as part of a slit-based expansion structure 1120. The slit-based expansion structure 1120 is an elongated section of material, such as plastic, polymer, steel, alloyed steel, titanium alloy, cobalt alloy, nitinol, and any other suitable biocompatible material, with an interior lumen permitting the slit-based expansion structure to be positioned over the inner shaft 1130. The slit-based expansion structure 1120 includes a plurality of slits 1111 at a distal end of the slit-based expansion structure 1120 and a plurality of slits 1112 at a proximal end of the slit-based expansion structure 1120. The plurality of slits 1111 divide the slit-based expansion structure 1120 into a plurality of expansion strips 1121. The slits 1111 and 1112 are arranged longitudinally on the slit-based expansion structure 1120 to create the expansion strips 1121 and 1122. The slits 1111 and 1112 and expansion strips 1121 and 1122 form the axial force expandable retention bumpers 1101 and 1102, respectively. When the slit-based expansion structure 1120 is not axially compressed, as shown in FIG. 11A, the axial force expandable retention bumpers 1101 and 1102 have a first radially unexpanded size.

Each expansion strip 1121 further includes one or more flex portions 1131. When the slit-based expansion structure 1120 is axially compressed, the expansion strips 1121 bend, flex, or fold around the flex portions 1131 and, because they are separated from the rest of the expansion strips 1121, they expand radially away from the central axis of the slit-based expansion structure 1120. In an embodiment, each expansion strip 1121 includes three flex portions 1131. For each expansion strip 1121, a first flex portion 1131 may be disposed at a first end of the expansion strip 1121 where it connects to the remainder of the slit-based expansion structure 1120, a second flex portion 1131 may be disposed at a second end of the slits 1111 where it connects to the remainder of the slit-based expansion structure 1120, and a third flex portion 1131 may be disposed between the first and second ends of the expansion strip 1121. Each flex portion 1131 may be a portion of material that is configured for flexing, bending, and/or folding, and may be, for example, a living hinge consisting of a more flexible material and/or a smaller cross-section of material with respect to the remainder of the expansion strip 1121. When the expansion strips 1121 are axially compressed and radially expanded, the axial force expandable retention bumper 1101 expands to the second radially expanded size. Similarly, the axial force expandable retention bumper 1102 has a second radially expanded size when the expansion strips 1122 are placed under inward axial force, which causes radial expansion via bending, flexing, or folding of the expansion strips 1122 around the flex portions 1132. The flex portions 1132 are similar to the flex portions 1131 as described above. Appropriate compressive force may be applied during assembly via any suitable means. For example, one or more inward axial force tools including tubular structures may be disposed over the inner shaft to apply compressive force to both ends of the slit-based expansion structure 1120. The inward axial force tools may have an outer diameter smaller than the balloon opening 1149 of the balloon and may therefore be inserted into the balloon during the inward axial force process. In embodiments, the axial force expandable retention bumpers 1101 and 1102 may have a natural state of radial expansion, due, for example, to a spring mechanism (e.g., thin nitinol wire/strip) within the axial force expandable retention bumpers 1101 and 1102 applying the compressive force permanently. On assembly, a tensile force may be applied to radially collapse the bumpers and allow assembly within the balloon. On correct positioning of the radially unexpanded bumpers within the balloon, the tensile force is released and the inward axial force is reinstated by the spring mechanism. Other methods of applying a compressive force include but are not limited to the use of stainless steel mandrels, custom tools to conform to the profile and application of the force, and temporary structures initially attached to either end of the slit-based expansion structure 1120 that may be detached on full radial expansion of the bumpers and may then be removed from the assembly.

In embodiments, one end of the slit-based expansion structure 1120 may be secured, e.g., via adhesive, crimp, clamp, etc., prior to the application of inward axial force. As such, inward axial force may be applied from a single end of the slit-based expansion structure 1120 to cause radial expansion.

After radial expansion, the slit-based expansion structure 1120 may be secured in the axially compressed and radially expanded position by securement to the inner shaft 1130. Securement to the inner shaft 1130 may be accomplished via the use of adhesives, crimps, or other securing means. The slit-based expansion structure 1120 is secured to the inner shaft while inside the balloon. Adhesives may be applied, for example, via syringe through the balloon opening 1149 of the balloon and/or through the open distal end of the balloon 1110 In further embodiments, securement may be achieved through laser bonding or welding, e.g., laser bonding or welding the slit-based expansion structure 1120 to the inner shaft 1130 through the balloon 1110 via laser transmission welding to prevent balloon damage. In further embodiments, securement may be achieved via induction welding, mechanical fixtures, and/or a male/female fitting between the expanding structure 1120 and the inner shaft 1030. After the slit-based expansion structure 1120 is secured to the inner shaft 1130, the balloon 1110 is secured to the outer shaft 1140. As discussed above with respect to axial force expandable retention bumpers 901 and 902, the axial force expandable retention bumpers 1101 and 1102 may be expanded at any suitable time during the assembly process after insertion into the balloon 1110.

During use, inflation fluid is delivered to the balloon via a lumen between the outer shaft 1140 and the inner shaft 1130. In embodiments, portions of the slit-based expansion structure 1120 may be disposed within the balloon opening 1149. Inflation fluid delivered to the balloon 1110 via the outer shaft 1140 may flow around the slit-based expansion structure 1120 within the balloon opening 1149. In embodiments, the slit-based expansion structure 1120 defines a lumen between the slit-based expansion structure 1120 and the inner shaft 1130 to provide a pathway for inflation fluid flowing from a proximal end of the balloon 1110 to a distal end of the balloon 1110. In such embodiments, the expanding structure 1120 inflation fluid is delivered to the balloon at least partially through the expanding structure 1120. In further embodiments, the expanding structure 1120 may be disposed within the balloon 1110 such that inflation fluid flow from the outer shaft 1140 into the balloon 1110 is not substantially impeded.

FIGS. 12A-12E illustrate axial force expandable retention bumpers according to embodiments hereof. The axial force expandable retention bumpers 1201 and 1202 are configured for expanding under inward axial force and may be employed with a balloon catheter 1200. The balloon catheter 1200 includes at least a balloon 1210, an inner shaft 1230, and an outer shaft 1240. The balloon catheter 1200 is configured for delivering a prosthetic heart valve (not pictured) and may include any or all features and aspects of the balloon catheter 400. The balloon catheter 1200 further includes a distal portion 1285, within which the balloon 1210 is disposed, and a proximal portion 1290.

The axial force expandable retention bumpers 1201 and 1202 are configured to expand from a first radially unexpanded size (illustrated in FIG. 12A) to a second radially expanded size (illustrated in FIGS. 12C and 12E) when subject to inward axial force. The axial force expandable retention bumpers 1201 and 1202 have the first radially unexpanded size with a narrow enough diameter to fit into a balloon opening 1249 of the balloon 1210, e.g., between approximately 0.1 inches and 0.25 inches, while the second radially expanded size has a great enough diameter to secure the prosthetic heart valve during a delivery operation, e.g., between approximately 0.25 inches and 0.35 inches. The axial force expandable retention bumpers 1201 and 1202 are formed from slit-based expansion structures 1219 and 1220, respectively. The slit-based expansion structure 1219 includes slits 1211, expansion strips 1221, and flex portions 1231. The slit-based expansion structure 1220 includes slits 1212, expansion strips 1222, and flex portions 1232. Each slit-based expansion structure 1219 and 1220 operates similarly to the slit-based expansion structure 1120, as described above. Because this embodiment employs two slit-based expansion structures 1219 and 1220, each must be partially secured to the inner shaft 1230 prior to inward axial force and radial expansion to prevent movement of the slit-based expansion structures on the inner shaft 1230.

FIG. 12B illustrates the securement of slit-based expansion structure 1219 to the inner shaft 1230. The illustration of FIG. 12B is limited to one expansion strip 1221 to better illustrate the securing adhesives. The slit-based expansion structures 1219 and 1220 are secured to the inner shaft by a pre-expansion adhesive 1244 and a post-expansion adhesive 1245. The pre-expansion adhesive 1244 is applied to secure one end of the slit-based expansion structures 1219 and 1220 to the inner shaft 1230 prior to expansion. The pre-expansion adhesive 1244 is applied to the end of each slit-based expansion structures 1219 and 1220 that is closer to the interior of the balloon 1210 (e.g., the proximal end for slit-based expansion structure 1219 and the distal end for the slit-based expansion structure 1220). When secured with the pre-expansion adhesive 1244, the balloon 1210 is positioned over the distal portion 1285. Axial compressive forces are applied to the slit-based expansion structures 1219 and 1220 to cause their radial expansion from a first radially unexpanded size to a second radially expanded size. Appropriate compressive force may be applied during assembly via any suitable means. For example, one or more inward axial force tools including tubular structures may be disposed over the inner shaft to apply compressive force to the slit-based expansion structures 1219 and 1220. The inward axial force tools may have an outer diameter smaller than the balloon opening 1249 of the balloon 1210 and may therefore be inserted into the balloon during the inward axial force process. In embodiments, the axial force expandable retention bumpers 1201 and 1202 may have a natural state of radial expansion, due, for example, to a spring mechanism (e.g., thin nitinol wire/strip) within the axial force expandable retention bumpers 1201 and 1202 applying the compressive force permanently. On assembly, a tensile force may be applied to radially collapse the bumpers and allow assembly within the balloon. On correct positioning of the radially unexpanded bumpers within the balloon, the tensile force is released and the inward axial force is reinstated by the spring mechanism. Other methods of applying a compressive force include but are not limited to the use of stainless steel mandrels, custom tools to conform to the profile and application of the force, and temporary structures initially attached to either end of the slit-based expansion structures 1219 and 1220 that may be detached on full radial expansion of the bumpers and may then be removed from the assembly.

After expansion, a post-expansion adhesive 1245 is applied to the slit-based expansion structures 1219 and 1220 at the ends closer to the exterior of the balloon 1210 (e.g., the distal end for slit-based expansion structure 1219 and the proximal end for the slit-based expansion structure 1220) to secure the slit-based expansion structures 1219 and 1220 in the radially expanded positions to serve as axial force expandable retention bumpers 1201 and 1202. The adhesive may be applied, for example, via syringe through the balloon opening 1249 of the balloon 1210 and/or through the open distal end of the balloon 1210. In other examples, the slit-based expansion structures 1219 and 1220 may be laser welded or bonded to the inner shaft 1230 through the balloon 1210 via laser transmission welding to prevent balloon damage. In further embodiments, securement may be achieved via induction welding, mechanical fixtures, and/or a male/female fitting between the slit-based expansion structures 1219 and 1220 and the inner shaft 1230. After the axial force expandable retention bumpers 1201 and 1202 are radially expanded and secured, the balloon 1210 is secured to the outer shaft 1240. As discussed above with respect to axial force expandable retention bumpers 1201 and 1202, the axial force expandable retention bumpers 1201 and 1202 may be radially expanded at any suitable time during the assembly process after insertion into the balloon 1210. In further embodiments, the slit-based expansion structures 1219 and 1220 may be secured via means other than adhesives, such as crimps, clamps, etc.

During use, inflation fluid is delivered to the balloon via a lumen between the outer shaft 1240 and the inner shaft 1230. In embodiments, portions of the slit-based expansion structures 1219 and 1220 may be disposed within a neck of the balloon 1210. Inflation fluid delivered to the balloon 1210 via the outer shaft 1240 may flow around the slit-based expansion structures 1219 and 1220 within the neck of the balloon. In embodiments, the adhesive or other means securing the slit-based expansion structures 1219 and 1220 to the inner shaft 1230 does not eliminate the space between the inner shaft 1230 and the slit-based expansion structures 1219 and 1220. In such embodiments, inflation fluid may flow between the slit-based expansion structures 1219 and 1220 and the inner shaft 1230. In further embodiments, the slit-based expansion structures 1219 and 1220 may be disposed within the balloon 1210 such that inflation fluid flow from the outer shaft 1240 into the balloon 1210 is not substantially impeded.

FIGS. 13A-13B illustrate axial force expandable retention bumpers according to embodiments hereof. The axial force expandable retention bumpers 1301 and 1302 are configured for radially expanding under axial force and may be employed with a balloon catheter 1300. The balloon catheter 1300 includes at least a balloon 1310, an inner shaft 1330, and an outer shaft 1340. The balloon catheter 1300 is configured for delivering a prosthetic heart valve (not pictured) and may include any or all features and aspects of the balloon catheter 400. The balloon catheter 1300 further includes a distal portion 1385, within which the balloon 1310 is disposed, and a proximal portion 1390.

The axial force expandable retention bumpers 1301 and 1302 are configured to radially expand from a first radially unexpanded size (illustrated in FIG. 13A) to a second radially expanded size (illustrated in FIG. 13B) when subject to inward axial force. As discussed with respect to axial force expandable retention bumpers 1201 and 1202, the first radially unexpanded size is narrow enough diameter to fit into a balloon opening 1349 of the balloon 1310, e.g., between approximately 0.1 inches and 0.25 inches, while the second radially expanded size may have a great enough diameter to secure the prosthetic heart valve during a delivery operation, e.g., between approximately 0.25 inches and 0.35 inches. The axial force expandable retention bumpers 1301 and 1302 are formed from one or more materials, such as alloyed steels, aluminum, and rigid polymers, and shaped such that inward axial force causes radial expansion. For example, the axial force expandable retention bumpers 1301 and 1302 may be formed from one or more materials having a high Poisson's ratio. Poisson's ratio is a ratio of an amount of expansion in one axis caused by force in another. Materials with a high Poisson's ratio will expand significantly in a radial direction when compressed axially.

The axial force expandable retention bumpers 1301 and 1302 are slidably disposed over the inner shaft 1330. To ensure that inward axial force may be applied, the axial force expandable retention bumpers 1301 and 1302 are secured to the inner shaft 1330, via bonding, adhesive, or other suitable means. The axial force expandable retention bumpers 1301 and 1302 are secured to the inner shaft at the end of the axial force expandable retention bumpers 1301 and 1302 that is interior to the balloon. The remainder of the axial force expandable retention bumpers 1301 and 1302 may remain slidably disposed so as to permit partial movement of the bumpers when inward axial force is applied.

Thus, when axial force is applied, as shown by the arrows in FIG. 13B, the axial force expandable retention bumpers 1301 and 1302 are compressed axially and expand radially from a first radially unexpanded size to a second radially expanded size. Appropriate compressive force may be applied during assembly via any suitable means. For example, one or more inward axial force tools including tubular structures may be disposed over the inner shaft to apply compressive force to the axial force expandable retention bumpers 1301 and 1302. The inward axial force tools may have an outer diameter smaller than the balloon opening 1349 of the balloon 1310 and may therefore be inserted into the balloon during the inward axial force process.

After securement to the inner shaft 1330, the balloon 1310 is passed over the axial force expandable retention bumpers 1301 and 1302 for assembly. After expansion, the axial force expandable retention bumpers 1301 and 1302 may be secured to the inner shaft 1330 a second time to ensure that the inward axial force and radial expansion are retained. The axial force expandable retention bumpers 1301 and 1302 are secured a second time via adhesive, bonding, clamps, crimps, or other suitable means. Such securement may be achieved via the use of tools inserted into the balloon 1310 via the balloon opening 1349 and/or the open distal end of the balloon 1310 before positioning of the outer shaft 1340. In other examples, the axial force expandable retention bumpers 1301 and 1302 may be laser welded to the inner shaft 1330 through the balloon 1310 via laser transmission welding to prevent balloon damage. Next, the balloon 1310 is secured to the outer shaft 1340. In embodiments, a portion of the axial force expandable retention bumpers 1301 and 1302 may extend out of the balloon 1310 to facilitate application of inward axial force. In further embodiments, the entirety of each axial force expandable retention bumper 1301 and 1302 may remain inside of the balloon 1310. After the retention bumpers are secured to the inner shaft 1330, the balloon 1310 is sealed to the outer shaft 1340 and folded, and the prosthetic heart valve is crimped to the balloon 1310.

During use, inflation fluid is delivered to the balloon via a lumen between the outer shaft 1340 and the inner shaft 1330. In embodiments, portions of the axial force expandable retention bumpers 1301 and 1302 may be disposed within a neck of the balloon 1310. Inflation fluid delivered to the balloon 1310 via the outer shaft 1340 may flow around axial force expandable retention bumpers 1301 and 1302 within the balloon opening 1349. In further embodiments, the axial force expandable retention bumpers 1301 and 1302 may be disposed within the balloon 1310 such that inflation fluid flow from the outer shaft 1340 into the balloon 1310 is not substantially impeded.

FIGS. 14A-14D illustrate tension expandable retention bumpers according to embodiments hereof. The tension expandable retention bumpers 1401 and 1402 are configured for radially expanding under tension and may be employed with balloon catheter 1400. The balloon catheter 1400 includes at least a balloon 1410, an inner shaft 1430, and an outer shaft 1440. The balloon catheter 1400 is configured for delivering a prosthetic heart valve (not pictured) and may include any or all features and aspects of the balloon catheter 400. The balloon catheter 1400 further includes a distal portion 1485, within which the balloon 1410 is disposed, and a proximal portion 1490.

The tension expandable retention bumpers 1401 and 1402 are configured to expand from a first radially unexpanded size (illustrated in FIG. 14A) to a second radially expanded size (illustrated in FIG. 14B) when subject to axial tension. As discussed with respect to axial force expandable retention bumpers 1301 and 1302, the first radially unexpanded size has a narrow enough diameter to fit into a balloon opening 1449 of the balloon 1410, e.g., between approximately 0.1 inches and 0.25 inches, while the second radially expanded size has a great enough diameter to secure the prosthetic heart valve during a delivery operation, e.g., between approximately 0.25 inches and 0.35 inches. The tension expandable retention bumpers 1401 and 1402 are structured such that axial tension causes radial expansion. For example, the tension expandable retention bumpers 1401 and 1402 may have an origami-like structure 1450, as illustrated in FIG. 14C. The origami-like structure 1450 is a structure comprising a plurality of hinges and links between the hinges arranged such that tension applied in an axial direction causes expansion in a radial direction. In another example, the tension expandable retention bumpers 1401 and 1402 may comprise auxetic materials or structures. Auxetic materials and structures have a negative Poisson's ratio, meaning that they expand in one direction when tension is applied in a transverse direction. In the tension expandable retention bumpers 1401 and 1402, an axially applied tension causes a radial expansion. For example, as illustrated in FIG. 14D, auxetic structure 1451 includes a plurality of elastic cords 1470 wrapped with tension line 1471. When the elastic cords 1470 are stretched, the tension lines 1471 maintain their position and cause the radial expansion of the elastic cords 1470.

The tension expandable retention bumpers 1401 and 1402 are slidably disposed over the inner shaft 1430. To ensure that tension may be applied, the tension expandable retention bumpers 1401 and 1402 are secured to the inner shaft 1430, via bonding, adhesive, clamping, crimping, or other suitable means. The tension expandable retention bumpers 1401 and 1402 are secured to the inner shaft at the end of the tension expandable retention bumpers 1401 and 1402 that is interior to the balloon. The remainder of the tension expandable retention bumpers 1401 and 1402 may remain slidably disposed so as to permit partial movement of the bumpers when tension is applied.

Appropriate tension force may be applied during assembly via any suitable means. For example, one or more tools may be employed to grasp the protruding ends of the tension expandable retention bumpers 1401 and 1402 to exert tension.

After securement to the inner shaft 1430, the balloon 1410 is passed over the tension expandable retention bumpers 1401 and 1402 for assembly. Thus, when axial force is applied, the tension expandable retention bumpers 1401 and 1402 are put into tension axially and expand radially from a collapsed first size to an expanded second size. After expansion, the tension expandable retention bumpers 1401 and 1402 may be secured to the inner shaft 1430 a second time to ensure that the expansion is retained. The tension expandable retention bumpers 1401 and 1402 are secured a second time via adhesive, bonding, clamps, crimps, or other suitable means. Such securement may be achieved via the use of tools (e.g., an adhesive containing syringe) inserted into the balloon 1410 via the balloon opening 1449 and/or through the open distal end of the balloon 1410 before positioning of the outer shaft 1440. In other examples, the tension expandable retention bumpers 1401 and 1402 may be laser welded to the inner shaft 1430 through the balloon 1410 via laser transmission welding to prevent balloon damage. The balloon 1410 may then be secured to the outer shaft 1440. In embodiments, a portion of the tension expandable retention bumpers 1401 and 1402 may extend out of the balloon 1410 to facilitate tension. In further embodiments, the entirety of each tension expandable retention bumper 1401 and 1402 may remain inside of the balloon 1410. As discussed above with respect to axial force expandable retention bumpers 1201 and 1202, the tension expandable retention bumpers 1401 and 1402 may be expanded to a second radially expanded size at any suitable time during the assembly process after insertion into the balloon 1410.

During use, inflation fluid is delivered to the balloon via a lumen between the outer shaft 1440 and the inner shaft 1430. In embodiments, portions of the tension expandable retention bumpers 1401 and 1402 may be disposed within a neck of the balloon 1410. Inflation fluid delivered to the balloon 1410 via the outer shaft 1440 may flow around tension expandable retention bumpers 1401 and 1402 within the balloon opening 1449. In further embodiments, the tension expandable retention bumpers 1401 and 1402 may be disposed within the balloon 1410 such that inflation fluid flow from the outer shaft 1440 into the balloon 1410 is not substantially impeded.

FIGS. 15A and 15B illustrate settable retention bumpers according to embodiments hereof. The settable retention bumpers 1501 and 1502 are configured to be elastically radially compressed for insertion into the balloon 1510 and are composed of a settable material that may be processed to reduce its elastic properties. The balloon catheter 1500 includes at least a balloon 1510, an inner shaft 1530, and an outer shaft 1540. The balloon catheter 1500 is configured for delivering a prosthetic heart valve (not pictured) and may include any or all features and aspects of the balloon catheter 400. The balloon catheter 1500 further includes a distal portion 1585, within which the balloon 1510 is disposed, and a proximal portion 1590.

Also in the distal portion 1585 are disposed settable retention bumpers 1501 and 1502. The settable retention bumpers 1501 and 1502 are formed from a material that is initially elastic before undergoing a processing step. The settable retention bumpers 1501 and 1502 have a first radially collapsed size and a second radially expanded size. The first radially collapsed size of the settable retention bumpers 1501 and 1502 is illustrated in FIG. 15A and is small enough to enter the balloon 1510 through the balloon opening 1549, which may have a diameter of approximately 0.2 inches. In further embodiments, the balloon opening 1549 may have a diameter between 0.1 and 0.25 inches. To reach the first radially collapsed size, the settable retention bumpers 1501 and 1502 are elastically deformed from the second radially expanded size when subject to radial pressure.

After insertion into the balloon 1510, the settable retention bumpers 1501 and 1502 are released from the radial pressure and permitted to expand back to the second radially expanded size, as shown in FIG. 15B. The second radially expanded size of the settable retention bumpers 1501 and 1502, as illustrated in FIG. 15B, is large enough to provide valve retention during a delivery operation. For example, the second radially expanded size, may be approximately 0.3 inches. In further embodiments, the second radially expanded size of the bumpers may have a diameter between 0.25 and 0.35 inches.

In a process of assembling the balloon catheter 1500, the settable retention bumpers 1501 and 1502 are positioned within the balloon 1510 while at the first radially collapsed size. The bumpers 1501 and 1502 are radially collapsed for insertion into the balloon 1510 through the application of radial pressure. Radial force may be applied, for example, via manual manipulation, via a crimping tool, via a tubular sheath, and/or via any other suitable means. The settable retention bumpers 1501 and 1502 are then expanded to the second radially expanded size through release of the radial pressure maintaining the first radially collapsed size. After expansion, the settable retention bumpers 1501 and 1502 are processed to cause the material of the bumpers to set or harden, causing a decrease in the elasticity of the settable retention bumpers 1501 and 1502. The settable retention bumpers 1501 and 1502 may be cured or set via thermal processing, gas processing, UV processing, or any suitable curing/setting approach. After processing, the settable retention bumpers 1501 and 1502 are locked into the second radially expanded size and can no longer be compressed to the first radially collapsed size.

The settable retention bumpers 1501 and 1502 may be secured to the inner shaft 1530 before or after insertion into the balloon 1510. The settable retention bumpers 1501 and 1502 are secured to the inner shaft 1530 via any suitable means, including adhesives, bonding, clamps, crimping, over molding, etc. If secured after insertion into the balloon 1510, tools may be deployed through the balloon opening 1549 and/or the open distal end of the balloon 1510 to apply the securement means. In other examples, the settable retention bumpers 1501 and 1502 may be laser welded to the inner shaft 1530 through the balloon 1510 via laser transmission welding to prevent balloon damage. After the settable retention bumpers 1501 and 1502 are secured to the inner shaft 1530 and cured/set at the second radially expanded size, the balloon 1510 is secured to the outer shaft 1540. The balloon 1510 may then be folded. A prosthetic heart valve is then crimped onto the balloon catheter 1500 between the settable retention bumpers 1501 and 1502. In further embodiments, settable retention bumpers 1501 and 1502 may remain uncured or unset until after the balloon catheter 1500 is fully assembled.

The settable retention bumpers 1501 and 1502 are illustrated in FIGS. 15A and 15B as having a conical shape with collapsible legs. The settable retention bumpers 1501 and 1502 are not limited to a specific shape or configuration, however, and any suitable shape or configuration may be employed.

During use, inflation fluid is delivered to the balloon via a lumen between the outer shaft 1540 and the inner shaft 1530. In embodiments, portions of the settable retention bumpers 1501 and 1502 may be disposed within a neck of the balloon 1510. Inflation fluid delivered to the balloon 1510 via the outer shaft 1540 may flow around axial force expandable retention bumpers 1501 and 1502 within neck of the balloon 1510. In further embodiments, the axial force expandable retention bumpers 1501 and 1502 may be disposed within the balloon 1510 such that inflation fluid flow from the outer shaft 1540 into the balloon 1510 is not substantially impeded.

Figure 16C:
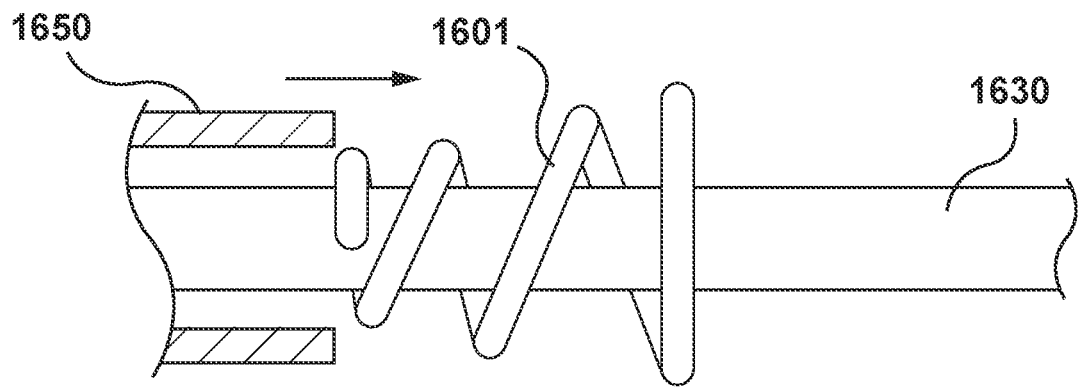

FIGS. 16A-16G and 17A-17D illustrate spring retention bumpers. The spring retention bumpers 1601 and 1602 are configured for collapsing to a first radially collapsed size when pulled axially or squeezed radially, as described below, and returning to a second radially expanded size when released. The spring retention bumpers 1601 and 1602 may be employed with a balloon catheter 1600. The balloon catheter 1600 includes at least a balloon 1610, an inner shaft 1630, and an outer shaft 1640. The balloon catheter 1600 is configured for delivering a prosthetic heart valve (not pictured) and may include any or all features and aspects of the balloon catheter 400. The balloon catheter 1600 further includes a distal portion 1685, within which the balloon 1610 is disposed, and a proximal portion 1690. FIGS. 16A-16B illustrate the spring retention bumpers 1601 and 1602 as assembled and secured to the inner shaft 1630 with the balloon 1610 positioned around the spring retention bumpers 1601 and 1602. FIGS. 16C-16G illustrate an assembly process for positioning the spring retention bumpers 1601 and 1602 on the balloon catheter 1600. FIGS. 17A-17D provide a close-up view of an alternative assembly process for positioning the spring retention bumpers 1601 and 1602 on the balloon catheter 1600.

The spring retention bumpers 1601 and 1602 are formed from a coil of elastic material, such as steel, and others. In an embodiment, the spring retention bumpers 1601 and 1602 each have a tapered shape, with a narrow end 1621/1622 and a wide end 1611/1612. The wide end 1611/1612 of the retention bumpers 1601/1602 has a diameter larger than a balloon opening 1649 and large enough to serve as a retention bumper to maintain a position of a prosthetic heart valve during a delivery operation, e.g., between approximately 0.25 inches and 0.35 inches. The narrow end 1621/1622 of the retention bumpers 1601/1602 has a diameter of an appropriate size for secure attachment to the inner shaft 1630. The narrow end 1621/1622 is also narrow enough to fit into the balloon opening 1649. The narrow end 1621/1622 is secured to the inner shaft 1630, for example, by adhesive, by bonding, by crimping, and/or by clamping. FIGS. 16A and 16B illustrate the spring retention bumpers 1601 and 1602 secured to the inner shaft 1630 and having differing amounts of axial compression. In embodiments, the spring retention bumpers 1601 and 1602 may be axially compressed after securement to the inner shaft 1630 (as shown in FIG. 16B) to secure the prosthetic heart valve in place once it is crimped over the balloon 1610. In embodiments, the spring retention bumpers 1601 and 1602 may be permitted to extend to their natural uncompressed length (as shown in FIG. 16A) to secure the prosthetic heart valve in place once it is crimped onto the balloon 1610.

Figure 16D:
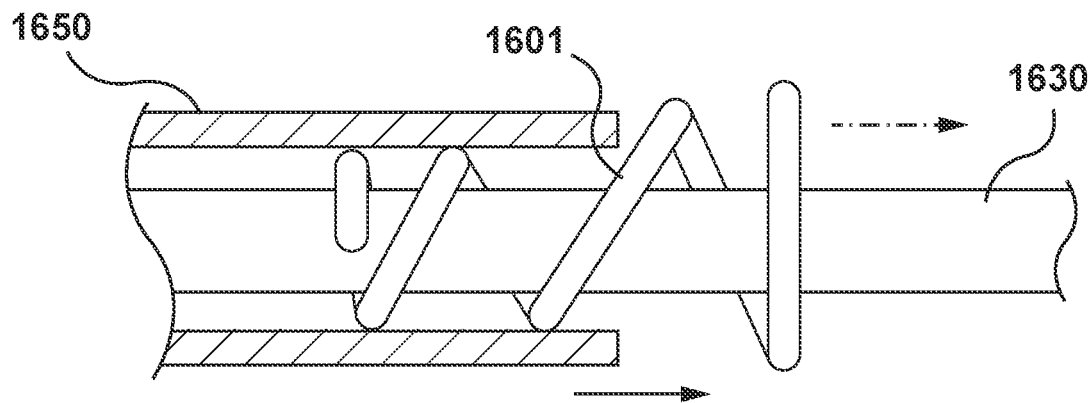
Figure 16E:
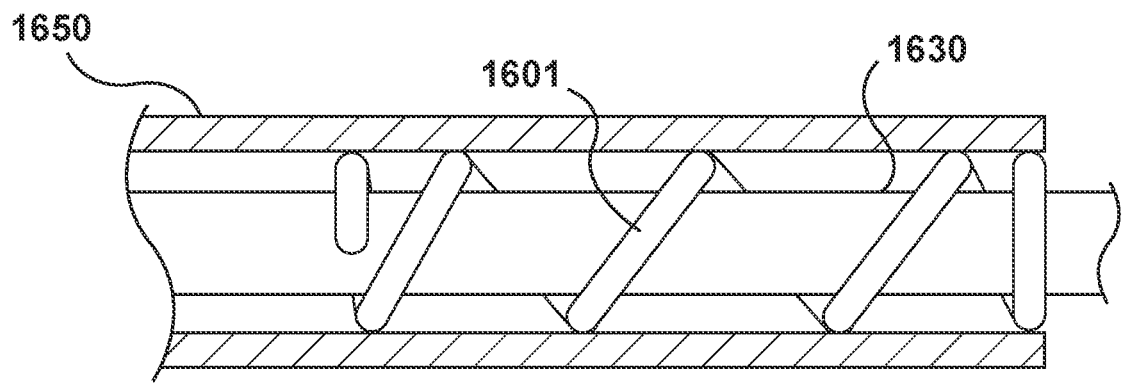
Figure 16F:
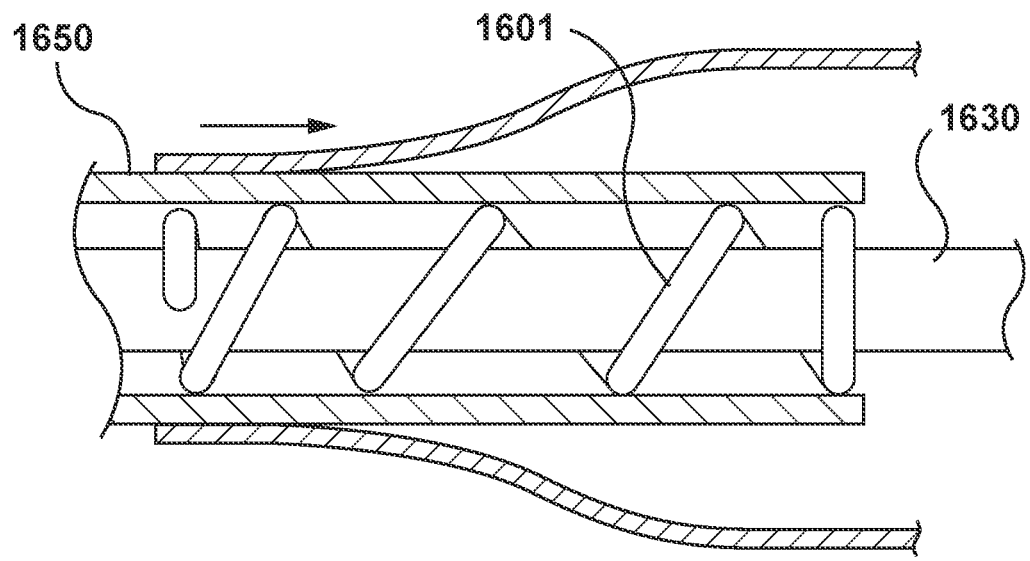
Figure 16G:
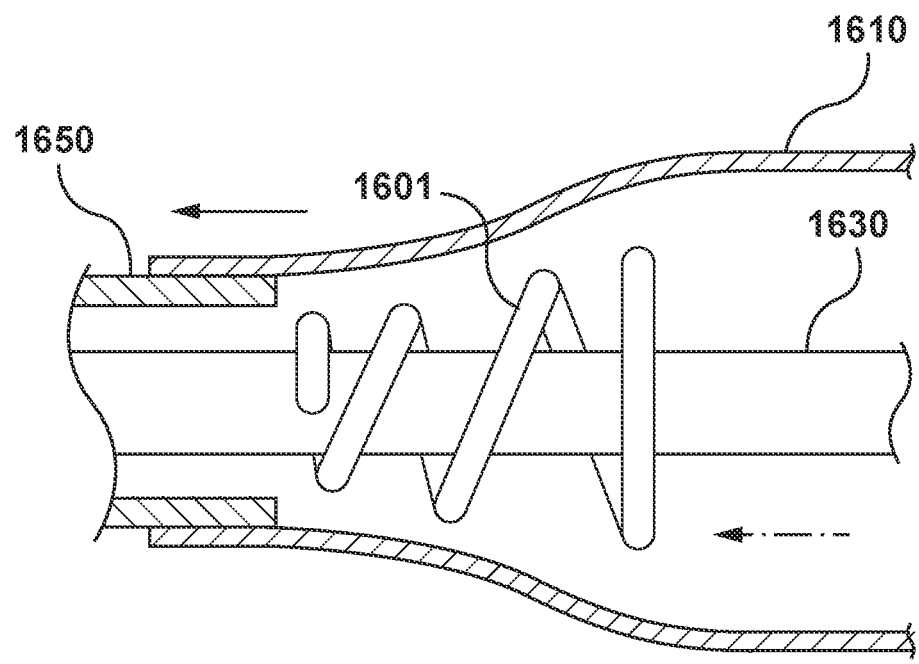

FIGS. 16C-16E illustrate a series of steps for collapsing one of the spring retention bumpers 1601 to the first radially collapsed size. A sleeve tube 1650 having an inner diameter larger than the narrow end 1621 of the spring retention bumper 1601 and an outer diameter smaller than the balloon opening 1649 is passed over the spring retention bumper 1601. As the leading edge of the sleeve tube 1650 reaches the wide end 1611, the spring retention bumper 1601 elongates and narrows in diameter. Because the narrow end 1621 of the spring retention bumper 1601 is secured to the inner shaft 1630, the spring retention bumper 1601 does not slide along the inner shaft 1630. The sleeve tube 1650 is then passed over the wide end 1611, which forces the spring retention bumper 1601 into the first radially collapsed size, e.g., between approximately 0.1 inches and 0.25 inches in diameter, as shown in FIG. 16E. The balloon 1610 is then passed over the sleeve tube 1650 containing the spring retention bumper 1601 for assembly. After the balloon 1610 is positioned, the sleeve tube 1650 is removed (FIGS. 16F-16G), permitting the spring retention bumper 1601 to return to the second radially expanded size so it may function to maintain a position of a prosthetic heart valve. A similar procedure is carried out for the spring retention bumper 1602 at the other side of the balloon 1610. Two sleeve tubes 1650 may be used simultaneously to hold both spring retention bumpers 1601 and 1602 at the first radially collapsed size while the balloon 1610 is positioned over them.

After the balloon 1610 is positioned over the spring retention bumpers 1601 and 1602 secured to the inner shaft 1630, the assembly of the balloon catheter 1600 may be completed. The balloon 1610 may be sealed to the outer shaft 1640 and folded. The prosthetic heart valve is then crimped onto the balloon 1610.

Figure 17A:
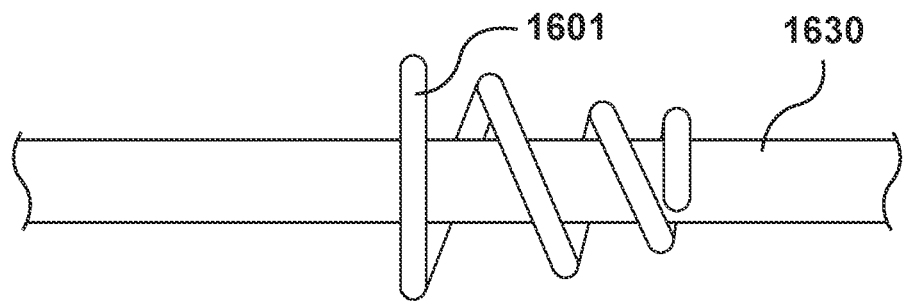
FIGS. 17A-17D illustrate spring retention bumpers according to embodiments hereof.
Figure 17B:
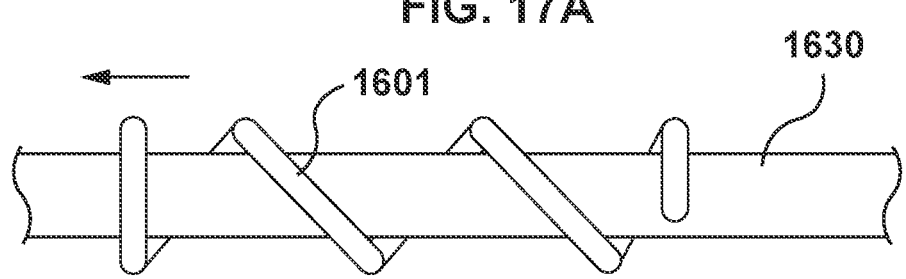
Figure 17C:
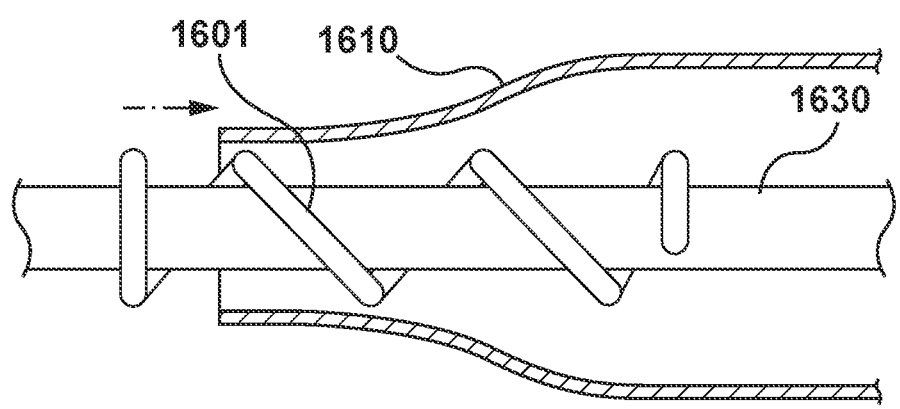
Figure 17D:
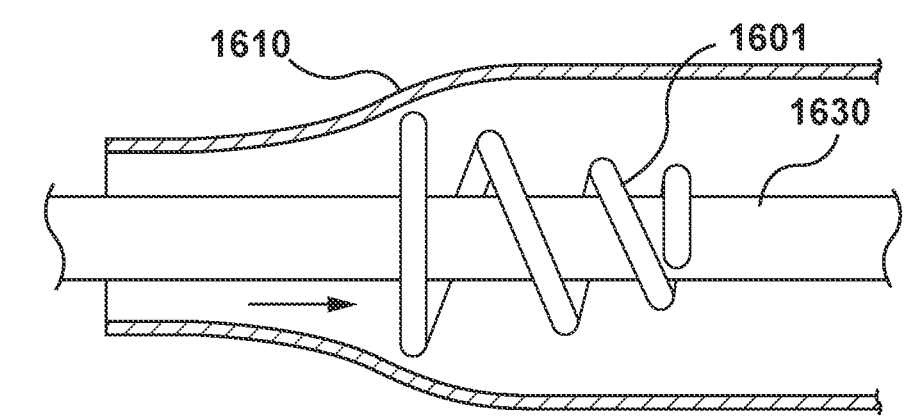

FIGS. 17A-17D illustrate an alternative method of collapsing the spring retention bumper to the first radially collapsed size to the second radially expanded size. As discussed above, the narrow end 1621 of the spring retention bumper 1601 is secured to the inner shaft 1630 (FIG. 17A). The wide end 1611 of the spring retention bumper 1601 is then pulled or stretched (FIG. 17B), causing the spring retention bumper 1601 to elongate and to narrow to the first radially collapsed size, e.g., between approximately 0.1 inches and 0.25 inches in diameter. The spring retention bumper 1601 may be pulled or stretched manually, through the use of simple tools such as pliers, or through any other suitable means. In embodiments, a tube or sheath similar to sleeve tube 1650 may be employed to maintain the spring retention bumper 1601 in the first radially collapsed size. In further embodiments, a wire or rod inserted through the balloon opening 1649 may be used to provide axial tension on the spring retention bumper 1601 to stretch it during insertion into the balloon 1610. The balloon 1610 is positioned over the spring retention bumper 1601 (FIG. 17C) and the spring retention bumper 1601 is released (FIG. 17D) to return to the second radially expanded size. This operation may be performed on both spring retention bumpers 1601 and 1602 at the same time, and/or may be performed one by one.

During use, inflation fluid is delivered to the balloon via a lumen between the outer shaft 1640 and the inner shaft 1630. In embodiments, portions of the spring retention bumpers 1601 and 1602 may be disposed within or near the balloon opening 1649. Inflation fluid delivered to the balloon 1610 via the outer shaft 1640 may flow around and/or through the spring retention bumpers 1601 and 1602 within or near the neck of the balloon 1610.

FIGS. 18A and 18B illustrate foldable retention bumpers according to embodiments hereof. The foldable retention bumpers 1801 and 1802 are configured to fold closed from a first radially unexpanded size to a second radially expanded size. The balloon catheter 1800 includes at least a balloon 1810, an inner shaft 1830, and an outer shaft 1840. The balloon catheter 1800 is configured for delivering a prosthetic heart valve (not pictured) and may include any or all features and aspects of the balloon catheter 400. The balloon catheter 1800 further includes a distal portion 1885, within which the balloon 1810 is disposed, and a proximal portion 1890.

Also in the distal portion 1885 are disposed the foldable retention bumpers 1801 and 1802. The folding of the foldable retention bumpers 1801 and 1802 is facilitated by a living hinge 1805 separating a first section 1806 from a second section 1807 of each of the foldable retention bumpers 1801 and 1802. In an open position, the first section 1806 and the second section 1807 line up axially so as to have a reduced cross-section at the first radially unexpanded size. In a closed position, the second section 1807 rotates around the living hinge 1805 so as to line up radially with the first section 1806, thereby causing the foldable retention bumpers 1801 and 1802 to have an expanded cross-section at the second radially expanded size. The foldable retention bumpers 1801 and 1802 further include a locking feature 1820, which includes a first locking portion 1821 and a second locking portion 1822. When the foldable retention bumpers 1801 and 1802 are folded closed, the first locking portion 1821 engages the second locking portion 1822 to secure the foldable retention bumpers 1801 and 1802 in the closed position. In embodiments, the first locking portion 1821 is a cavity disposed in the first section 1806 and the second locking portion 1822 is a projection disposed on the second section 1807. In further embodiments, the locking feature 1820 may comprise additional or different physical structures configured to lock the foldable retention bumpers 1801 and 1802 into a folded position. The first radially unexpanded size of the foldable retention bumpers 1801 and 1802 is illustrated in FIG. 18A and is small enough to enter the balloon 1810 through the balloon opening 1849, which may have a diameter of approximately 0.2 inches. In further embodiments, the balloon opening 1849 may have a diameter between 0.1 and 0.25 inches.

After insertion into the balloon 1810, the foldable retention bumpers 1801 and 1802 are folded closed and secured at the second radially expanded size, as shown in FIG. 18B. The second radially expanded size of the foldable retention bumpers 1801 and 1802, as illustrated in FIG. 18B, is large enough to provide valve retention during a delivery operation. For example, the second radially expanded size, may be approximately 0.3 inches. In further embodiments, the second radially expanded size of the bumpers may have a diameter between 0.25 and 0.35 inches.

In a process of assembling balloon catheter 1800, the foldable retention bumpers 1801 and 1802 are positioned within the balloon 1810 while at the first radially unexpanded size. The foldable retention bumpers 1801 and 1802 are then expanded to the second radially expanded size through folding. A tool may be inserted into the balloon 1810 through the balloon opening 1849 and/or through the open distal end of the balloon 1810 to manipulate the foldable retention bumpers 1801 and 1802 into the second radially expanded size. Alternatively, in embodiments, due to the flexible nature of the balloon 1810, the foldable retention bumpers 1801 and 1802 may be manipulated into the second radially expanded size manually from the outside of the balloon 1810. In embodiments, the foldable retention bumpers 1801 and 1802 may be elastically biased towards the closed, second radially expanded size. In such embodiments, the foldable retention bumpers 1801 and 1802 may held in a first radially unexpanded size, e.g., manually or via a tool, during insertion into the balloon 1810. Releasing the foldable retention bumpers 1801 and 1802 would then cause them to snap back or return to the second radially expanded size. The foldable retention bumpers 1801 and 1802 may be secured to the inner shaft 1830 before or after insertion into the balloon 1810. The foldable retention bumpers 1801 and 1802 are secured via adhesive, bonding, crimping, clamping, over molding, and/or any other suitable means. After the foldable retention bumpers 1801 and 1802 are secure to the inner shaft 1830 and secured at the second radially expanded size, the balloon 1810 is secured to the outer shaft 1840. The balloon 1810 may then be folded. A prosthetic heart valve is then crimped to balloon catheter 1800 between the foldable retention bumpers 1801 and 1802.

During use, inflation fluid is delivered to the balloon via a lumen between the outer shaft 1840 and the inner shaft 1830. In embodiments, the foldable retention bumpers 1801 and 1802 may be disposed within or near the balloon opening 1849. Inflation fluid delivered to the balloon 1810 via the outer shaft 1840 may flow around the foldable retention bumpers 1801 and 1802 such that the inflation fluid flow is not substantially impeded.

FIGS. 19A-19D illustrate collapsible retention bumpers 1901 and 1902 according to embodiments hereof. The collapsible retention bumpers 1901 and 1902 include elastic arms 1903 configured to radially collapse under pressure from a second radially expanded size to a first radially collapsed size. The balloon catheter 1900 includes at least a balloon 1910, an inner shaft 1930, and an outer shaft 1940. The balloon catheter 1900 is configured for delivering a prosthetic heart valve (not pictured) and may include any or all features and aspects of the balloon catheter 400. The balloon catheter 1900 further includes a distal portion 1985, within which the balloon 1910 is disposed, and a proximal portion 1990.

Also in the distal portion 1985 are disposed the collapsible retention bumpers 1901 and 1902. The arms 1903 of the collapsible retention bumpers 1901 and 1902 are elastic and can be radially collapsed under pressure into the first radially collapsed size. Each collapsible retention bumper 1901 and 1902 may have a plurality of arms 1903, e.g., three, four, five, six, or more arms. The arms 1903 are secured to a hub 1904 which is configured with a central cavity for disposition over the inner shaft 1930. The arms 1903 are arranged around the perimeter of the hub 1904 and extend radially outwards. Under pressure, the arms 1903 are configured to collapse radially inwards, as illustrated in FIG. 19B. Pressure for collapsing the collapsible retention bumpers 1901 and 1902 is provided by a sheath 1905, which is temporarily disposed over the collapsible retention bumpers 1901 and 1902 during assembly of the balloon catheter 1900.

Figure 19C:
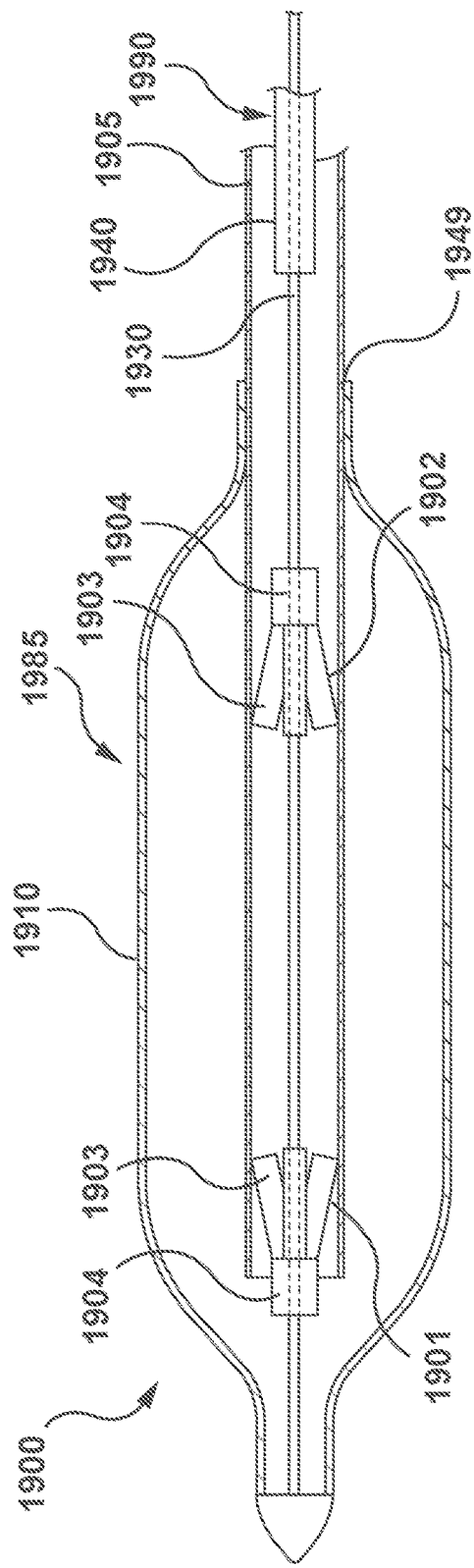
Figure 19D:
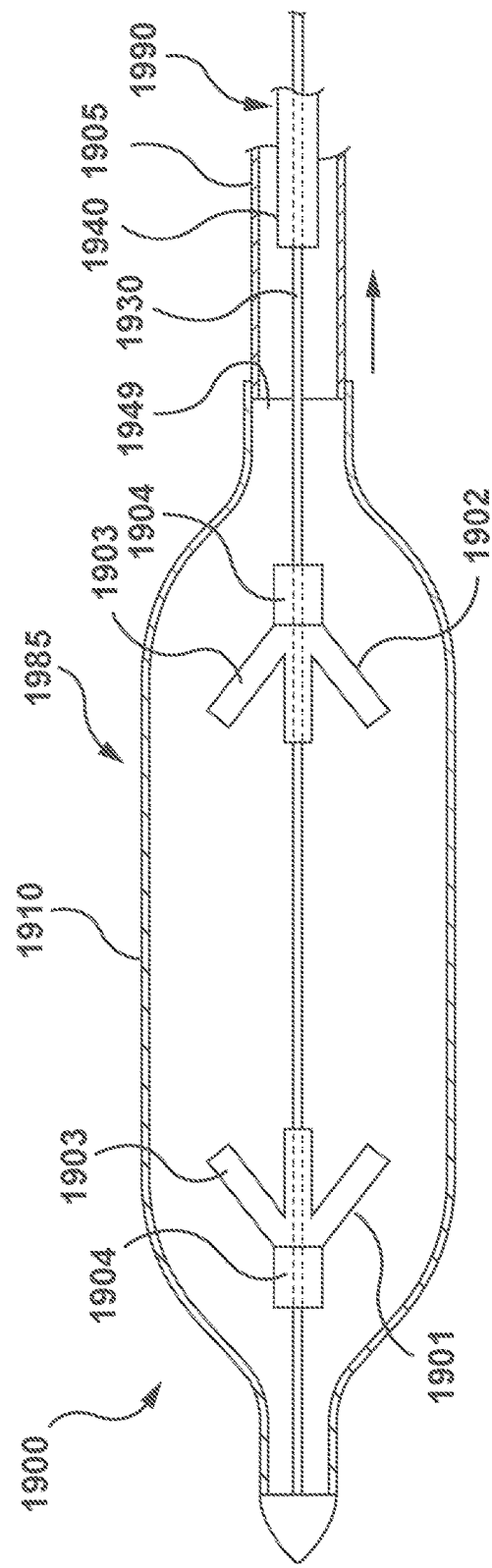

In FIG. 19A, the collapsible retention bumpers 1901 and 1902 are shown at their second radially expanded size, with arms 1903 extending radially outwards, prior to insertion into the balloon 1910. The sheath 1905 is used to collapse the collapsible retention bumpers 1901 and 1902 to the first radially collapsed size through radial force or pressure, as shown in FIG. 19B. The sheath 1905 causes the arms 1903 to bend radially inwards. The sheath/bumper assembly is then positioned inside the balloon 1910, as shown in FIG. 19C. After positioning inside the balloon 1910, the sheath 1905 is removed, permitting the collapsible retention bumpers 1901 and 1902 to expand to the second radially expanded size, as shown in FIG. 19D.

The first radially collapsed size of the collapsible retention bumpers 1901 and 1902 is illustrated in FIGS. 19B and 19C and is small enough to enter the balloon 1910 through the balloon opening 1949, which may have a diameter of approximately 0.2 inches. In further embodiments, the balloon opening 1949 may have a diameter between 0.1 and 0.25 inches. The second radially expanded size of the collapsible retention bumpers 1901 and 1902, as illustrated in FIGS. 19A and 19D, is large enough to provide valve retention during a delivery operation. For example, the second radially expanded size, may be approximately 0.3 inches. In further embodiments, the second radially expanded size of the bumpers may have a diameter between 0.25 and 0.35 inches.

In a process of assembling balloon catheter 1900, the collapsible retention bumpers 1901 and 1902 are disposed inside the sheath 1905 and positioned within the balloon 1910 while at the first radially collapsed size. The collapsible retention bumpers 1901 and 1902 are then expanded to the second radially expanded size through removal of the sheath 1905. The collapsible retention bumpers 1901 and 1902 are secured to the inner shaft 1930, e.g., via adhesives, bonding, crimping, clamping, over molding, or any other suitable means, prior to disposal within the sheath 1905. In other examples, the collapsible retention bumpers 1901 and 1902 may be laser welded to the inner shaft 1930 through the balloon 1910 via laser transmission welding to prevent balloon damage. After the collapsible retention bumpers 1901 and 1902 are positioned inside the balloon 1910 and are at the second radially expanded size, the balloon 1910 is secured to the outer shaft 1940. The balloon 1910 may then be folded. A prosthetic heart valve is then crimped to balloon catheter 1900 between the collapsible retention bumpers 1901 and 1902.

During use, inflation fluid is delivered to the balloon via a lumen between the outer shaft 1940 and the inner shaft 1930. In embodiments, the collapsible retention bumpers 1901 and 1902 may be disposed within or near the balloon opening 1949. Inflation fluid delivered to the balloon 1910 via the outer shaft 1940 may flow around the collapsible retention bumpers 1901 and 1902 such that the inflation fluid flow is not substantially impeded.

Figure 20A:
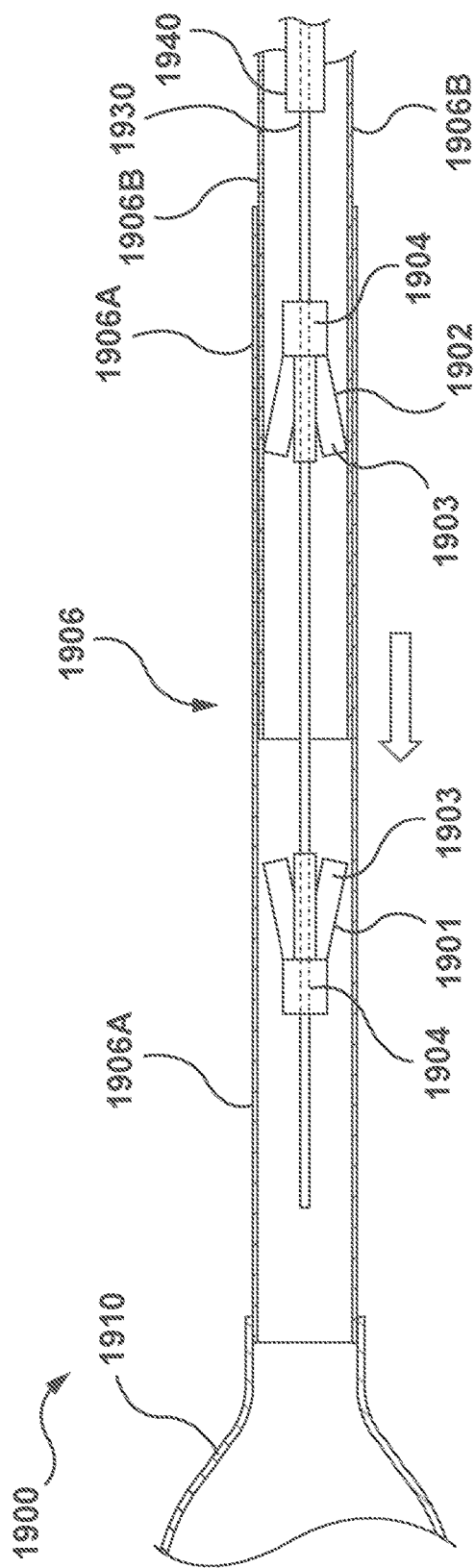
FIGS. 20A and 20B illustrate additional embodiments of a sheath for use with the collapsible retention bumpers.
Figure 20B:
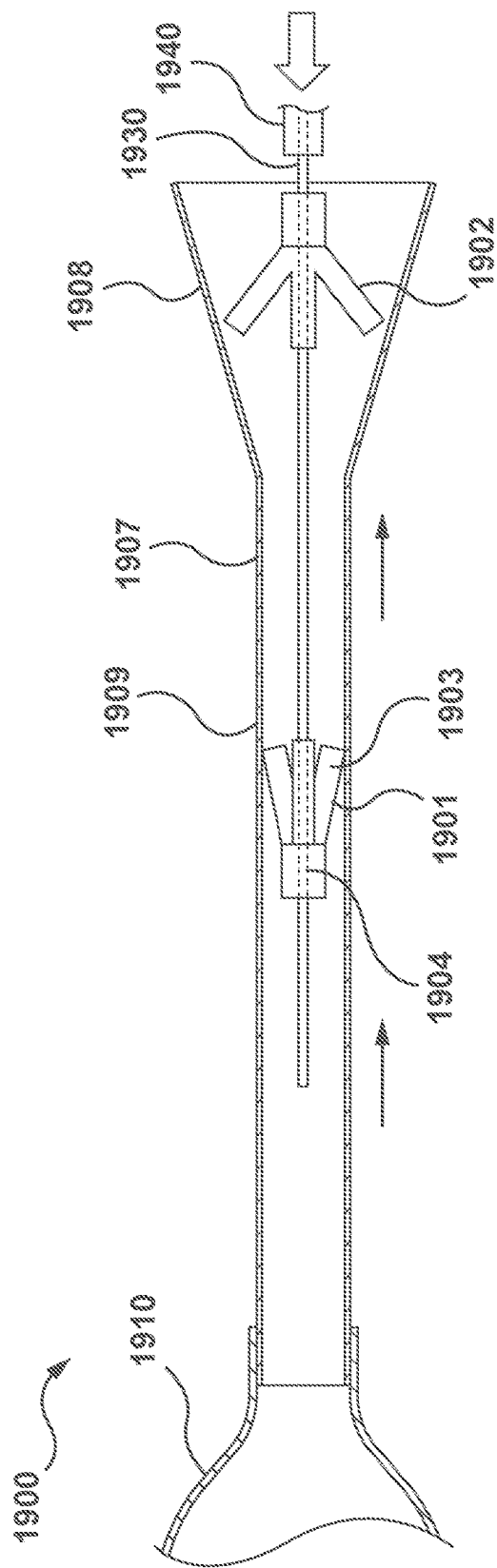

FIGS. 20A and 20B illustrate additional embodiments of a sheath for use with the collapsible retention bumpers 1901 and 1902. FIG. 20A illustrates a two-part sheath 1906 configured for use with the collapsible retention bumpers. The two-part sheath 1906 includes a first sheath part 1906A and a second sheath part 1906B. The first sheath part 1906A and the second sheath part 1906B are tubes with an interior lumen sized and configured to collapse the collapsible retention bumpers 1901 and 1902 to the first radially collapsed size. The first sheath part 1906A is configured to around the second sheath part 1906B. The assembled two-part sheath 1906 is disposed over the collapsible retention bumpers 1901 and 1902. Each of the first sheath part 1906A and the second sheath part 1906B may be assembled from opposing ends of the collapsible retention bumpers 1901 and 1902 secured on the inner shaft 1930. The first sheath part 1906A is disposed over the collapsible retention bumper 1901 from the distal side while the second sheath part 1906B is disposed over the collapsible retention bumper 1902 from the proximal side. Assembling from the opposing ends permits each sheath part 1906A, 1906B to radially collapse the collapsible retention bumper 1901/1902 over which it is disposed. For example, as illustrated in FIG. 20A, the first sheath part 1906A is disposed over the collapsible retention bumper 1901 from the direction of the hub 1904 of the collapsible retention bumper 1901. This permits the first sheath part 1906A to collapse the arms 1903 of the collapsible retention bumper 1901 as it is pushed into place over the arms 1903. Similarly, the second sheath part 1906B is disposed over the collapsible retention bumper 1902 from the direction of the hub 1904 of the retention bumper 1902. After insertion into the two-part sheath 1906, the entire assembly is disposed inside of the balloon 1910, after which the two-part sheath 1906 is removed, permitting the collapsible retention bumpers 1901 and 1902 to expand. The first sheath part 1906A and the second sheath part 1906B are removed from the same directions from which they were assembled over the collapsible retention bumpers 1901 and 1902.

FIG. 20B illustrates a funnel sheath 1907 for use with the collapsible retention bumpers 1901 and 1902. The funnel sheath 1907 includes a funnel 1908 and a shaft 1909. The funnel 1908 is a hollow tapered cone that narrows from a first large diameter to a second small diameter to meet the shaft 1909. The shaft 1909 is sized to collapse the collapsible retention bumpers 1901 and 1902 to the first radially collapsed size. The collapsible retention bumpers 1901 and 1902, after being secured to the inner shaft 1930, are inserted into the funnel sheath 1907 by way of the funnel 1908, which acts to facilitate the collapse of the retention bumpers 1901 and 1902 from the second radially expanded size to the first radially collapsed size. After insertion into the funnel sheath 1907, the shaft 1909 of the funnel sheath 1907 is disposed inside of the balloon 1910, after which the funnel sheath 1907 is removed, permitting the collapsible retention bumpers 1901 and 1902 to expand.

Figure 21A:
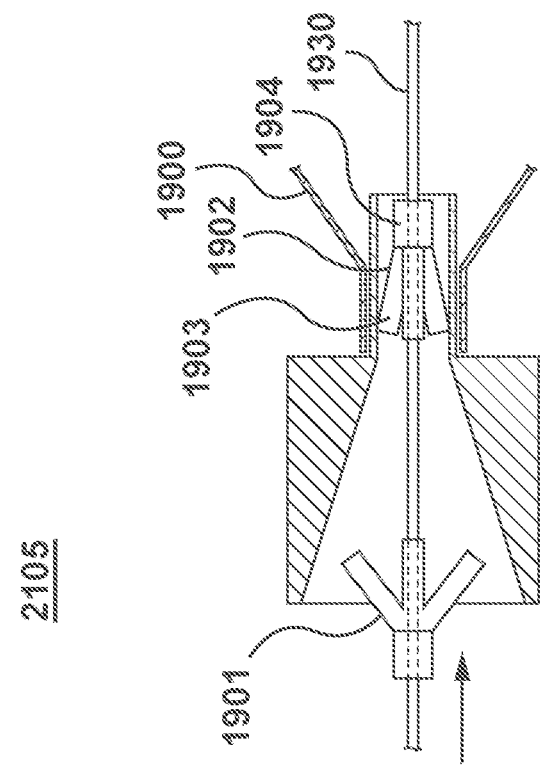
FIGS. 21A and 21B illustrate a loading cone configured for use with collapsible retention bumpers.
Figure 21B:
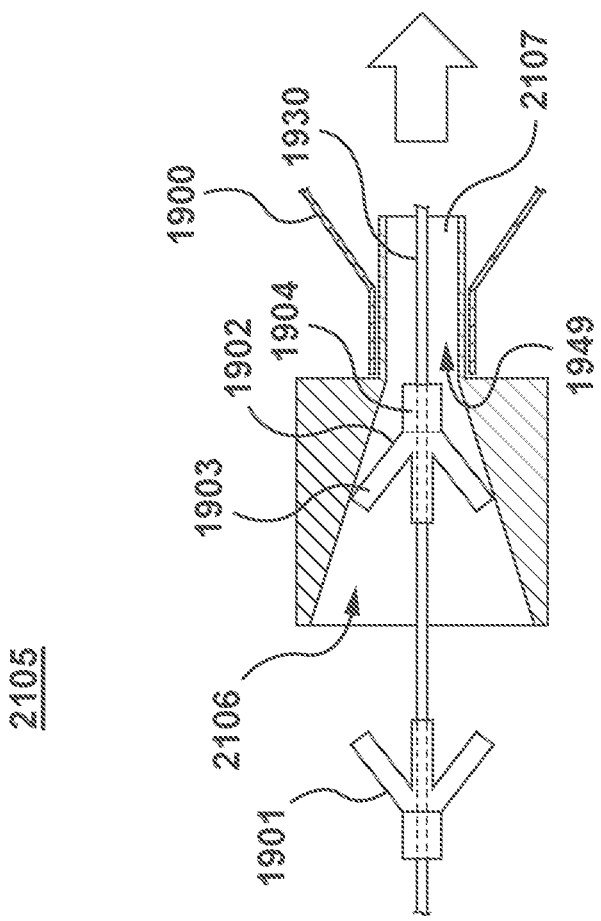

FIGS. 21A and 21B illustrate a loading cone 2105 configured for use with the collapsible retention bumpers 1901 and 1902. The loading cone 2105 includes a tapered portion 2106 and a shaft portion 2107. The tapered portion 2106 has a hollow funnel shaped interior with walls tapering from a first large diameter to a second small diameter. The tapered portion 2106 may include any suitable material and be of any suitable shape to support the hollow funnel shaped interior. The second small diameter is shared with the interior diameter of the shaft portion 2107. The second small diameter is selected in accordance with the first radially collapsed size of the collapsible retention bumpers 1901 and 1902. The outer diameter of the shaft portion 2107 is selected such that it will fit into the opening 1949 of the balloon 1910. To use the loading cone 2105 in the assembly of balloon catheter 1900, the shaft portion 2107 is disposed inside the balloon opening 1949 of the balloon 1910. The inner shaft 1930 with the collapsible retention bumpers 1901 and 1902 is then inserted into the balloon through the loading cone 2105, as shown in FIG. 21A. The tapered portion 2106 facilitates the collapse of the collapsible retention bumpers 1901 and 1902 from the second radially expanded size to the first collapsible size, as shown in FIG. 21B. After each collapsible retention bumper 1901 and 1902 passes through the shaft portion 2107, it expands from the first radially collapsed size to the second radially expanded size. After the collapsible retention bumper 1902 expands to the second radially expanded size it is moved through the unexpanded balloon 1910 as the collapsible retention bumper 1901 is passed through the loading cone 2105.

FIGS. 22A-22D illustrate collapsible retention bumpers according to embodiments hereof. The collapsible retention bumpers 2201 and 2202 are configured to collapse under radial pressure from a second radially expanded size to a first radially collapsed size. The balloon catheter 2200 includes at least a balloon 2210, an inner shaft 2230, and an outer shaft 2240. The balloon catheter 2200 is configured for delivering a prosthetic heart valve (not pictured) and may include any or all features and aspects of the balloon catheter 400. The balloon catheter 2200 further includes a distal portion 2285, within which the balloon 2210 is disposed, and a proximal portion 2290.

Figure 22A:
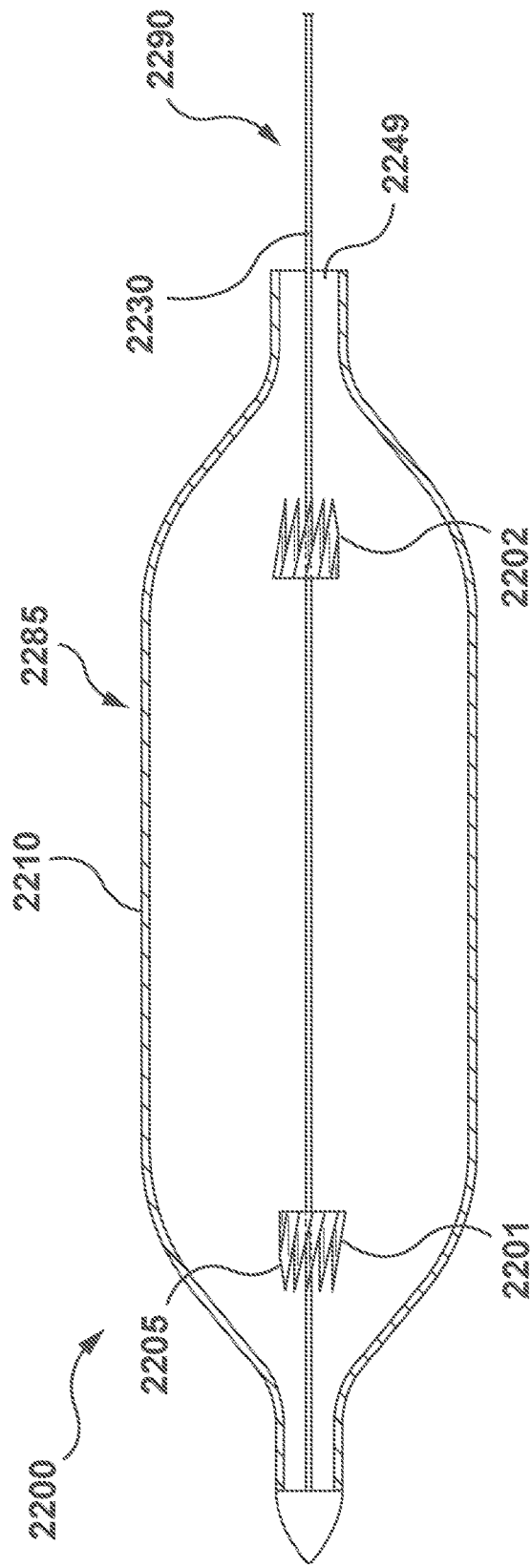

Also in the distal portion 2285 are disposed the collapsible retention bumpers 2201 and 2202. The collapsible retention bumpers 2201 and 2201 include a central hub 2206 and a plurality of radial arms 2205. The radial arms 2205 are relatively flat and are each attached to the central hub 2206 at one end. The radial arms 2205 have a length dimension extending radially away from the central hub 2206, a width dimension extending axially along the central hub 2206, and a depth dimension in a circumferential direction of the central hub 2206. The depth dimension is significantly smaller than the length and width dimensions. The several radial arms 2205 are disposed around the circumference of the central hub 2206. The shape of the radial arms 2205 allows flexibility around the circumference of the central hub 2206 and permits the radial arms to collapse under radial pressure and fold around the circumference of the central hub 2206 to achieve the first radially collapsed size. When released from the radial pressure, the radial arms 2205 are configured to elastically return to an initial position extending radially away from the central hub 2206 such that the collapsible retention bumpers 2201 and 2202 achieve the second radially expanded size. The collapsible retention bumpers 2201 and 2202 are radially collapsed for insertion into the balloon 2210 through the application of radial pressure. Radial force may be applied, for example, via manual manipulation, via a crimping tool, via a tubular sheath, and/or via any other suitable means. Due to the greater size of the radial arms 2205 in the length dimension (radially along the hub), the radial arms 2205 are configured to withstand force directed axially along the central hub 2206 (i.e., forces exerted on the radial arms by the prosthetic valve during insertion). In embodiments, the radial arms 2205 may be triangular in profile, with a narrow portion at one end of the central hub 2206 and a wide portion at the other end of the central hub 2206, as illustrated in FIG. 22A. The narrow portion of the radial arms 2205 may taper to a point such that combined diameter of the central hub 2206 and the radial arms 2205 is equal to the diameter of the central hub 2206. The wide portion of the radial arms 2205 may be such that, when the radial arms are extended, the combined diameter of the central hub and the radial arms 2205 is equal to the second radially expanded diameter. In further embodiments, the radial arms 2205 may be rectangular, square, or any other shape in profile.

Figure 22B:
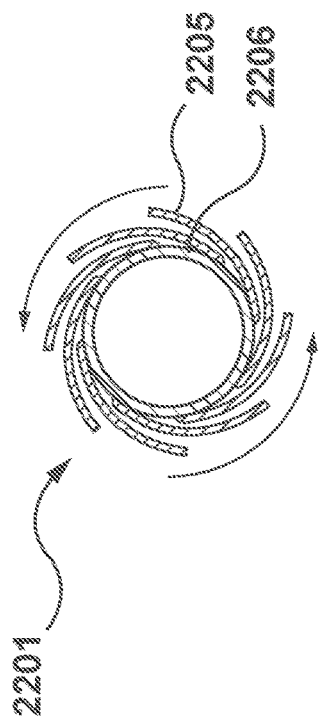

In FIG. 22A, the collapsible retention bumpers 2201 and 2202 are shown at their first radially collapsed size, after insertion into the balloon 2210. FIG. 22B shows the collapsible retention bumpers 2201 and 2202 in cross-section at the first radially collapsed size. FIG. 22C shows the collapsible retention bumpers 2201 and 2202 at their second radially expanded size after insertion into the balloon 2210 and released from radial pressure. FIG. 22D shows the collapsible retention bumpers 2201 and 2202 in cross-section at the second radially expanded size.

The first radially collapsed size of the collapsible retention bumpers 2201 and 2202 is illustrated in FIGS. 22A and 22B and is small enough to enter the balloon 2210 through the balloon opening 2249, which may have a diameter of approximately 0.2 inches. In further embodiments, the balloon opening 2249 may have a diameter between 0.1 and 0.25 inches. The second radially expanded size of the collapsible retention bumpers 2201 and 2202, as illustrated in FIGS. 22C and 22D, is large enough to provide valve retention during a delivery operation. For example, the second radially expanded size, may be approximately 0.3 inches. In further embodiments, the second radially expanded size of the bumpers may have a diameter between 0.25 and 0.35 inches.

In a process of assembling balloon catheter 2200, the collapsible retention bumpers 2201 and 2202 are positioned within the balloon 2210 while at the first radially collapsed size. The collapsible retention bumpers 2201 and 2202 may be secured to the inner shaft 2230 prior to positioning within the balloon 2210 or after positioning within the balloon 2210. The collapsible retention bumpers 2201 and 2202 may be secured to the inner shaft 2230 via any suitable means, including adhesives, bonding, clamps, crimping, over molding, etc. If secured after insertion into the balloon 2210, tools may be deployed through the opening of the balloon 2210 and/or the open distal end of the balloon 2210 to apply the securement means. In other examples, the collapsible retention bumpers 2201 and 2202 may be laser welded to the inner shaft 2230 through the balloon 2210 via laser transmission welding to prevent balloon damage. The collapsible retention bumpers 2201 and 2202 are then expanded to the second radially expanded size when radial pressure is released. In some embodiments, a sheath, multiple sheaths, and/or loading cone (such as those depicted in FIGS. 19A-D, 20A-B, and 21A-B) may be employed to provide the radial pressure to maintain the first radially collapsed size of the collapsible retention bumpers 2201 and 2202. After the collapsible retention bumpers 2201 and 2202 are positioned inside the balloon 2210 at the second radially expanded size, the balloon 2210 is secured to the outer shaft 2240. The balloon 2210 may then be folded. A prosthetic heart valve is then crimped onto the balloon catheter 2200 between the collapsible retention bumpers 2201 and 2202.

During use, inflation fluid is delivered to the balloon via a lumen between the outer shaft 2240 and the inner shaft 2230. In embodiments, the collapsible retention bumpers 2201 and 2202 may be disposed within or near the balloon opening 2249. Inflation fluid delivered to the balloon 2210 via the outer shaft 2240 may flow around the collapsible retention bumpers 2201 and 2202 such that the inflation fluid flow is not substantially impeded.

FIGS. 23A-23B illustrate elongated retention bumpers according to embodiments hereof. The elongated retention bumpers 2301 and 2302 are non-circular and are elongated in a first dimension and narrower in a second dimension perpendicular to the first dimension. A balloon catheter 2300 includes at least a balloon 2310, an inner shaft 2330, and an outer shaft 2340. The balloon catheter 2300 is configured for delivering a prosthetic heart valve (not pictured) and may include any or all features and aspects of the balloon catheter 400. The balloon catheter 2300 further includes a distal portion 2385, within which the balloon 2310 is disposed, and a proximal portion 2390.

Also in the distal portion 2385 are disposed the elongated retention bumpers 2301 and 2302. The elongated retention bumpers 2301 and 2302 are elongated in a first dimension compared to a second dimension. The first dimension is perpendicular to the second dimension. The first and second dimensions define a cross-sectional plane of the elongated retention bumpers 2301 and 2302, as shown in FIG. 23C. The elongated retention bumpers 2301 and 2302 may have a rectangular, oval, elliptical, or any other cross-sectional shape that is longer in a first dimension than a second dimension. The elongated shape of the elongated retention bumpers 2301 and 2302 facilitate entry into the balloon 2310. The elongated retention bumpers 2301 and 2302 have a perimeter similar in length to an inner circumference of the balloon opening 2349. The balloon opening 2349 may be distorted into a shape similar to that of the elongated retention bumpers 2301 and 2302. Due to the similarity in perimeters, the elongated retention bumpers 2301 and 2302 may be inserted into the balloon opening 2349 once it is distorted. In further embodiments, the elongated retention bumpers 2301 and 2302 may have a perimeter slightly smaller than the perimeter of the balloon opening 2349. In other embodiments, the elongated retention bumpers 2301 and 2302 may have a perimeter larger than the perimeter of the balloon opening 2349, and the balloon opening 2349 may be stretched to permit entry of the elongated retention bumpers 2301 and 2302.

In FIG. 23A, the elongated retention bumpers 2301 and 2302 are shown after insertion into the balloon 2310. FIG. 23B shows the elongated retention bumpers 2301 and 2302 immediately prior to insertion into the balloon 2310. FIG. 23C shows the elongated retention bumpers 2301 in cross-section.

Optionally, the elongated retention bumpers 2301 and 2302 may include one or more channels 2305. The channels 2305 may permit the elongated retention bumpers 2301 and 2302 to be squeezed into a smaller cross-section to facilitate insertion into the balloon 2310. The channels 2305 may further facilitate flow of inflation fluid during valve deployment.

The second dimension of the elongated retention bumpers 2301 and 2302 is small enough to enter the balloon 2310 through the balloon opening 2349 when the balloon opening is distorted into a shape similar to that of the elongated retention bumpers 2301 and 2302. The balloon opening 2349 may have a diameter of approximately 0.2 inches prior to distortion. In further embodiments, the balloon opening 2349 may have a diameter between 0.1 and 0.25 inches. The first dimension of the elongated retention bumpers 2301 and 2302 is large enough to provide valve retention during a delivery operation. For example, the first dimension, may be approximately 0.3 inches. In further embodiments, the first dimension of the elongated retention bumpers 2301 and 2302 may have a diameter between 0.25 and 0.35 inches.

In a process of assembling balloon catheter 2300, the elongated retention bumpers 2301 and 2302 are positioned within the balloon 2310. The elongated retention bumpers 2301 and 2302 may be secured to the inner shaft 2330 prior to positioning within the balloon 2310 or after positioning within the balloon 2310. The elongated retention bumpers 2301 and 2302 may be secured to the inner shaft 2330 via any suitable means, including adhesives, bonding, clamps, crimping, over molding, etc. In other examples, the elongated retention bumpers 2301 and 2302 may be laser welded to the inner shaft 2330 through the balloon 2310 via laser transmission welding to prevent balloon damage. If secured after insertion into the balloon 2310, tools may be deployed through the balloon opening 2349 and/or the open distal end of the balloon 2310 to apply the securement means. After the elongated retention bumpers 2301 and 2302 are positioned inside the balloon 2310, the balloon 2310 is secured to the outer shaft 2340. The balloon 2310 may then be folded. A prosthetic heart valve is then crimped onto the balloon catheter 2300 between the elongated retention bumpers 2301 and 2302.

During use, inflation fluid is delivered to the balloon via a lumen between the outer shaft 2340 and the inner shaft 2330. In embodiments, the elongated retention bumpers 2301 and 2302 may be disposed within or near the balloon opening 2349. Inflation fluid delivered to the balloon 2310 via the outer shaft 2340 may flow around the elongated retention bumpers 2301 and 2302 such that the inflation fluid flow is not substantially impeded.

FIGS. 24A-27B illustrate multipart retention bumpers. Each part of the multipart retention bumpers is small enough to fit inside a balloon opening. Thus, when separate, the multiple parts of the multipart retention bumpers have a first radially collapsed size. When coupled to one another inside of the balloon, the multiple parts of the retention bumpers form a bumper with a second radially expanded size suitable to be employed to maintain the position of a prosthetic heart valve.

Figure 24D:
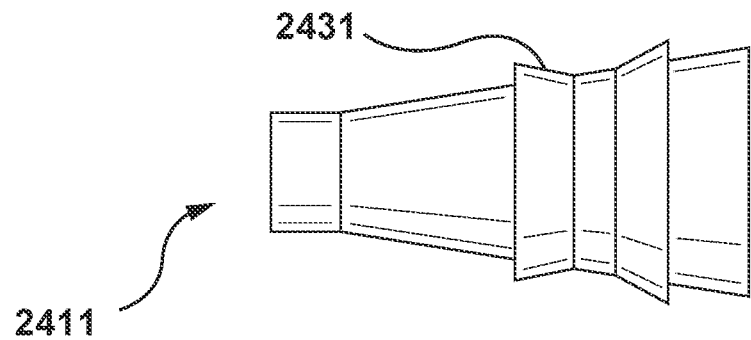
Figure 24E:
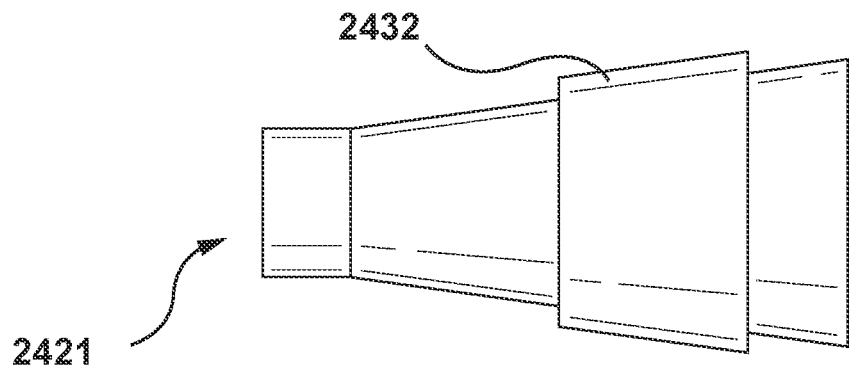
Figure 24F:
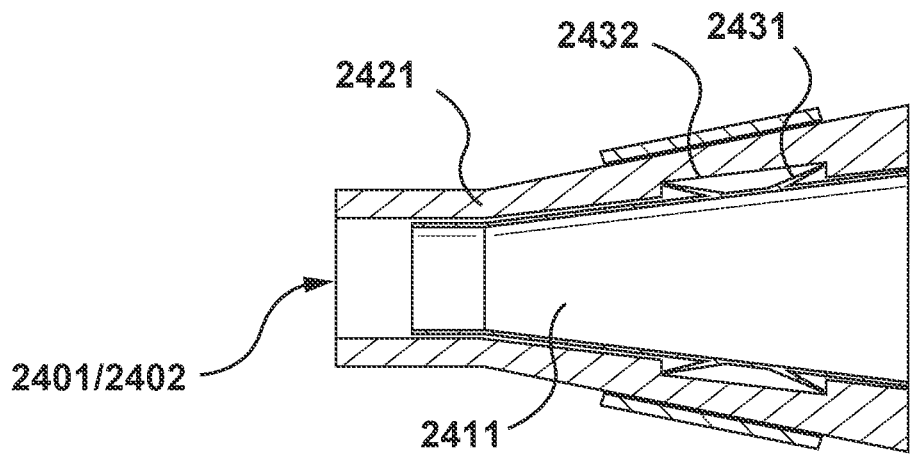

FIGS. 24A-24F illustrate multipart retention bumpers 2401 and 2402. The multipart retention bumpers 2401 and 2402 are configured for expanding when assembled and may be employed with a balloon catheter 2400. The balloon catheter 2400 includes at least a balloon 2410, an inner shaft 2430, and an outer shaft 2440. The balloon catheter 2400 is configured for delivering a prosthetic heart valve (not pictured) and may include any or all features and aspects of balloon catheter 400. The balloon catheter 2400 further includes a distal portion 2485, within which the balloon 2410 is disposed, and a proximal portion 2490. FIGS. 24A-24C illustrate the multipart retention bumpers 2401 and 2402 in various positions during an assembly process. FIGS. 24D-24F provide a close-up of various aspects of the multipart retention bumpers 2401 and 2402.

The multipart retention bumpers 2401 and 2402 each includes two interlocking parts. In a first configuration, the two interlocking parts of each of the multipart retention bumpers 2401 and 2402 are not interlocked and each of the two interlocking parts has a first radially unexpanded size smaller than the balloon opening 2449 of the balloon 2410, e.g., between approximately 0.1 inches and 0.25 inches (although each interlocking part need not have the same first radially unexpanded size). In a second configuration, the two interlocking parts of each of the multipart retention bumpers 2401 and 2402 are interlocked such that each multipart retention bumper 2401 and 2401 has a second radially expanded size larger than the first radially unexpanded size and of sufficient size to maintain an axial position of a prosthetic heart valve during a delivery operation, e.g., between approximately 0.25 inches and 0.35 inches.

The multipart retention bumpers 2401 and 2402 each include a first inner part 2411 and a second outer part 2421. The first inner part 2411 is generally tapered in profile and includes an axial cavity in the center to accommodate the inner shaft 2430. The first inner part 2411 further includes an interlocking feature 2431, illustrated in FIG. 24D. The interlocking feature 2431 includes at least one projection or protrusion and may include multiple projections or protrusions. The second outer part 2421 is also generally tapered in profile and includes an axial cavity in the center to accommodate the first inner part 2411. The second outer part 2421 is formed from an elastic material and is configured to stretch around and over the first inner part 2411. When stretched over the first inner part 2411, the second outer part 2421 takes on a radially expanded size. In some embodiments, the second outer part 2421 is formed from an elastic material and is configured to be compressed to fit through the balloon opening 2449. The second outer part 2421 further includes, in its interior, an interlocking feature 2432 configured to mate with the interlocking feature 2431 of the first inner part 2411. The interlocking feature 2432 is a recess sized and shaped to accommodate the interlocking feature 2431. After the second outer part 2421 is interlocked with the first inner part 2411, the multipart retention bumpers 2401 and 2402 are in the second configuration having the second radially expanded size.

The first inner parts 2411 are each secured to the inner shaft 2430. During an assembly process, after securement of the first inner parts 2411 to the inner shaft 2430, the balloon 2410 is disposed over the first inner parts 2411. The first inner parts 2411 may be secured to the inner shaft 2430 via any suitable means, including adhesives, bonding, clamps, crimping, over molding, etc. If secured after insertion into the balloon 2410, tools may be deployed through the balloon opening 2449 and/or the open distal end of the balloon 2410 to apply the securement means. The second outer parts 2421 are then inserted into the balloon opening 2449 and/or through the open distal end of the balloon 2410 and stretched around the first inner parts 2411 to interlock. The insertion and interlocking of the second outer parts 2421 may be facilitated via the use of tools and/or via manual manipulation applied through the flexible balloon 2410. Interlocking of the outer parts 2421 and the inner parts 2411 may be secured, for example, via snap fit or adhesives. Once interlocked in the second radially expanded size, the multipart retention bumpers 2401 and 2402 have a diameter large enough to appropriately prevent migration of the prosthetic heart valve during deployment. After interlocking the first inner parts 2411 and the second outer parts 2421, the balloon 2410 may be sealed to the outer shaft 2440, before the folding and crimping operations are carried out. As discussed above with respect to expandable retention bumpers disclosed herein, the multipart retention bumpers 2401 and 2402 may be interlocked and expanded to a second radially expanded size at any suitable time during the assembly process after insertion into the balloon 2410.

During use, inflation fluid is delivered to the balloon via a lumen between the outer shaft 2440 and the inner shaft 2430. In embodiments, the multipart retention bumpers 2401 and 2402 may be disposed within or near the balloon opening 2449. Inflation fluid delivered to the balloon 2410 via the outer shaft 2440 may flow around the multipart retention bumpers 2401 and 2402 such that the inflation fluid flow is not substantially impeded.

Figure 25D:
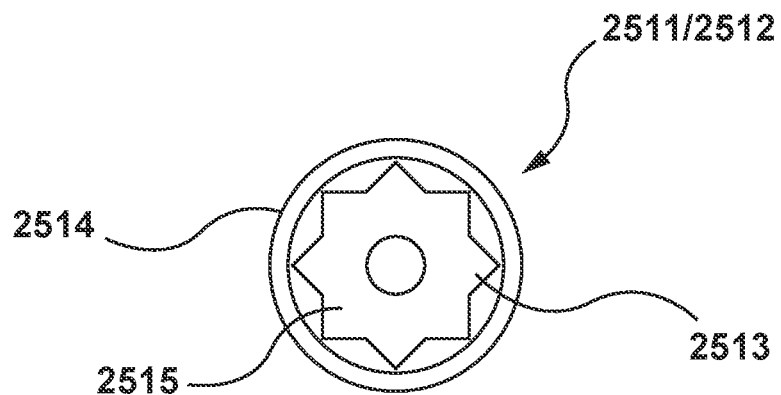
Figure 25E:
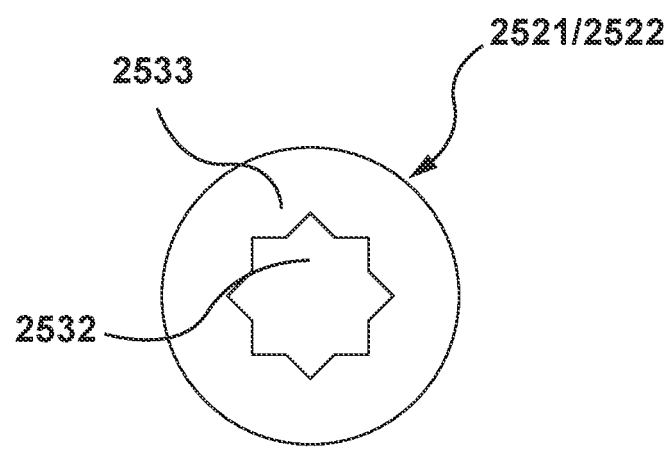

FIGS. 25A-25E illustrate multipart retention bumpers 2501 and 2502. The multipart retention bumpers 2501 and 2502 are configured for expanding when assembled and may be employed with a balloon catheter 2500. The balloon catheter 2500 includes at least a balloon 2510, an inner shaft 2530, and an outer shaft 2540. The balloon catheter 2500 is configured for delivering a prosthetic heart valve (not pictured) and may include any or all features and aspects of the balloon catheter 400. The balloon catheter 2500 further includes a distal portion 2585, within which the balloon 2510 is disposed, and a proximal portion 2590. FIGS. 25A-25C illustrate the multipart retention bumpers 2501 and 2502 in various positions during an assembly process. FIGS. 25D-25E provide a close-up of various aspects of the multipart retention bumpers 2501 and 2502.

The multipart retention bumpers 2501 and 2502 each includes two interlocking parts. In a first configuration, the two interlocking parts of the multipart retention bumpers 2501 and 2502 are not interlocked and each has a first radially unexpanded size smaller than the balloon opening 2549 of the balloon 2510, e.g., between approximately 0.1 inches and 0.25 inches (although each interlocking part need not have the same first radially unexpanded size). In a second configuration, the two interlocking parts of each of the multipart retention bumpers 2501 and 2502 are interlocked such that each multipart retention bumper 2501 and 2502 has a second radially expanded size of sufficient size to maintain an axial position of a prosthetic heart valve during a delivery operation, e.g., between approximately 0.25 inches and 0.35 inches.

The multipart retention bumper 2501 includes a first inner part 2511 and a second outer part 2521. Likewise, the multipart retention bumper 2502 includes a first inner part 2512 and a second outer part 2522. The first inner parts 2511 and 2512 are generally cylindrical in shape and have an axial interior cavity to accommodate disposition over the inner shaft 2530. The first inner parts 2511 and 2512 each further include a central hub 2515 and one or more hub rims 2514. The central hub 2515 is an annulus of material surrounding the axial interior cavity. One or more interlocking ridges 2513 extend radially from the central hub 2515 and include at least one projection or protrusion and may include multiple projections or protrusions. In embodiments, the interlocking ridge 2513 may include a single projection while in other embodiments the interlocking ridges 2513 may include a series of radially spaced projections disposed around the entire diameter of the central hub 2515. The hub rim 2514 is disposed at one end of the central hub 2515 and has a diameter larger than the central hub 2515 of the first inner parts 2511 and 2512. The second outer parts 2521 and 2522 are also generally cylindrical in profile and include an axial cavity 2532 in the center to accommodate the first inner parts 2511 and 2512, respectively. The second outer parts 2521 and 2522 are formed from an elastic material and are configured to stretch around and over the first inner parts 2511 and 2512. The second outer parts 2521 and 2522 further include, in the axial cavity 2532, one or more interlocking recesses 2533 configured to mate with the interlocking ridges 2513 of the first inner parts 2511 and 2512. Each interlocking recess 2533 is a recess sized and shaped to accommodate a corresponding interlocking ridge 2513. After the second outer parts 2521 and 2522 are interlocked with the first inner parts 2511 and 2512, the multipart retention bumpers 2501 and 2502 are in the second configuration having the second radially expanded size.

When interlocked with the first inner parts 2511 and 2512, the outer diameter of the second outer parts 2521 and 2522 is equal to the second radially expanded size. As discussed above, the second outer parts 2521 and 2522 are formed from an elastic material. Prior to interlocking with the first inner parts 2511 and 2512, the outer diameter of the second outer parts 2521 and 2522 may be similar to or smaller than the second radially expanded size. If the outer diameter of the second outer parts 2521 and 2522 is smaller than the second radially expanded size prior to interlocking, stretching the second outer parts 2521 and 2522 to interlock with the first inner parts 2511 and 2512 may cause the outer diameter of the second outer parts to expand and equal the second radially expanded size. If the outer diameter of the second outer parts 2521 and 2522 is similar to the second radially expanded size prior to interlocking, the second outer parts 2521 and 2522 may be manually compressed so as to fit through the balloon opening 2549. In embodiments, the second outer parts 2521 and 2522 are manually compressed to fit through the balloon opening 2549 and also expand when stretched over the first inner parts 2511 and 2512. After interlocking, the hub rims 2514 of the first inner parts 2511 and 2512 act to maintain the lateral positioning of the second outer parts 2521 and 2522.

The first inner parts 2511 and 2512 are each secured to the inner shaft 2530. During an assembly process, after securement of the first inner parts 2511 and 2512 to the inner shaft 2530, the balloon 2510 is disposed over the first inner parts 2511 and 2512. The first inner parts 2511 and 2512 are secured to the inner shaft 2530 via any suitable means, including adhesives, bonding, clamps, crimping, over molding, etc. If secured after insertion into the balloon 2510, tools may be deployed through the balloon opening 2549 and/or the open distal end of the balloon 2510 to apply the securement means. The second outer parts 2521 and 2522 are then inserted into the balloon opening 2549 and/or through the open distal end of the balloon 2510 and stretched around the first inner parts 2511 and 2512 to interlock. The insertion and interlocking of the second outer parts 2521 may be facilitated via the use of tools and/or via manual manipulation applied through the flexible balloon 2510. Interlocking of the outer parts 2521 and the inner parts 2511 may be secured, for example, via snap fit or adhesives. Once interlocked in the second expanded configuration, the multipart retention bumpers 2501 and 2502 have a diameter large enough to appropriately prevent migration of the prosthetic heart valve during deployment. As discussed above with respect to other expandable retention bumpers discussed herein, the multipart retention bumpers 2501 and 2502 may be interlocked and expanded to a second radially expanded size at any suitable time during the assembly process after insertion into the balloon 2510.

During use, inflation fluid is delivered to the balloon via a lumen between the outer shaft 2540 and the inner shaft 2530. In embodiments, the multipart retention bumpers 2501 and 2502 may be disposed within or near the balloon opening 2549. Inflation fluid delivered to the balloon 2510 via the outer shaft 2540 may flow around the multipart retention bumpers 2501 and 2502 such that the inflation fluid flow is not substantially impeded.

Figure 26E:
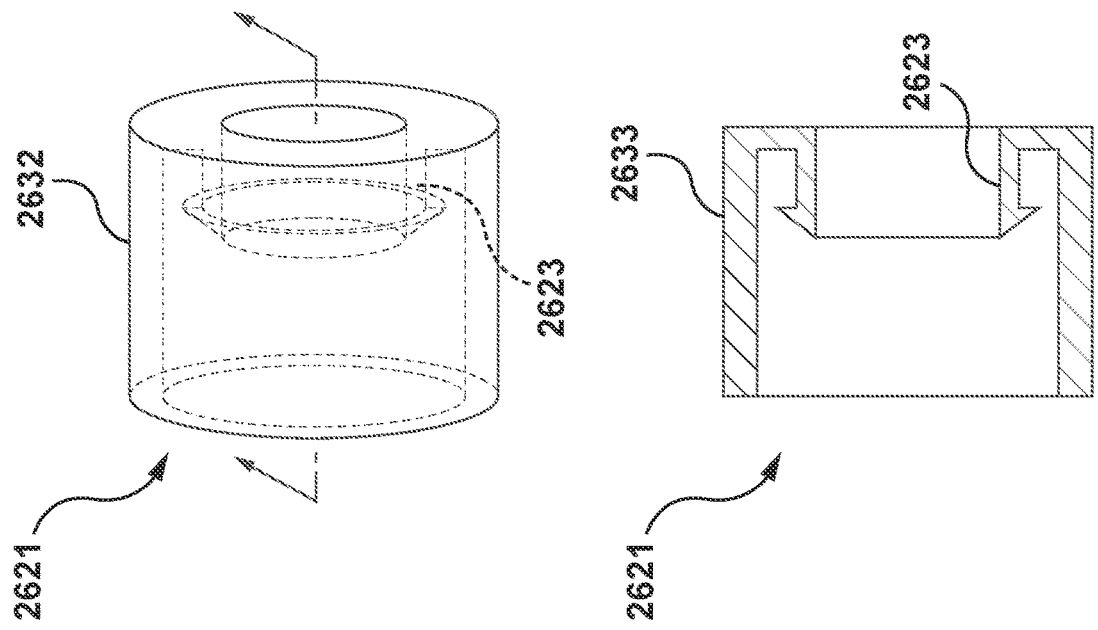
Figure 26D:
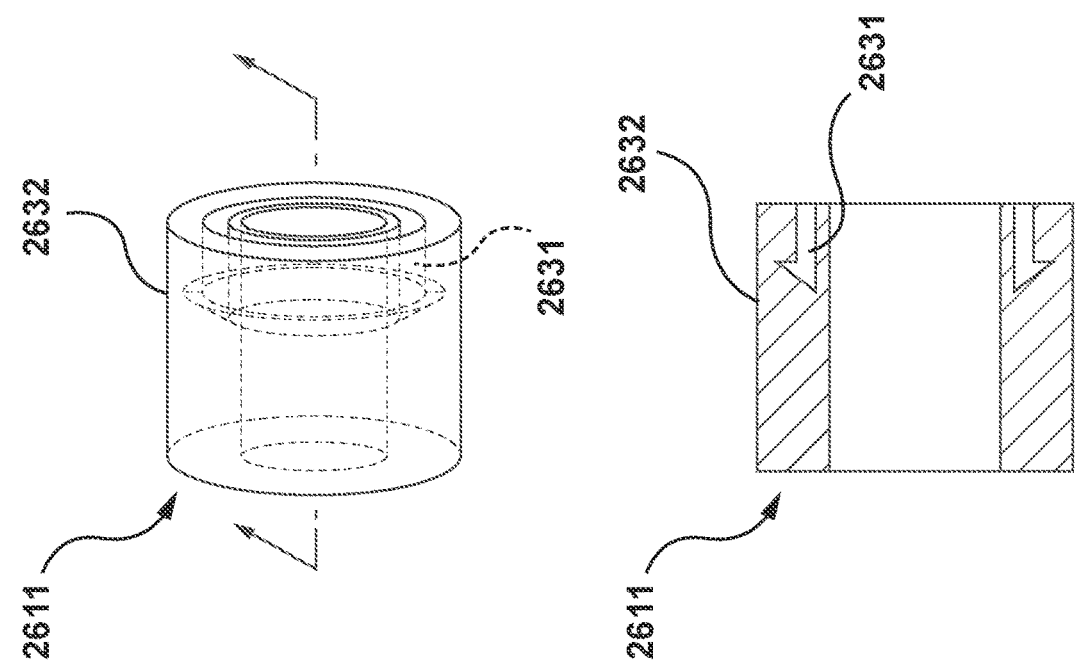

FIGS. 26A-26E illustrate multipart retention bumpers 2601 and 2602. The multipart retention bumpers 2601 and 2602 are configured for assembly into a larger size and may be employed with a balloon catheter 2600. The balloon catheter 2600 includes at least a balloon 2610, an inner shaft 2630, and an outer shaft 2640. The balloon catheter 2600 is configured for delivering a prosthetic heart valve (not pictured) and may include any or all features and aspects of the balloon catheter 400. The balloon catheter 2600 further includes a distal portion 2685, within which the balloon 2610 is disposed, and a proximal portion 2690. FIGS. 26A-26C illustrate the multipart retention bumpers 2601 and 2602 in various positions during an assembly process. FIGS. 26D-26E provide a close-up of various aspects of the multipart retention bumpers 2601 and 2602.

The multipart retention bumpers 2601 and 2602 each include two interlocking parts. In a first configuration, the multipart retention bumpers 2601 and 2602 are not interlocked and have a first radially unexpanded size smaller than the balloon opening 2649 of the balloon 2610, e.g., between approximately 0.1 inches and 0.25 inches. In a second configuration, the multipart retention bumpers 2601 and 2602 are interlocked and a have a second radially expanded size of sufficient size to maintain an axial position of a prosthetic heart valve during a delivery operation, e.g., between approximately 0.25 inches and 0.35 inches.

The multipart retention bumpers 2601 and 2602 each include a first inner part 2611 and a second outer part 2621. The first inner parts 2611, illustrated in detail in FIG. 26D, are generally cylindrical in shape each include an annular prism body 2632, at least one interlocking slot 2631, and an axial interior cavity to accommodate disposition over the inner shaft 2630. The interlocking slot 2631 is a recess configured to accommodate a barb or tab shaped projection. The second outer parts 2621, illustrated in detail in FIG. 26E, are also generally cylindrical in profile and include a body portion 2633 having an axial cavity in the center of to accommodate the first inner parts 2611. The second outer parts 2621 are formed from an elastic material and are configured to stretch around and over the first inner parts 2611. The second outer parts 2621 further include, in their interior, one or more interlocking barbs 2623 configured to mate with the interlocking slot 2631 of the first inner parts 2611. The interlocking barb 2623 is a barbed projection extending from the body portion 2633 into the axial cavity. The interlocking barb 2623 is sized and shaped to fit within the interlocking slot 2631. The barb portion of the interlocking barb 2623 is configured to hold the first inner parts 2611 and second outer parts 2621 together once interlocked. After the second outer parts 2621 are interlocked with the first inner parts 2611, the multipart retention bumpers 2601 and 2602 are in the second configuration having the second radially expanded size.

When interlocked with the first inner parts 2611, the outer diameter of the second outer parts 2621 is equal to the second radially expanded size. As discussed above, the second outer parts 2621 are formed from an elastic material. Prior to interlocking with the first inner parts 2611, the outer diameter of the second outer parts 2621 may be similar to or smaller than the second radially expanded size. If the outer diameter of the second outer parts 2621 is smaller than the second radially expanded size prior to interlocking, stretching the second outer parts 2621 to interlock with the first inner parts 2611 may cause the outer diameter of the second outer parts to expand and equal the second radially expanded size. If the outer diameter of the second outer parts 2621 is similar to the second radially expanded size prior to interlocking, the second outer parts 2621 may be manually compressed so as to fit through the balloon opening 2649. In embodiments, the second outer parts 2621 are manually compressed to fit through the balloon opening 2649 and also expand when stretched over the first inner parts 2611.

For assembly, the first inner parts 2611 are each secured to the inner shaft 2630. During an assembly process, after securement to the inner shaft, the balloon 2610 is disposed over the first inner parts 2611. The first inner parts 2611 are secured to the inner shaft 2630 via any suitable means, including adhesives, bonding, clamps, crimping, over molding, etc. If secured after insertion into the balloon 2610, tools may be deployed through the balloon opening 2649 and/or the open distal end of the balloon 2610 to apply the securement means. The second outer parts 2621 are then inserted into the balloon opening 2649 and/or through the open distal end of the balloon 2610 and stretched around the first inner parts 2611 to interlock. The insertion and interlocking of the second outer parts 2621 may be facilitated via the use of tools and/or via manual manipulation applied through the flexible balloon 2610. Interlocking of the outer parts 2621 and the inner parts 2611 may be secured, for example, via snap fit or adhesives. The second outer parts 2621 are then inserted into the balloon opening 2649 and stretched around the first inner parts 2611 to interlock. Once interlocked in the second radially expanded size, the multipart retention bumpers 2601 and 2602 have a diameter large enough to appropriately prevent migration of the prosthetic heart valve during deployment. As discussed above with respect to axial force expandable retention bumpers 901 and 902, the multipart retention bumpers 2601 and 2602 may be interlocked and expanded to a second radially expanded size at any suitable time during the assembly process after insertion into the balloon 2610.

During use, inflation fluid is delivered to the balloon via a lumen between the outer shaft 2640 and the inner shaft 2630. In embodiments, the multipart retention bumpers 2601 and 2602 may be disposed within or near the balloon opening 2649. Inflation fluid delivered to the balloon 2610 via the outer shaft 2640 may flow around the multipart retention bumpers 2601 and 2602 such that the inflation fluid flow is not substantially impeded.

Figure 27A:
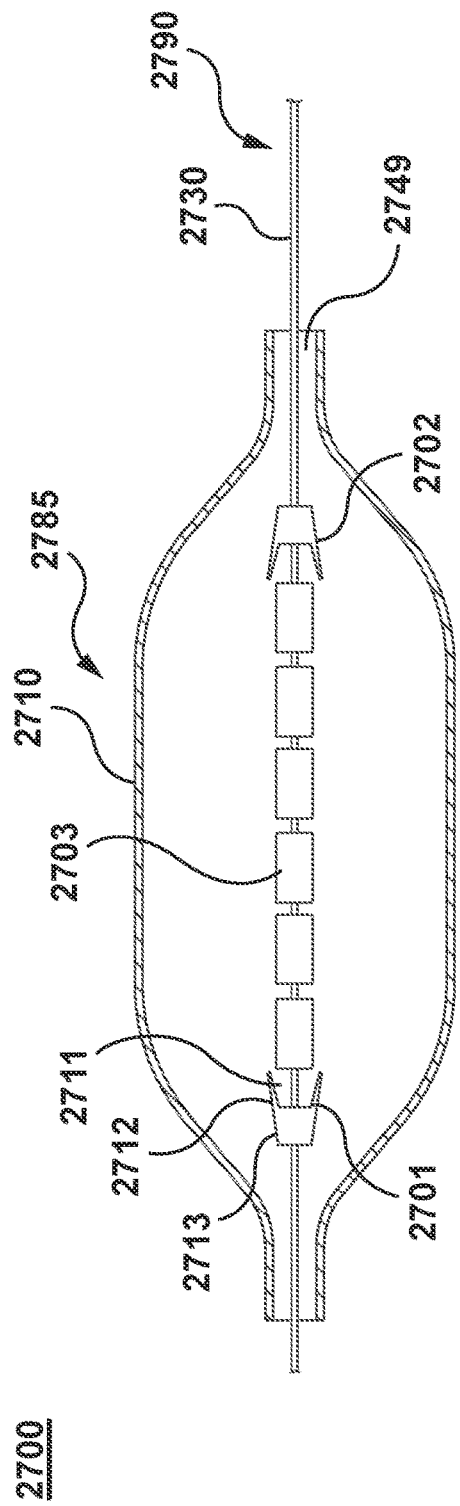
FIGS. 27A and 27B illustrate multipart retention bumpers according to embodiments hereof.
Figure 27B:
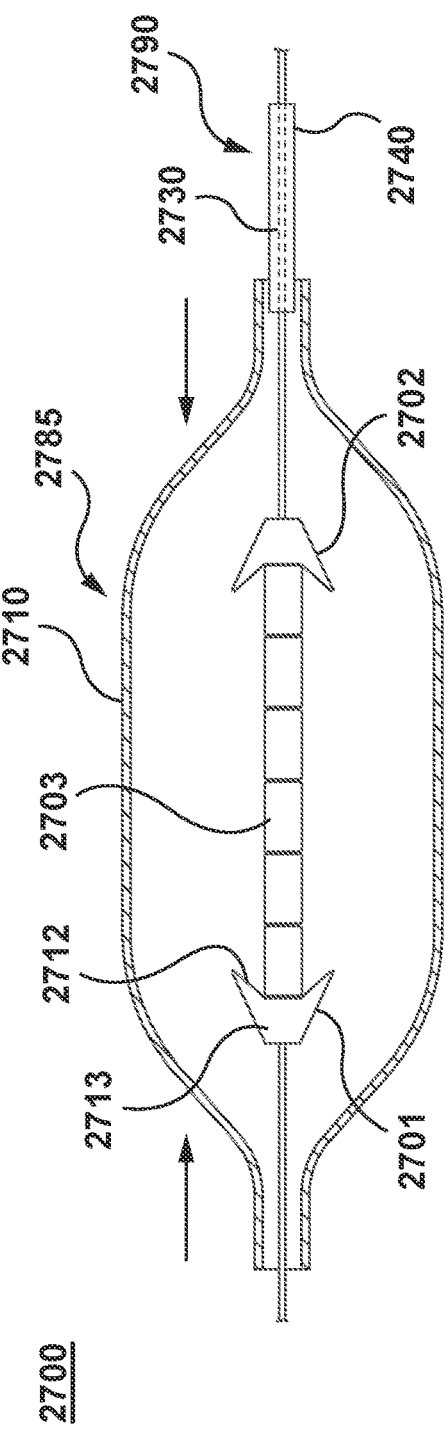

FIGS. 27A and 27B illustrate multipart retention bumpers 2701 and 2702. The multipart retention bumpers 2701 and 2702 are configured for interlocking into a larger size and may be employed with a balloon catheter 2700. The balloon catheter 2700 includes at least a balloon 2710, an inner shaft 2730, and an outer shaft 2740. The balloon catheter 2700 is configured for delivering a prosthetic heart valve (not pictured) and may include any or all features and aspects of the balloon catheter 400. The balloon catheter 2700 further includes a distal portion 2785, within which the balloon 2710 is disposed, and a proximal portion 2790.

The multipart retention bumpers 2701 and 2702 are each configured to interlock with one or more of a plurality of interlocking portions 2703. In a first configuration, the multipart retention bumpers 2701 and 2702 are not interlocked with the interlocking portions 2703 and have a first radially unexpanded size smaller than the balloon opening 2749 of the balloon 2710, e.g., between approximately 0.1 inches and 0.25 inches. In a second configuration, the multipart retention bumpers 2701 and 2702 are interlocked with interlocking portions 2703 and a have a second radially expanded size of sufficient size to maintain an axial position of a prosthetic heart valve during a delivery operation, e.g., between approximately 0.25 inches and 0.35 inches. The multipart retention bumpers 2701 and 2702 and the interlocking portions 2703 are each disposed over the inner shaft 2730, with the multipart retention bumpers 2701 and 2702 disposed at either end of a plurality of interlocking portions 2703.

The multipart retention bumpers 2701 and 2702 have a tapered shape with an axial cavity to permit disposition over the inner shaft 2730. The multipart retention bumpers 2701 and 2702 further include a flange 2712 extending from a central portion 2713 and a recess or cavity 2711 surrounded by the flange 2712. The multipart retention bumpers 2701 and 2702 are formed from a flexible material and are shaped and configured such that the ends of the flange 2712 flare outwardly when pressed from within the cavity 2711. Thus, the interlocking portions 2703 may be pressed into the cavity 2711 to cause the flange to flare outward, thereby moving the multipart retention bumpers 2701/2702 from the first radially unexpanded position to the second radially expanded position. The interlocking portion 2703 may be held in place to maintain the flared position of the flange 2712 by inward pressure from the flange 2712 attempting to return to its original position. In additional embodiments, the interlocking portion 2703 holding the flange 2712 in an expanded position may be secured to the inner shaft 2730 via adhesive, crimping, or the like.

When force is applied to the multipart retention bumpers 2701 and 2702, they slide along the inner shaft 2730 towards the interior of the balloon 2710. The interlocking portions 2703 press against one another, as shown in FIG. 27B, and the interlocking portions 2703 closest to the multipart retention bumpers 2701 and 2702 presses into the cavity 2711 of each of the multipart retention bumpers 2701 and 2702 to cause the flanges 2712 to flare and the multipart retention bumpers 2701 and 2702 to move to a second expanded position.

In an assembly process, the multipart retention bumpers 2701 and 2702 and the interlocking portions 2703 may all be disposed on the inner shaft 2730. The balloon 2710 may then be positioned over the multipart retention bumpers 2701 and 2702 and the interlocking portions 2703. The multipart retention bumpers 2701 and 2702 may be expanded at any later point in the assembly process by applying inward axial force from either end. Such force may be applied, for example, via manual manipulation through the balloon 2710 and/or via suitable tools inserted through the balloon opening 2749 and open distal end of the balloon 2710. Suitable tools include, for example, tubes configured for disposal over the inner shaft 2730. In particular, the multipart retention bumpers 2701 and 2702 may be expanded after disposition of the balloon 2710. After the multipart retention bumpers 2701 and 2702 are expanded, the balloon 2710 may be sealed to the outer shaft 2740, folded, and then a prosthetic heart valve crimped thereon. After expansion, the multipart retention bumpers 2701 and 2702 may be secured to the inner shaft via adhesive, crimping, clamping, or other means so that they may be employed to maintain the position of a prosthetic heart valve during a delivery operation. The multipart retention bumpers 2701 and 2702 may be secured through the use of one or more tools, such as adhesive applying syringes, inserted through the balloon opening 2749 and/or the open distal end of the balloon 2710. In other examples, the multipart retention bumpers 2701 and 2702 may be laser welded to the inner shaft 2730 through the balloon 2710 via laser transmission welding to prevent balloon damage.

During use, inflation fluid is delivered to the balloon via a lumen between the outer shaft 2740 and the inner shaft 2730. In embodiments, the multipart retention bumpers 2701 and 2702 may be disposed within or near the balloon opening 2749. Inflation fluid delivered to the balloon 2710 via the outer shaft 2740 may flow around the multipart retention bumpers 2701 and 2702 such that the inflation fluid flow is not substantially impeded.

Figure 28A:
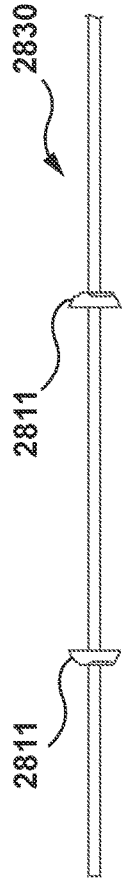
FIGS. 28A-28C illustrate multipart retention bumpers according to embodiments hereof.
Figure 28B:
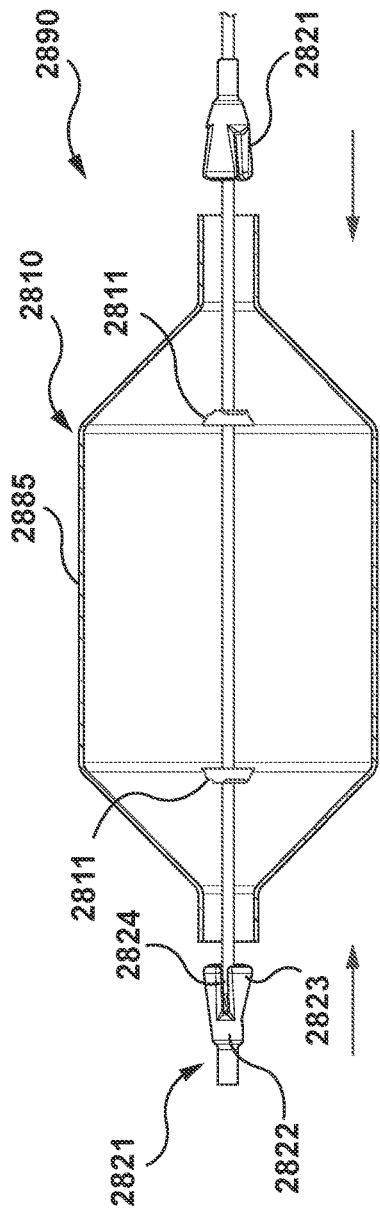
Figure 28C:
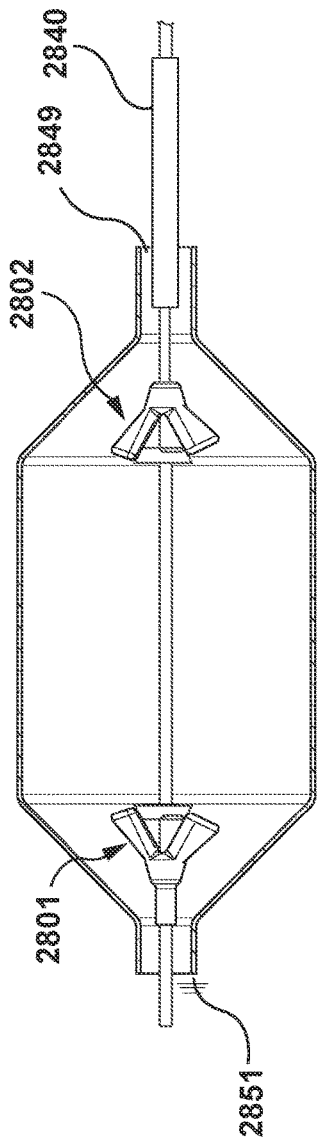

FIGS. 28A-28C illustrate multipart retention bumpers 2801 and 2802. The multipart retention bumpers 2801 and 2802 are configured for expanding from a first radially unexpanded size when disassembled to a second radially expanded size when assembled and may be employed with a balloon catheter 2800. The balloon catheter 2800 includes at least a balloon 2810, an inner shaft 2830, and an outer shaft 2840. The balloon catheter 2800 is configured for delivering a prosthetic heart valve (not pictured) and may include any or all features and aspects of the balloon catheter 400. The balloon catheter 2800 further includes a distal portion 2885, within which the balloon 2810 is disposed, and a proximal portion 2890. FIGS. 28A-28C illustrate the multipart retention bumpers 2801 and 2802 in various positions during an assembly process.

The multipart retention bumpers 2801 and 2802 each includes two interlocking parts. In a first configuration, the multipart retention bumpers 2801 and 2802 are not interlocked or assembled and each part has a first radially unexpanded size smaller than the balloon opening 2849 of the balloon 2810, e.g., between approximately 0.1 inches and 0.25 inches. In a second configuration, the two interlocking parts of each of the multipart retention bumpers 2801 and 2802 are interlocked such that each multipart retention bumper has a second radially expanded size of sufficient size to maintain an axial position of a prosthetic heart valve during a delivery operation, e.g., between approximately 0.25 inches and 0.35 inches.

The multipart retention bumpers 2801 and 2802 each include a first inner part 2811 and a second outer part 2821. The first inner part 2811 is generally tapered in profile and includes an axial cavity in the center to accommodate the inner shaft 2830. In embodiments, the first inner part 2811 has different cross-sections, as discussed below with respect to FIGS. 30A-30F. The tapered profile is provided to facilitate interlocking or assembly with the second outer part 2821. The second outer part 2821 is also generally tapered in profile and includes a central hub 2822 having an axial cavity to accommodate the inner shaft 2830 and a plurality of extension arms 2823 surrounding a hollow portion 2824 configured to accommodate the first inner part 2811. The extension arms 2823 extend axially and radially from the central hub 2822 to form the cone or tapered profile and define the hollow portion 2824. The multiple extension arms 2823 are disconnected from each other along their lengths so as to permit radial expansion when interlocked with the first inner part 2811.

Interlocking the first inner part 2811 with the second outer part 2821 is accomplished by pressing the tapered shaped first inner part 2811 into the hollow portion 2824 of the second outer part 2821. The tapered shaped of the first inner part 2811 causes the extension arms 2823 to expand radially, thus enlarging the diameter of the second outer part 2821 from the first radially unexpanded size to the second radially expanded size. At the second radially expanded size, the interlocked multipart retention bumpers 2801 and 2802 are able to act to maintain valve position during a delivery operation. The second outer parts 2821 are interlocked with the first inner parts 2811 while inside of the balloon 2810. Interlocking may be accomplished via manual manipulation through the balloon 2810 and/or via one or more tools inserted through the balloon opening 2849 and/or through the open distal end of the balloon 2810.

In some embodiments, the second outer part 2821 is formed from an elastic material and is configured to be compressed to fit through the balloon opening 2849. The hollow portion 2824 permits the extension arms 2823 to be pushed inwards to reduce the overall diameter of the second outer part 2821.

In some embodiments, the extension arms 2823 include, at their ends, interlocking hooks extending inward towards the hollow portion 2824. When the second outer part 2821 is disposed over the first inner part 2811, the interlocking hooks snap into place over the first inner part 2811, preventing the multipart retention bumpers 2801 and 2802 from being disassembled.

During use, inflation fluid is delivered to the balloon via a lumen between the outer shaft 2840 and the inner shaft 2830. In embodiments, the multipart retention bumpers 2801 and 2802 may be disposed within or near the balloon opening 2849. Inflation fluid delivered to the balloon 2810 via the outer shaft 2840 may flow around the multipart retention bumpers 2801 and 2802 such that the inflation fluid flow is not substantially impeded.

FIGS. 29A-29F illustrate stages of an assembly process for the balloon catheter 2800 employing the multipart retention bumpers 2801 and 2802. The assembly process described below may be completed prior to assembly of other portions of the balloon catheter 2800, e.g., the distal tip 2860, the outer shaft 2840, and the proximal handle (not shown) such that these portions of the balloon catheter 2800 do not interfere with assembly of the multipart retention bumpers 2801 and 2802.

During assembly, the first inner parts 2811 are each secured to the inner shaft 2830 and the second outer parts 2821 are disposed on the inner shaft 2830, but not secured. The first inner part 2811 and second outer part 2821 of the multipart retention bumper 2802 are then disposed in the balloon 2810, as shown in FIG. 29A. Because the second outer parts 2821 are not yet expanded, they may be inserted into the proximal balloon opening 2849 or the distal balloon opening 2851. FIG. 29A illustrates assembly through a distal balloon opening 2851, but assembly may be completed through a proximal balloon opening 2849 as well, or through both proximal and distal openings. The second outer part 2821 of the multipart retention bumper 2802 is then coupled with the first inner part 2811, as shown in FIG. 29B. Coupling the inner and outer parts 2811 and 2821 of the multipart retention bumper 2802 causes the outer part 2821 to expand from a first radially unexpanded size to a second radially expanded size. Coupling may be achieved through manual manipulation through the balloon 2810 and/or via the use of one or more tools (e.g., a tube disposed over the inner shaft 2830) inserted into the proximal balloon opening 2849. The first inner part 2811 and the second outer part 2821 of the retention bumper 2801 are then inserted into the balloon 2810, via the distal balloon opening 2851, as shown in FIG. 29C. The first inner part 2811 and the second outer part 2821 of the retention bumper 2801 are then assembled and the multipart retention bumper 2801 achieves the second radially expanded size. Once interlocked in the second radially expanded size, the multipart retention bumpers 2801 and 2802 each have a diameter large enough to appropriately prevent migration of the prosthetic heart valve during deployment. After interlocking the first inner parts 2811 and the second outer parts 2821 for both multipart retention bumpers 2801 and 2802, the balloon 2810 may be sealed to the outer shaft 2840 and the distal tip 2860, as shown successively in FIGS. 29D-29F, before the balloon folding and prosthetic heart valve crimping operations are carried out. As discussed above with respect to other retention bumpers described herein, the multipart retention bumpers 2801 and 2802 may be interlocked and expanded to a second radially expanded size at any suitable time during the assembly process after insertion into the balloon 2810.

The foregoing description applies to an embodiment wherein the first inner parts 2811 are secured and the second outer parts 2821 are slidable and wherein the parts of the multi part retention bumpers 2801 and 2802 are configured to snap lock together. Alternative embodiments may vary aspects of the foregoing description.

In further embodiments, the secured portions of the multi part retention bumpers 2801 and 2802 may vary. In embodiments, the second outer parts 2821 are secured to the inner shaft 2830 while the first inner parts 2811 are permitted to slide along the inner shaft 2830. In further embodiments, either the first inner part 2811 or the second outer part 2821 of each multipart retention bumper 2801 and 2802 are secured to the inner shaft, permitting the other part to be slidably disposed. Securing the first inner part 2811 or the second outer part 2821 may be accomplished through any suitable means, including adhesives, bonding, over molding, crimping, clamping, etc. Various aspects of the assembly process may differ somewhat according to which parts of the multipart retention bumpers 2801 and 2802 are secured.

In further embodiments, the respective second outer parts 2821 may be formed integrally with the outer shaft 2840 and the distal tip 2860 and manipulation of these may facilitate interlocking the first inner parts 2811 and second outer parts 2821. In such embodiments, the multipart retention bumpers 2801 and 2802 may include features allowing inflation fluid to flow through, as discussed below with respect to FIGS. 30A-30F.

In further embodiments, alternative means of interlocking the first inner part 2811 or the second outer part 2821 of each multipart retention bumper 2801 and 2802 may be employed. For example, the first inner part 2811 or the second outer part 2821 may be configured for a screw fit.

In further embodiments, the first inner parts 2811 may each be secured to a flow guide (e.g., similar to the flow guide 4170, discussed below) disposed over the inner shaft 2830.

In still further embodiments, the inner shaft 2830 may be configured with raised stops having an increased diameter to assist in positioning the first inner part 2811 or the second outer part 2821 during assembly by preventing the respective first inner part 2811 or the second outer part 2821 from sliding past the raised stops.

FIGS. 30A-30F illustrate several different configurations for first inner parts of the multipart retention bumpers 2801 and 2802. FIGS. 30A-B illustrate the first inner parts 2811, as also shown in FIGS. 28A-28C and 29A-29F. The first inner parts 2811 include the axial cavity 2817 for accommodating the inner shaft 2830. Optionally, the first inner parts 2811 may also include fluid flow lumens 2818 to promote the flow of inflation fluid within the balloon 2810. In profile, the first inner parts 2811 have a tapered shape with a flat truncated top. In cross-section, the first inner parts 2811 are circular. FIGS. 30C-D illustrate a first inner part 3011. The first inner part 3011 includes an axial cavity 3017. The first inner part 3011 is configured with a cog-like shape in cross-section, having a plurality of projections 3018 extending radially from a central hub 3019. The gaps 3020 between the projections 3018 of the first inner part 3011 may promote the flow of inflation fluid within the balloon 2810. In profile, the first inner parts 3011 have a tapered shape with a flat truncated top. The first inner part 3011 is compatible with the second outer parts 2821 illustrated in FIGS. 28A-28C. FIGS. 30E-F illustrate first inner parts 3031. The first inner parts 3031 include an axial cavity 3037 for accommodating the inner shaft 2830. Optionally, the first inner parts 3031 may also include fluid flow lumens 3038 to promote the flow of inflation fluid within the balloon 2810. In profile, the first inner parts 3031 have an extended tapered shape. In cross-section, the first inner parts 3031 are circular. The first inner part 3021 is compatible with the second outer parts 2821 illustrated in FIGS. 28A-28C.

FIGS. 31-33 illustrate balloon catheter embodiments including modified balloons to facilitate balloon catheter assembly. The modified balloons of these embodiments may be employed or combined with any of the expandable retention bumpers described herein, and/or may be employed or combined with non-expandable retention bumpers.

FIGS. 31A and 31B illustrate a balloon catheter 3100 configured for balloon processing during assembly. Some balloon catheters are assembled after manufacturing of the balloon is complete. In the method of manufacturing the balloon catheter 3100, manufacture of the balloon 3110 is only partially completed prior to the initiation of assembly of the balloon catheter 3100. After assembly of the balloon catheter 3100 is begun, e.g., after insertion of the retention bumpers 3101 and 3102 and inner shaft 3130 into the balloon catheter 3100, manufacturing of the balloon 3110 is then completed. The balloon catheter 3100 includes at least a balloon 3110, retention bumpers 3101 and 3102, an inner shaft 3130, and an outer shaft 3140. The retention bumpers 3101 and 3102 may be any type of retention bumper as discussed herein. The balloon 3110 has a balloon opening 3149 at its proximal end. The balloon catheter 3100 is configured for delivering a prosthetic heart valve (not pictured) and may include any or all features and aspects of the balloon catheter 400. The balloon catheter 3100 further includes a distal portion 3185, within which the balloon 3110 is disposed, and a proximal portion 3190.

The balloon 3110 of the balloon catheter 3100 is configured for additional processing or manufacturing during assembly of the balloon catheter 3100. The balloon 3110 is initially produced with a balloon neck 3145 and the balloon opening 3149 large enough to admit entry of the retention bumpers 3101 and 3102 having a diameter large enough to be employed for maintaining a position of a prosthetic heart valve during a delivery operation. Thus, prior to the initiation of the assembly of the balloon catheter 3100, the manufacturing of the balloon 3110 is not fully completed. In an example, the balloon opening 3149 may initially have a diameter larger than approximately 0.25 inches. After the retention bumpers 3101 and 3102, which may have a diameter between approximately 0.25 and 0.35 inches, are secured to the inner shaft 3130 and the balloon 3110 is arranged over the retention bumpers 3101 and 3102, the balloon 3110 may be further processed to reduce the size of the balloon neck 3145 and the balloon opening 3149. The diameter of the reduced balloon neck 3145 and balloon opening 3149 may be approximately 0.1 to 0.25 inches in embodiments. Processes such as hot die necking, thermal reduction of the balloon neck using heat shrink tubing, laser welding, hot jaw welding, induction welding, or other suitable manufacturing processes may be employed to reduce the size of the balloon neck 3145 to a size appropriate for the final balloon catheter 3100. After reduction of the size of the balloon neck 3145, the balloon may be sealed to the outer shaft 3140 and folded. The prosthetic valve is then crimped onto the balloon 3110 to complete assembly of the balloon catheter 3100. During use, inflation fluid is provided to the balloon 3100 via the lumen disposed between the inner shaft 3130 and the outer shaft 3140.

Figure 32A:
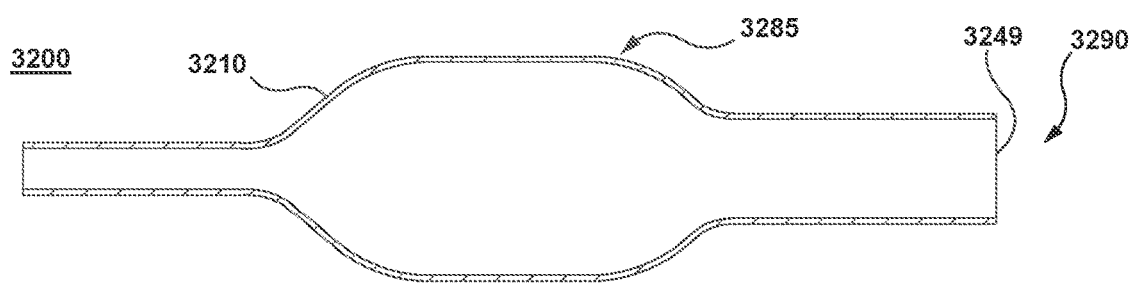
FIGS. 32A-32C illustrate a balloon catheter configured for balloon processing during assembly according to embodiments hereof.
Figure 32B:
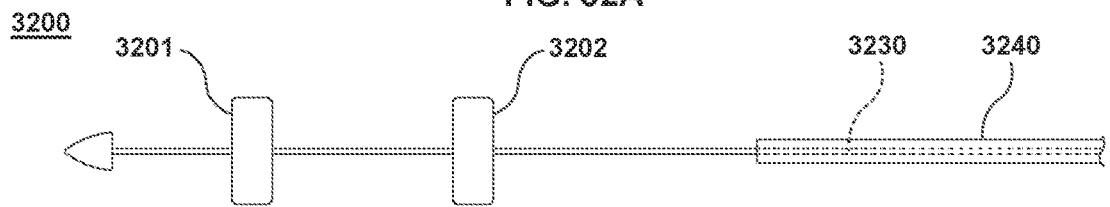
Figure 32C:
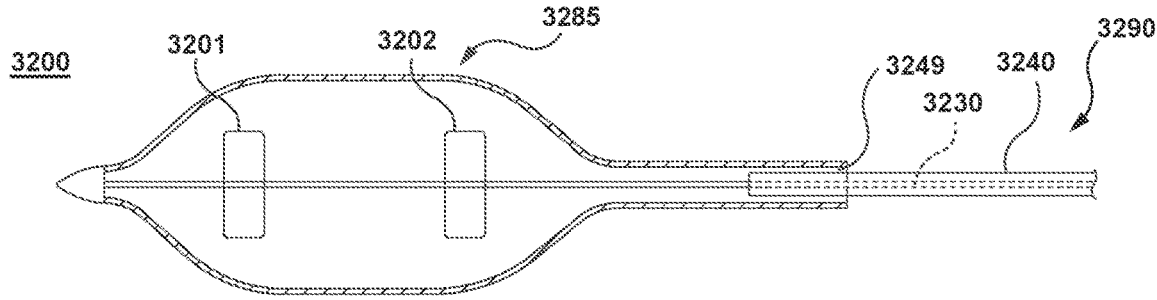

FIGS. 32A-32C illustrate a balloon catheter 3200 configured for balloon processing during assembly. As discussed above, some balloon catheters are assembled after manufacturing of the balloon is complete. In the method of manufacturing the balloon catheter 3200, manufacture of the balloon 3210 is only partially completed prior to the initiation of assembly of the balloon catheter 3200. After assembly of the balloon catheter 3200 is begun, e.g., after insertion of the retention bumpers 3201 and 3202 and inner shaft 3230 into the balloon 3200, manufacturing of the balloon 3210 is then completed. The balloon catheter 3200 includes at least a balloon 3210, retention bumpers 3201 and 3202, an inner shaft 3230, and an outer shaft 3240. The retention bumpers 3201 and 3202 may be any type of retention bumper as discussed herein. The balloon 3210 has a balloon opening 3249 at its proximal end. The balloon catheter 3200 is configured for delivering a prosthetic heart valve (not pictured) and may include any or all features and aspects of the balloon catheter 400. The balloon catheter 3200 further includes a distal portion 3285, within which the balloon 3210 is disposed, and a proximal portion 3290.

The balloon 3210 of the balloon catheter 3200 is configured for additional processing during assembly of the balloon catheter 3200. During blow molding of the balloon 3210, the balloon 3210 is initially extruded and blown to a size and shape configured to permit the entry of the retention bumpers 3201 and 3202 secured to the inner shaft 3230 into the balloon opening 3249 (FIGS. 32A-B). At this stage, the balloon opening 3249 has an opening diameter of approximately 0.3 inches or more. In further embodiments, the balloon opening 3249 has an opening diameter of anywhere between approximately 0.25 inches and 0.35 inches. At this point, further manufacturing of the balloon 3210 is halted and assembly is begun. The inner shaft 3230 with retention bumpers 3201 and 3202 secured thereon is inserted into the partially completed balloon 3210 to begin the assembly process. After this insertion, processing or manufacturing of the balloon may then be resumed. The assembly of the inner shaft 3230 and the balloon 3210 are placed in a manufacturing mold and the blow molding process is resumed. The blow molding process of the balloon 3210 is then completed such that the balloon 3210 is blown to its final size (FIG. 32C). Assembly of the balloon catheter 3200 is then completed by sealing the balloon opening 3249 to an outer shaft and a distal tip, folding the balloon 3210, and crimping a prosthetic heart valve onto the balloon 3210. During use, inflation fluid is provided to the balloon 3210 via the lumen disposed between the inner shaft 3230 and the outer shaft 3240.

Figure 32D:
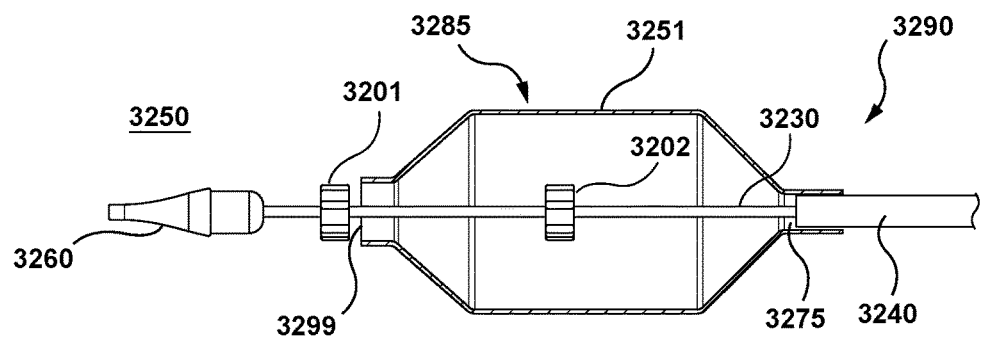
FIGS. 32D-32F illustrate a balloon catheter configured for balloon processing during assembly according to embodiments hereof.
Figure 32E:
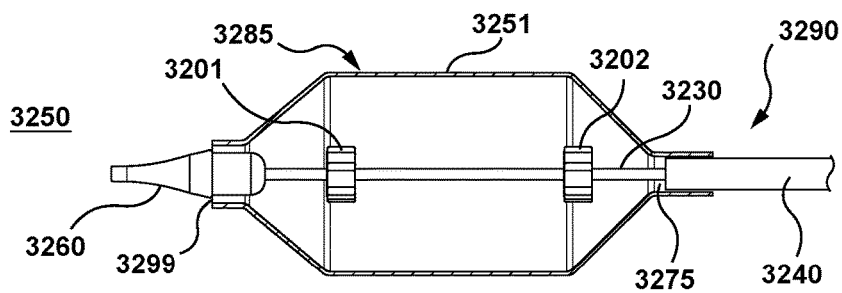
Figure 32F:
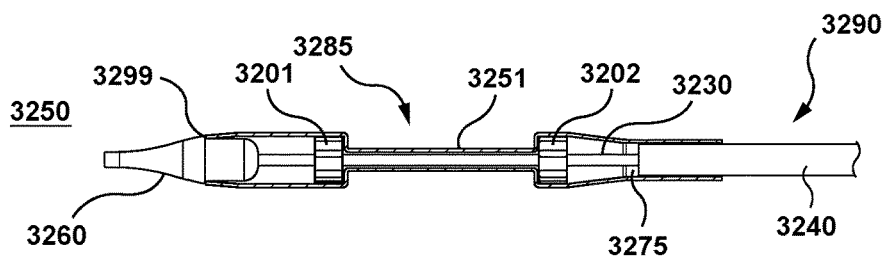

FIGS. 32D-F illustrate a balloon catheter 3250 configured for balloon processing during assembly. Similar to the method of manufacturing the balloon catheter 3200, during the manufacture of the balloon catheter 3250, processing of the balloon 3251 is only partially completed prior to the initiation of assembly of the balloon catheter 3250. Manufacture of the balloon catheter 3250 differs from manufacture of the balloon catheter 3200 in that the additional balloon processing during balloon catheter assembly occurs at a distal balloon opening 3299, as discussed below.

After assembly of the balloon catheter 3250 is begun, e.g., after insertion of the retention bumpers 3201 and 3202 and inner shaft 3230 into the balloon 3251, manufacturing of the balloon 3251 is then completed. The balloon catheter 3250 includes at least a balloon 3251, a distal tip 3260, retention bumpers 3201 and 3202, an inner shaft 3230, and an outer shaft 3240. The retention bumpers 3201 and 3202 may be any type of retention bumper as discussed herein. The balloon 3251 has a distal balloon opening 3299 at its distal end. The balloon catheter 3250 is configured for delivering a prosthetic heart valve (not pictured) and may include any or all features and aspects of the balloon catheter 400. The balloon catheter 3250 further includes a distal portion 3285, within which the balloon 3251 is disposed, and a proximal portion 3290.

The balloon 3251 of the balloon catheter 3250 is manufactured as a sub-assembly of the balloon catheter 3250. During blow molding (or other suitable manufacturing technique) of the balloon 3251, the balloon 3251 is extruded, stretched, and blown to a size and shape configured to permit the entry of the retention bumpers 3201 and 3202 secured to the inner shaft 3230 into the distal balloon opening 3299 (FIGS. 32D-E). As manufactured, the distal balloon opening 3299 has an opening diameter of approximately 0.3 inches or more. In further embodiments, the distal balloon opening 3299 has an opening diameter of anywhere between approximately 0.25 inches and 0.35 inches. The balloon 3251 is secured or bonded to a distal end of the outer shaft 3240 to begin assembly of the distal portion 3285. The inner shaft 3230 with retention bumpers 3201 and 3202 and distal tip 3260 secured thereon, for example, via over molding or adhesives as discussed herein, is inserted into the partially completed balloon 3251 via the distal balloon opening 3299. After insertion of the inner shaft 3230 into the balloon 3251, the balloon 3251 then receives further processing.

Further processing is applied to the balloon 3251 to reduce the diameter of the distal balloon opening 3299 to a size compatible with bonding to the distal tip 3260. In embodiments, the assembly of the inner shaft 3230, the outer shaft 3240, and the balloon 3251 are placed in a manufacturing mold and a further blow molding process is initiated. The blow molding process of the balloon 3251 is then completed such that the balloon 3251 is blown to its final size.

Assembly of the balloon catheter 3250 is then completed by sealing the balloon opening 3299 to the distal tip 3260 and pleating and folding the balloon 3251 (FIG. 32E). Finally, a prosthetic heart valve is crimped onto the balloon 3251. During use, inflation fluid is provided to the balloon 3251 via the lumen 3275 disposed between the inner shaft 3230 and the outer shaft 3240.

Figure 33A:
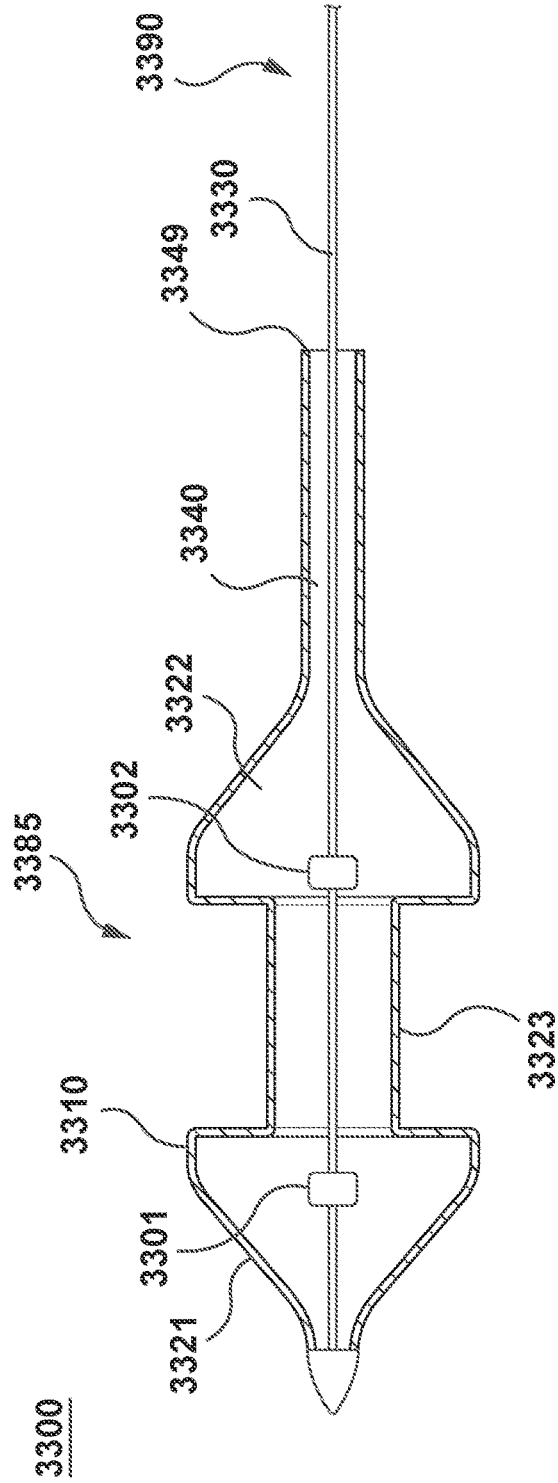
FIGS. 33A and 33B illustrate a balloon catheter having a balloon manufactured to function as a retention bumper.
Figure 33B:
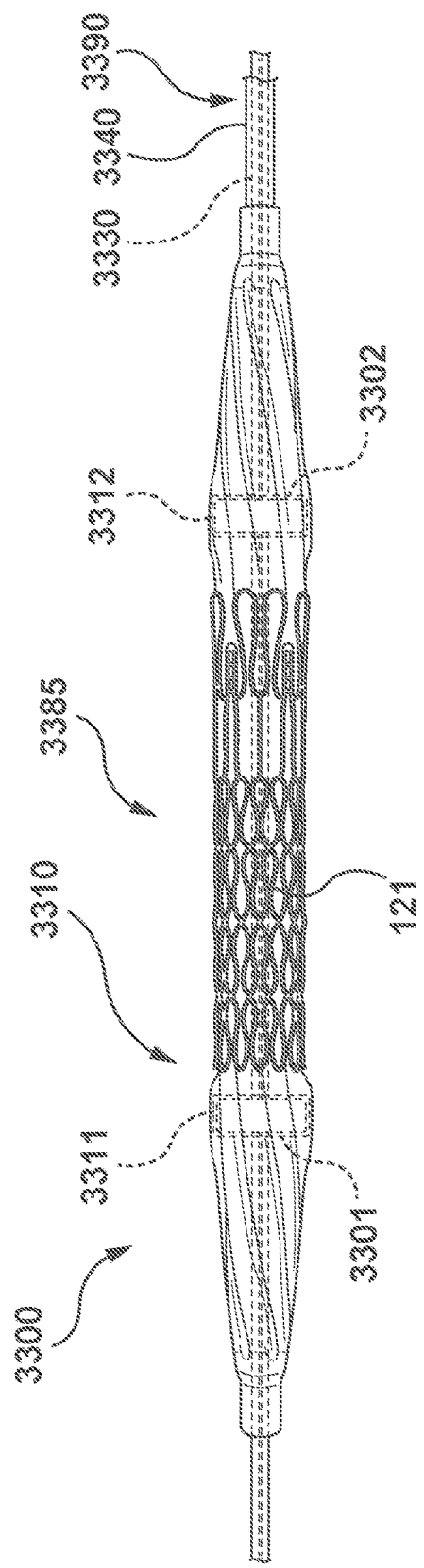

FIGS. 33A and 33B illustrate a balloon catheter 3300 having a balloon 3310 manufactured to function as a retention bumper. The balloon catheter 3300 includes at least the balloon 3310, partial retention bumpers 3301 and 3302, an inner shaft 3330, and an outer shaft 3340. The balloon 3310 has a balloon opening 3349 at its proximal end. When fully assembled, the balloon catheter 3300 further includes combined retention bumpers 3311 and 3312. The balloon catheter 3300 is configured for delivering a prosthetic heart valve (not pictured) and may include any or all features and aspects of the balloon catheter 400. The balloon catheter 3300 further includes a distal portion 3385, within which the balloon 3310 is disposed, and a proximal portion 3390.

FIG. 33A illustrates the balloon catheter 3300 prior to prosthetic heart valve crimping. The partial retention bumpers 3301 and 3302 are sized and configured for insertion into the balloon opening 3349. Each of the partial retention bumpers 3301 and 3302, alone, has a diameter representing a first radially unexpanded size of the combined retention bumpers 3311 and 3312, e.g., between approximately 0.1 inches and 0.25 inches. The partial retention bumpers 3301 and 3302 are secured to the inner shaft 3330 and this assembly is inserted into the balloon 3310. The balloon 3310 is shaped with a narrow central portion 3323 and enlarged end portions 3321 and 3322. When the balloon 3310 is folded into place on the balloon catheter 3300 with the prosthetic heart valve 120 crimped onto it, as shown in FIG. 33B, the additional size and balloon material present in the enlarged end portions 3321 and 3322 of the balloon 3310 serve to combine with the partial retention bumpers 3301 and 3302 to form the combined retention bumpers 3311 and 3312, having a diameter of a second radially expanded size sufficient to prevent migration of the prosthetic heart valve during a delivery operation. For example, the combined retention bumpers 3311 and 3312 may have a diameter of approximately 0.25 inches to 0.35 inches. Thus, the partial retention bumpers 3301 and 3302 are provided on the inner shaft 3330 with the smaller first radially unexpanded size so that they may fit into the balloon opening 3349. When combined with the excess material of the enlarged end portions 3321 and 3322 of the balloon 3310, the larger combined retention bumpers 3311 and 3312, having the second radially expanded size, are formed. During use, inflation fluid is delivered to the balloon 3310 via the lumen between the inner shaft 3330 and the outer shaft 3340.

Figure 34A:
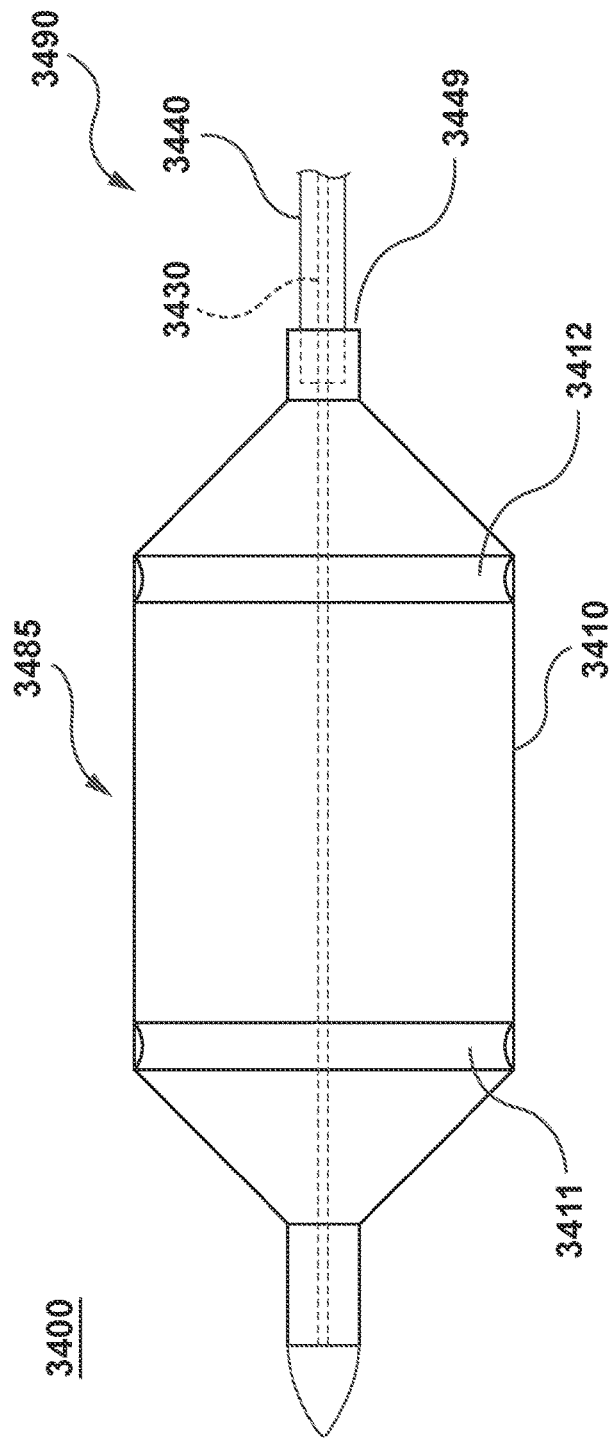
FIGS. 34A and 34B illustrate a balloon catheter having a balloon manufactured to function as a retention bumper.
Figure 34B:
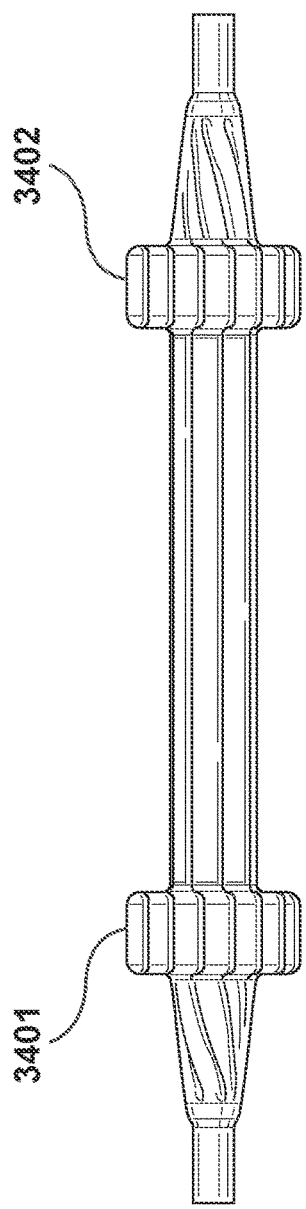

FIGS. 34A and 34B illustrate a balloon catheter 3400 having a balloon 3410 manufactured to function as a retention bumper. The balloon catheter 3400 includes at least the balloon 3410, an inner shaft 3430, and an outer shaft 3440. The balloon 3410 has a balloon opening 3449 at its proximal end. When fully assembled, the balloon catheter 3400 further includes retention bumpers 3401 and 3402. The balloon catheter 3400 is configured for delivering a prosthetic heart valve (not pictured) and may include any or all features and aspects of the balloon catheter 400. The balloon catheter 3400 further includes a distal portion 3485, within which the balloon 3410 is disposed, and a proximal portion 3490.

FIG. 34A illustrates the balloon catheter 3400 prior to prosthetic heart valve crimping. The balloon 3410 is similar to the above-described balloon 3310, in that the balloon 3410 includes extra portions of material, such that, when the balloon 3410 is folded, retention bumpers are created. Unlike balloon 3310, however, the balloon 3410 does not require the use of partial retention bumpers. Instead, the balloon retention bumpers 3401 and 3402 are formed entirely from excess material portions 3411 and 3412 during balloon folding. Excess material portions 3411 and 3412 are bands or strips of additional material located on the balloon 3410 at locations distal and proximal to the portion of the balloon 3410 configured to receive the prosthetic heart valve (not pictured). The excess material portions 3411 and 3412 may include portions of material that are secured to the interior or exterior of the balloon 3410 via bonding, adhesives, printing, or other process. In some embodiments, the excess material portions 3411 and 3412 may be formed from the same material as the balloon 3410 or by a different material than the balloon 3410. In embodiments, the excess material portions 3411 and 3412 may be integral to the balloon 3410, consisting of thickened portions of the balloon 3410. In embodiments, the excess material portions 3411 and 3412 may extend uniformly around an inner and/or outer circumference of the balloon 3410. In further embodiments, the excess material portions 3411 and 3412 may be non-uniform around the inner and/or outer circumference of the balloon 3410. For example, the excess material portions 3411 and 3412 may vary in thickness and width around the inner and/or outer circumference of the balloon 3410. The excess material portions 3411 and 3412 may also be present only intermittently around the inner and/or outer circumference of the balloon 3410.

FIG. 34B illustrates the balloon 3410 after folding. As shown, the excess material portions 3411 and 3412 form the balloon retention bumpers 3401 and 3402. After the balloon 3410 is folded, a transcatheter valve may be crimped onto the balloon 3410. During use, inflation fluid is delivered to the balloon 3410 via the lumen between the inner shaft 3430 and the outer shaft 3440.

FIGS. 35A-F illustrate balloon folding patterns configured to preserve a fluid flow pathway from the proximal end of a balloon to the distal end of the balloon. In some balloon catheters, inflation fluid is delivered to a proximal portion of the balloon via an inflation lumen between an inner shaft and an outer shaft. Due to folding of the balloon around the inner shaft, flow of inflation fluid from the proximal end of the balloon to the distal end of the balloon may be inhibited. Such inhibition of inflation fluid flow from the proximal end of the balloon to the distal end of the balloon can result in asymmetric valve deployment due to asymmetric balloon inflation. Preserving fluid flow pathways from the proximal end of the balloon to the distal end of the balloon may therefore facilitate symmetric and accurate valve deployment.

In some balloon catheters, the balloon may be wrapped or folded around the inner shaft the through pleating and compression processes. In a pleating process, pleating dies are closed around the balloon used to create pleats or folds in the balloon. In some systems, the pleating dies may be heated. Following pleating, during a compression step, compression dies are closed around the balloon to complete the wrapping or folding process and compress the balloon around the inner shaft. Subsequently, a prosthetic heat valve is crimped onto the balloon. Various other techniques exist to carry out balloon wrapping and folding.

Figure 35A:
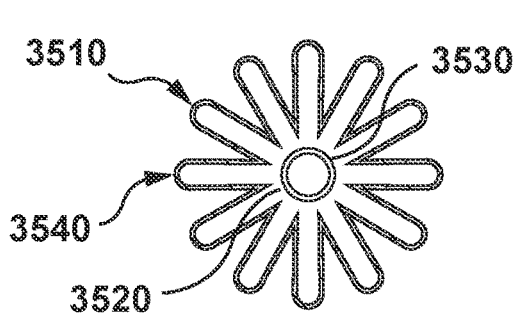
FIGS. 35A-35F illustrate balloon folding patterns configured to preserve a fluid flow pathway from the proximal end of a distal portion to the distal end of a distal portion.
Figure 35B:
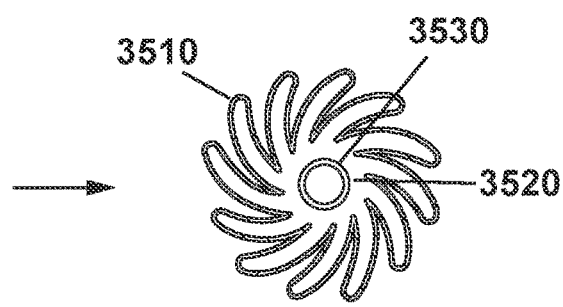

FIGS. 35A and 35B illustrate a spoked folding pattern for a balloon 3510 around an inner shaft 3530. The inner shaft 3530 is consistent with the inner shaft 430 as shown in FIG. 4A and with other inner shafts described throughout this disclosure. The balloon 3510 and inner shaft 3530 may be employed with a balloon catheter consistent with balloon catheters described throughout this disclosure. The spoked folding pattern of the balloon 3510 includes a plurality of spokes 3540 created by inward folds of the balloon 3510. The inward folds of the balloon 3510 are configured to leave an annular space 3520 around the inner shaft 3530 at the center of the balloon. The spoked folding pattern of the balloon 3510 may be created through the use of pleating dies configured for creating the specific folding pattern having a plurality of spokes 3540 and permitting an annular space 3520 at the center of the balloon 3510. Any other suitable means for creating the spoked folding pattern may also be employed. Before the valve is crimped to the balloon 3510, the spokes 3540 are folded and wrapped circumferentially, e.g., through the use of compression dies, around the inner shaft 3530, as shown in FIG. 35B. This folding pattern leaves the annular space 3520 at the center of the folded balloon 3510 open to permit fluid flow during valve deployment.

Figure 35C:
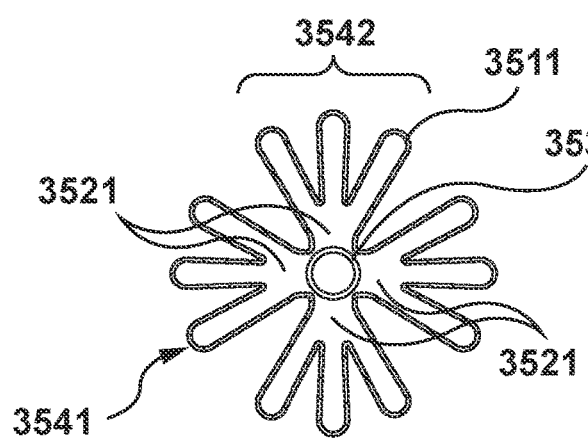
Figure 35D:
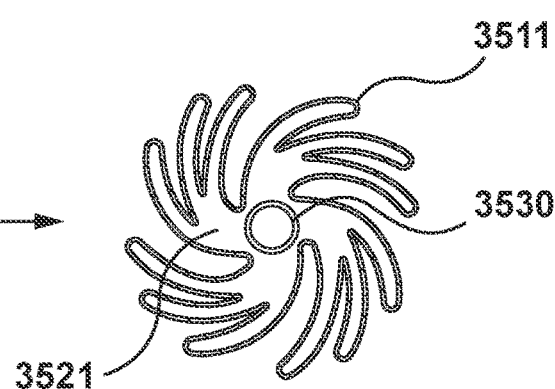

FIGS. 35C and 35D illustrate a tree folding pattern for a balloon 3511 around an inner shaft 3530. The inner shaft 3530 is consistent with the inner shaft 430 as shown in FIG. 4A and with other inner shafts described throughout this disclosure. The balloon 3511 and inner shaft 3530 may be employed with a balloon catheter consistent with balloon catheters described throughout this disclosure. The tree folding pattern of balloon 3511 includes a plurality of branches 3541 grouped into multiple branch sets 3542 created by inward folds of the balloon 3511. The inward folds of the balloon 3511 are configured to leave a plurality of open spaces 3521 at the base of each branch set 3542. The tree folding pattern of the balloon 3511 may be created through the use of pleating dies configured for creating the specific folding pattern having a plurality of branches 3541 and branch sets 3542 and leaving the plurality of open spaces 3521 at the center of the balloon 3511. Any other suitable means for creating the spoked folding pattern may also be employed. Before the valve is crimped to the balloon 3511, the branches 3541 are folded and wrapped circumferentially, e.g., through the use of compression dies, around the inner shaft 3531, as shown in FIG. 35D. This folding pattern leaves the open spaces 3521 at the bases of the branch sets 3542 open to permit fluid flow during valve deployment.

Figure 35E:
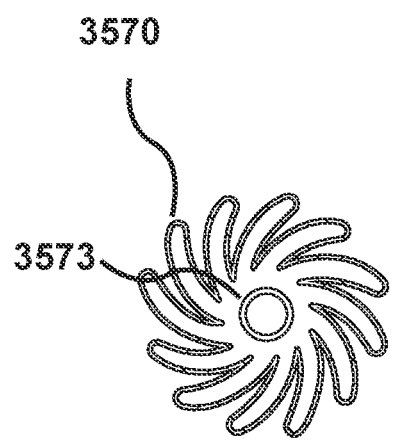
Figure 35F:
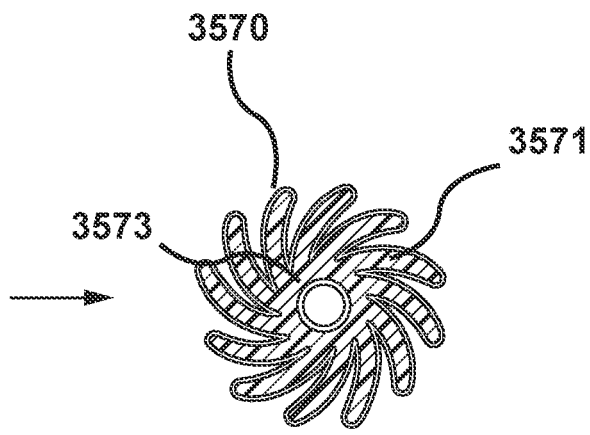

FIGS. 35E and 35F illustrate a gel filled balloon 3570 around an inner shaft 3573. The inner shaft 3573 is consistent with the inner shaft 430 as shown in FIG. 4A and with other inner shafts described throughout this disclosure. The gel filled balloon 3570 and inner shaft 3573 may be employed with a balloon catheter consistent with balloon catheters described throughout this disclosure. The gel filled balloon 3570 is partially filled with a gel 3571 or other viscous fluid material prior to crimping of a transcatheter valve. The gel 3571 may be disposed in the balloon before, during, or after completion of folding the balloon. The gel 3571 occupies space between the folds of the gel filled balloon 3570 and acts to maintain fluid passageways from a proximal end of the balloon to a distal end of the balloon after crimping pressure from the valve is applied. The gel 3571 prevents the gel filled balloon 3570 from being compressed to the extent that fluid passageways from the proximal end to the distal end are blocked during valve crimping. The gel filled balloon 3570 may be folded according to any suitable folding pattern.

Figure 36A:
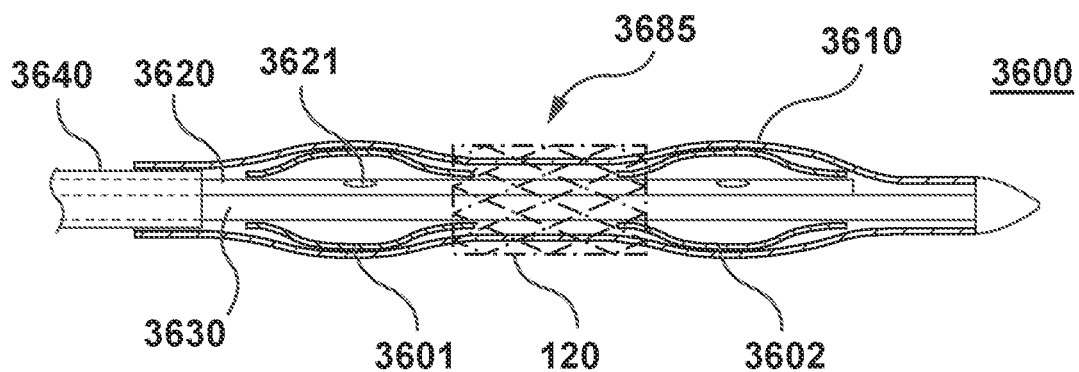
FIGS. 36A-36C illustrate a triple balloon catheter configured to provide valve stability during delivery and deployment.
Figure 36B:
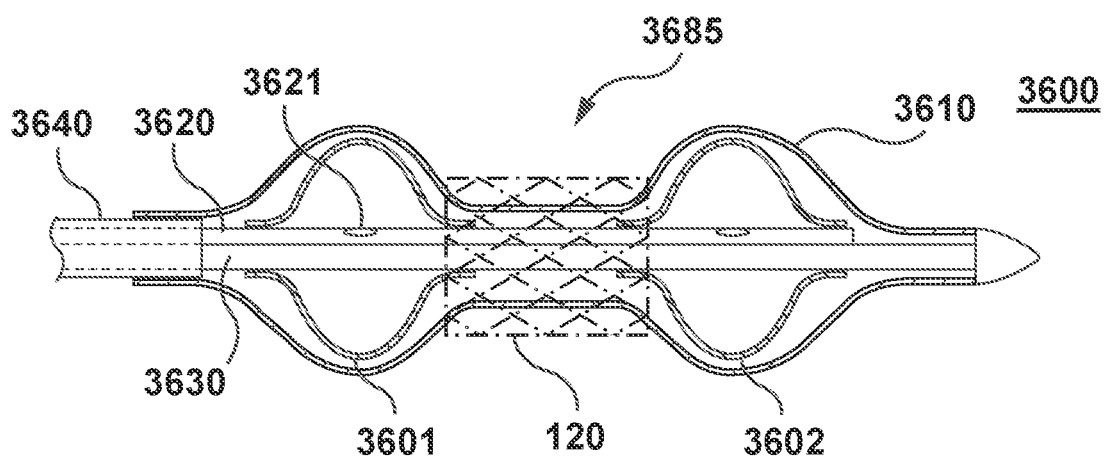
Figure 36C:
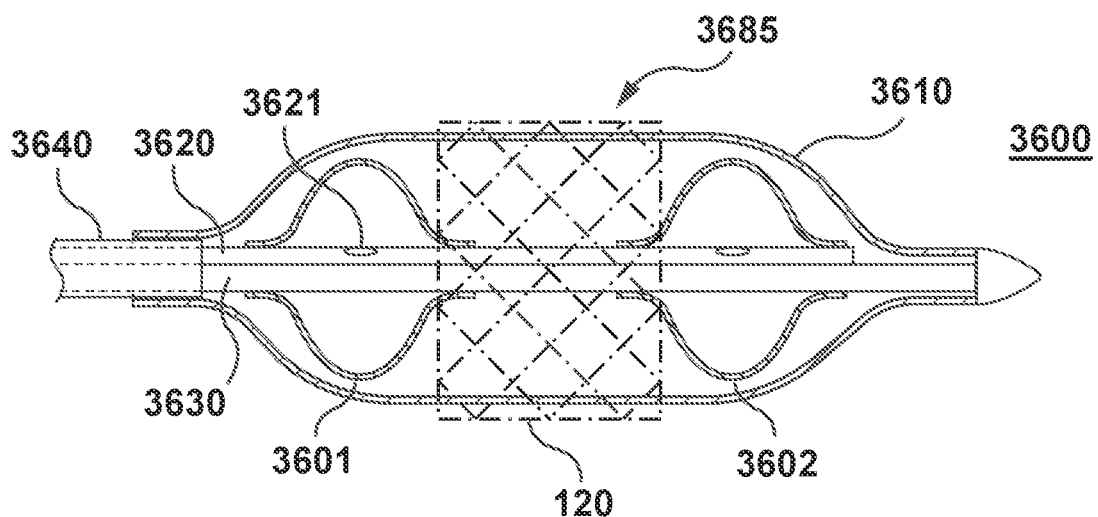

FIGS. 36A-36C illustrate a triple balloon catheter 3600 configured to provide valve stability during delivery and deployment. The balloon catheter 3600 includes at least a balloon 3610, retention balloons 3601 and 3602, an inner shaft 3630, an inflation shaft 3620, and an outer shaft 3640. The balloon catheter 3600 is configured for delivering a prosthetic heart valve 120 and may include any or all features and aspects of the balloon catheter 400. The balloon catheter 3600 further includes a distal portion 3685, within which the balloon 3610 is disposed.

The retention balloons 3601 and 3602 are flexible inflatable structures sealed around the inner shaft 3630 and inflation shaft 3620 on either side of the prosthetic heart valve 120. The retention balloons 3601 and 3602 may be inflated via fluid pressure applied through the injection of inflation fluid through the inflation ports 3621. The inflation ports 3621 are ports, holes, skives, or openings in the inflation shaft 3620 that permit inflation fluid to flow into the interior of the retention balloons 3601 and 3602. Each retention balloon 3601 and 3602 may have one or more inflation ports 3621 associated with it.

The retention balloons 3601 and 3602 may be configured to act as retention bumpers during valve delivery. The retention balloons 3601 and 3602 may act as retention bumpers during valve delivery at various inflation levels, as discussed below.

In embodiments, the retention balloons 3601 and 3602 may be inflated from a first radially unexpanded size to a second radially expanded size having a diameter large enough to maintain an axial position of the prosthetic heart valve 120 during a delivery operation. During a valve delivery procedure, the retention balloons 3601 and 3602 may be inflated prior to insertion of the balloon catheter 3600 into a guide catheter. The first radially unexpanded size of the retention balloons 3601 and 3602 is illustrated in FIG. 36A. As shown in FIG. 36A, at the first radially unexpanded size, the additional material of the retention balloons 3601 and 3602 causes a bulge in the balloon 3610, which may serve as a retention bumper to maintain the position of the prosthetic heart valve 120 during a delivery operation. In further embodiments, the retention balloons 3601 and 3602 may be wrapped in a lower profile such that the balloon 3610 does not bulge around the retention balloons 3601 and 3602. The second radially expanded size of the retention balloons 3601 and 3602 is illustrated in FIG. 36B. The retention balloons 3601 and 3602 are shown larger than actual size for the purposes of illustration and are not drawn to scale with the other aspects of the catheter 3600. The first radially unexpanded size may have a diameter of approximately 0.2 inches to correspond with a size of the balloon opening. In further embodiments, the first radially unexpanded size may have a diameter between 0.1 and 0.25 inches. The second radially expanded size of the retention balloons 3601 and 3602 is large enough to provide valve retention during a delivery operation. For example, the second radially expanded size, illustrated in FIG. 36B, may be approximately 0.3 inches. In further embodiments, the second radially expanded size of the retention balloons 3601 and 3602 may have a diameter between 0.25 and 0.35 inches. In embodiments, even when un-inflated, additional material of the retention balloons 3601 and 3602 may create a retention bumper, e.g., as shown in FIG. 36A. In embodiments, the retention balloons 3601 and 3602 may be un-inflated, partially inflated, or fully inflated during a delivery operation.

The retention balloons 3601 and 3602 are further configured to maintain an axial position of the prosthetic heart valve 120 during a valve deployment procedure. After navigating the balloon catheter 3600 to a treatment site, the prosthetic heart valve 120 is deployed. As discussed above, balloon catheter deployment can cause inaccuracies in deployment due to asymmetric balloon inflation. During a valve deployment procedure using the balloon catheter 3600, the retention balloons 3601 and 3602 are inflated prior to inflation of the balloon 3610. As discussed above, inflation may occur prior to valve delivery. If embodiments, the retention balloons 3601 and 3602 may be further inflated after valve delivery and prior to valve deployment. Inflation of the retention balloons 3601 and 3602 serves to stabilize the prosthetic heart valve 120 and maintain its axial position during deployment. After delivery of the prosthetic heart valve 120 to the target location, the balloon 3610 is inflated. FIG. 36C shows the balloon 3610 in a fully inflated configuration. As noted above, the retention balloons 3601 and 3602 are not shown to scale. In use, the balloon 3610 may be inflated to a diameter significantly larger than the second radially expanded diameter of the retention balloons 3601 and 3602. Even if balloon 3610 inflates asymmetrically or unevenly, the prosthetic heart valve 120 cannot migrate axially during deployment due to the inflated retention balloons 3601 and 3602.

Although the second radially expanded size of the retention balloons 3601 and 3602 is large enough to serve as a retention bumper, the second radially expanded size may not represent a maximum inflation size of the retention balloons 3601. In embodiments, the retention balloons 3601 and 3602 may be inflated to the second radially expanded size during valve delivery to maintain a position of the prosthetic heart valve. Then, prior to valve deployment, the retention balloons 3601 and 3602 may be inflated further, to an expanded deployment size. The expanded deployment size is larger than the second radially expanded size and is not used during valve delivery because it may be too large to fit through a guide catheter. In further embodiments, the retention balloons 3601 and 3602 may be employed with any or all of the various retention bumpers disclosed herein. In such embodiments, the retention balloons 3601 and 3602 may be used either during valve delivery to augment the function of the retention bumpers or during valve deployment to increase deployment accuracy.

During use, inflation fluid may be provided to the balloon 3610 via several different means. In embodiments, the lumen defined by the space in the outer shaft 3640 not occupied by the inner shaft 3630 and the inflation shaft 3620 may be used to deliver inflation fluid to the balloon 3610. In embodiments, the inflation shaft 3620 may be provided with additional inflation ports to supply inflation fluid to the balloon 3610. In embodiments, such additional inflation ports may open only when a specific level of pressure within the inflation shaft is achieved, as discussed below with respect to the proximal valved inflation ports 3952 of FIGS. 39A-39D.

FIGS. 37A-37B illustrate a balloon catheter 3700 having a protected balloon inflation lumen. FIG. 37A shows the balloon catheter 3700 in profile, while FIG. 37B shows a cross-section of the balloon catheter 3700. The balloon catheter 3700 includes at least a balloon 3710, retention bumpers 3701 and 3702, an inner shaft 3730, and an outer shaft 3740. Further, the balloon catheter 3700 includes a balloon inflation lumen 3731 having one or more inflation ports 3732. The one or more inflation ports 3732 may be located at a distal end of the balloon 3710. In further embodiments, one or more inflation ports 3732 may be located in several places along the length of the inner shaft 3730 inside the balloon 3710. The balloon inflation lumen 3731 is included in the inner shaft 3730 running at least the length of the balloon 3710. Also included in the inner shaft 3730 is a guidewire lumen 3765. The balloon inflation lumen 3731 may be defined by an additional shaft inside of the inner shaft 3730 and/or may be enclosed or defined by an additional wall of the inner shaft 3730, as shown in FIG. 37B. In embodiments, the balloon inflation lumen 3731 runs the entire length of the catheter 3700 and receives inflation fluid at the proximal handle. In embodiments, the outer shaft 3740 delivers additional inflation fluid to the proximal portion of the balloon via an annular lumen between the inner shaft 3730 and the outer shaft 3740. In embodiments, the balloon inflation lumen 3731 begins at any location between the proximal handle and the balloon 3710 and receives inflation fluid transported via the outer shaft 3740 through one or more openings or ports. The balloon catheter 3700 is configured for delivering a prosthetic heart valve (not pictured) and may include any or all features and aspects of the balloon catheter 400.

As discussed above, among the reasons that retention bumpers may be necessary in a balloon catheter is that the prosthetic heart valve is not crimped tightly enough to the balloon to prevent migration during a delivery operation. The prosthetic heart valve is often loosely crimped to the balloon to prevent the tight crimping from causing uneven fluid flow during inflation of the balloon. Some balloon catheters are inflated from a proximal end of the balloon. If the balloon is tightly folded to the inner shaft with a prosthetic heart valve tightly crimped around it to compress it further, it can interfere with fluid flow to the distal end of the balloon. Such interference results in greater pressure at the proximal end of the balloon and uneven balloon inflation, which can cause prosthetic heart valve migration during the inflation procedure. The balloon inflation lumen 3731 is protected by virtue of being interior to the inner shaft 3730. During use, inflation fluid is supplied to the balloon 3710 via the balloon inflation lumen 3731 through the one or more inflation ports 3732. The prosthetic valve can therefore be crimped tightly to the balloon 3710 without concern that fluid flow to the distal end of the balloon 3710 will be inhibited. The tighter crimping permits the use of smaller retention bumpers 3701 and 3702 sized such that they will fit into the balloon 3710 through the balloon opening during assembly. Retention bumpers 3701 and 3702 may be sized and configured such that they can readily be inserted into an opening of the balloon 3710 during the assembly process without need for expansion of either the balloon opening or the retention bumpers 3701/3702. For example, the retention bumpers 3701 and 3702 may have a diameter between approximately 0.1 inches and 0.25 inches.

Figure 38A:
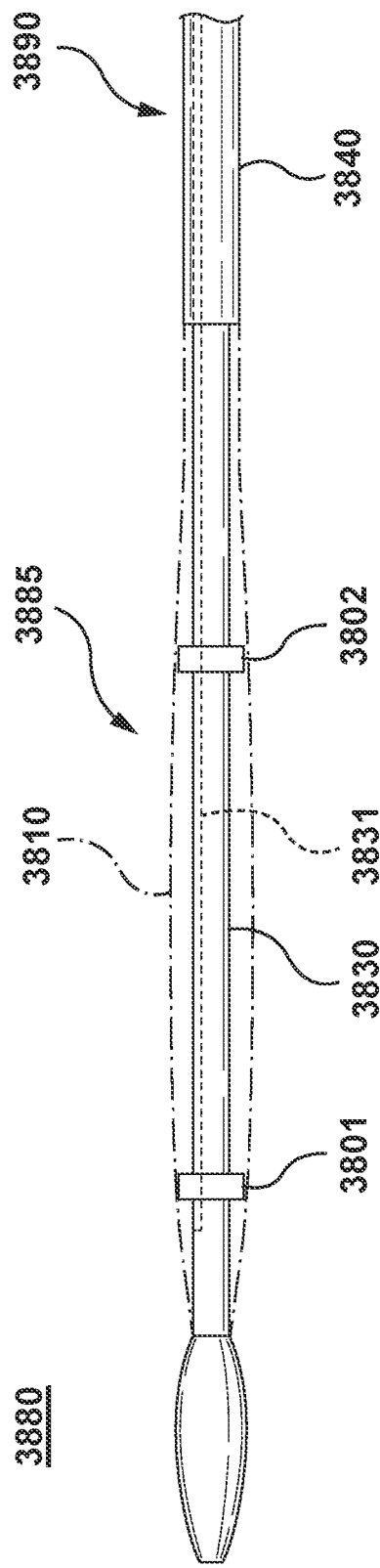
FIGS. 38A and 38B illustrate a balloon catheter having a protected balloon inflation lumen.
Figure 38B:
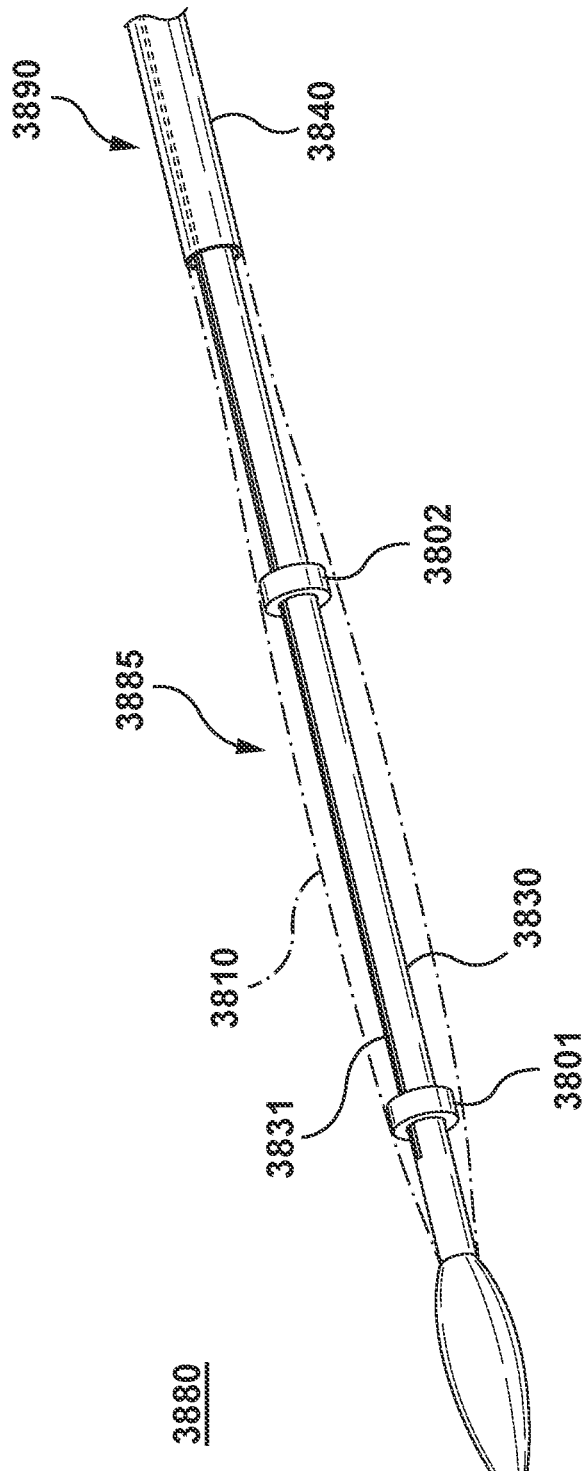

FIGS. 38A and 38B illustrate a balloon catheter 3800 having a protected balloon inflation lumen. The balloon catheter 3800 includes at least a balloon 3810, retention bumpers 3801 and 3802, an inner shaft 3830, and an outer shaft 3840. Further, the inner shaft 3830 includes one or more inflation channels 3831. The inflation channel 3831 is a slot or channel cut into the side of the inner shaft 3830 running the length of the balloon 3810. The balloon catheter 3800 is configured to deliver and deploy a prosthetic heart valve (not pictured) and may include any or all features and aspects of the balloon catheter 400. Balloon catheter 3800 further includes a distal portion 3885, within which the balloon 3810 is disposed, and a proximal portion 3890.

The inflation channel 3831 operates in a fashion similar to that described above with respect to inflation lumen 3731. The inflation channel 3831, by virtue of being a channel or slot cut into the inner shaft 3830, is protected from interference by a tightly folded balloon 3810 with a prosthetic heart valve tightly crimped around it to compress it further. Even if the balloon 3810 is tightly folded to the inner shaft 3830 with a prosthetic heart valve tightly crimped around it, the recessed area of the inflation channel 3831 continues to provide an unimpeded flow pathway to the distal end of the balloon 3810 to facilitate even inflation. The unimpeded flow pathway within the inflation channel 3831 provides a low pressure pathway from the proximal end of the balloon 3810 to the distal end of the balloon 3810. The pressure of the wrapped balloon keeps the inflation fluid in the inflation channel 3831 until the pressure within is high enough to cause the balloon 3810 to begin expanding. At that point, pressure from the inflation fluid will be supplied across the entire length of the inflation channel 3831. Accordingly, because the balloon may be crimped tighter, the retention bumpers 3801 and 3802 may be of a smaller diameter sufficient to be inserted into a balloon opening. Retention bumpers 3801 and 3802 may be sized and configured such that they can readily be inserted into an opening of the balloon 3810 during the assembly process without need for expansion of either the balloon opening or the retention bumpers 3801/3802. For example, the retention bumpers 3801 and 3802 may have a diameter between approximately 0.1 inches and 0.25 inches.

Throughout the foregoing description, the previously discussed bumpers are described as being secured to an inner shaft of a balloon catheter. In some designs, a balloon catheter may have different or alternative shaft designs running through the balloon. For example, an inflation shaft with inflation holes may run through the balloon of the balloon catheter. All of the retention bumper embodiments, as discussed herein, as well as the balloon processing methods and structural balloon designs, may be modified for use with any shaft or component that runs through the balloon of the balloon catheter, and are not limited to use with an inner shaft as described in FIG. 4A.

Described above are multiple prosthetic valve retention bumper systems, embodied variously to include expandable retention bumpers, balloon alterations, and fluid delivery alterations. None of the above-described embodiments are exclusive and each may be employed in a balloon catheter with any other valve retention bumper system described herein. For example, a balloon catheter may employ both an expandable retention bumper and an altered balloon. In another example, two different types or styles of retention bumpers may be employed to prevent proximal migration. Any suitable combination of valve retention bumper systems may be employed.

FIGS. 39A-39D illustrate a valved balloon inflation shaft 3950. The balloon inflation shaft 3950 is compatible with balloon catheters described herein and functions similarly to the balloon inflation shaft 3620. The balloon inflation shaft 3950 may be used in conjunction with an inner shaft 3930 similar to inner shafts described herein. The balloon inflation shaft 3950 may be configured at a proximal end to receive inflation fluid delivered to the inflation lumen 3947 between the inflation shaft 3950 and the inner shaft 3930. The following description describes the balloon inflation shaft 3950 as employed with the balloon catheter 3700, but its use is not limited to the balloon catheter 3700. The balloon inflation shaft 3950 is configured to preferentially provide inflation fluid to a distal portion of the balloon 3710 to prevent asymmetrical balloon inflation. The balloon inflation shaft 3950 includes one or more distal inflation ports 3951 and one or more proximal valved inflation ports 3952 covered by an inflation valve 3953. The one or more distal inflation ports 3951 are configured to provide fluid access to a distal portion of the balloon 3710 during valve deployment. The distal inflation ports 3951 are unobstructed. The one or more proximal valved inflation ports 3952 are configured to provide fluid access to a proximal portion of the balloon 3710. The proximal valved inflation ports 3952 each include an inflation valve 3953.

The flap valve cover 3933 includes at least one flap configured to give way when an interior pressure threshold of the inflation lumen inside the balloon inflation shaft 3950 is reached. The flap valve cover 3933 may be formed by one or more devices attached to the exterior of the balloon inflation shaft 3950 over the proximal inflation valve 3953. In embodiments, the flap valve cover 3933 is formed by weakening portions of the balloon inflation shaft 3950.

During prosthetic heart valve deployment, inflation fluid is pumped through the balloon inflation shaft 3950. Due to the lack of obstruction at the distal inflation port 3951, the fluid preferentially flows to the distal inflation port 3951. As the inflation fluid exits the distal inflation port 3951, it encounters resistance from the balloon 3710, causing the pressure of the inflation fluid to increase. When the inflation fluid pressure passes a threshold, the inflation valve 3953 of the proximal valved inflation ports 3952 gives way, as shown in FIGS. 39C and 39D, permitting inflation fluid to enter the proximal portion of the balloon 3710. An open proximal valved inflation port 3952 is illustrated in FIGS. 39C and 39D. The valved inflation shaft 3950 therefore functions to permit a fluid pathway to the distal portion of the balloon 3710 to be established prior to the proximal portion of the balloon 3710 beginning inflation. This reduces the possibility of asymmetric inflation caused by lack of inflation fluid flow to the distal portion of the balloon 3710. The pressure threshold required for the inflation valve 3953 to give way may be varied depending on a desired inflation profile of the balloon 3710. For example, if it is desired that the proximal and distal portions of the balloon 3710 begin inflating at the same time, the pressure threshold may be set equal to or slightly below the pressure required to begin initial inflation of the balloon. If it is desired that the distal portion of the balloon 3710 begin inflating before the proximal portion, the pressure threshold may be set such that the required pressure to open the inflation valve 3953 is not achieved until after initiation of balloon inflation at the distal portion.

Figure 40:
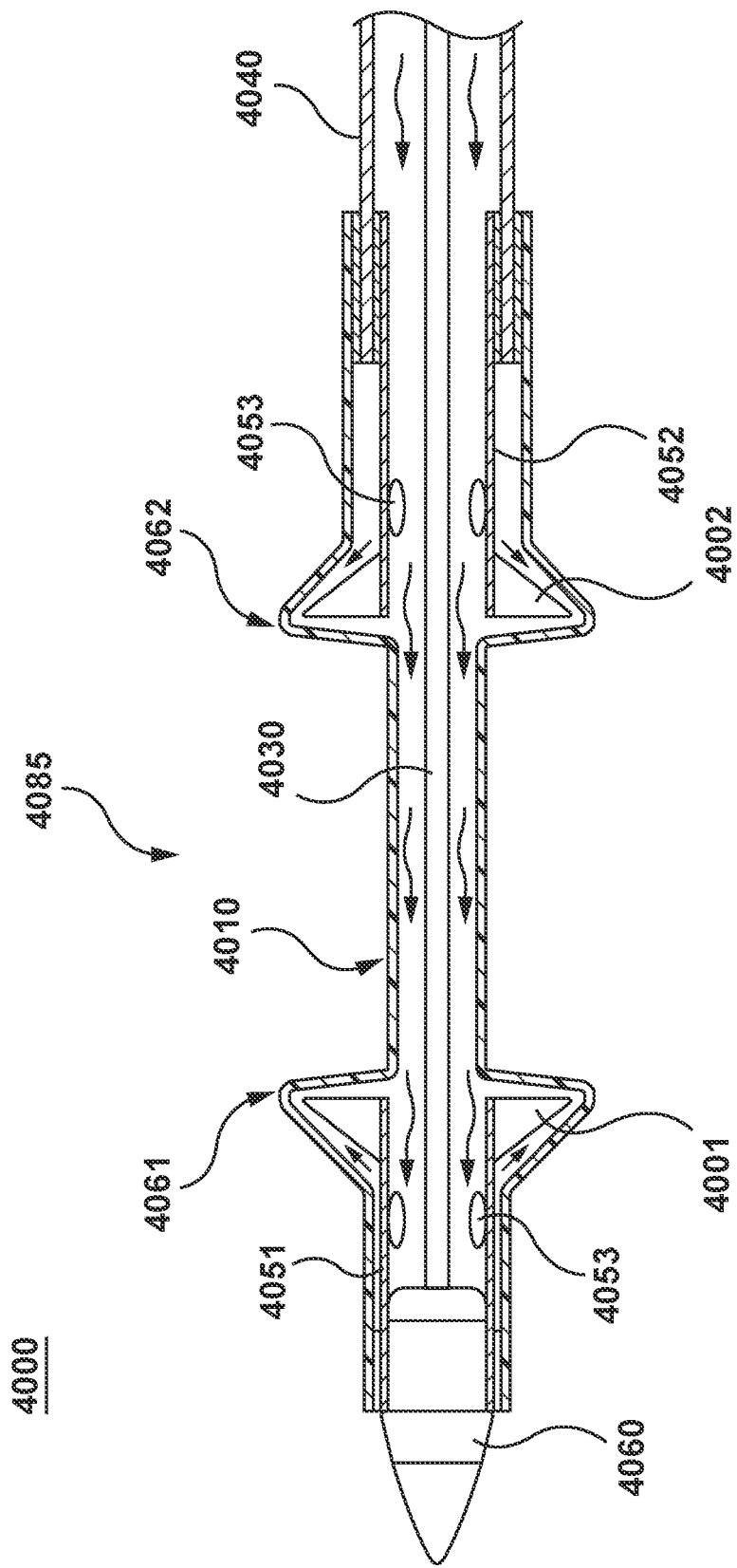
FIG. 40 illustrates a balloon catheter employing a combination of retention bumpers and flow improvement aspects.

FIG. 40 illustrates a balloon catheter 4000 employing a combination of retention bumpers and flow improvement aspects. The balloon catheter 4000 include at least a balloon 4010, retention bumpers 4001 and 4002, a distal tip 4060, an inner shaft 4030, an outer shaft 4040, a proximal flow guide 4052 and a distal flow guide 4051. The balloon catheter 4000 is configured for delivering a prosthetic heart valve and may include any or all features and aspects of the balloon catheter 400. The balloon catheter 4000 further includes a distal portion 4085, within which the balloon 4010 is disposed. The retention bumpers 4001 and 4002 are secured to the distal flow guide 4051 and the proximal flow guide 4052, respectively. The retention bumpers 4001 and 4002 may be any of the retention bumpers described herein. The balloon 4010 is secured over and around the retention bumpers 4001 and 4002, thereby forming cone portions 4061 and 4062 in the portions covering the retention bumpers 4001 and 4002. The balloon catheter 4000 is configured to deliver and deploy a prosthetic heart valve (not pictured) and may include any or all features and aspects of the balloon catheter 400.

The proximal flow guide 4052 and the distal flow guide 4051 each include one or more fluid guide ports 4053. The fluid guide ports 4053 are located or positioned so as to provide preferential fluid flow to the cone portions 4061 and 4062 of the balloon 4010 in the vicinity of the retention bumpers 4001 and 4002. Such preferential flow causes the cone portions 4061 and 4062 to inflate before the remainder of the balloon 4010 during valve deployment. Early inflation of the cone portions 4061 and 4062 provides stabilization of the prosthetic valve during deployment, preventing migration either axially or distally.

Figure 41:
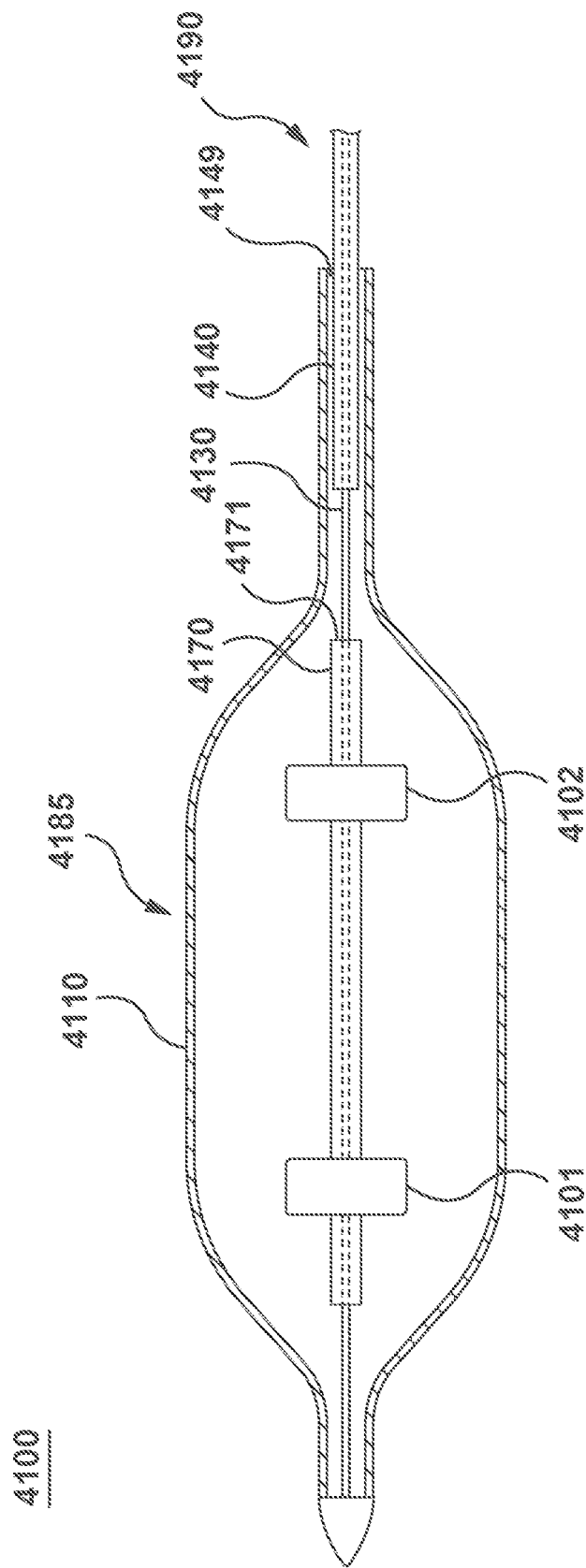
FIG. 41 illustrates a balloon catheter including a flow guide and retention bumpers.

FIG. 41 illustrates a balloon catheter 4100 including a flow guide and retention bumpers. The balloon catheter 4100 include at least a balloon 4110, retention bumpers 4101 and 4102, an inner shaft 4130, an outer shaft 4140, and a flow guide 4170. The balloon catheter 4100 is configured for delivering a prosthetic heart valve and may include any or all features and aspects of the balloon catheter 400. The balloon catheter 4100 further includes a distal portion 4185, within which the balloon 4110 is disposed. The retention bumpers 4101 and 4102 are secured to the flow guide 4170. The retention bumpers 4101 and 4102 may be any of the retention bumpers described herein. The balloon catheter 4100 is configured to deliver and deploy a prosthetic heart valve (not pictured) and may include any or all features and aspects of the balloon catheter 400.

The flow guide 4170 runs from a proximal end to a distal end of the balloon 4110 and is disposed over the inner shaft 4130. Between the flow guide 4170 and the inner shaft 4130, an annular lumen 4171 is formed. The flow guide 4170 traverses the distal portion 4185 of the balloon catheter 4100. The flow guide 4170 is secured to the inner shaft 4130, for example, via adhesives or bonding or other techniques that still permit the annular lumen 4171 to carry inflation fluid. The annular lumen 4171 preserves a fluid channel from the proximal portion of the balloon 4110 to the distal portion of the balloon 4110. Inflation fluid is supplied to the balloon 4110 via a lumen between the inner shaft 4130 and the outer shaft 4140. The inflation fluid is released in a proximal portion of the balloon 4110. The flow guide 4170 ensures that an unimpeded fluid channel is provided between the proximal portion of the balloon 4110 and the distal portion of the balloon 4110, and thereby prevent preferential inflation of the proximal portion of the balloon 4110, where the inflation fluid is delivered via the outer shaft 4140, to the distal end of the balloon 4110. The fluid channel provided by the annular lumen 4171 is not minimized or eliminated by the crimping of a prosthetic heart valve over the balloon 4110. Thus, the annular lumen 4171 permits balanced inflation fluid delivery between the proximal and distal portions of the balloon 4110. In additional embodiments, the flow guide 4170 may be configured with one or more inflation ports similar to the fluid guide ports 4053 described with respect to FIG. 40.

FIGS. 42A and 42B illustrate a balloon catheter 4200 including a ported flow guide and retention bumpers. The balloon catheter 4200 includes at least a balloon 4210, retention bumpers 4201 and 4202, an inner shaft 4230, an outer shaft 4240, and a ported flow guide 4270. The balloon catheter 4200 is configured for delivering a prosthetic heart valve and may include any or all features and aspects of the balloon catheter 400. The balloon catheter 4200 further includes a distal portion 4285, within which the balloon 4210 is disposed. The retention bumpers 4201 and 4202 are secured to the ported flow guide 4270. The retention bumpers 4201 and 4202 may be any of the retention bumpers described herein. The balloon catheter 4200 is configured to deliver and deploy a prosthetic heart valve (not pictured) and may include any or all features and aspects of the balloon catheter 400.

The flow guide 4270 runs from a proximal end to a distal end of the balloon 4210 and is disposed over the inner shaft 4130. The proximal end of the flow guide 4270 may extend into the outer shaft 4240 and/or terminate prior to reaching the outer shaft 4240. Between the flow guide 4270 and the inner shaft 4230, an annular lumen 4272 is formed. Similar to the annular lumen 4171 described above, the annular lumen 4271 preserves an inflation fluid channel between the proximal end and the distal end of the balloon 4210.

The ported flow guide 4270 includes one or more inflation fluid ports 4271. The inflation fluid ports 4271 may be holes, skives, cut-outs, notches, or any other form or shape of opening in the ported flow guide 4270. The inflation fluid ports 4271 are arranged along the length of the ported flow guide 4270 to direct flow of the inflation fluid for valve deployment. The inflation fluid ports 4271 may be arranged to provide balanced inflation fluid flow to the balloon 4210 during valve deployment. For example, the inflation fluid ports 4271 may be arranged such that there are more or larger inflation fluid ports 4271 at the distal end of the ported flow guide 4270 to facilitate flow to the distal end of the balloon 4210. This reduces the pressure required for inflation fluid to reach the distal end of the balloon 4210, thereby resulting in more balanced fluid flow between the proximal ends and distal ends of the balloon 4210. In embodiments, the ported flow guide 4270 may be a hypo tube and the inflation fluid ports 4271 may be laser cut for ease of manufacture. Use of a hypo tube may provide additional resistance to crushing forces. In further embodiments, the ported flow guide 4270 may be made of any suitable material and the inflation fluid ports 4271 may be formed by any suitable means.

Figure 43A:
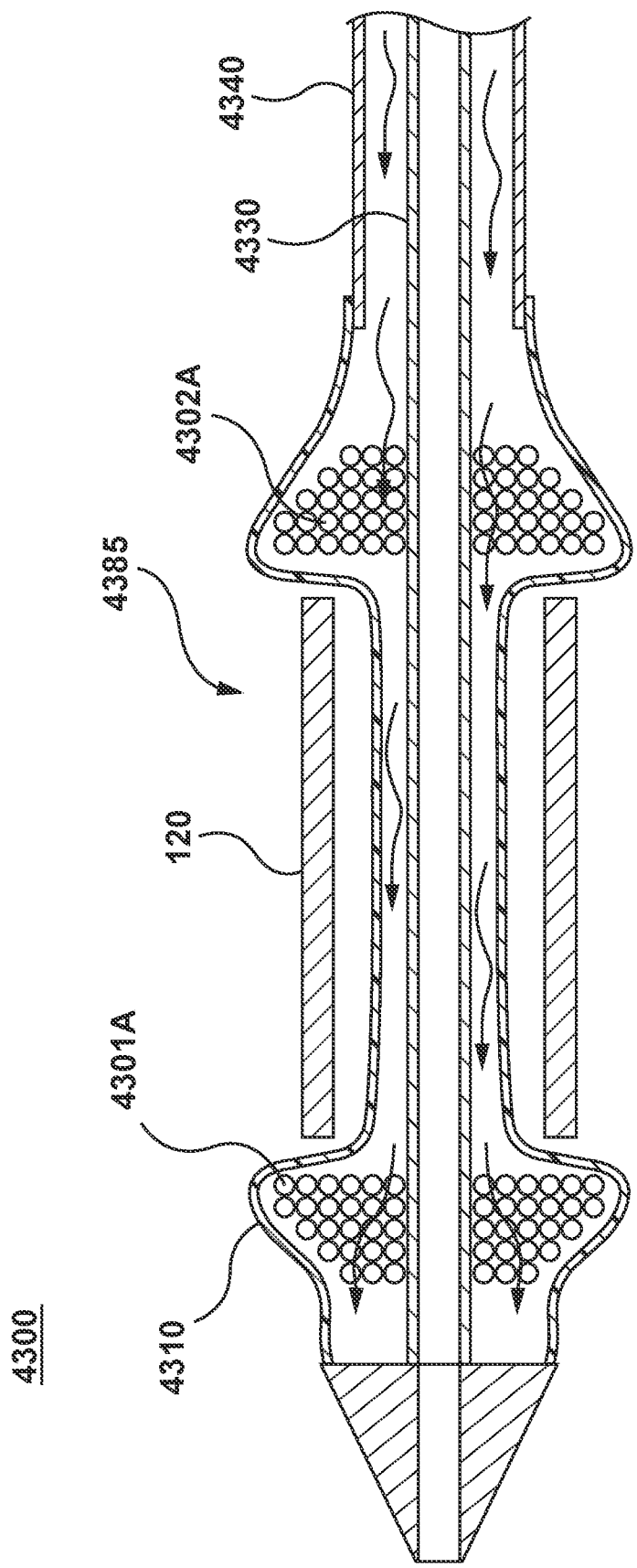
FIGS. 43A-43C illustrate a balloon catheter employing flow through retention bumpers.
Figure 43B:
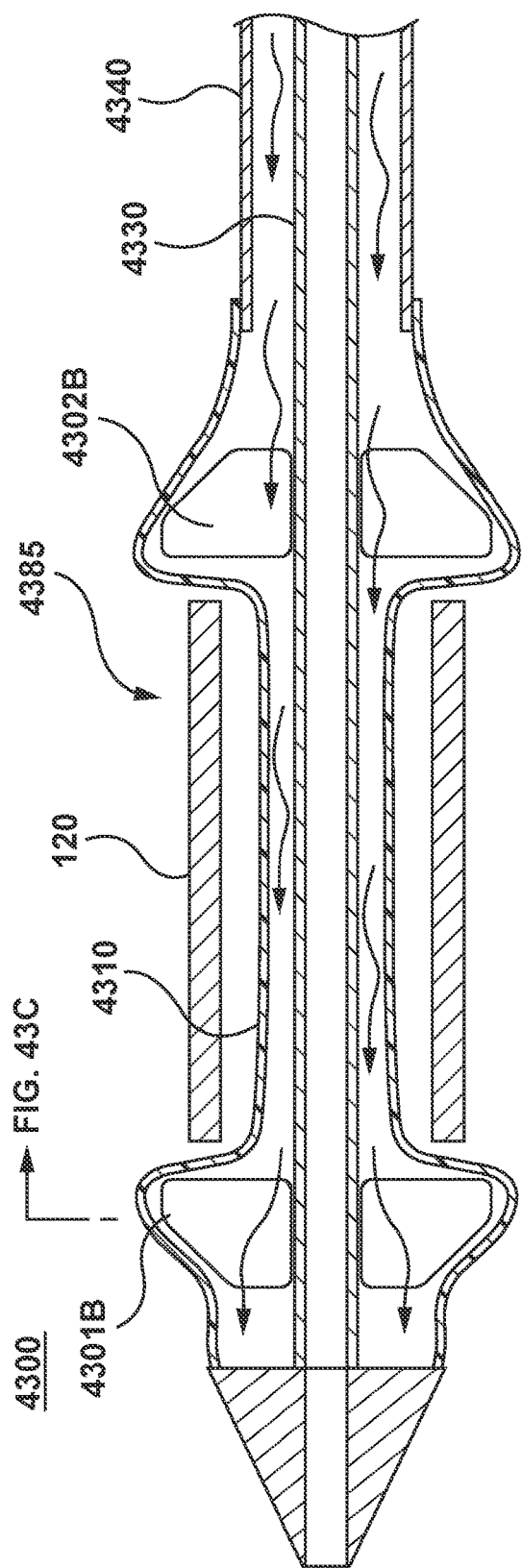
Figure 43C:
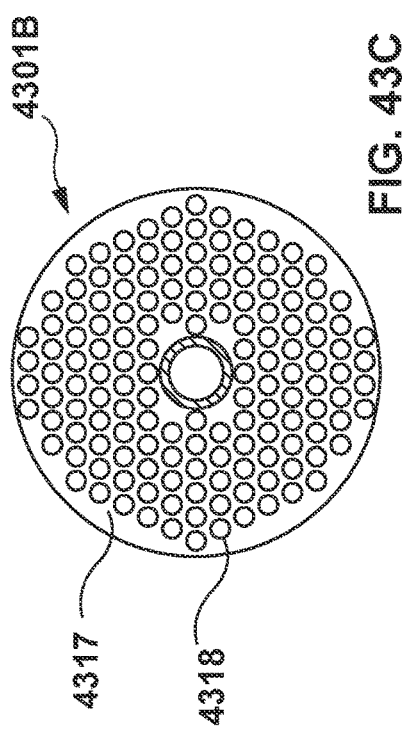

FIGS. 43A-43C illustrate a balloon catheter 4300 employing flow through retention bumpers. The balloon catheter 4300 of FIG. 43A includes at least a balloon 4310, flow through retention bumpers 4301A and 4302A, an inner shaft 4330, an outer shaft 4340. The balloon catheter 4300 is configured for delivering a prosthetic heart valve and may include any or all features and aspects of the balloon catheter 400. The balloon catheter 4300 further includes a distal portion 4385, within which the balloon 4310 is disposed. The balloon catheter 4300 is configured to deliver and deploy a prosthetic heart valve (not pictured) and may include any or all features and aspects of the balloon catheter 400.

The flow through retention bumpers 4301A and 4302A are made of a porous material that permits fluid flow. The flow through retention bumpers 4301A and 4302A may be made of, for example, an open-celled foam material, a cellulose material, and any other material that permits fluid to flow through. In embodiments, the flow through retention bumpers 4301A and 4302A may include sintered ceramic or metallic (e.g., bronze) filters, selective laser sintered polymers, In embodiments, the flow through retention bumpers 4301A and 4302A may be configured with the size, shape, and functionality of any retention bumpers discussed herein. The flow through retention bumpers 4301A and 4302A permit inflation fluid to flow through them. This feature facilitates symmetric inflation of the balloon 4310 because the fluid flow permitted by the flow through retention bumpers 4301A and 4302B serves to aid fluid delivery to both proximal and distal portions of the balloon 4310 in a balanced fashion.

FIG. 43B illustrates flow through retention bumpers 4301B and 4302B. The flow through retention bumper 4301B is illustrated in FIG. 43C in cross-section. The flow through retention bumpers 4301B and 4302B are configured with a honeycomb structure having support portions 4317 and flow channels 4318. The flow through retention bumpers 4301B and 4302B may be formed, for example, of aluminum, steel, titanium, and/or suitable plastics or polymers. The support portions 4317 provide the honeycomb structure with structural stability while also permitting inflation fluid to flow through the bumper via the flow channels 4318. The honeycomb structure of flow through retention bumpers 4301A and 4302B may include any shape or pattern of support portions 4317 and flow channels 4318 and are not limited to the hexagonal structure.

Figure 44D:
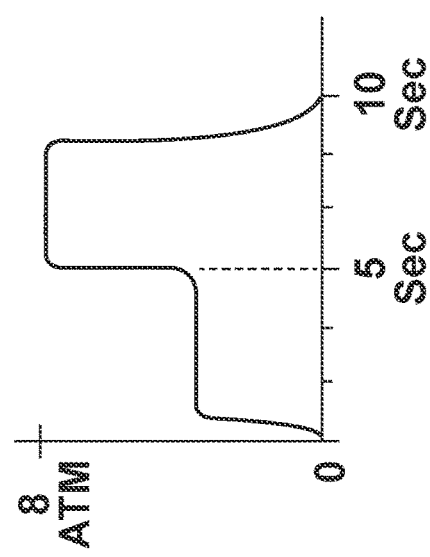

FIGS. 44A-44E illustrate a pressure control system for a balloon catheter 4400. As shown in FIG. 44A, the balloon catheter 4400 includes at least a balloon 4410, retention bumpers 4401 and 4402, an inner shaft 4430, an outer shaft 4440. The balloon catheter 4400 is configured for delivering a prosthetic heart valve and may include any or all features and aspects of the balloon catheter 400. The balloon catheter 4400 further includes a distal portion 4485, within which the balloon 4410 is disposed. The balloon catheter 4400 may include any and all features described herein with respect to the various embodiments of balloon catheters and retention bumpers.

As with other balloon catheters described herein, the outer shaft 4440 of the balloon catheter 4400 extends proximally and is connected to a pressure source 4475. The pressure source 4475 may be a syringe, pump, or any other suitable means for providing pressure to cause inflation fluid to flow through the outer shaft 4440 and into the balloon 4410. Between the pressure source 4475 and the outer shaft 4440 is arranged a pressure control valve 4476. The pressure control valve 4476 operates to regulate the pressure of the inflation fluid injected into the balloon 4410. The pressure control valve 4476 may be configured to reduce an initial pressure rise of the inflation fluid.

FIG. 44B illustrates inflation fluid pressure rise in a balloon catheter operating without the pressure control valve 4476. As shown, the initial pressure rise is sharp leading to a pressure plateau that is maintained to cause inflation of the balloon and deployment of the prosthetic valve. The sharp initial pressure rise may cause asymmetric balloon inflation due to delays in inflation fluid reaching the distal portion of the balloon 4410. The sharp pressure rise provides enough immediate pressure to inflate the proximal portion of the balloon 4410 before the inflation fluid has time to reach the distal portion of the balloon 4410. This may cause asymmetric inflation, as shown in FIG. 44C.

Figure 44E:
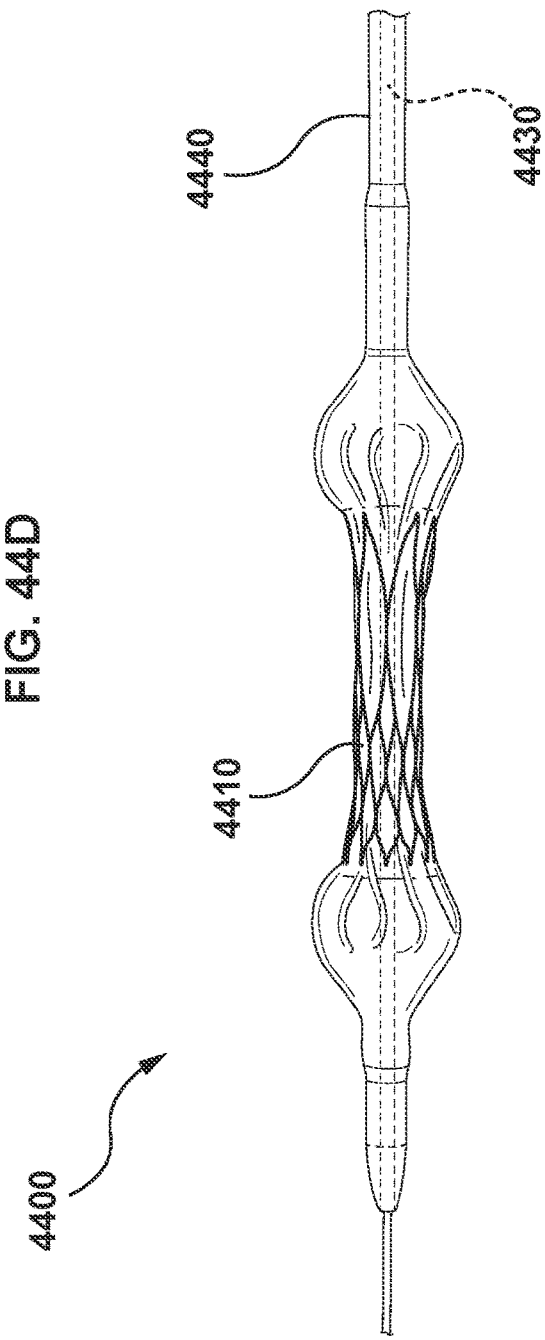

FIG. 44D illustrates inflation fluid pressure rise in the balloon 4410 operating with the pressure control valve 4476. The stepped inflation fluid pressure rise illustrated in FIG. 44D is an example only, and the pressure control valve 4476 may be employed to reduce an initial pressure rise in different patterns, include linear ramps, curved ramps, multiple steps, and other patterns. The reduced initial pressure rise provided by the pressure control valve 4476 reduces the pressure of the inflation fluid initially delivered. The initial pressure of the inflation fluid may be provided at a level great enough to begin balloon inflation but not high enough to begin valve expansion. This control permits time for the inflation fluid to begin expanding the portion of the balloon 4410 distal of the prosthetic heart valve before the heart valve begins to deploy. Thus, both proximal and distal portions of the balloon are permitted time to begin inflation before the pressure is increased to a level that permits valve expansion, as shown in FIG. 44E. Accordingly, operation of the pressure control valve 4476 may facilitate symmetric balloon inflation through pressure control.

FIG. 44A illustrates catheter 4400 including a pressure source 4475 and a pressure control valve 4476 as separate devices. In further embodiments, a controlled pressure source may be employed in place of the separate pressure source 4475 and pressure control valve 4476. For example, a pressure controlled pump may be employed to provide a pressure profile configured to cause symmetric inflation of the balloon 4410.

Figure 45:
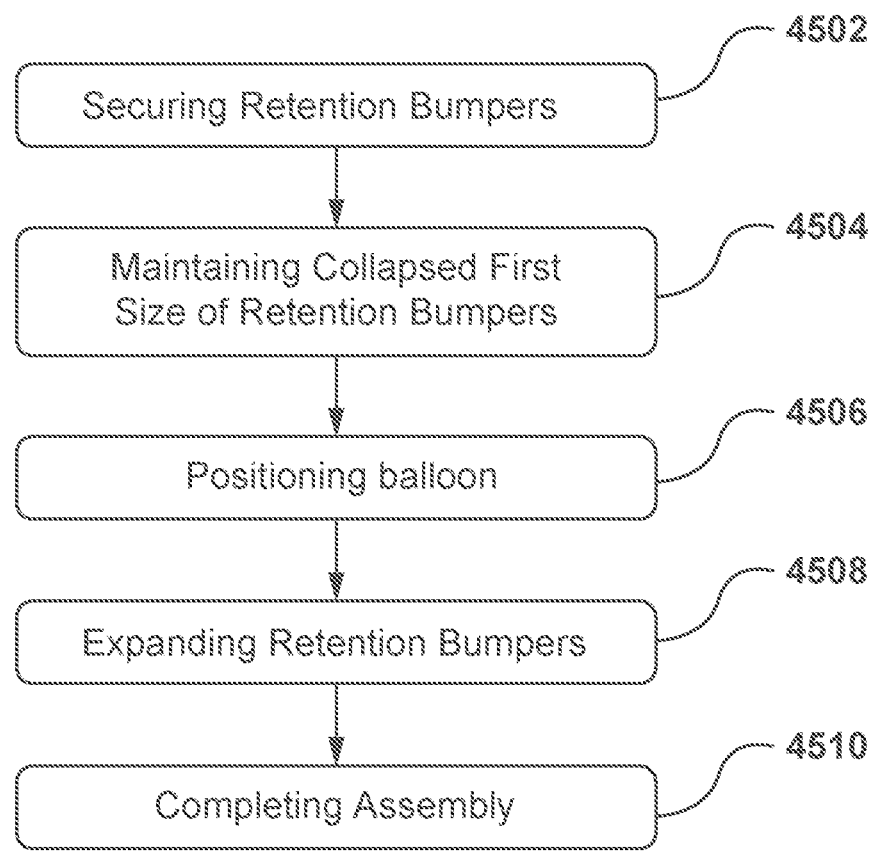
FIG. 45 is a flow chart of a balloon catheter assembly process for assembly of a balloon enabled prosthetic heart valve delivery and deployment system consistent with embodiments described herein.

FIG. 45 is a flow chart of a balloon catheter assembly process 4500 for assembly of a balloon enabled prosthetic heart valve delivery and deployment system consistent with embodiments described herein. The devices and structures described herein reduce or prevent prosthetic heart valve migration during valve delivery. Methods of assembling a balloon catheter described below are consistent with any of the embodiments described herein. In particular, the process 4500 is compatible with embodiments that employ expandable retention bumpers, for example, those embodiments associated with FIGS. 5A-30F, and with any combination of the embodiments described herein. It is not necessary that the following operations of process 4500 occur in the order in which they are described.

In an operation 4502 of balloon catheter assembly process 4500, one or more retention bumpers are secured to an inner shaft of a balloon catheter. As discussed above, in alternative embodiments, the retention bumpers may be secured to any suitable shaft running through the balloon of an assembled balloon catheter.

In an operation 4504, the one or more retention bumpers are maintained at a first radially unexpanded or first radially collapsed size. In embodiments, maintaining the retention bumpers at a first radially collapsed size may involve providing force, pressure, tension, axial force, or another suitable mechanism to prevent the retention bumper from expanding to the second radially expanded size from the first radially collapsed size capable of fitting into an opening of a balloon. In further embodiments, maintaining the retention bumpers at a first radially unexpanded size may involve not providing the force, pressure, tension, axial force, or other suitable mechanism to expand the retention bumpers from the first radially unexpanded size to the second radially expanded size. In further embodiments, maintaining the retention bumpers at the first radially unexpanded size may include not assembling multipart retention bumpers.

In an operation 4506, a balloon of the balloon catheter is disposed over the retention bumpers such that both retention bumpers are inside the balloon. The operation 4506 occurs after the operation 4504, and the retention bumpers at the first radially collapsed or the first radially unexpanded size may be inserted into an opening of the balloon. The operation 4506 may occur before or after the retention bumpers are secured to the inner shaft.

In an operation 4508, the retention bumpers are expanded from the first radially collapsed or the first radially unexpanded size to the second radially expanded size. In embodiments, expanding the retention bumpers to the second radially expanded size may involve providing force, pressure, tension, inward axial force, or another suitable mechanism to cause the retention bumper to expand from the first radially unexpanded size capable of fitting into an opening of a balloon to the second radially expanded size capable of restraining movement of the prosthetic heart valve. In further embodiments, expanding the retention bumpers to the second radially expanded size may involve releasing the force, pressure, tension, inward axial force, or other mechanism that is maintaining the retention bumpers at the first radially collapsed size. In further embodiments, expanding the retention bumpers to the second radially expanded size may involve assembling a multipart bumper.

In an operation 4510, assembly of the balloon catheter is completed. Completing balloon catheter assembly may involve steps such as folding the balloon, attaching the inner shaft and the outer shaft to a proximal handle, sealing the balloon to the outer shaft, attaching a distal tip to the balloon catheter, crimping a prosthetic heart valve over the balloon, and any other step required to complete assembly of the balloon catheter.

Figure 46:
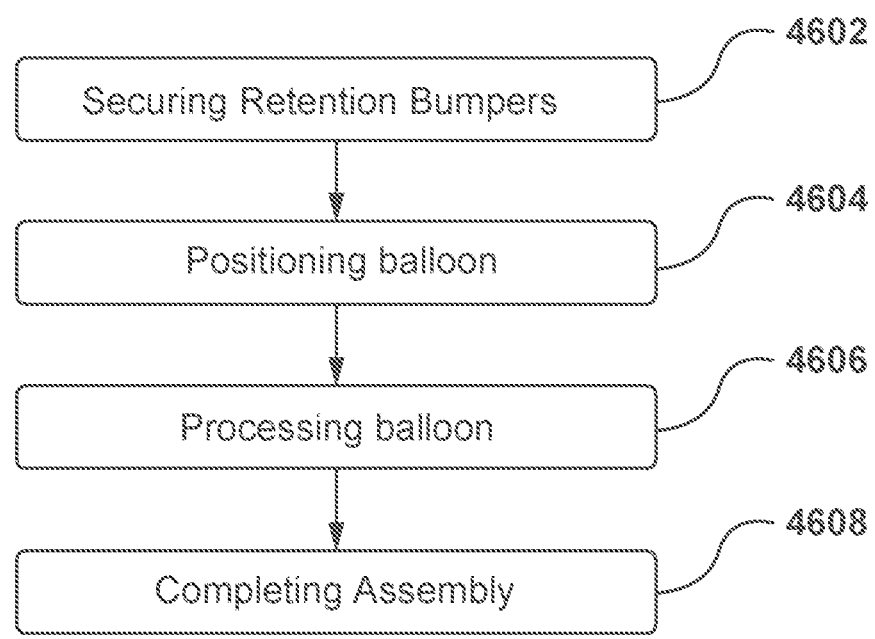
FIG. 46 is a flow chart of a balloon catheter assembly process for a balloon enabled prosthetic heart valve delivery and deployment system consistent with embodiments described herein.

FIG. 46 is a flow chart of a balloon catheter assembly process 4600 for a balloon enabled prosthetic heart valve delivery and deployment system consistent with embodiments described herein. The devices and structures described herein reduce or prevent prosthetic heart valve migration during valve delivery. Methods of assembling a balloon catheter described below are consistent with any of the embodiments described above, and with any combination of the embodiments described herein. In particular the balloon catheter assembly process 4600 is compatible with balloon catheters that include additional processing during assembly, such as those embodiments associated with FIGS. 31A-34B. It is not necessary that the following operations of process 4600 occur in the order in which they are described. In the following discussion of process 4600, the retention bumpers are referred to as "large" and "small." Large retention bumpers as discussed with respect to process 4600 have a diameter equivalent to that previously discussed with respect to the second radially expanded size, e.g., approximately 0.25 inches to 0.35 inches, capable of functioning to prevent migration of a prosthetic heart valve. Small retention bumpers as discussed with respect to process 4600 have a diameter equivalent to that previously discussed with respect to the first radially collapsed or radially unexpanded size, e.g., approximately 0.1 inches to 0.25 inches, capable of insertion into the opening of a balloon sized for secure attachment to a balloon catheter.

In an operation 4602, one or more retention bumpers are secured to an inner shaft of a balloon catheter. Depending on the balloon catheter embodiment being assembled, these may be large or small retention bumpers. As discussed above, in alternative embodiments, the retention bumpers may be secured to any suitable shaft running through the balloon of an assembled balloon catheter.

In an operation 4604, a balloon of the balloon catheter is positioned over the retention bumpers such that both of the retention bumpers are inside the balloon. The opening of the balloon, at this stage of the assembly process, has a diameter of sufficient size to admit the retention bumpers, whether they are large or small.

In an operation 4606, the balloon is further processed. In embodiments, neck portions of the balloon may be further processed to reduce their diameter from a size capable of admitting large retention bumpers to a size capable of providing secure inflation, e.g., as discussed with respect to FIGS. 18A-18B. In another embodiment, the entire balloon may be further processed via a blow molding technique, e.g., as discussed with respect to FIGS. 32A-32C, to reduce the size of a balloon opening from a size capable of admitting large retention bumpers to a size capable of providing secure inflation and to finish processing other portions of the balloon. In other embodiments, further processing of the balloon may involve folding the balloon and crimping a prosthetic valve over the balloon such that small retention bumpers, in conjunction with the folded balloon and position of the crimped prosthetic valve, are able to adequately prevent migration of the prosthetic heart valve during a trans vascular delivery operation.

In an operation 4608, assembly of the balloon catheter is completed. Completing balloon catheter assembly may involve steps such as folding the balloon, attaching the inner shaft and the outer shaft to a proximal handle, sealing the balloon to the outer shaft, attaching a distal tip to the balloon catheter, crimping a prosthetic heart valve over the balloon, and any other step required to complete assembly of the balloon catheter.

Further embodiments of balloon catheters consistent with embodiments hereof including one or more valve retention devices configured to prevent or reduce valve migration during delivery are presented herein with respect to FIGS. 47A-57.

FIG. 47A illustrates a balloon catheter 400A employing retention bumpers as valve retention devices according to embodiments hereof. Retention bumpers 401A, 402A act as valve retention devices to maintain the position of a prosthetic heart valve mounted on the balloon catheter 4700A. Balloon catheter 4700A further includes a balloon 4710A an inner shaft 4730A and an outer shaft 4740A. The balloon catheter 4700A further includes a distal portion 4785A and a proximal portion 4790A. Also illustrated in FIG. 47A is the prosthetic heart valve 120 crimped onto the balloon 4710A. The retention bumpers 4701A, 4702A are disposed in the distal portion 4785A of the balloon catheter 4700A beneath the balloon 4710A. The retention bumpers 4701A, 4702A are attached to the inner shaft 4730A. In further embodiments, retention bumpers 4701A, 4702A may be secured via alternative means. The balloon catheter 4700A is configured to deliver and deploy a prosthetic heart valve (not pictured) and may include any or all features and aspects of the balloon catheter 400.

The retention bumpers 4701A, 4702A function to maintain an axial position of the prosthetic heart valve 120. The retention bumpers 4701A, 4702A are positioned adjacent to the prosthetic heart valve 120 so as to maintain an axial position, i.e., prevent or reduce axial migration, through contact. In particular, as shown in FIG. 47A, the retention bumper 4701A is positioned adjacent the proximal end 122 of the prosthetic heart valve 120 and the retention bumper 4702A is positioned adjacent the distal end 121 of the prosthetic heart valve 120. When subject to proximal or distal forces, the prosthetic heart valve 120 presses up against the portion of the balloon 4710A raised by the retention bumpers 4701A, 4702A, which arrests the movement of the prosthetic heart valve 120.

The retention bumpers 4701A, 4702A may also function to reduce forces acting on the prosthetic heart valve 120. The retention bumpers may be sized such that they (or the balloon 4710A covering them) extend further radially outward than the prosthetic heart valve 120. Thus, the features of the balloon catheter 4700A having the largest diameter are the retention bumpers and not the prosthetic heart valve 120. When inserted into an introducer, the retention bumpers 4701A, 4702A therefore are the portion of the balloon catheter 4700A that contacts the introducer wall, thereby preventing the wall of the introducer from contacting the prosthetic heart valve 120 and reducing the amount of force acting on the prosthetic heart valve from the inner walls of the introducer.

FIG. 47B illustrates a balloon catheter employing retention bumpers as valve retention devices according to embodiments hereof. Retention bumpers 4701B, 4702B act as valve retention devices in the balloon catheter 4700B. The balloon catheter 4700B further includes a balloon 4710B and an inner shaft 4730B and an outer shaft 4740B. The balloon catheter 4700B includes a distal portion 4785B and a proximal portion 4790B. Also illustrated in FIG. 47B is prosthetic heart valve 120 crimped to balloon 4710B. The retention bumpers 4701B, 4702B are disposed in a distal portion 4785B of the balloon catheter 4700B over the balloon 4710B. The retention bumpers 4701B, 4702B function similarly to the retention bumpers 4701A, 4702A. The balloon catheter 4700B is configured to deliver and deploy a prosthetic heart valve (not pictured) and may include any or all features and aspects of the balloon catheter 400.

Figure 48:
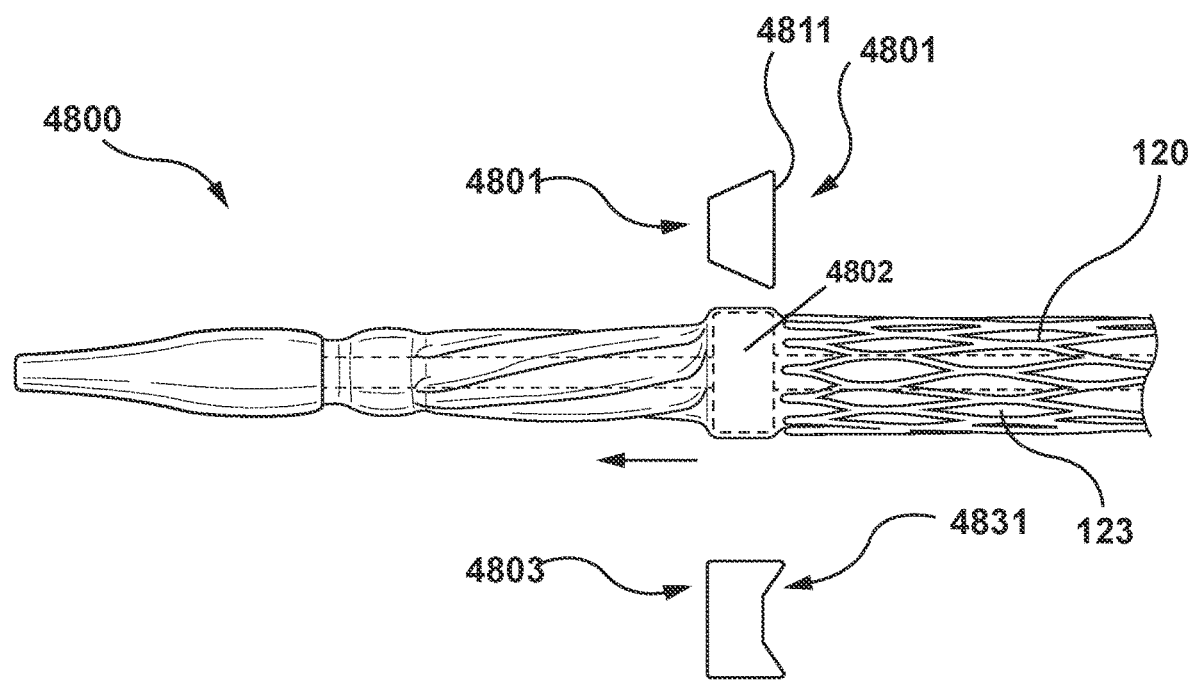
FIG. 48 illustrates alternative cross-sections of retention bumpers according to embodiments hereof.
Figure 49:
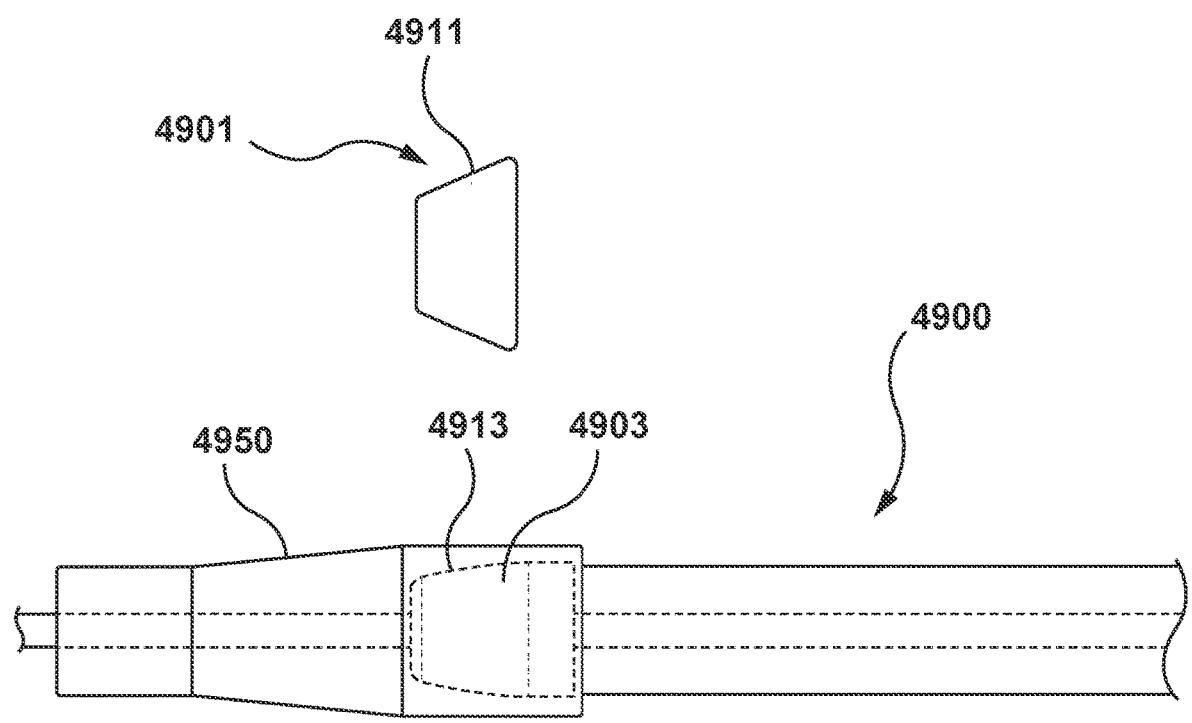
FIG. 49 illustrates a retention bumper having a tapered profile according to embodiments hereof.

In embodiments, the retention bumpers 4701A/4702A or 4701B/4702B may differ in size and/or shape from those illustrated as well as from one another. Although the retention bumpers 4701A/4702A and 4701B/4702B have rectangular profiles, such profiles are not required. FIGS. 48-50 illustrate examples of retention bumpers having different sizes and shapes. Balloon catheters consistent with embodiments hereof may have one or more retention bumper of any type disclosed herein, and there is no implicit or explicit limitation to the combinations of retention bumpers that may be selected.

FIGS. 48 and 49 illustrate various alternative retention bumper cross-sectional profiles. FIG. 48 illustrates prosthetic heart valve frame facing edge profiles and FIG. 49 illustrates edge profiles facing away from the prosthetic heart valve.

Referring now to FIG. 48, retention bumpers 4801 and 4803 for use with balloon catheter 4800 are illustrated. The balloon catheter 4800 may include any or all of the features of other balloon catheters described herein. The balloon catheter 4800 is illustrated with retention bumper 4802, having a rectangular profile with rounded corners. The rounded corners of retention bumper 4802 may facilitate assembly of the balloon catheter 4800 and insertion of the balloon catheter 4800 into an introducer. Although retention bumper 4802 is illustrated in a position underneath the balloon of the balloon catheter 4800, all of the retention bumpers 4801, 4802, 4803 may be positioned internal or external to the balloon as appropriate. The balloon catheter 4800 is configured to deliver and deploy a prosthetic heart valve (not pictured) and may include any or all features and aspects of the balloon catheter 400.

FIG. 48 further illustrates features of frame facing edge profiles of retention bumpers that face the frame 123 of a prosthetic heart valve 120. For a retention bumper located distal to the prosthetic heart valve, the frame facing edge profiles of retention bumpers 4801 and 4803 apply to a proximal facing side of the retention bumper when assembled with the balloon catheter 4800. For a retention bumper located proximal to the prosthetic heart valve, the frame facing edge profiles of retention bumpers 4801 and 4803 apply to a distal facing side of the retention bumper when assembled with the balloon catheter 4800.

The retention bumper 4801 includes a square edge 4811 facing the frame 123 of the prosthetic heart valve 120. The square edge 4811 of a retention bumper 4801 disposed on a proximal side of the prosthetic heart valve 120 is oriented to be facing distally, while the square edge 4811 of a retention bumper 4801 disposed on a distal side of the prosthetic heart valve 120 is oriented to be facing proximally. When the frame 123 of the prosthetic heart valve 120 contacts the square edge 4811 of the retention bumper 4801, the squared edge 4811 does not induce expansion of the prosthetic heart valve 120. In contrast, a retention bumper having a tapered edge facing the frame 123 may induce the frame 123 to flare open and expand during delivery. The increased diameter of the frame 123 in such a situation may lead to increased forces on and thus increased migration of the prosthetic heart valve 120.

In another embodiment, retention bumper 4803 includes a concave edge 4831 facing the frame 123 of the prosthetic heart valve 120. The concave edge 4831 of a retention bumper 4803 disposed on a proximal side of the prosthetic heart valve 120 may be oriented to be facing distally, while the concave edge 4831 of a retention bumper 4803 disposed on a distal side of the prosthetic heart valve 120 is oriented to be facing proximally. When the frame 123 of the prosthetic heart valve 120 contacts the concave edge 4831 of the retention bumper 4803, the concave edge 4831 applies force to the struts of the frame 123 that tends to force the frame closed. The edge profiles of retention bumpers 4801 and 4803 that face away from the frame 123 may be varied appropriately consistent with other embodiments discussed herein.

Referring now to FIG. 49, retention bumpers 4901 and 4903 for use with balloon catheter 4900 are illustrated. The balloon catheter 4900 may include any or all of the features of other balloon catheters described herein. FIG. 49 illustrates features edges profile of the retention bumpers 4901 and 4903 that face away from the frame 123 of a prosthetic heart valve 120. For a retention bumper located distal to the prosthetic heart valve, the frame facing edge profiles of retention bumpers 4901 and 4903 apply to a distal facing side of the retention bumper when assembled with a balloon catheter. For a retention bumper located proximal to the prosthetic heart valve, the frame facing edge profiles of retention bumpers 4901 and 4903 apply to a proximal facing side of the retention bumper when assembled with a balloon catheter. The balloon catheter 4900 is configured to deliver and deploy a prosthetic heart valve 120 and may include any or all features and aspects of the balloon catheter 400.

The retention bumper 4901 has a leading edge tapered profile according to embodiments hereof. The retention bumper 4901 includes a tapered leading edge 4911. The tapered leading edge 4911, which is oriented away from the prosthetic heart valve 120 during assembly, may facilitate insertion or withdrawal of the balloon catheter 4900. When the balloon catheter 4900 is inserted into an introducer 4950, the tapered leading edge 4911 provides a smooth insertion into the introducer 4950, which may have a diameter similar in size or smaller in size than the widest portion of the balloon catheter 4900. The tapered leading edge 4911 also facilitates advancement through the introducer 4950. When the balloon catheter 4900 is withdrawn from the introducer 4950, the tapered leading edge 4911 of a proximally placed retention bumper 4901 serves to ease passage in a reverse direction.

In another embodiment, the retention bumper 4903 includes a tapered leading edge 4913 to facilitate insertion of the balloon catheter 4900 into the introducer 4950 as described above with respect to the retention bumper 4901. Retention bumpers consistent with embodiments herein may include any type of tapered profile wherein the end positioned away from the prosthetic heart valve 120 is has a smaller diameter than the end positioned close to the prosthetic heart valve. The tapered profile may be conical, curved, straight, or any other suitable shape. The retention bumpers 4901 and 4903, when positioned distal to the prosthetic heart valve, are arranged such that the respective leading edge 4911 or 4913 also faces distally to assist with insertion of the balloon catheter. The retention bumpers 4901 and 4903, when positioned proximal to the prosthetic heart valve, are arranged such that the tapered leading edge 4911 or 4913 also faces proximally to assist with withdrawal of the balloon catheter.

The edge profile embodiments of FIGS. 48 and 49 may be combined. Either of square edge 4811 and concave edge 4831 may be combined with either of tapered leading edge 4911 or tapered curve leading edge 4913 in a retention bumper that incorporates these advantageous edge profiles on both sides.

Figure 50A:
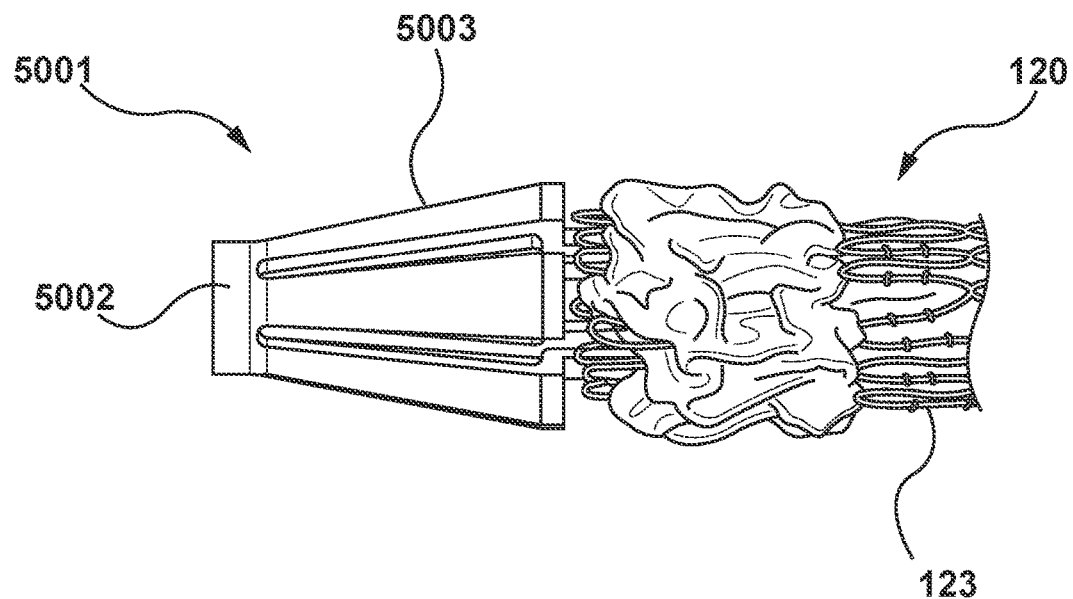
FIGS. 50A and 50B illustrate a flexible retention bumper according to embodiments hereof.
Figure 50B:
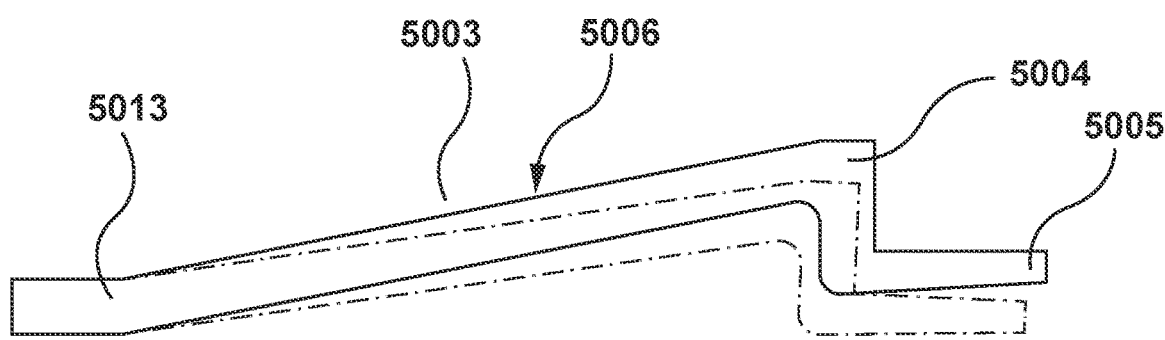

FIGS. 50A and 50B illustrate a dynamic retention bumper 5001 according to embodiments hereof. The dynamic retention bumper 5001 includes a hub 5002 from which extends a plurality of flexible tabs 5003. The flexible tabs 5003 extend both radially and axially away from the hub 5002 and are shaped with an extension portion 5006, an outer diameter portion 5004, and a frame ledge 5005. The flexible tabs 5003 are connected to hub 5002 at hinges 5013, which are living hinges. The extension portions 5006 of the flexible tabs 5003 extend radially outwards and axially away from the hub 5002. At the ends of the extension portions 5006 away from the hub 5002, the outer diameter portions 5004 extend radially inwards. The frame ledges 5005 extend axially from the outer diameter portions 5004 closest to the central axis of the hub 5002 in a direction away from the hub 5002. The dynamic retention bumper 5001 may include three, four, five, six, or more flexible tabs 5003, each spaced apart from one another such that they may move independently of one another. When assembled, the prosthetic heart valve 120 is positioned and crimped over the frame ledge 5005. The outer diameter portions 5004 define the outer diameter of the dynamic retention bumper 5001 where they connect to the extension portions 5006. During procedural use of the balloon catheter, the prosthetic heart valve 120 frame 123 may be subject to forces that change its shape. Specifically, as the frame 123 is tracked through vasculature of the patient on the balloon catheter, the prosthetic heart valve 120 may exhibit uneven compression, i.e., fish-mouthing and/or flaring, as the balloon catheter is tracked through bends in the introducer catheter. Compression of the prosthetic heart valve 120 in one dimension causes an ovalization and associated decrease in diameter of the dynamic retention bumper 5001 in the same dimension while causing an increase in diameter in the orthogonal dimension. The change in shape of the dynamic retention bumper 5001 is due to added or reduced force on the frame ledge 5005 provided by the altered shape prosthetic heart valve 120, which causes each flexible tab 5003 to rotate around its respective hinge 5013. Thus, the dynamic retention bumper 5001 is configured for dynamic changes in shape in response to changes in shape of a prosthetic heart valve crimped over the dynamic retention bumper 5001. Because the outer diameter portion 5004 of each flexible tab 5003 expands axially when the frame 123 expands in the same direction, the dynamic retention bumper 5001 is able to prevent any portion of the frame 123 from expanding past the largest diameter of the dynamic retention bumper 5001.

Figure 51A:
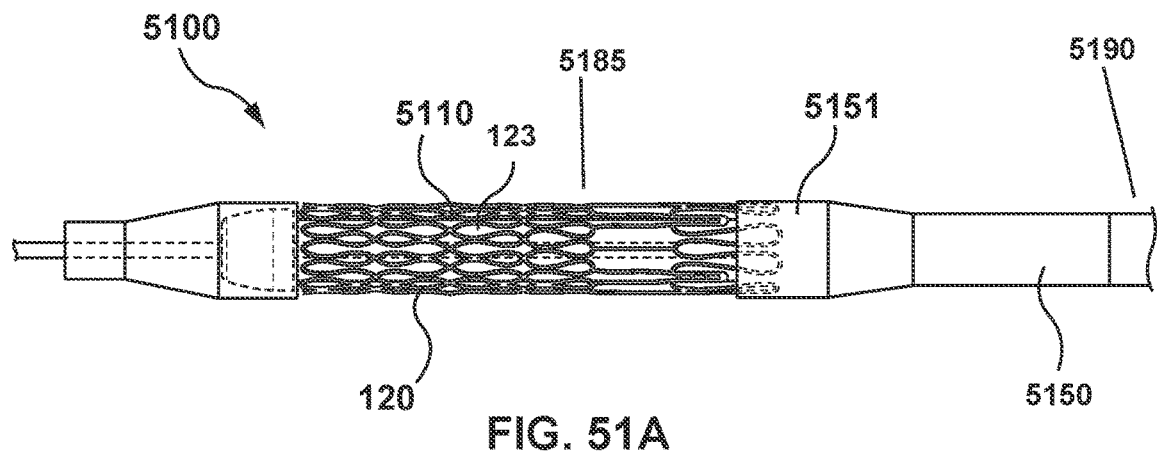
FIGS. 51A-51D illustrate a retention sheath as a valve retention device according to embodiments hereof.
Figure 51B:
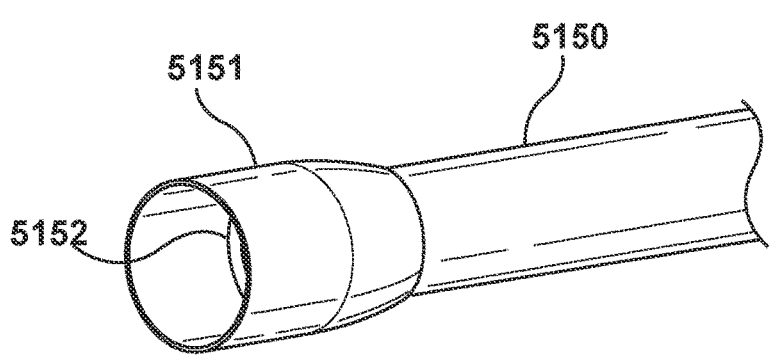
Figure 51C:
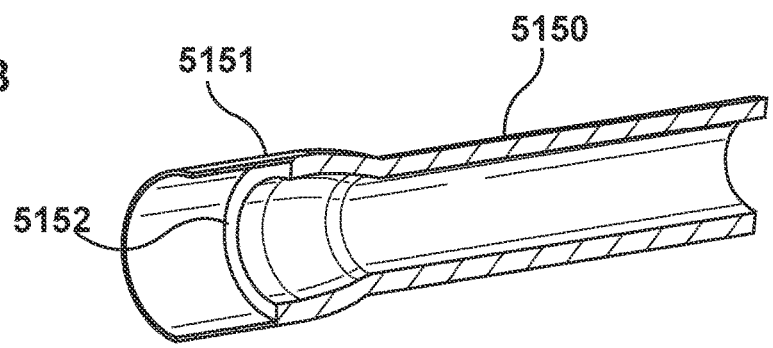

FIGS. 51A-51C illustrate a retention sheath 5150 as a valve retention device for a balloon catheter 5100 according to embodiments hereof. The balloon catheter 5100 includes a proximal portion 5190 and a distal portion 5185, an inflatable balloon 5110 disposed on the distal portion 5185, and the retention sheath 5150 disposed at a distal end of the proximal portion 5190. the prosthetic heart valve 120 is crimped over the balloon 5110 for intravascular delivery. The balloon catheter 5100 is configured to deliver and deploy a prosthetic heart valve 120 and may include any or all features and aspects of the balloon catheter 400.

Figure 51D:
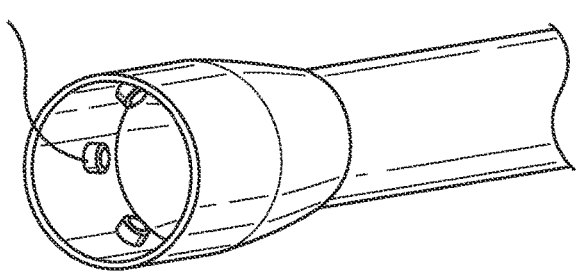

The retention sheath 5150 includes a shroud 5151 and a backstop 5152. The shroud 5151 of the retention sheath 5150 is configured to extend over or enclose at least a portion of the prosthetic heart valve 120. In some embodiments, the shroud 5151 extends over an entirety of the prosthetic heart valve 120 during delivery. The backstop 5152 has a smaller diameter than the rest of the retention sheath 5150 and is arranged to contact the frame 123 of the prosthetic heart valve 120 during delivery. The backstop 5152 acts to prevent the prosthetic heart valve 120 from migrating proximally due to forces encountered during delivery. The shroud 5151, covering the prosthetic heart valve 120, prevents the prosthetic heart valve 120 from expanding and slipping past the backstop 5152 during delivery. When the prosthetic heart valve 120 is appropriately positioned for deployment, the retention sheath 5150 may be retracted proximally by the operator to expose the prosthetic heart valve 120 and permit its expansion for deployment. In further embodiments, the retention sheath 5150 may be configured with perforations such that, during balloon expansion for valve deployment, the retention sheath 5150 splits open to permit the prosthetic heart valve 120 to expand. In such embodiments, retraction of the sheath is unnecessary. In additional embodiments, as illustrated in FIG. 51D the shroud 5151 of the retention sheath 5150 further includes bosses 5153. The bosses 5153 are configured to engage with the crowns 125 of the frame 123 of the prosthetic heart valve 120 to further secure the prosthetic heart valve 120 within the shroud 5151.

Figure 52A:
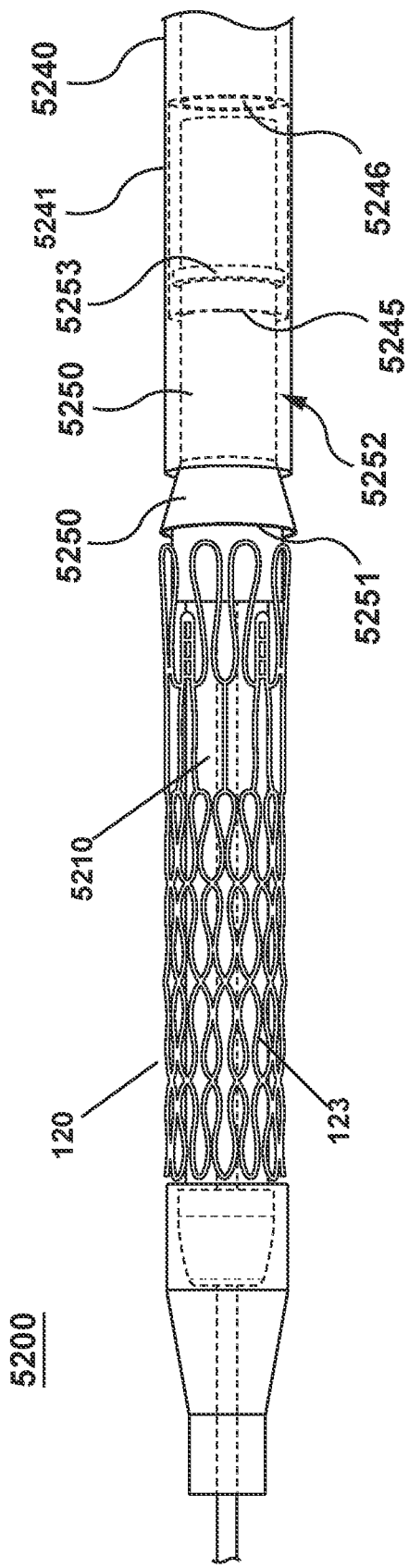
FIGS. 52A-52B illustrate a retention collet as a valve retention device according to embodiments hereof.
Figure 52B:
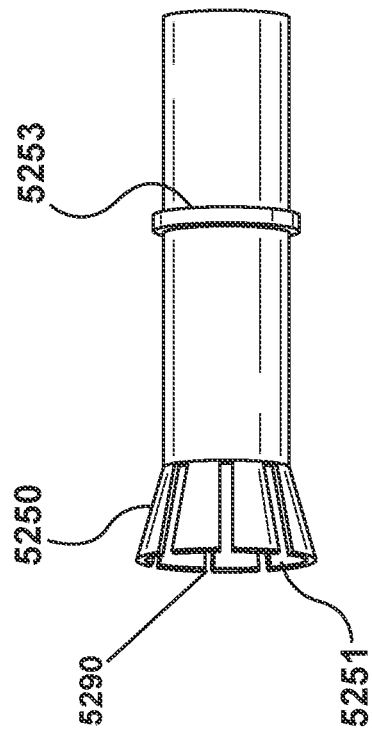

FIGS. 52A-52B illustrate a balloon catheter 5200 including a retention collet 5250 as a valve retention device according to embodiments hereof. The retention collet 5250 operates similarly to the retention sheath 5150 described above. In addition to covering the prosthetic heart valve 120 to prevent valve expansion, the retention collet 5250 also exerts normal force on the prosthetic heart valve 120 to increase friction on the valve to prevent axial migration. The balloon catheter 5200 is configured to deliver and deploy a prosthetic heart valve 120 and may include any or all features and aspects of the balloon catheter 400.

The balloon catheter 5200 includes a catheter shaft 5240, an inner shaft (not shown), an inflatable balloon 5210, and the retention collet 5250. The prosthetic heart valve 120 is crimped over the balloon 5210 for intravascular delivery. The retention collet 5250 includes a funnel 5251, an extension portion 5252, and a retention ring 5253. The extension portion 5252 is slidably engaged with a distal end 5241 of the catheter shaft 5240. The retention ring 5253 is configured to engage with a proximal stopper 5246 and a distal stopper 5245 of the catheter shaft 5240. The distal stopper 5245 prevents the retention collet 5250 from extending too far distally and the proximal stopper 5246 prevents the retention collet 5250 from being pressed too far proximally into the catheter shaft 5240.

The funnel 5251 is less rigid than the distal end 5241, either through thinner walls, softer materials, or both. The retention collet 5250 is configured to extend over or enclose at least a portion of the prosthetic heart valve 120. During assembly, the prosthetic heart valve 120 is inserted into the retention collet 5250 via the funnel 5251. The retention collet 5250 is then slid further into the distal end 5241 of the catheter shaft 5240 such that the funnel 5251 enters the distal end 5241 of the catheter shaft 5240. As the funnel 5251 is pushed into the distal end 5241, the funnel 5251 is forced to close and tighten on the prosthetic heart valve 120 within by the interior walls of the distal end 5241 of the catheter shaft 5240. The increase in crimping or compression force on the prosthetic heart valve 120 creates additional friction between the prosthetic heart valve 120 and the balloon 5210, serving to reduce or prevent migration of the prosthetic heart valve 120 either proximally or distally during delivery when the balloon catheter 5200 is used. The funnel 5251 further acts to prevent the frame 123 of the prosthetic heart valve 120 from prematurely expanding. When the prosthetic heart valve 120 is appropriately positioned for deployment, the retention collet 5250 is retracted proximally by the operator to expose the prosthetic heart valve 120 and permit its expansion.

FIG. 52B illustrates optional features of retention collet 5250 consistent with embodiments hereof. In embodiments, the funnel 5251 includes slots 5290 cut into the sides. The slots 5290 serve to facilitate the inward collapse of the walls of the funnel 5251 when the retention collet 5250 is pressed into the distal end 5241 of the catheter shaft 5240.

Figure 53A:
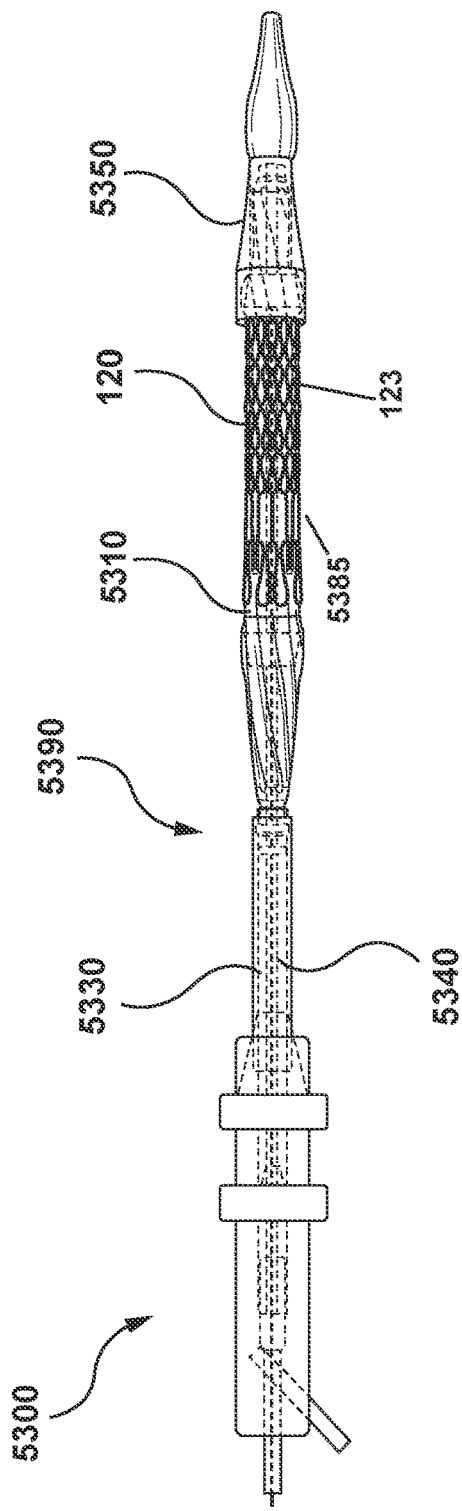
FIGS. 53A-53B illustrate a distal sheath as a valve retention device according to embodiments hereof.
Figure 53B:
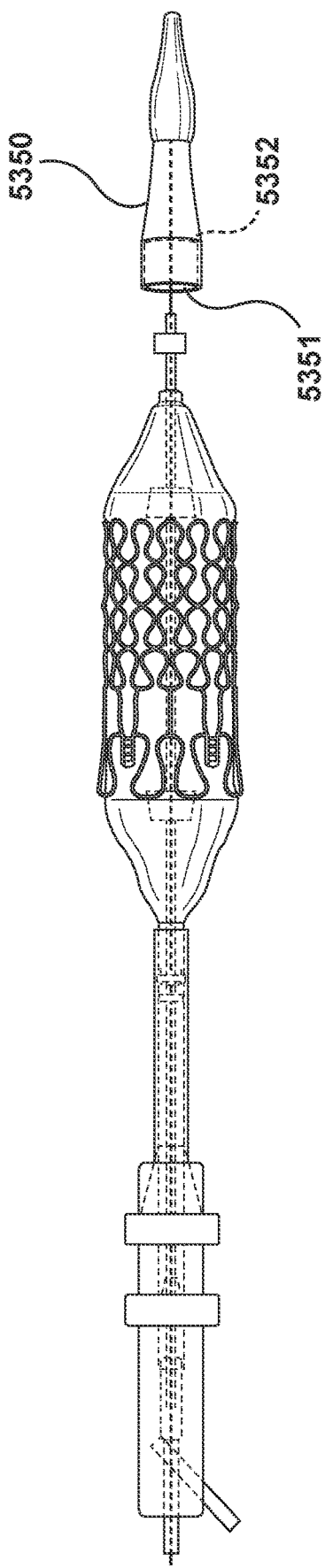

FIGS. 53A-53B illustrate a balloon catheter 5300 including a retention sheath 5350 as a valve retention device according to embodiments hereof. The balloon catheter 5300 includes an inner shaft 5330, an outer shaft 5340, a proximal portion 5390, an inflatable balloon 5310 disposed over a distal portion 5385, and a retention sheath 5350. The prosthetic heart valve 120 is be crimped over the balloon 5310 for intravascular delivery. The balloon catheter 5300 is configured to deliver and deploy a prosthetic heart valve 120 and may include any or all features and aspects of the balloon catheter 400.

The retention sheath 5350 includes a shroud 5351 and a backstop 5352, similar to those of retention sheath 5350. The backstop 5352 has a smaller diameter than the rest of the retention sheath 5350. The shroud 5351 of the retention sheath is configured to extend over or enclose at least a portion of the prosthetic heart valve 120. In some embodiments, the shroud 5351 extends over an entirety of the prosthetic heart valve 120 during delivery. The backstop 5352 is arranged to contact the frame 123 of the prosthetic heart valve 120 during delivery. The backstop 5352 acts to prevent the prosthetic heart valve 120 from migrating distally due to forces encountered during delivery. The shroud 5351, covering the prosthetic heart valve 120, prevents the prosthetic heart valve 120 from expanding and slipping past the backstop 5352 during delivery. When the prosthetic heart valve 120 is appropriately positioned for deployment, the retention sheath 5350 may be advanced distally by the operator to expose the prosthetic heart valve 120 and permit its expansion. In some embodiments, the retention sheath 5350 may be configured with perforations such that, during balloon expansion, the retention sheath 5350 splits open to permit the prosthetic heart valve 120 to expand. In such embodiments, extension of the sheath is unnecessary. In some embodiments, the retention sheath 5350 may be used in a balloon catheter in combination with the retention sheath 5150. In some embodiments, the retention sheath 5350 may be used in a balloon catheter in combination with retention bumpers as described herein.

Figure 54A:
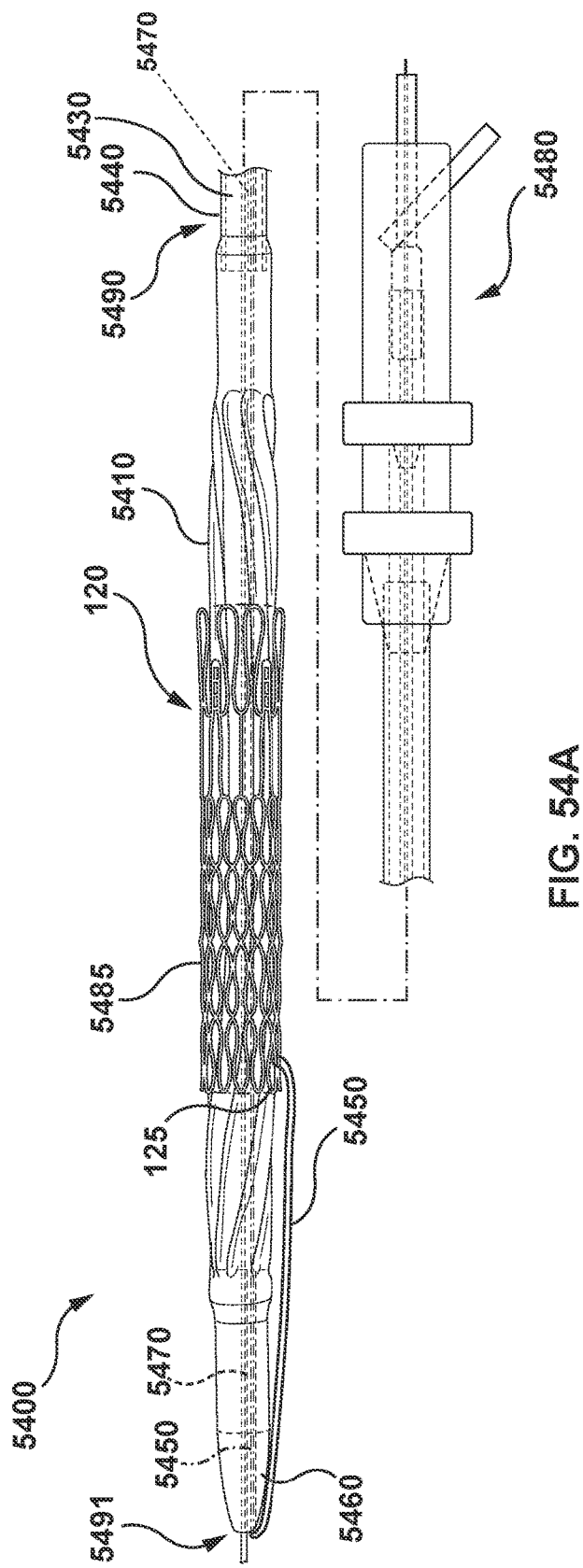
FIGS. 54A-54B illustrate a suturing system as a valve retention device according to embodiments hereof.
Figure 54B:
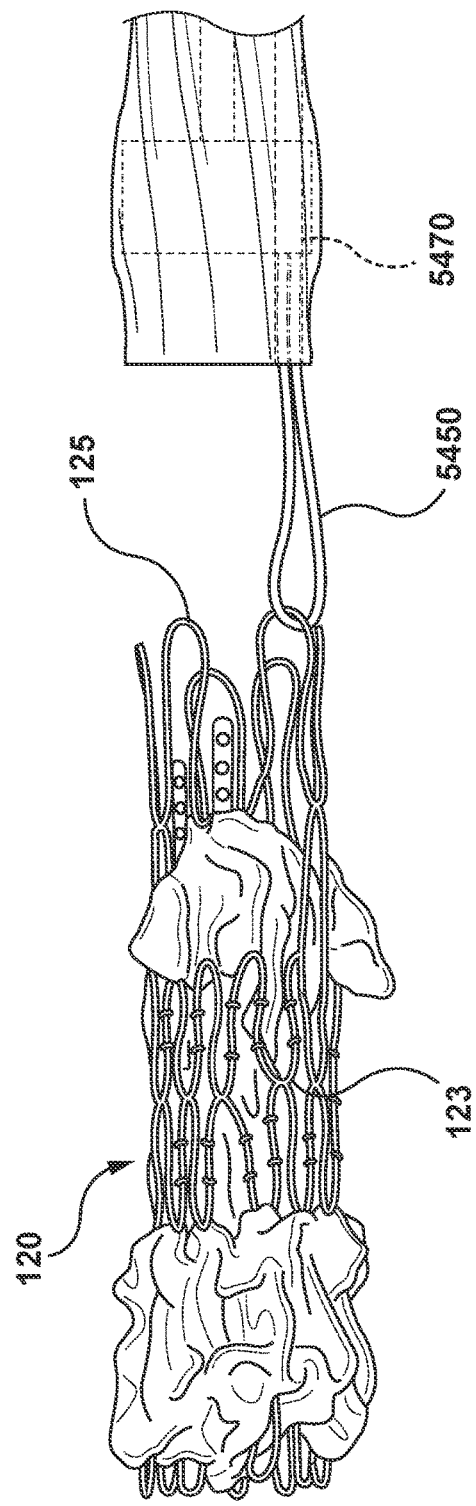

FIGS. 54A-54B illustrate a balloon catheter 5400 including a tethering system as a valve retention device according to embodiments hereof. The balloon catheter 5400 includes a proximal handle 5480, an outer shaft 5440 and an inner shaft 5430, an inflatable balloon 5410, a distal tip 5460, and one or more valve tethers 5450. The balloon catheter 5400 is configured to deliver and deploy a prosthetic heart valve 120 and may include any or all features and aspects of the balloon catheter 400.

The prosthetic heart valve 120 having a frame 123 including multiple crowns 125 is crimped onto the inflatable balloon 5410 at a distal portion 5485. A proximal portion 5490 of the balloon catheter 5400 extends proximally from the distal portion 5485. The outer shaft 140 and the distal tip 5460 each include one or more tether lumens 5470 formed therein. The tether lumens 5470 may be constructed as lumens within the walls of the outer shaft 5440 and within the distal tip 5460. In some embodiments, the inflation lumen between the inner shaft 5430 and the outer shaft 5440 may serve as a tether lumen 5470 in the proximal portion 5490 of the balloon catheter 5400. The tether 5450 is constructed of any flexible or malleable material, including suture, filament, wire, etc. The tether 5450 is configured to be looped around or otherwise releasably attached to a crown 125 of the frame 123 of the prosthetic heart valve 120. The tether 5450 may be looped around either a proximal or distal crown 125 of the prosthetic heart valve 120. The tether 5450 is secured to the proximal handle 5480 of the balloon catheter 5400. In embodiments, a plurality of tethers 5450 may each be looped around crowns 125 of the prosthetic heart valve 120 and secured to the proximal handle 5480. The tether(s) 5450, accordingly, restrain the prosthetic heart valve 120 from migrating during delivery.

As illustrated in FIG. 54A, the tether 5450 may extend past the prosthetic heart valve 120 and be looped around a distal crown 125 of the prosthetic heart valve 120. The tether 5450 exits the tether lumen 5470 at the end of the outer shaft 5440 and travels underneath the balloon 5410 through the distal portion 5485. The tether 5450 exits the interior of the balloon catheter 5400 at a tether support portion 5491 located in the distal tip 5460 of the balloon catheter 5400, allowing the tether 5450 to exert a distally directed force on the prosthetic heart valve 120. Such a force prevents the prosthetic heart valve from migrating proximally during delivery. The tether support portion 5491 may be a notch near the hole at the end of the distal tip 5460 or may be a hole in the side of the distal tip 5460 permitting the tether 5450 to exit the interior of the balloon catheter 5400.

As illustrated in FIG. 54B, in some embodiments, the tether 5450 may be looped around a proximally located crown 125 of the prosthetic heart valve 120, providing a proximally directed force on the prosthetic heart valve 120. Such a force prevents the prosthetic heart valve 120 from migrating distally during delivery.

In either embodiment, the tether 5450 may be released by an operation of the proximal handle 5480 by the operator. After release, the tether 5450 may be retracted so as to allow the prosthetic heart valve 120 free movement to expand during deployment.

Figure 55:
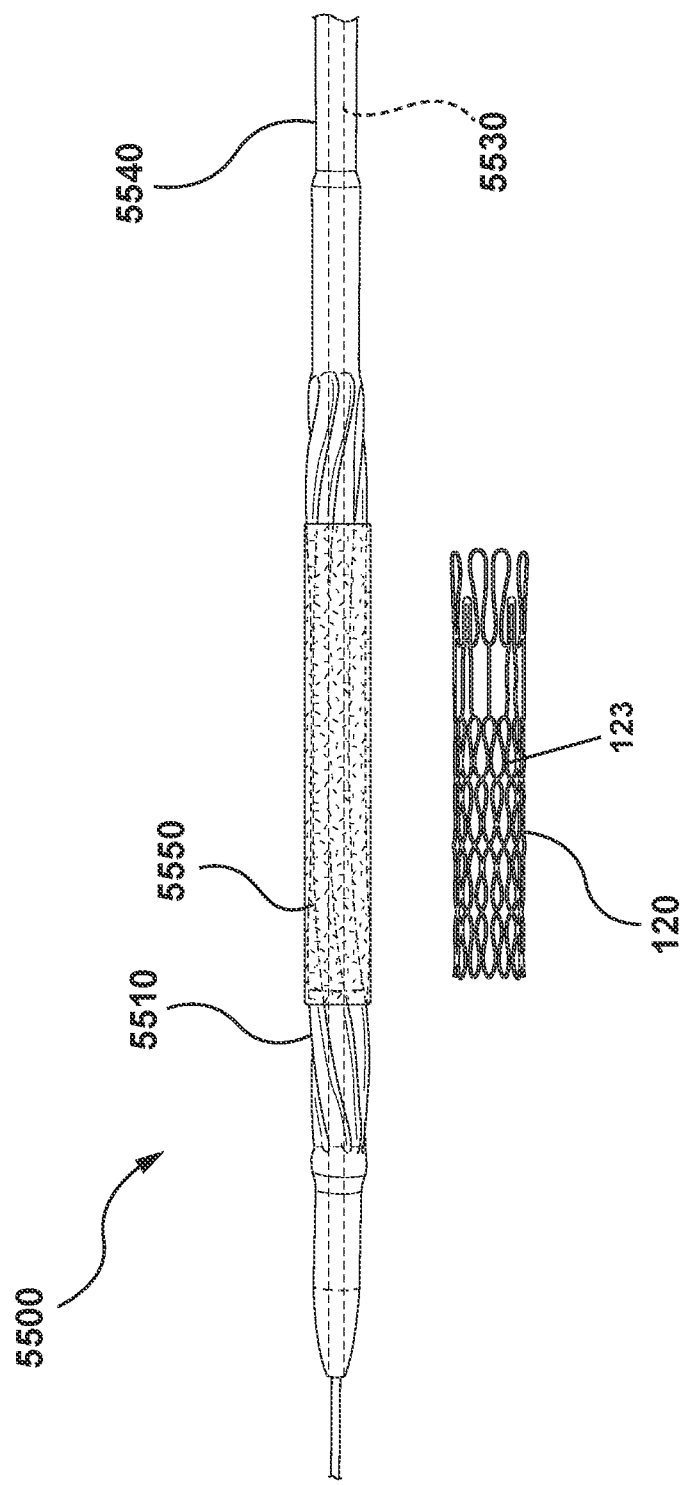
FIG. 55 illustrates an impressionable material as a valve retention device according to embodiments hereof.

FIG. 55 illustrates a balloon catheter 5500 including an impressionable material restraint 5550 as a valve retention device according to embodiments hereof. The balloon catheter 5500 includes an inner shaft 5530 and an outer shaft 5540, an inflatable balloon 5510, and an impressionable material restraint 5550. The impressionable material restraint 5550 is an elastic or plastic compressible material located between the balloon 5510 and a prosthetic heart valve 120. The balloon catheter 5500 is configured to deliver and deploy a prosthetic heart valve 120 and may include any or all features and aspects of the balloon catheter 400.

In alternative embodiments, the balloon 5510 is configured to act as the impressionable material restraint 5550. When the prosthetic heart valve 120 is crimped onto the balloon 5510, the frame 123 of the prosthetic heart valve 120 is pressed into the impressionable material restraint 5550. The impressionable material restraint 5550 yields to the prosthetic heart valve 120 and develops impressions or indentations that accommodate the compressed frame. The impressions or indentations provide mechanical resistance to prevent the prosthetic heart valve 120 from migrating laterally during delivery. In some embodiments, the impressionable material restraint 5550 is formed of a non-slip or high friction material to increase the mechanical locking effect. In some embodiments, the impressionable material restraint 5550 may be located underneath the balloon 5510. In such cases, crimping of the prosthetic heart valve 120 serves to impress or imprint the prosthetic heart valve 120 into the material of the balloon 5510 and to impress or imprint the balloon 5510 into the impressionable material restraint 5550.

Described above are multiple valve retention devices, embodied variously as retention bumpers, retention sheaths, retention collets, and retention tethers. None of the above-described embodiments are exclusive and each may be employed in a balloon catheter with any other valve retention device described herein. For example, a balloon catheter may employ a proximal retention collet and a distal retention bumper. In another example, a retention tether attached to a proximal end of the prosthetic heart valve may prevent distal migration while a proximal retention bumper may be employed to prevent proximal migration. Any suitable combination of valve retention devices may be employed.

Figure 56:
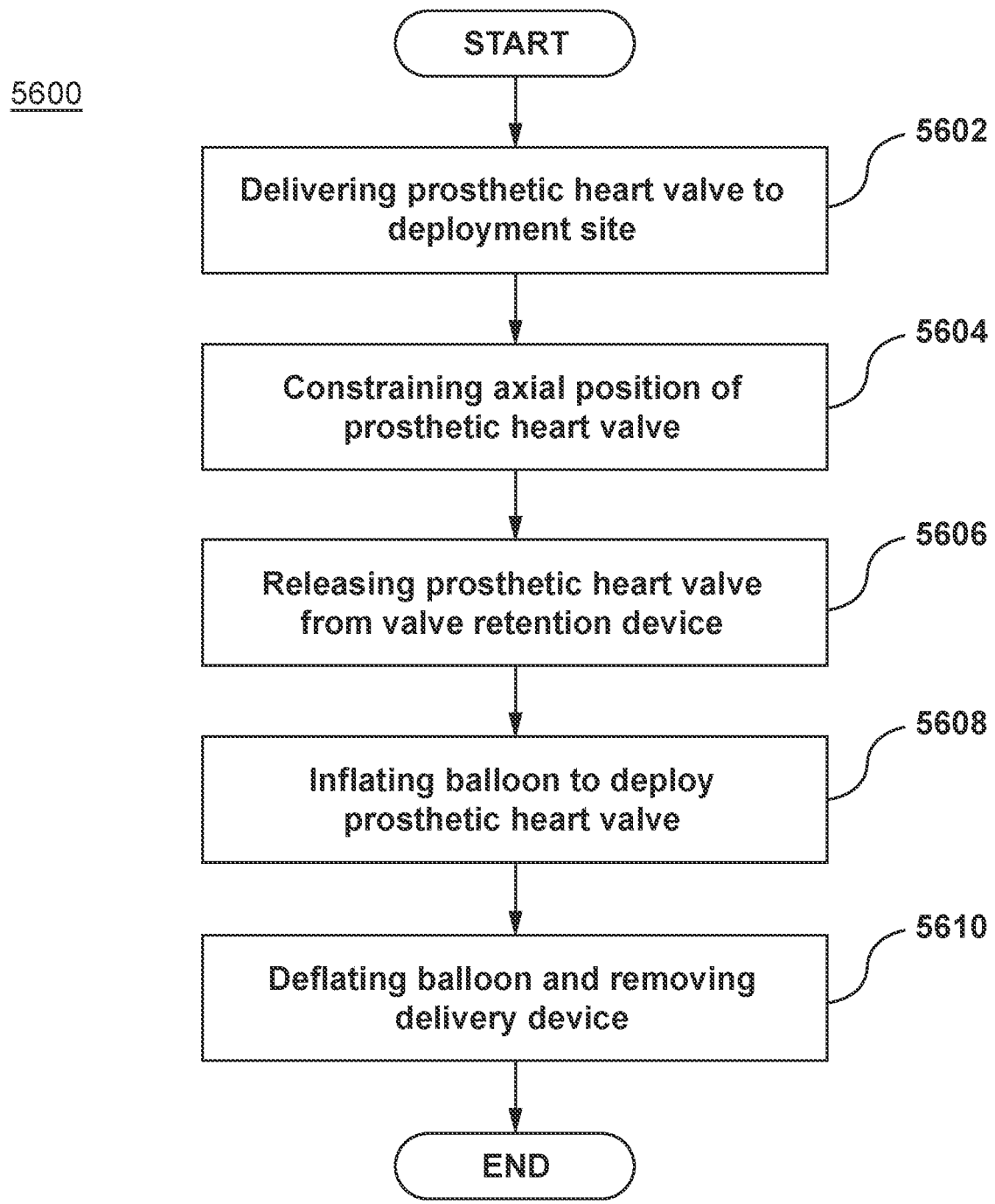
FIG. 56 is a flow chart of a method of balloon enabled delivery and deployment of a prosthetic heart valve consistent with embodiments described herein.

FIG. 56 is a flow chart of a method 5600 of balloon enabled delivery and deployment of a prosthetic heart valve consistent with embodiments described herein. The devices and structures described herein reduce or prevent prosthetic heart valve migration during valve delivery. Methods of delivering and deploying a prosthetic heart valve to a determined location may be carried out it with any of the embodiments described herein, and with any combination of the embodiments described herein.

In an operation 5602, a prosthetic heart valve is delivered to a deployment site. A balloon catheter is manipulated to navigate a distal portion of the balloon catheter to the prosthetic heart valve deployment site. The balloon catheter is navigated through a procedural catheter, a guide catheter, and/or an introducer catheter to deliver the prosthetic heart valve to the site for deployment of the prosthetic heart valve. In some embodiments, the balloon catheter is delivered via a guidewire that has previously been inserted into the patient vasculature.

In an operation 5604, one or more valve retention devices are employed to constrain an axial position of the prosthetic heart valve. Operation 5604 may occur simultaneously to operation 5602. Constraining axial migration may include preventing or reducing valve migration in either the proximal or distal directions. While the operator of the balloon catheter navigates the balloon catheter, the valve retention devices of the balloon catheter constrain movement of the prosthetic heart valve in a proximal direction, a distal direction, and/or both. Valve retention devices consistent with this operation may include any combination of valve retention devices described herein.

In an operation 5606, the prosthetic heart valve is released from the valve retention device. Releasing the valve from the valve retention device permits the prosthetic heart valve to expand and deploy in the vasculature of a patient. In some embodiments, the prosthetic heart valve may be released from the valve retention device at the outset of balloon inflation. For example, where the prosthetic heart valve is retained by retention bumpers, inflating the balloon, and expanding the frame of the prosthetic heart valve causes release of the prosthetic heart valve from the valve retention device. When the frame expands past the diameter of the retention bumpers, the retention bumpers no longer constrain the frame. In further embodiments, release of the prosthetic heart valve from the valve retention device may involve retraction or advancement of a sheath or collet, splitting open of a sheath, and/or release from a tether.

In an operation 5608, the balloon is inflated to expand the prosthetic heart valve to a full deployment configuration. The balloon inflation continues until the prosthetic heart valve is fully expanded and engaged with the native patient anatomy.

In an operation 5610, the balloon is deflated and the balloon catheter is removed from the patient. The prosthetic heart valve remains in the expanded and deployed position while the balloon catheter is removed from the local site and from the patient.

Figure 57B:
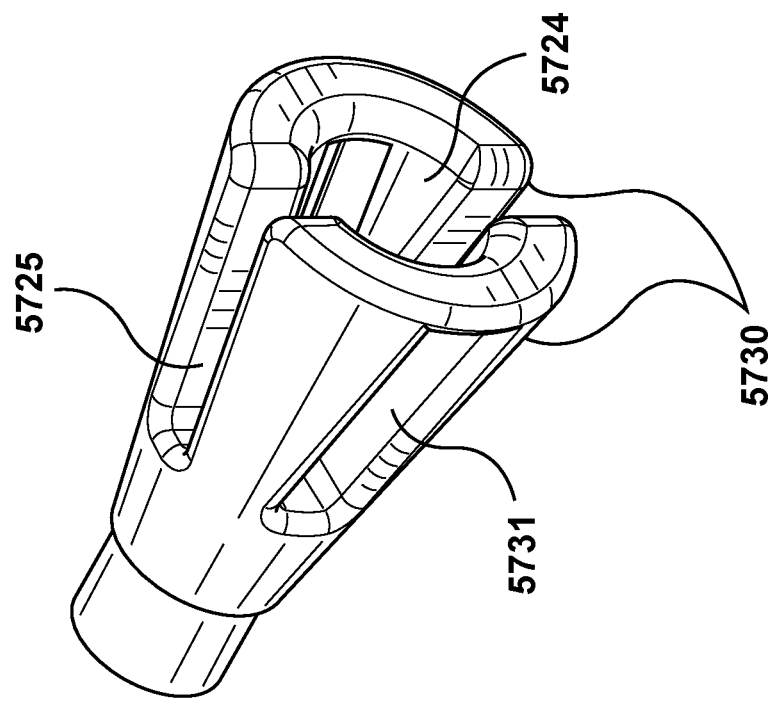
FIGS. 57A-F illustrate multipart retention bumpers consistent with embodiments hereof.
Figure 57A:
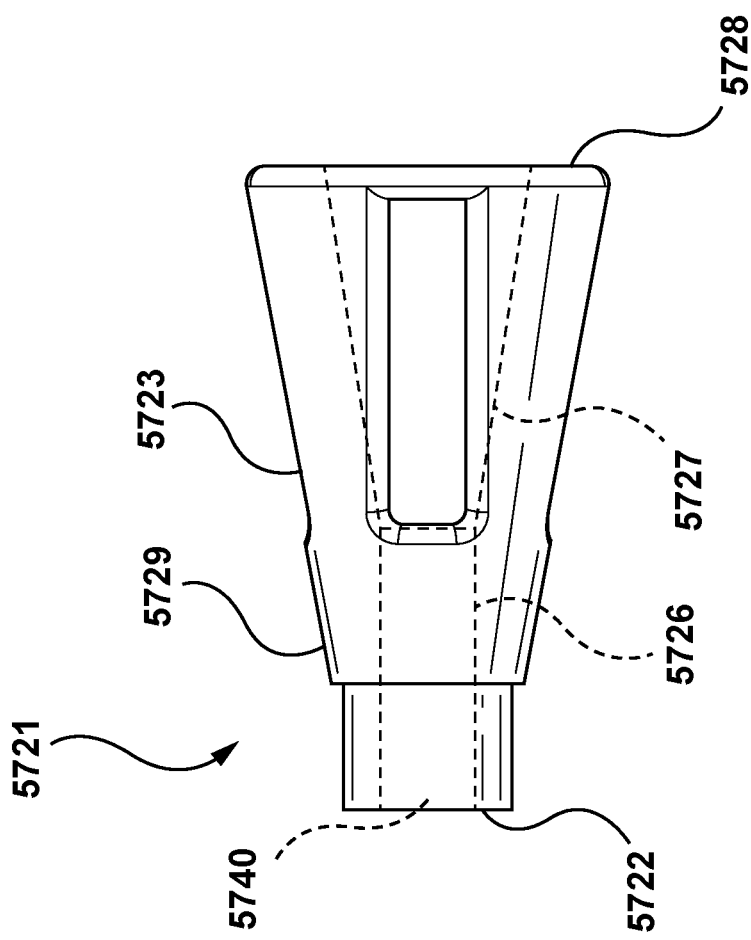
Figure 57D:
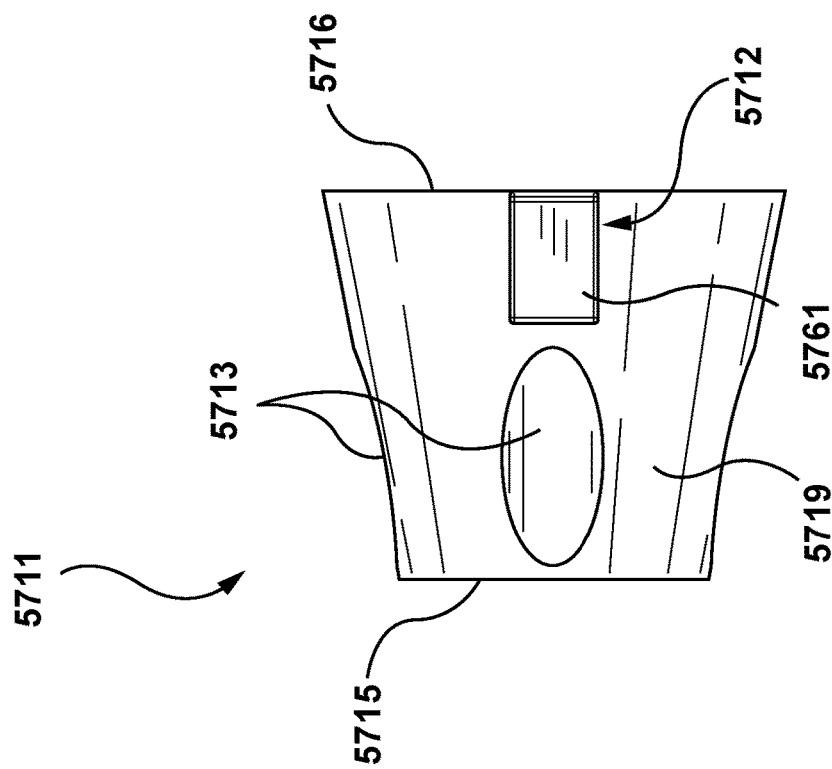
Figure 57C:
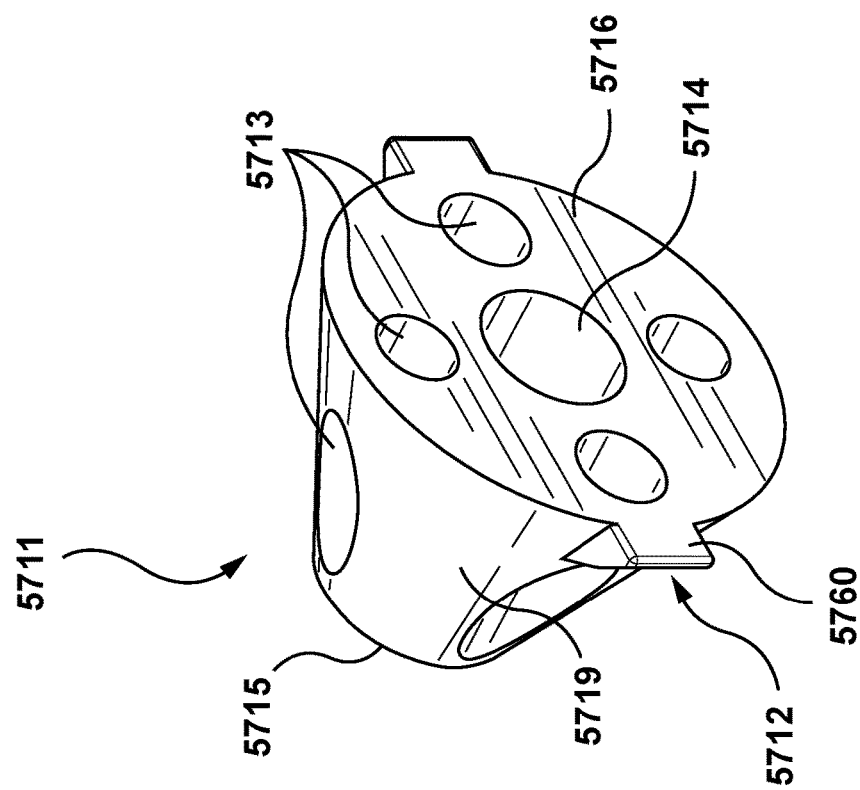
Figure 57F:
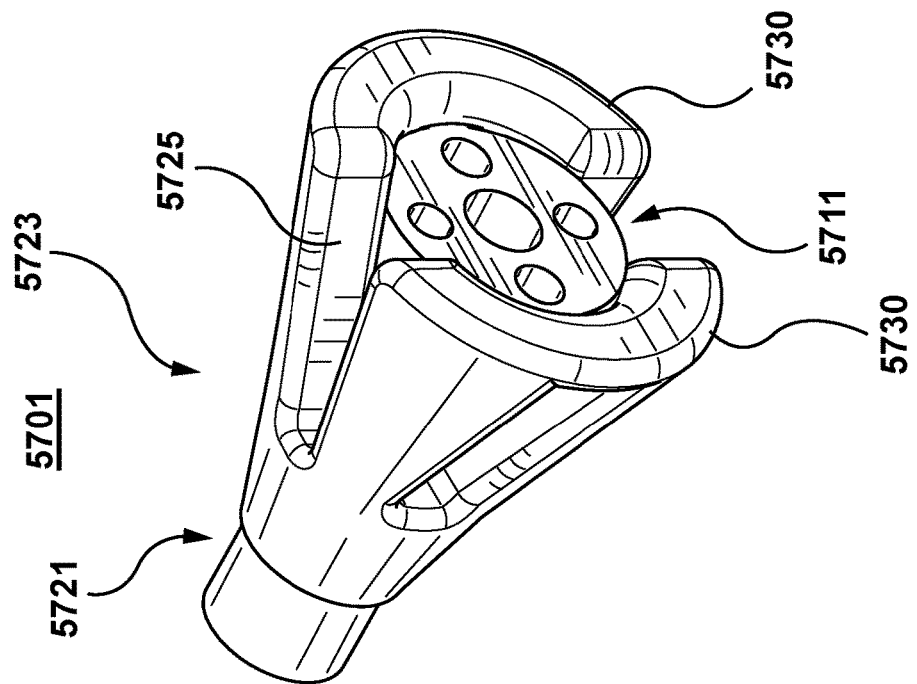
Figure 57E:
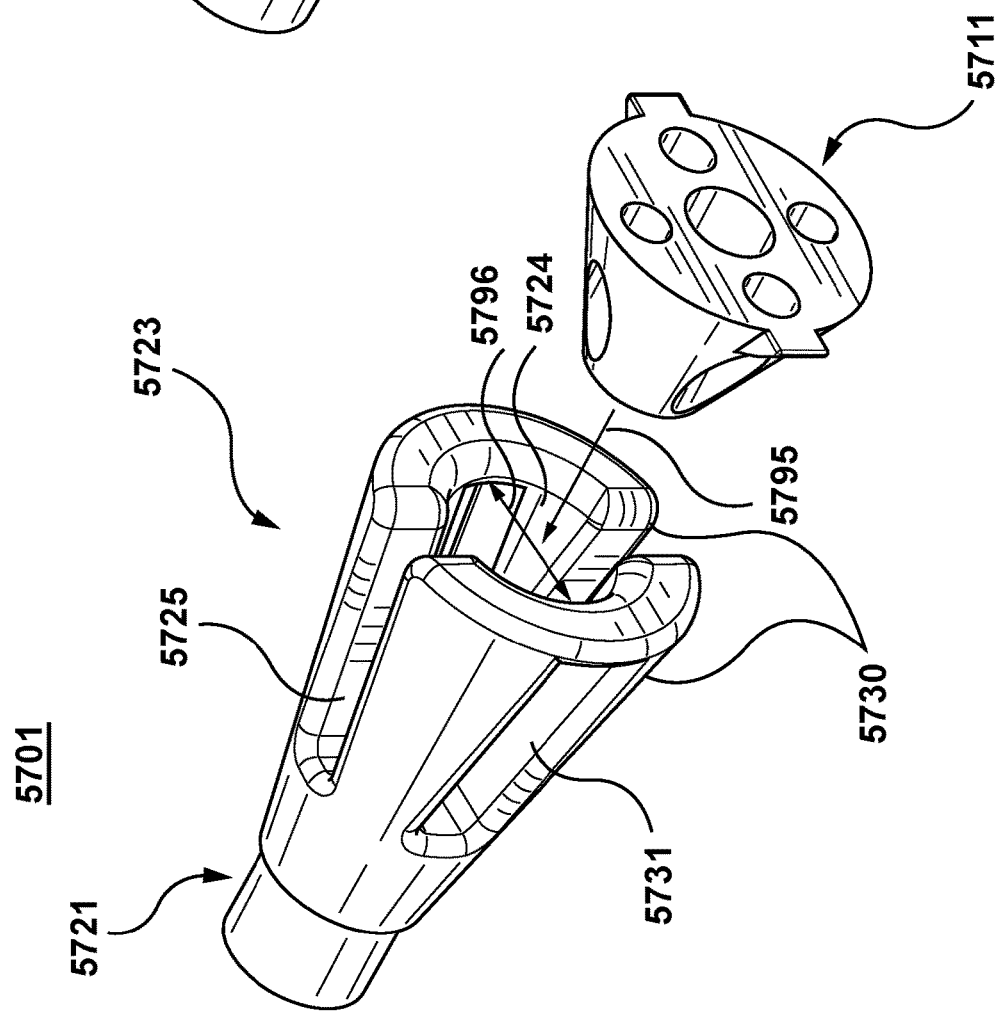

FIGS. 57A-57F illustrate multipart retention bumpers 5701 according to embodiments hereof. The multipart retention bumpers 5701 include inner portions, i.e., inner wedges 5711, and outer portions, i.e., outer bumpers 5721. FIGS. 57A and 57B illustrate plan and perspective views of the outer bumper 5721. FIGS. 57C and 57D illustrate perspective and plan views of the inner wedge 5711. FIG. 57E is a perspective view of the outer bumper 5721 and the inner wedge 5711 being interlocked into the multipart retention bumper 5701. FIG. 57F is a perspective view of the interlocked multipart retention bumper 5701.

The multipart retention bumpers 5701 include the inner wedges 5711 and the outer bumpers 5721. The multipart retention bumpers 5701 are substantially non-compressible retention bumpers and include snap fit features to maintain interlock and designed to facilitate manufacturing. The inner wedges 5711 and the outer bumpers 5721 are configured such that, when interlocked, the maximum diameter of the outer bumpers 5721 (and thus the maximum diameter of the multipart retention bumpers 5701) expands from a first radially unexpanded size to a second radially expanded size, wherein the first radially unexpanded size is selected to fit within the neck of a balloon during assembly of a balloon catheter and the second radially expanded size is selected to permit the interlocked multipart retention bumper 5701 to maintain the axial position of a prosthetic heart valve crimped to the balloon, as discussed in greater detail below.

In an interlocked configuration, the multipart retention bumpers 5701 have an outer diameter at the second radially expanded size and are configured to maintain the axial position of a prosthetic heart valve crimped to the balloon. In a non-interlocked configuration, the constituent components of the multipart retention bumpers 5701, i.e., the inner wedges 5711 and the outer bumpers 5721, each have an outer diameter at the first radially unexpanded size. The first radially unexpanded size for the inner wedges 5711 and the first radially unexpanded size for the outer bumpers 5721 need not be equal. In embodiments, each of the inner wedges 5711 and outer bumpers 5721 are configured with maximum diameters, in a non-interlocked configuration, between approximately 0.1 inches and 0.25 inches, between 0.15 and 0.22 inches, between 0.19 and 0.21 inches, or approximately 0.2 inches. Such sizes, i.e., the first radially unexpanded sizes, may be suitable for entry into the opening of a balloon of a balloon catheter, as discussed in greater detail below with respect to FIGS. 59A-59F. In embodiments, the multipart retention bumpers 5701, in an interlocked configuration, may have a maximum diameter between 0.25 inches and 0.35 inches, between 0.27 and 0.33 inches, between 0.29 and 0.31 inches, or approximately 0.3 inches after the inner wedges 5711 and the outer bumpers 5721 are interlocked.

Referring now to FIGS. 57A and 57B, the outer bumper 5721 includes a central hub 5722 with a central hollow 5740 sized and adapted for disposition over an inner shaft, such as the inner shaft 5930 shown in FIGS. 59A-59F. Projecting from the central hub 5722 is a tapered retention body 5723. The tapered retention body 5723 is a hollow tapered body, projecting from and expanding outwardly from the central hub 5722. The central hub 5722 is located at an apex end 5729 of the tapered retention body 5723, i.e., the portion having a smaller diameter. The tapered retention body 5723 extends away from the central hub 5722 at the apex end 5729 to a base end 5728. Due to the tapered shape of the tapered retention body 5723, the diameter of the tapered retention body 5723 expands with increasing distance from the central hub 5722. For example, slices of the tapered retention body 5723 near to the central hub 5722 have a smaller diameter than slices farther away from the central hub 5722.

The tapered retention body 5723 is hollow, having an empty tapered interior space 5724. The tapered interior space 5724 has a smallest diameter at the apex end 5729. In embodiments, the tapered interior space 5724 has a cylindrical portion 5726 and a tapered portion 5727. The cylindrical portion 5726 has a diameter corresponding to that of the central hollow 5740 of the central hub 5722. The tapered portion 5727 has a smallest diameter corresponding to the diameter of the cylindrical portion 5726 near the apex end 5729 of the tapered retention body 5723 and expanding to a largest diameter at the base end 5728 of the tapered retention body 5723. In additional embodiments, the smallest diameter of the cylindrical portion 5726 has a larger diameter than the central hollow 5740 of the central hub 5722. In embodiments, the tapered portion 5727 is configured such that the walls of the tapered retention body 5723 are substantially the same thickness over the length of the tapered portion 5727. In additional embodiments, the tapered portion 5727 is configured such that the walls of the tapered retention body 5723 vary over the length of the tapered retention body 5723, either increasing or decreasing in thickness. In further embodiments, the tapered interior space 5724 is configured with no cylindrical portion 5726 and only a tapered portion 5727. Other suitable profiles of the tapered interior space 5724 may be provided without departing from the scope of this disclosure.

The tapered retention body 5723 further includes one or more expansion slots 5725. FIGS. 57A and 57B illustrate a tapered retention body 5723 having two expansion slots 5725. The expansion slots 5725 extend from the base end 5728 of the tapered retention body 5723. In embodiments, the expansion slots 5725 extend the entire length of the tapered portion 5727 to the cylindrical portion 5726. In further embodiments, the expansion slots 5725 extend into the cylindrical portion 5726 or stop short of the cylindrical portion 5726. The expansion slots 5725 divide the tapered retention body 5723 into multiple tapered retention body walls 5730. The expansion slots 5725 permit the multiple tapered retention body walls 5730 to expand away from each other when externally oriented radial force is provided by the tapered sides of the inner wedge 5711 inserted into the tapered interior space 5724. FIG. 57B illustrates a tapered retention body 5723 having two expansion slots 5725 and two tapered retention body walls 5730. In further embodiments, additional expansion slots 5725 and a commensurate number of tapered retention body walls 5730 may be included.

The multiple tapered retention body walls 5730 include interlock slots 5731 located therein. In embodiments, each tapered retention body wall 5730 has an interlock slot 5731. In additional embodiments, two tapered retention body walls 5730 include interlock slots 5731. In further embodiments, any appropriate number of tapered retention body walls 5730 may include an interlock slot 5731. An interlock slot 5731 is a slot through a tapered retention body wall 5730. In embodiments, interlock slots may be square, circular, rectangular, or any other suitable shape. The interlock slots 5731 are surrounded by the tapered retention body walls 5730. The interlock slots 5731 are configured to mate with one or more interlock projections 5712 (shown in FIG. 57C) extending from an inner wedge 5711. Thus, the interlock slots 5731 are at least partially enclosed at the base end by the base end 5728 of the tapered retention body 5723. In some embodiments, the interlock slots 5731 are fully surrounded by the tapered retention body walls 5730. In additional embodiments, the interlock slots 5731 are only partially surrounded by the tapered retention body walls 5730. The interlock slots 5731 may be further configured to permit inflation fluid to pass therethrough, as explained in greater detail with respect to FIGS. 59A-59F.

The inner wedges 5711, pictured in FIGS. 57C and 57D, include a truncated cone 5719 having tapered sides, one or more fluid passages 5713, a central hollow 5714, and one or more interlock projections 5712. The truncated cone 5719 is a hollow tapered body having an apex end 5715 and a base end 5716. The central hollow 5714 shares a central longitudinal axis with the truncated cone 5719 and runs the entire length of the truncated cone 5719. The central hollow 5714 is sized and adapted to permit disposition of the inner wedge 5711 over an inner shaft of a balloon catheter, such as the inner shaft 5930, discussed further below. The diameter of the truncated cone 5719 at an apex end 5715 is at least as large as the diameter of the central hollow 5714. The diameter of the truncated cone 5719 at a base end 5716 is selected to expand the outer bumper 5721 from the first radially unexpanded size to the second radially expanded size, wherein the first radially unexpanded size is selected to fit within the neck of a balloon during assembly and the second radially expanded size is selected to permit the interlocked multipart retention bumper 5701 to maintain the axial position of a prosthetic heart valve, as discussed in greater detail throughout. The one or more fluid passages 5713 are axial passageways, each with an opening in the base end 5716 of the inner wedge 5711 and an opening on the tapered exterior wall of the inner wedge 5711. The one or more fluid passages 5713 are substantially parallel to the central hollow 5714 and are configured to permit longitudinal flow of inflation fluid therethrough. Substantially parallel, as used herein, refers to structures that are within 10 degrees, within 5 degrees, or within 1 degree of parallel.

The inner wedges 5711 further include one or more interlock projections 5712 projecting from the truncated cone 5719. The interlock projections 5712 are wedge shaped projections having a projection base 5760 approximately parallel to and on same plane as the base end 5716 of the truncated cone 5719. A slope of a leading edge 5761 of the interlock projections 5712 is less steep than that of the truncated cone 5719, with respect to the base end 5716, which permits the interlock projections 5712 to extend outward away from the truncated cone 5719. The leading edge 5761 facilitates the expansion of the outer bumpers 5721 when the inner wedges 5711 and the outer bumpers 5721 are interlocked, as discussed below. The shape of the interlock projections 5712 facilitates various molding manufacturing processes. Projecting shapes, such as the interlock projections 5712, may be easier to manufacture through molding processes than other shapes, for example, shapes having undercuts. The combination of the shape of the interlock projections 5712 and the interlock slots 5731 do not require any undercut shapes, and thus may increase manufacturability.

In further embodiments, the interlock projections 5712 may be positioned such that the projection base 5760 is not parallel to the base end 5716 of the truncated cone 5719 and/or does not intersect the plane of the base end 5716 of the truncated cone 5719. The interlock projections 5712, as discussed above, are configured to interlock with the interlock slots 5731 of the outer bumpers 5721, and the slope and angles of the leading edge 5761 and the projection base 5760 may be adjusted in various ways while still permitting interlock with the interlock slots 5731.

The inner wedges 5711 and outer bumpers 5721 may be composed of any suitable material. For example, suitable plastics or polymers may include high density polyethylene, thermoplastic elastomers, Pebax®, etc. In embodiments, the inner wedges 5711 and/or the outer bumpers 5721 each have a relatively high durometer so as to be substantially non-compressible during conditions expected to accompany manufacture, assembly, or use. As used herein, substantially non-compressible during conditions expected to accompany manufacture, assembly, or use means that the inner wedges 5711 and/or the outer bumpers 5721 show less than 5%, less than 3%, and/or less than 1% strain when subject to forces or stresses common during manufacture, assembly, and/or use. For example, a suitable durometer may be in excess of 60D, in excess of 65D, in excess of 70D, or in excess of 75D.

In embodiments, the material of the inner wedges 5711 or the outer bumpers 5721 may include a radiopaque material, such as barium sulfate, to increase imaging visibility during valve delivery and deployment operations. In embodiments, the inner wedges 5711 and the outer bumpers 5721 may be injection molded and/or over molded to an inner shaft, such as the inner shaft 5930, as discussed below with respect to FIGS. 59A-59F. The inner wedges 5711 or the outer bumpers 5721 may be over molded according to an assembly method selection, as discussed below with respect to FIGS. 59A-59F.

In embodiments, the inner wedge 5711 may be sized and configured to achieve a specific outer diameter of the multipart retention bumper 5701 after interlock. Multiple inner wedges 5711 having different sizes may be employed to interlock with the outer bumpers 5721 and expand the outer bumpers 5721 to different final diameters. Thus, the outer bumper 5721 is configured to expand to different second radially expanded sizes depending on the size of the inner wedge 5711 with which it is interlocked. Different inner wedges 5711 may be selected to customize the final radially expanded size according to a sizing of a prosthetic heart valve to be crimped onto a balloon catheter employing the multipart retention bumpers 5701.

FIGS. 57E and 57F illustrate the assembly and interlock of an outer bumper 5721 and an inner wedge 5711 to form the multipart retention bumper 5701. FIG. 57E illustrates the inner wedge 5711 prior to interlock with the outer bumper 5721. During the interlock process, the inner wedge 5711 will follow arrow 5795 while the tapered retention body walls 5730 will expand according to arrow 5796. As the outer bumper 5721 and the inner wedge 5711 are advanced towards one another, the tapered retention body walls 5730 are pressed outward due to the taper of the truncated cone 5719 of the inner wedge 5711. The leading edge 5761 of the interlock projections 5712 serves to press the tapered retention body walls 5730 out further. When the inner wedge 5711 has advanced far enough into the tapered interior space 5724 for the interlock projections 5712 to project into the interlock slots 5731, the tapered retention body walls 5730 snap closed from the expanded position to maintain the position of the inner wedge 5711. After interlock, the inner wedge 5711 is prevented from exiting the tapered interior space 5724 by engagement between the interlock projections 5712 and the walls of the interlock slots 5731.

In the interlocked configuration, as shown in FIG. 57F, the diameter of the multipart retention bumper 5701 is expanded to the second radially expanded size, large enough to prevent axial migration of the prosthetic heart valve. In this configuration, the fluid passages 5713 are each radially aligned with either an interlock slot 5731 or an expansion slot 5725. The interlock slot 5731 and the expansion slot 5725 may thus act as flow slots for inflation fluid during inflation of a balloon associated with the balloon catheter employing the multipart retention bumpers 5701. At the proximal end of the distal portion of a balloon catheter employing the multipart retention bumpers 5701, inflation fluid passes through the flow slots and through the fluid passages 5713 into the interior of the balloon. At the distal end of the distal portion of a balloon catheter employing the multipart retention bumpers 5701, inflation fluid passes through the fluid passages and the flow slots into the distal end of the balloon.

Due to the relatively high durometer, the interlocked retention bumpers 5701 are substantially non-compressible. After interlocking, the inner wedges 5711 serve to support the outer bumpers 5721 and no significant compression can occur. As discussed above, the inner wedges 5711 are substantially non-compressible due to the material of which they are constituted. Although portions of the outer bumpers 5721 may be flexible to permit expansion of the tapered retention body walls 5730, the structure of the outer bumpers 5721 is non-compressible. Further, to facilitate further non-compressibility during a manufacturing or assembly step, the inner wedges 5711 and outer bumpers 5721 may be partially interlocked during insertion into the opening of a balloon of a balloon catheter. For example, the inner wedge 5711 may be pressed into the tapered interior space 5724 of the outer bumper 5721 to a degree such that the outer surface of the inner wedge 5711 contacts the tapered retention body walls 5730 without providing enough force or pressure to cause the tapered retention body walls 5730 to expand outwardly. Thus, the tapered retention body walls 5730 cannot bend inwards due to the presence of the inner wedge 5711. The inner wedge 5711, in this configuration, does not expand the tapered retention body walls 5730 of the outer bumper 5721, and thus the partially assembled retention bumper 5701 may still fit into the opening of the balloon.

FIGS. 58A-58H illustrate multipart retention bumpers 5801 according to embodiments hereof. The multipart retention bumpers 5801 include inner portions, i.e., inner wedges 5811, and outer portions, i.e., outer bumpers 5821. The multipart retention bumpers 5801 are non-compressible retention bumpers that facilitate substantially longitudinal flow of inflation fluid while limiting radial flow. Limiting radial flow may include reducing, minimizing, eliminating radial flow. As used herein, substantially longitudinal flow refers to fluid flows having streamlines approximately parallel to a designated longitudinal axis. For example, a longitudinal flow in a balloon catheter may have streamlines approximately parallel to a central longitudinal axis of the balloon catheter. Approximately parallel may include streamlines within 10 degrees, within 5 degrees, and/or within 1 degree of parallel. Longitudinal flows represent fluid flows along the length of the balloon catheter. Radial flows refer to fluid flows having streamlines that deviate from parallelism with a designated longitudinal axis, having a significant orthogonal vector component. A streamline with a significant orthogonal vector component may deviate from parallel by 10 degrees or more. Radial flows represent flows towards or away from the axial center of the balloon catheter. The inner wedges 5811 and outer bumpers 5821 are configured such that, when interlocked, the maximum diameter of the outer bumpers 5821 (and thus the maximum diameter of the multipart retention bumpers 5801) expands from a first radially unexpanded size to a second radially expanded size, wherein the first radially unexpanded size is selected to fit within the neck of a balloon during assembly of a balloon catheter and the second radially expanded size is selected to permit the interlocked multipart retention bumper 5801 to maintain the axial position of a prosthetic heart valve crimped to the balloon, as discussed in greater detail below.

In an interlocked configuration, the multipart retention bumpers 5801 have an outer diameter at the second expanded size and are configured to maintain the axial position of a prosthetic heart valve crimped to the balloon. In a non-interlocked configuration, the constituent components of the multipart retention bumpers 5801, i.e., the inner wedges 5811 and the outer bumpers 5821, each have an outer diameter at the first radially unexpanded size. The first radially unexpanded size for the inner wedges 5811 and the first radially unexpanded size for the outer bumpers 5821 need not be equal. In embodiments, each of the inner wedges 5811 and the outer bumpers 5821 are configured with maximum diameters in the first radially unexpanded size between approximately 0.1 inches and 0.25 inches, between 0.15 and 0.22 inches, between 0.19 and 0.21 inches, or approximately 0.2 inches. Such sizes may be suitable for entry into the opening of a balloon of a balloon catheter, as discussed in greater detail below with respect to FIGS. 59A-59F. In embodiments, the multipart retention bumpers 5801 may have a maximum diameter, in an interlocked configuration, between 0.25 inches and 0.35 inches, between 0.27 and 0.33 inches, between 0.29 and 0.31 inches, or approximately 0.3 inches after the inner wedges 5811 and the outer bumpers 5821 are interlocked.

Referring now to FIGS. 58A and 58B, the outer bumper 5821 includes a central hub 5822 with a central hollow 5827 sized and adapted for disposition over an inner shaft, such as the inner shaft 5930 shown in FIGS. 59A-59F. Projecting from the central hub 5822 is a plurality of retention branches 5823. Between each pair of retention branches 5823 is a flow slot 5816. The retention branches 5823 are arranged radially around the central hub 5822 and project from the central hub 5822 both axially and radially to collectively define a tapered retention body 5824. The tapered retention body 5824 has an apex end 5829 where the retention branches 5823 connect to the central hub 5822 and a base end 5828 at the ends of the retention branches 5823 located away from the central hub 5822. One or more of the retention branches 5823 include projections 5830 at their base end 5828. In embodiments, all of the retention branches 5823 include projections 5830 at their base ends 5828. As discussed in greater detail below, the projections 5830 are configured to interlock and/or engage with corresponding depressions 5831 in the inner wedges 5811.

The retention branches 5823 surround an empty tapered interior space 5825. The tapered interior space 5825 has a smallest diameter at the apex end 5829 of the tapered retention body 5824. The tapered interior space 5825 has a smallest diameter corresponding to the diameter of the central hollow 5827 expanding to a largest diameter at the base end 5828 of the tapered retention body 5824. In additional embodiments, the smallest diameter of the tapered interior space 5825 is larger than the diameter of the central hollow 5827. In embodiments, the retention branches 5823 are configured with walls of substantially the same thickness over the length of the tapered retention body 5824. In additional embodiments, the retention branches 5823 are configured such that their walls increase or decrease in thickness over their length.

FIGS. 58A and 58B illustrate an outer bumper 5821 having four flow slots 5816. The flow slots 5816 extend from the base end 5828 of the tapered retention body 5824 towards the apex end 5829 of the tapered retention body 5824. In embodiments, the flow slots 5816 extend the entire length of tapered retention body 5824 to the central hub 5822. In further embodiments, the flow slots 5816 stop short of the central hub 5822. The flow slots 5816 divide the retention branches 5823 from each other. The functionality of the flow slots 5816 is discussed in greater detail below with respect to the interlock with the inner wedges 5811.

Figures 58C, 58D:
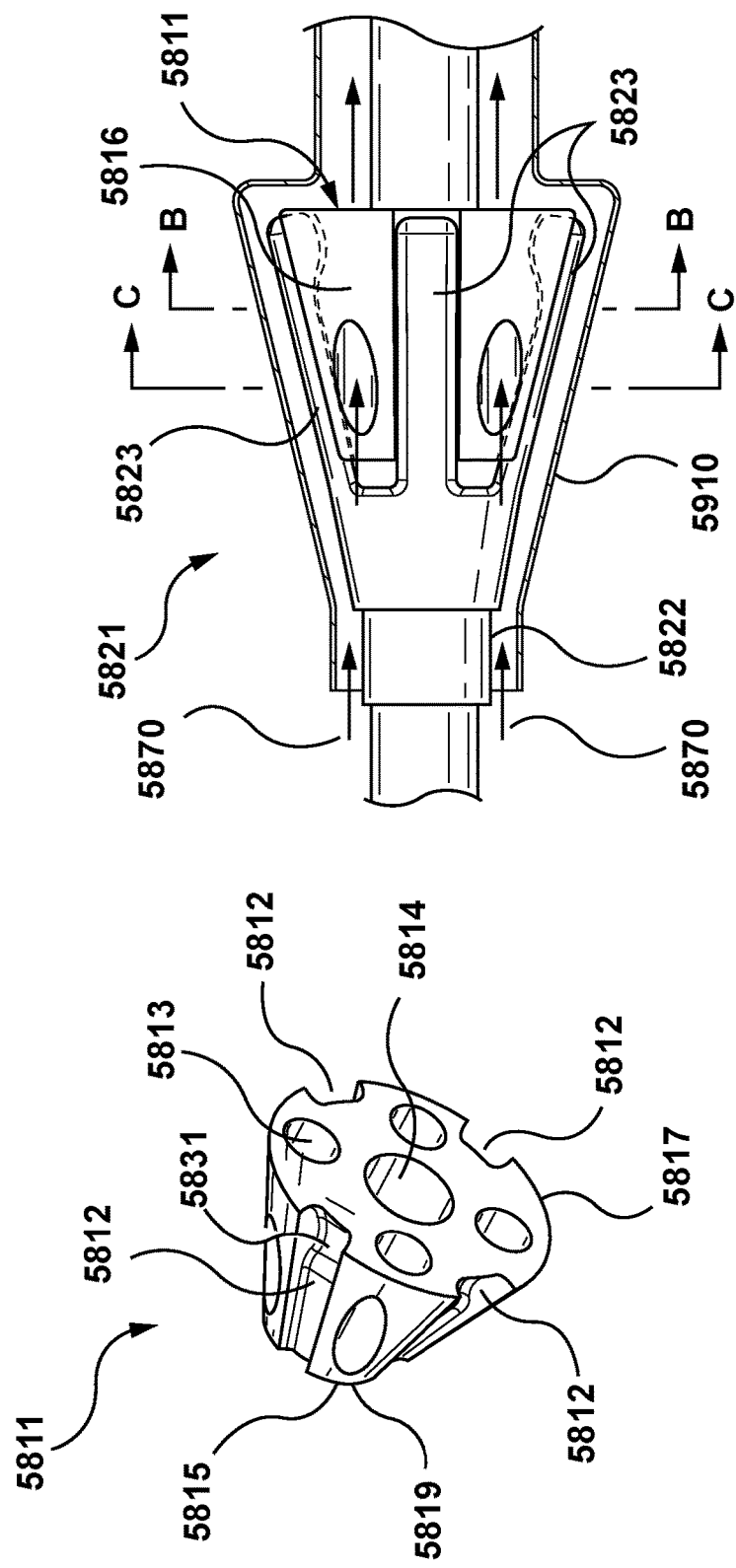
Figure 58E:
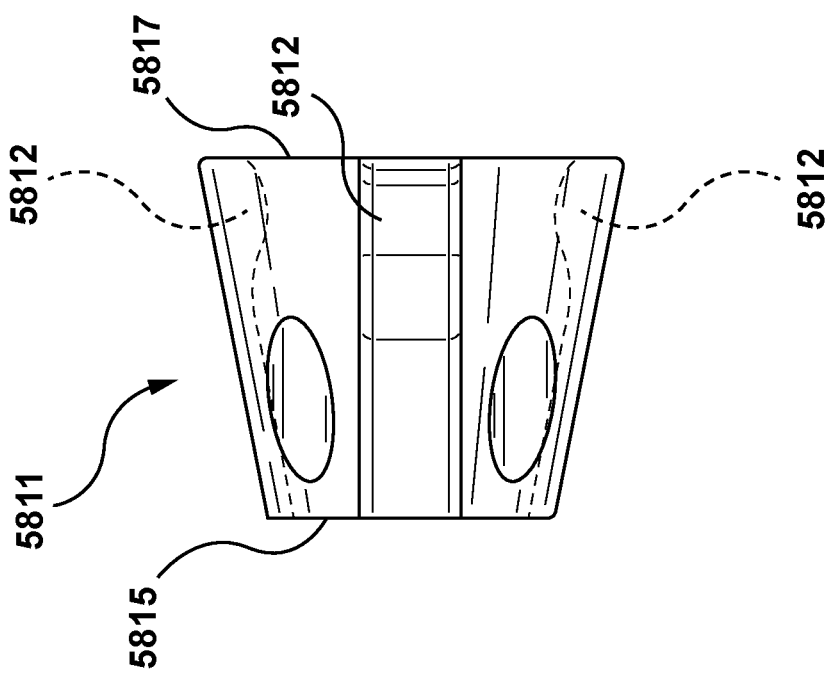

Referring now to FIGS. 58C and 58D, the inner wedges 5811 include a truncated cone 5819 having tapered sides, one or more fluid passages 5813, a central hollow 5814, and one or more retention grooves 5812. The truncated cone 5819 is a hollow tapered body having an apex 5815 and a base 5817. The central hollow 5814 shares a central longitudinal axis with the truncated cone 5819 and runs the entire length of the truncated cone 5819. The central hollow 5814 is sized and adapted to permit disposition of the inner wedge 5811 over an inner shaft of a balloon catheter, such as the inner shaft 5930, discussed further below. The diameter of the truncated cone 5819 at the apex 5815 is at least as large as the diameter of the central hollow 5814. The diameter of the truncated cone 5819 at the base 5817 is selected to expand the outer bumper 5821 from the first radially unexpanded size to the second radially expanded size, wherein the first radially unexpanded size is selected to fit within the neck of a balloon during assembly and the second radially expanded size is selected to permit the interlocked multipart retention bumper 5801 to maintain the axial position of a prosthetic heart valve, as discussed in greater detail below. The one or more fluid passages 5813 are axial passageways, each with an opening in the base 5817 of the inner wedge 5811 and an opening on the tapered exterior wall of the inner wedge 5811. The one or more fluid passages 5813 are substantially parallel to the central hollow 5814 and are configured to permit longitudinal flow of inflation fluid therethrough.

The inner wedges 5811 further include one or more retention grooves 5812 running the length of the truncated cone 5819. The retention grooves 5812 are depressions in the wall of the truncated cone 5819 sized and adapted to accommodate the retention branches 5823 of the outer bumpers 5821. When the inner wedges 5811 and the outer bumpers 5821 are interlocked, the retention branches 5823 are disposed inside the retention grooves 5812. At the base 5817 of the truncated cone 5819, the retention branches 5823 project radially outward from the outer diameter of the truncated cone 5819 to establish the second radially expanded size of the multipart retention bumpers 5801. In embodiments, the retention branches 5823 and retention grooves 5812 may be configured such that the retention branches 5823 sit flush with the outer wall of the truncated cone 5819, over at least a portion of their length. In such an embodiment, the retention branches 5823 project radially outward from the outer diameter of the truncated cone 5819 to establish the second radially expanded size of the multipart retention bumpers 5801 even if portions of the retention branches 5823 closer to the apex 5815 of the truncated cone 5819 are flush with the outer wall of the truncated cone 5819.

The contour of the retention branches 5823 and the retention grooves 5812 is configured such that the retention branches 5823 snap into place within the retention grooves 5812, as shown in FIG. 58D. One or more of the retention branches 5823 is configured with a projection 5830 configured to mate with the corresponding depression 5831 in the retention groove 5812.

FIG. 58D illustrates various functional aspects of the retention bumpers 5801. As shown in FIG. 58D, an inner wedge 5811 and an outer bumper 5821 are interlocked to form the multipart retention bumper 5801. The multipart retention bumper 5801 is illustrated as part of a balloon catheter, disposed over an inner shaft 5930 inside of a balloon 5910. The remainder of the distal end of the balloon catheter 5900 is illustrated in FIGS. 59A-59F. The multipart retention bumpers 5801 are interlocked and in the second radially expanded size. FIG. 58D further illustrates inflation fluid flow associated with the multipart retention bumpers 5801 in the form of flow paths 5870.

The flow slots 5816 may provide multiple functional results. The flow slots 5816 are configured to permit the expansion of the outer bumpers 5821 from the first radially unexpanded size to the second radially expanded size. The flow slots 5816 separate the retention branches 5823 and thus permit the retention branches 5823 to expand radially under outward radial pressure or force provided by the inner wedge 5811 during interlock.

FIGS. 58F and 58G are cross-sections taken at the line CC and the line BB, respectively, as shown in FIG. 58D. The flow slots 5816 are further configured to facilitate longitudinal flow of inflation fluid and limit radial flow of inflation fluid. The flow slots 5816 are configured to radially align with the fluid passages 5813 such that the areas around the proximal and distal axial openings of the fluid passages 5813 are unobstructed by the outer bumper 5821. This feature is illustrated in FIG. 58F, which is a cross-section of the multipart retention bumpers 5801 taken at the line CC shown in FIG. 58D. As shown in FIG. 58F, the retention branches 5823 do not obscure or obstruct the openings around the proximal and distal openings of the fluid passages 5813. Thus, because the flow slots 5816 radially align with the fluid passages 5813, the flow of inflation fluid may follow a longitudinal streamline without the need for radial flow. Such longitudinal flow paths 5870 are illustrated in FIG. 58D, which shows the interlocked multipart retention bumper 5801 positioned within a balloon 5810. Inflation fluid flows substantially longitudinally through the multipart retention bumpers 5801 without significant amounts of radial flow. The multipart retention bumpers 5801 limit radial flow. Limiting radial flow may include reducing, minimizing, or eliminating radial flow of inflation fluid therethrough.

The inner wedges 5811 and outer bumpers 5821 may be composed of any suitable material. For example, suitable plastics or polymers may include high density polyethylene, thermoplastic elastomers, Pebax®, etc. In embodiments, the inner wedges 5811 and/or the outer bumpers 5821 have a relatively high durometer so as to be substantially non-compressible during conditions expected to accompany manufacture, assembly, or use. As used herein, substantially non-compressible during conditions expected to accompany manufacture, assembly, or use means that the inner wedges 5811 and/or outer bumpers 5821 show less than 5%, less than 3%, and/or less than 1% strain when subject to forces or stresses common during manufacture, assembly, and/or use. For example, a suitable durometer may be in excess of 60D, in excess of 65D, in excess of 70D, or in excess of 75D. In embodiments, the material of the inner wedges 5811 or outer bumpers 5821 may include a radiopaque material, such as barium sulfate, to increase imaging visibility during valve delivery and deployment operations. In embodiments, the inner wedges 5811 and outer bumpers 5821 may be injection molded and/or over molded to an inner shaft, such as inner shaft 5930, as discussed below with respect to FIGS. 59A-59F. The determination of which of the inner wedges 5811 and/or outer bumpers 5821 may be over molded is based on a selected assembly method, as discussed below with respect to FIGS. 59A-59F.

Figure 58H:
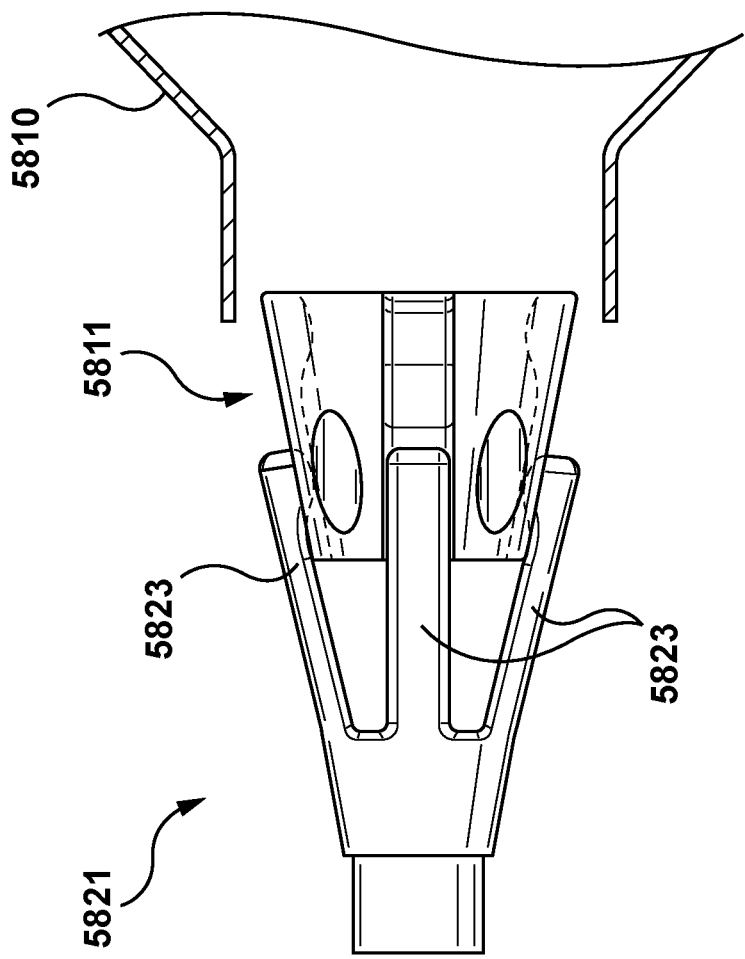

Due to the relatively high durometer, the interlocked retention bumpers 5801 are substantially non-compressible. After interlocking, the inner wedges 5811 serve to support the outer bumpers 5821 and no significant compression can occur. As discussed above, the inner wedges 5811 are substantially non-compressible due to the material of which they are constituted. Although portions of the outer bumpers 5821 may be flexible to permit expansion of the projections 5830, the structure of the outer bumpers 5821 is non-compressible. In embodiments, to facilitate non-compressibility during a manufacturing step, the inner wedges 5811 and outer bumpers 5821 may be partially interlocked, as illustrated in FIG. 58H, during insertion into the opening of a balloon of a balloon catheter. For example, the inner wedge 5811 may be pressed into the tapered interior space 5825 of the outer bumper 5821 to a degree such that the outer surface of the inner wedge 5811 contacts the retention branches 5823 without providing enough force or pressure to cause the retention branches 5823 to expand outwardly. Thus, the retention branches 5823 cannot bend inwards due to the presence of the inner wedge 5811. The inner wedge 5811, in this configuration, does not expand the retention branches 5823 of the outer bumper 5821, and thus the partially assembled retention bumper 5801 may still fit into the opening of the balloon.

In embodiments, the inner wedge 5811 may be sized and configured to achieve a specific outer diameter of the multipart retention bumper 5801 after interlock. Multiple inner wedges 5811 having different sizes may be employed to interlock with the outer bumper 5821 and expand it to different final diameters. Thus, the outer bumper 5821 is configured to expand to different second radially expanded sizes depending on the size of the inner wedge 5811 with which it is interlocked. Different inner wedges 5811 may be selected to customize the final radially expanded size according to a sizing of a prosthetic heart valve to be crimped onto a balloon catheter employing the multipart retention bumpers 5801.

FIGS. 59A-59F illustrate states of an assembly process for a balloon catheter employing multipart retention bumpers. FIGS. 59A-59F illustrate an assembly process employing the multipart retention bumpers 5701 for example purposes only. The assembly process of FIGS. 59A-59F may be suitable for the multipart retention bumpers 5701, the multipart retention bumpers 5801, and any other multipart retention bumpers discussed herein. The assembly process of FIGS. 59A-59F is by way of example only, and balloon catheters including multipart retention bumpers may be assembled using different steps in a different order without departing from the scope of the present disclosure.

Figure 59A:
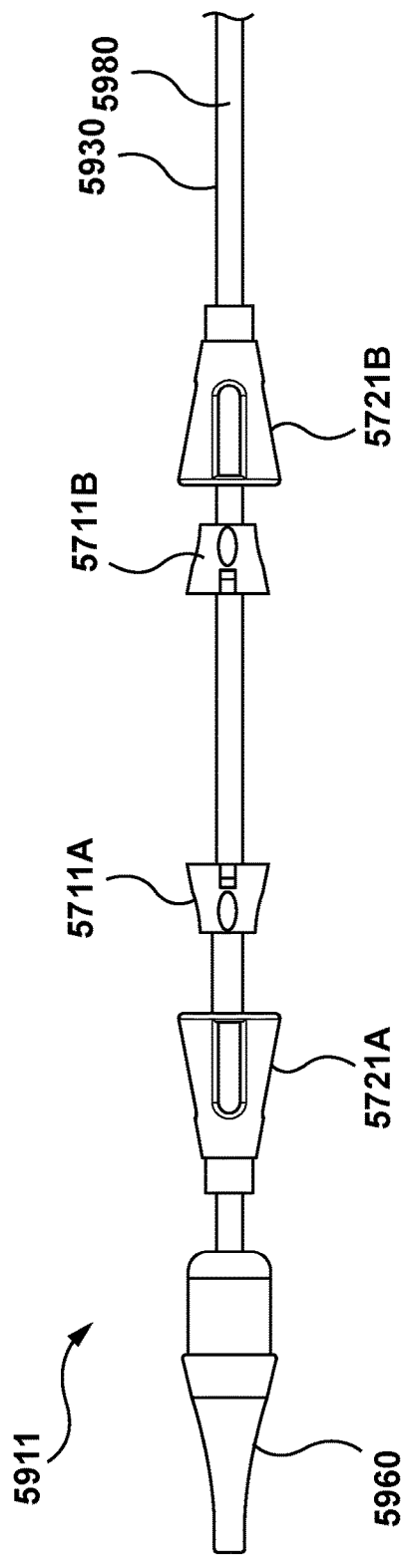

FIG. 59A illustrates a partial assembly 5911 prepared for balloon catheter assembly. The partial assembly 5911 includes the inner shaft 5930, the inner wedges 5711, the outer bumpers 5721, and a distal tip 5960. The distal tip 5960 is secured to the inner shaft 5930. Over molding of the distal tip may be selected to provide a sure connection throughout usage of the balloon catheter and to facilitate manufacturing. In further embodiments, the distal tip 5960 may be secured via other techniques, such as by bonding and/or adhesive.

In the partial assembly 5911, the distal and proximal outer bumpers 5721A and 5721B are secured to the inner shaft 5930. Over molding of the outer bumpers 5721 may be selected to provide a sure connection throughout usage of the balloon catheter, facilitate manufacturing, and insure accurate placement of the outer bumpers 5721 on the inner shaft 5930. In further embodiments, the outer bumpers 5721 may be secured via other techniques, such as by bonding and/or adhesive. The distal and proximal inner wedges 5711A and 5711B are loaded over the inner shaft 5930, but not secured thereto. In embodiments, the distal and proximal inner wedges 5711A and 5711B may be loaded over the inner shaft 5930 prior to an over molding process that assembles the distal and proximal outer bumpers 5721A and 5721B and the distal tip 5960.

In further embodiments, the distal inner wedge 5711A and the proximal outer bumper 5721B are secured to the inner shaft 5930, e.g., via over molding, bonding, and/or adhesive, while the distal outer bumper 5721A and the proximal inner wedge 5711B are unsecured to the inner shaft 5930. In further embodiments, both the distal inner wedge 5711A and the proximal inner wedge 5711B are over molded or otherwise secured to the inner shaft 5930 and the distal outer bumper 5721A and the proximal outer bumper 5721B are unsecured.

Figure 59B:
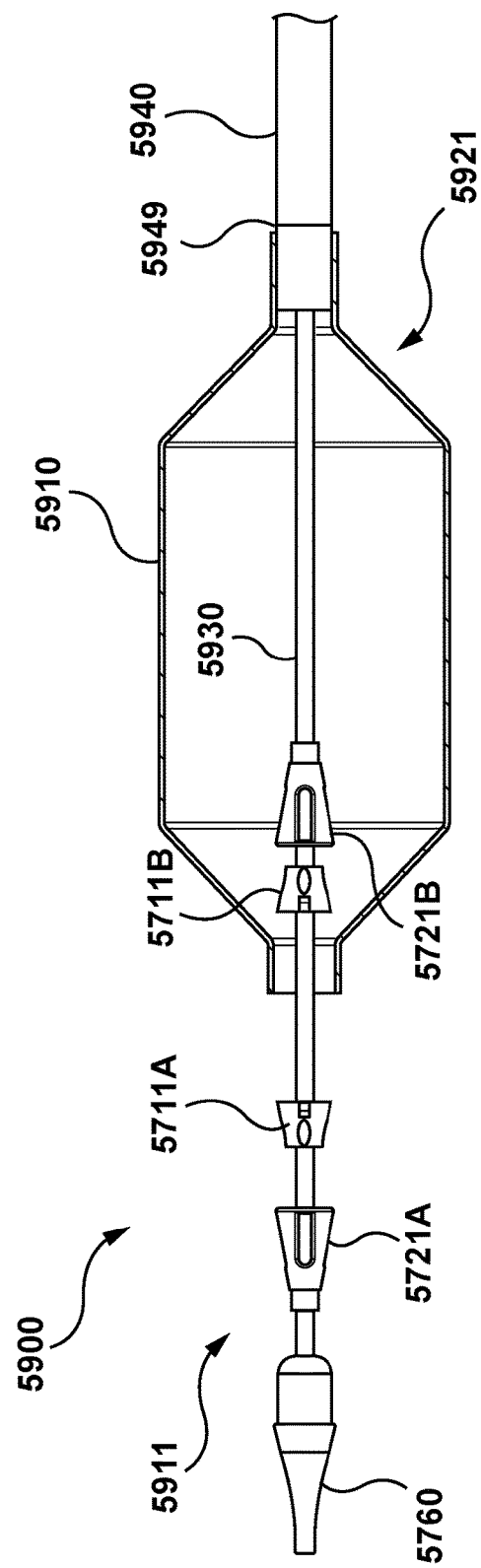

FIG. 59B illustrates the partial assembly 5911 being introduced to an outer assembly 5921. The outer assembly 5921 includes an outer shaft 5940 and a balloon 5910. A proximal end of the balloon 5910 is bonded to the outer shaft 5940 prior to insertion of the partial assembly 5911 into the balloon 5910 and insertion of the inner shaft 5930 into the outer shaft 5940. Bonding the balloon 5910 prior to insertion of the inner shaft 5930 into the outer shaft 5940 may facilitate the bonding process, because it alleviates a requirement for additional tooling, e.g., a mandrel, to support the inner shaft 5930 during such bonding. As discussed above, due to the sizing of the outer bumpers 5721, the partial assembly 5911 is configured to slide into the balloon opening 5949 of the balloon 5910 without compression.

In embodiments, prior to insertion of the partial assembly 5911 into the balloon 5910, the inner wedges 5711 may be partially interlocked with the outer bumpers 5721 so as to prevent unintended compression during the assembly and insertion process, as described above with respect to FIG. 58G.

Figure 59C:
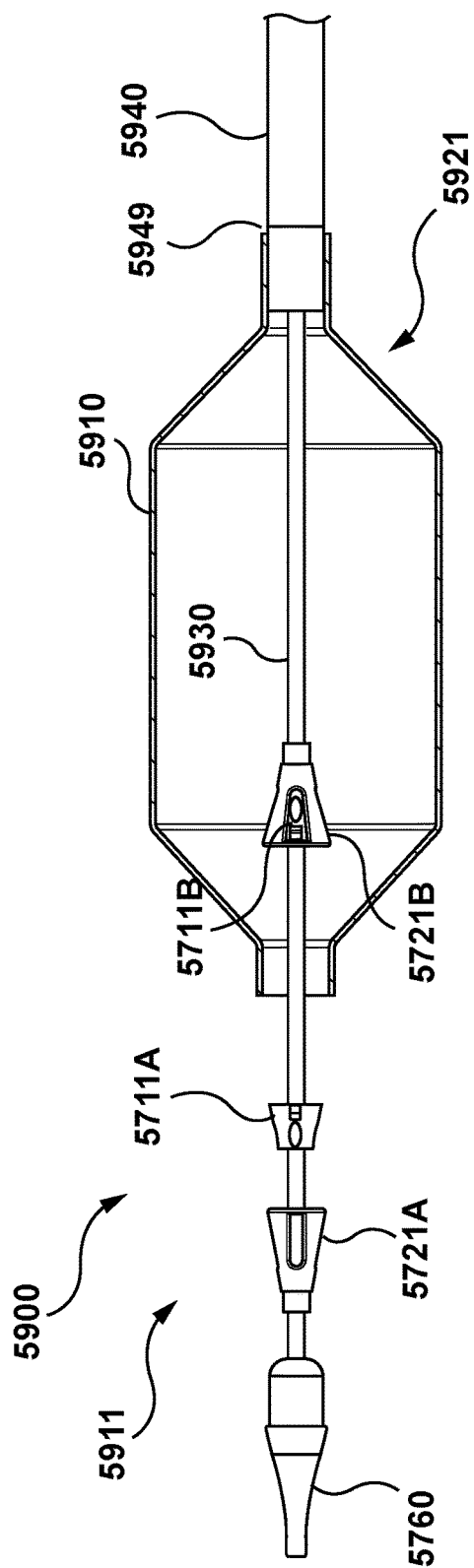

FIG. 59C illustrates interlocking the proximal inner wedge 5711B and the proximal outer bumper 5721B. The proximal outer bumper 5721B is secured to the inner shaft 5930, permitting the proximal inner wedge 5711B to be pushed into the tapered interior space 5724 of the proximal outer bumper 5721B. Pressing the proximal inner wedge 5711B into the tapered interior space 5724 of the proximal outer bumper 5721B causes the proximal outer bumper 5721B to expand from the first radially unexpanded size to the second radially expanded size. The proximal inner wedge 5711B may be pushed into the proximal outer bumper 5721B via the use of one or more tools configured to provide force to the proximal inner wedge 5711B through the balloon opening 5949 of the balloon 5910. Such tools, may include, for example, picks, hooks, mandrels, tubes, and other implements. The proximal inner wedge 5711B may click or snap into place inside the proximal outer bumper 5721B via the interlock of the interlock slots 5731 and the interlock projections 5712. In further embodiments employing alternate multipart retention bumpers, such as the multipart retention bumpers 5801, the inner wedges and outer bumpers may click or snap together through different means and/or may maintain interlock via pressure.

Figure 59D:
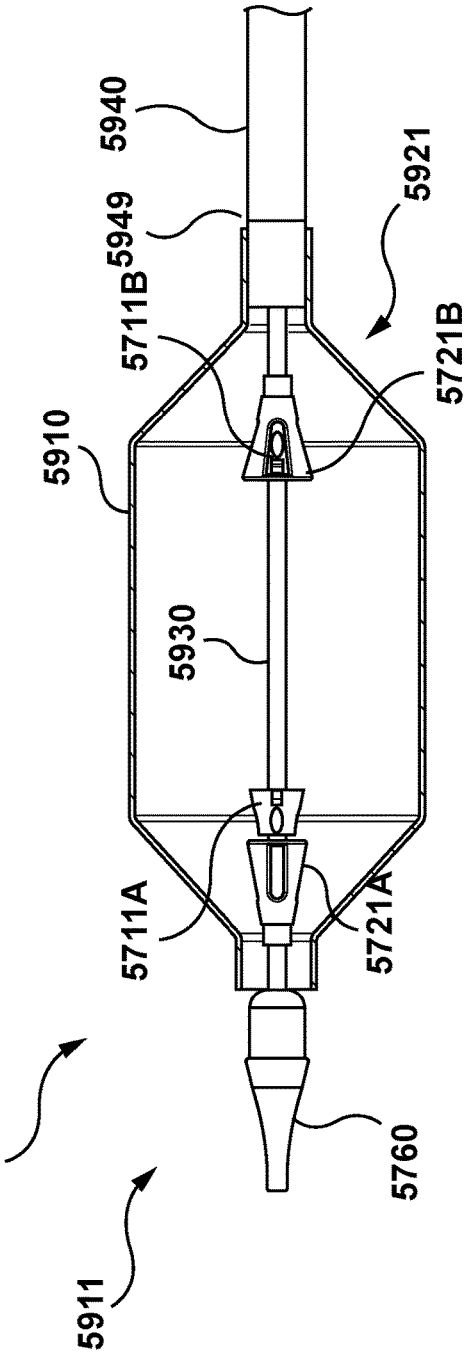

FIG. 59D illustrates the partial assembly 5911 being inserted further into the outer assembly 5921. As discussed above, due to the sizing of the outer bumpers 5721, the outer bumpers 5721 slide into the balloon opening 5949 of the balloon 5910 without compression. In embodiments, prior to further advancing the partial assembly 5911 into the balloon 5910, the inner wedges 5711 may be partially interlocked with the outer bumpers 5721 so as to prevent any inadvertent compression during the assembly and insertion process, as explained above with respect to FIG. 59G.

FIG. 59E illustrates the interlocking of the distal inner wedge 5711A and the distal outer bumper 5721A. In embodiments, the free moving distal inner wedge 5711A may be pulled into the secure outer distal bumper 5721A via a tool configured to be inserted through the balloon opening 5949. Such tools, may include, for example, picks, hooks, mandrels, tubes, and other implements. In further embodiments, where the distal inner wedge 5711A is secure, the free moving distal outer bumper 5721A is pushed over the secured distal inner wedge 5711A via a tool configured to be inserted through the balloon opening 5949. In further embodiments, the distal inner wedge 5711A and the distal outer bumper 5721A may be manually manipulated through the material of the balloon 5910 to achieve interlock.

The distal inner wedge 5711A may click or snap into place inside the distal outer bumper 5721A via the interlock of the interlock slots 5731 and the interlock projections 5712. In further embodiments employing alternate multipart retention bumpers, such as the multipart retention bumpers 5801, the inner wedges and outer bumpers may click or snap together through different means and/or may maintain interlock via pressure.

FIG. 59F illustrates completion of the assembly via bonding of the balloon 5910 to the distal tip 5960. The balloon 5910 is bonded to the distal tip 5960 via any suitable process, e.g., heat bonding, adhesion, etc., to finish construction of the distal delivery portion of the balloon catheter 5900. Assembly of the distal portion of the balloon catheter 5900 may then be completed by pleating and/or folding the balloon 5910 so that it may be closely wrapped to the inner shaft 5930 to permit the crimping of a prosthetic heart valve (not shown) in the space between the proximal and distal multipart retention bumpers 5701. After positioning of the inner shaft 5930 inside the outer shaft 5940, the inner shaft 5930 and the outer shaft 5940 define an inflation lumen 5975, through which inflation fluid may be passed to inflate the balloon 5910 during operation of the balloon catheter 5900. Further, the inner shaft 5930 defines a guidewire lumen 5980, through which a guidewire may be passed during operation of the balloon catheter 5900.

In variations of the assembly process, various steps may take place in a different order according to different requirements. For example, in embodiments, the balloon 5910 may be bonded to the outer shaft 5940 after insertion of multipart retention bumpers 5701 and inner shaft 5930 into the balloon 5910. This may permit access to the multipart retention bumpers 5701 from either end of the balloon 5910. In another example, the distal tip 5960 may be bonded to the inner shaft 5930 after insertion and interlock of the multipart retention bumpers 5701. This may facilitate access to the multipart retention bumpers 5701 through the balloon opening 5949. Other suitable variations may be employed.

Figure 60A:
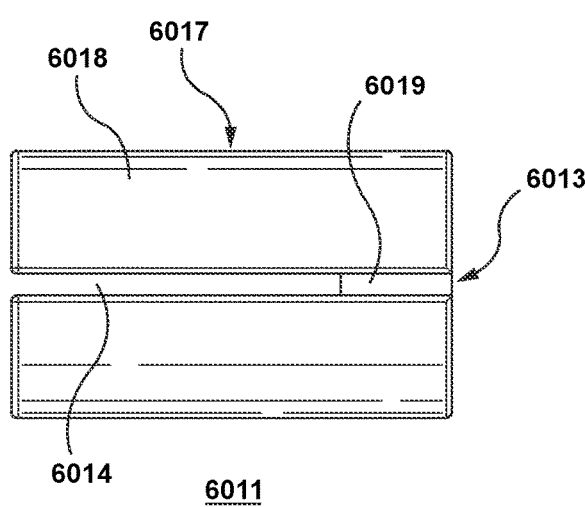
FIGS. 60A-E illustrate multipart retention bumpers consistent with embodiments hereof.
Figure 60B:
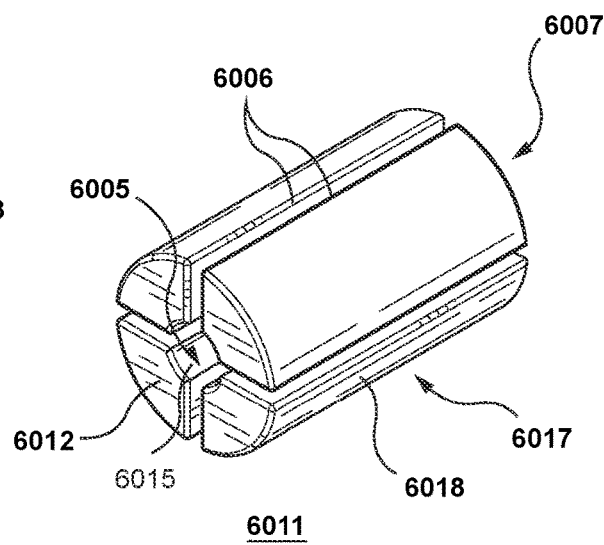
Figure 60C:
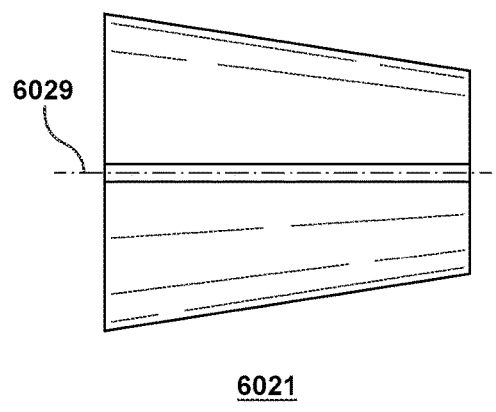
Figure 60D:
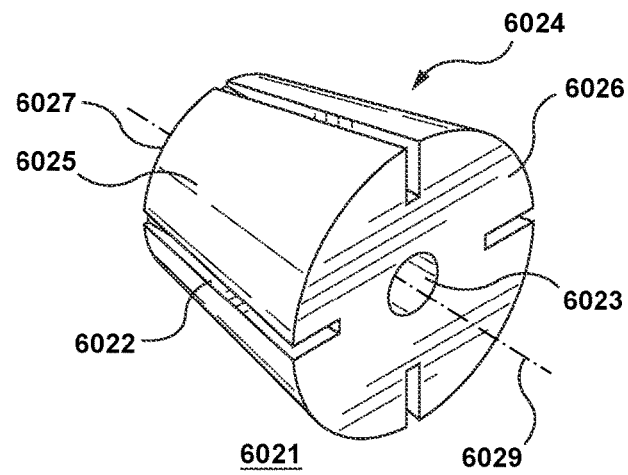
Figure 60E:
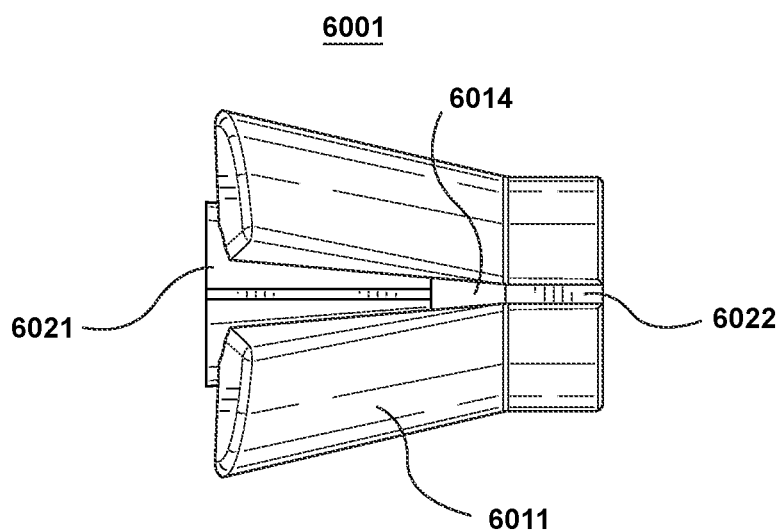

FIGS. 60A-E illustrate multipart retention bumpers 6001 according to embodiments hereof. The multipart retention bumpers 6001 include inner portions, i.e., inner wedges 6021, and outer portions, i.e., outer bumpers 6011. FIGS. 60A and 60B illustrate profile and perspective views of the outer bumper 6011. FIGS. 60C and 60D illustrate profile and perspective views of the inner wedge 6021. FIG. 60E is a profile view of the outer bumper 6011 and the inner wedge 6021 interlocked into the multipart retention bumper 6001. The multipart retention bumpers 6001 are compatible with embodiments of balloon catheters discussed herein, for example, the balloon catheter 5900, and may be assembled with the balloon catheter 5900 according to the assembly process described above with respect to FIGS. 59A-59F.

The multipart retention bumpers 6001 include the inner wedges 6021 and the outer bumpers 6011. The multipart retention bumpers 6001 are substantially non-compressible retention bumpers. The inner wedges 6021 and the outer bumpers 6011 are configured such that, when interlocked, the maximum diameter of the outer bumpers 6011 (and thus the maximum diameter of the multipart retention bumpers 6001) expands from a first radially unexpanded size to a second radially expanded size, wherein the first radially unexpanded size is selected to fit within the neck of a balloon during assembly of a balloon catheter and the second radially expanded size is selected to permit the interlocked multipart retention bumper 6001 to maintain the axial position of a prosthetic heart valve crimped to the balloon, as discussed in greater detail below.

In an interlocked configuration, the multipart retention bumpers 6001 have an outer diameter at the second radially expanded size and are configured to maintain the axial position of a prosthetic heart valve crimped to the balloon. In a non-interlocked configuration, the constituent components of the multipart retention bumpers 6001, i.e., the inner wedges 6021 and the outer bumpers 6011, each have an outer diameter at the first radially unexpanded size. The first radially unexpanded size for the inner wedges 6021 and the first radially unexpanded size for the outer bumpers 6011 need not be equal. In embodiments, each of the inner wedges 6021 and outer bumpers 6011 are configured with maximum diameters, in the non-interlocked configuration, between approximately 0.1 inches and 0.25 inches, between 0.15 and 0.22 inches, between 0.19 and 0.21 inches, or approximately 0.2 inches. Such sizes, i.e., the first radially unexpanded sizes, may be suitable for entry into the opening of a balloon of a balloon catheter, as discussed in greater detail above with respect to FIGS. 59A-59F. In embodiments, the multipart retention bumpers 6001, in the interlocked configuration, may have a maximum diameter between 0.25 inches and 0.35 inches, between 0.27 and 0.33 inches, between 0.29 and 0.31 inches, or approximately 0.3 inches after the inner wedges 6021 and the outer bumpers 6011 are interlocked.

Referring now to FIGS. 60A and 60B, the outer bumper 6011 is generally cylindrically shaped and includes a hub 6019 with a central hollow 6013 sized and adapted for disposition over an inner shaft, such as the inner shaft 5930 shown in FIGS. 59A-59F. Projecting radially and longitudinally from the hub 6019 are a plurality of retention arms 6017. The retention arms 6017 are defined by outer cylindrical surfaces 6018, inner surfaces 6015, retention surfaces 6012, end surfaces 6007, and sidewall surfaces 6006. The outer cylindrical surfaces 6018 of the retention arms 6017 are curved surfaces that define the generally cylindrical exterior of the outer bumper 6011. The inner surfaces 6015 of the retention arms 6017 are curved surfaces that define a retention hollow 6005 of the outer bumper 6011. Viewed in profile, the outer cylindrical surfaces 6018 and inner surfaces 6015 describe arc sections of coaxial circles. The retention hollow 6005 may be circular in profile, as shown in FIG. 60B to accommodate an inner wedge 6021, as discussed below. The retention arms 6017 further include retention surfaces 6012 disposed at an opposite longitudinal end of the retention arms 6017 from the hub 6019 and end surfaces 6007 disposed at the hub end of the retention arms 6017. Finally, the retention arms 6017 include sidewall surfaces 6006 extending between the retention surfaces 6012, the end surfaces 6007, the inner surfaces 6015, and the retention surfaces 6012. In embodiments, the retention surfaces 6012 may be substantially perpendicular to the outer cylindrical surfaces 6018, i.e., radial with respect to the retention hollow 6005, as shown in FIGS. 60A and 60B. In further embodiments, the retention surfaces 6012 may form a non-perpendicular angle with respect to the outer cylindrical surfaces 6018 such that, when the outer bumper 6011 is interlocked with an inner wedge 6021, the retention surfaces 6012 are substantially perpendicular to a longitudinal axis of the outer bumper 6011.

The retention arms 6017 are separated from one another by flow slots 6014. The flow slots 6014 are defined by the sidewall surfaces 6006 of neighboring retention arms 6017. In embodiments, the sidewall surfaces 6006 defining each flow slot 6014 may be substantially parallel to one another. The flow slots 6014 may serve multiple purposes. The flow slots 6014 provide separation between the retention arms 6017 such that, when the outer bumper 6011 and the inner wedge 6021 are interlocked, the retention arms 6017 are permitted to flex or hinge outwards from the hub 6019. Further, the flow slots 6014 permit inflation fluid to pass therethrough during operation of a balloon catheter employing the multipart retention bumpers 6001 as discussed in greater detail below with respect to FIG. 60E.

The inner wedges 6021, pictured in FIGS. 60C and 60D, include a tapered body 6024 having a base 6026 and an apex 6027 joined by tapered surfaces 6025. The tapered body 6024 further includes one or more flow passages 6022, and a central hollow 6023. The tapered surfaces 6025, which define the external surfaces of the inner wedge 6021, are separated one from another by the flow passages 6022. The tapered body 6024 is circular in profile and tapers from a first smaller diameter at the apex 6027 to a second larger diameter at the base 6026. The central hollow 6023 shares a central longitudinal axis with the tapered body 6024 and runs the entire length of the tapered body 6024.

The central hollow 6023 is sized and adapted to permit disposition of the inner wedge 6021 over an inner shaft of a balloon catheter, such as the inner shaft 5930, discussed above. The diameter of the tapered body 6024 at the apex 6027 is at least as large as the diameter of the central hollow 6023. The diameter of the tapered body 6024 at the base 6026 is selected to expand the outer bumper 6011 from the first radially unexpanded size to the second radially expanded size, wherein the first radially unexpanded size is selected to fit within the neck of a balloon during assembly and the second radially expanded size is selected to permit the interlocked multipart retention bumper 6001 to maintain the axial position of a prosthetic heart valve, as discussed in greater detail throughout.

The one or more flow passages 6022 are axial channels, each with an opening in the base 6026 of the tapered body 6024, an opening on the exterior wall of the tapered body 6024 (i.e., separating the tapered surfaces 6025), and an opening at the apex 6027 of the tapered body 6024. The one or more flow passages 6022 are substantially parallel to a central longitudinal axis 6029 of the tapered body and are configured to permit longitudinal flow of inflation fluid therethrough. Substantially parallel, as used herein, refers to structures that are within 10 degrees, within 5 degrees, or within 1 degree of parallel.

The inner wedges 6021 and outer bumpers 6011 may be composed of any suitable material. For example, suitable plastics or polymers may include high density polyethylene, thermoplastic elastomers, Pebax®, etc. In embodiments, the inner wedges 6021 and/or the outer bumpers 6011 each have a relatively high durometer so as to be substantially non-compressible during conditions expected to accompany manufacture, assembly, or use. As used herein, substantially non-compressible during conditions expected to accompany manufacture, assembly, or use means that the inner wedges 6021 and/or the outer bumpers 6011 show less than 5%, less than 3%, and/or less than 1% strain when subject to forces or stresses common during manufacture, assembly, and/or use. For example, a suitable durometer may be in excess of 60D, in excess of 65D, in excess of 70D, or in excess of 75D.

FIG. 60E illustrates the assembly and interlock of the outer bumper 6011 and the inner wedge 6021 to form the multipart retention bumper 6001. As the outer bumper 6011 and the inner wedge 6021 are advanced towards one another, the retention arms 6017 are pressed outward due to the taper of the tapered body 6024 of the inner wedge 6021. The apex 6027 of the tapered body 6024 of the inner wedge 6021 is sized and configured for entry into the retention hollow 6005 of the outer bumper 6011. The inner wedge 6021 remains within the outer bumper 6011 due to pressure from the outer bumper 6011. In further embodiments, the inner wedge 6021 or the outer bumper 6011 may include features configured to facilitate an interlock or snap fit, as discussed above, e.g., with respect to FIGS. 57A-58H. In further embodiments, the retention hollow 6005 may include a tapered opening to accommodate the apex 6027 of the inner wedge 6021.

In the interlocked configuration the diameter of the multipart retention bumper 6011 is expanded to the second radially expanded size, large enough to prevent axial migration of the prosthetic heart valve. In this configuration, the flow passages 6022 of the inner wedge 6021 are each radially aligned with a flow slot 6014 of the outer bumper 6011. The flow passages 6022 and flow slots 6014 combine as flow slots for inflation fluid during inflation of a balloon associated with the balloon catheter employing the multipart retention bumpers 6001. At the proximal end of the distal portion of a balloon catheter employing the multipart retention bumpers 6001, inflation fluid passes through the flow slots 6014 and the flow passages 6022 into the interior of the balloon. At the distal end of the distal portion of a balloon catheter employing the multipart retention bumpers 6001, inflation fluid passes through the flow slots 6014 and flow passages 6022 into the distal end of the balloon. The combination of flow passages 6022 and flow slots 6014 are further configured to facilitate longitudinal flow of inflation fluid and limit radial flow of inflation fluid. Inflation fluid flows substantially longitudinally, i.e., in parallel with the central longitudinal axis 6029, through the multipart retention bumpers 6001.

Due to the relatively high durometer, the interlocked retention bumpers 6001 are substantially non-compressible. After interlocking, the inner wedges 6021 serve to support the outer bumpers 6011 and no significant compression can occur. As discussed above, the inner wedges 6021 are substantially non-compressible due to the material of which they are constituted. Although portions of the outer bumpers 6011 may be flexible to permit expansion of the retention arms 6017 the structure of the outer bumpers 6011 is non-compressible. Further, to facilitate further non-compressibility during a manufacturing or assembly step, the outer bumpers 6011 may have a diameter selected to fit through an opening of a balloon during an assembly process.

FIGS. 61A-61B and FIGS. 62A-62B illustrate retention bumpers configured for incompressibility and longitudinal flow promotion.

Figure 61A:
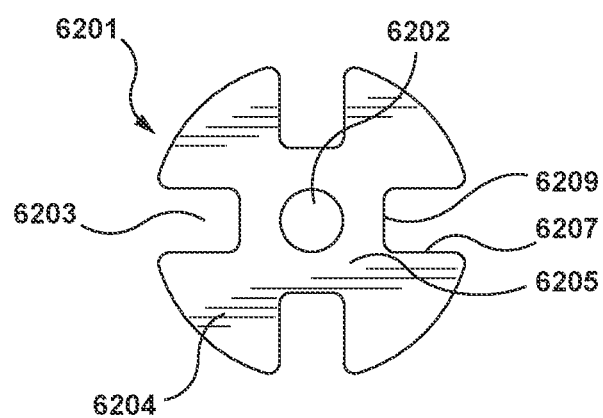
FIG. 61A-B illustrate aspects of assembly of a balloon catheter employing multipart retention bumpers consistent with embodiments hereof.
Figure 61B:
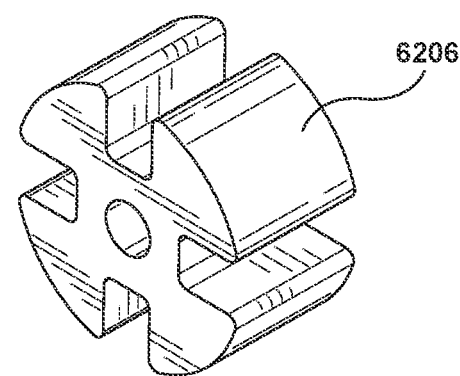

FIGS. 61A-61B illustrate a retention bumper 6201. The retention bumper 6201 includes a central hub 6205 surrounding a central hollow 6202. Extending from the central hub 6205 are one or more radial projections 6204, separated from one another by hub faces 6209. The central hollow 6202 is sized to accommodate disposition over an inner shaft of a balloon catheter, as discussed herein. The one or more radial projections 6204 each have an exterior face 6206 that, collectively, define a broken outer circumference of the retention bumper 6201. The one or more radial projections 6204 further include radial faces 6207 extending between the central hub 6205 and the exterior faces 6206. The breaks in the broken outer circumference of the retention bumper 6201 provide flow passages 6203. The flow passages 6203, which are defined by the hub faces 6209 and the radial faces 6207, are channels cut into the retention bumper 6201 between each pair of radial projections 6204. The hub faces 6209 and the radial faces 6207 are each surfaces substantially parallel to the central axis of the retention bumper 6201. Further, the hub faces 6209 may be perpendicular to the radial faces 6207. Accordingly, the flow passages 6203 run substantially parallel to the central axis of the retention bumper 6201. The cross-sectional dimensions of the flow passages 6203 are substantially constant through the entire length (in the axial direction) of the retention bumper 6201. By substantially constant it is meant that the cross-sectional dimensions are maintained within appropriate manufacturing tolerances, e.g., within 5%, 3%, and/or within 1% of constant. The flow passages 6203 may be approximately square or rectangular cut-outs in the retention bumper 6201, as shown in FIG. 61A. In further embodiments, the flow passages 6203 may be defined by other shapes, including, for example, curved or angled walls.

The broken outer circumference of the retention bumper 6201, defining the effective diameter, may have a diameter between 0.25 inches and 0.35 inches, between 0.27 and 0.33 inches, between 0.29 and 0.31 inches, or approximately 0.3 inches. The effective diameter of the retention bumpers 6201 may be larger than a balloon opening configured for being secured to an outer shaft and/or a distal tip. Accordingly, assembly of the retention bumpers 6201 to the inner shaft of a balloon catheter may occur while the balloon is undergoing processing. For example, the balloon catheter assembly methods discussed with respect to FIGS. 32A-32F, wherein a neck or opening of a balloon is processed to a smaller size after insertion of the retention bumpers, may be used with the retention bumpers 6201.

The retention bumper 6201 is configured to be substantially non-compressible. The retention bumper is 6201 formed from a suitable rigid material, including suitable plastics or polymers, including high density polyethylene (HDPE), TPE, Pebax® and any other suitable rigid material. In embodiments, the material of the retention bumper 6201 is selected so as to be substantially non-compressible during conditions expected to accompany manufacture, assembly, or use. As used herein, substantially non-compressible during conditions expected to accompany manufacture, assembly, or use means that the retention bumper 6201 shows less than 5%, less than 3%, and/or less than 1% strain when subject to forces or stresses common during manufacture, assembly, and/or use. For example, a suitable durometer may be in excess of 60D, in excess of 65D, in excess of 70D, or in excess of 75D.

The retention bumper 6201 is further configured to promote substantially longitudinal flow of inflation fluid and suppress, minimize, or eliminate radial flow of inflation fluid. As discussed above, the flow passages 6203 in the retention bumper 6201 have a substantially constant cross-section throughout the retention bumper 6201 length. Accordingly, the flow of inflation fluid through the flow passages 6203 may pass in substantially longitudinal streamlines with minimal or no radial flow.

Figures 62A, 62B:
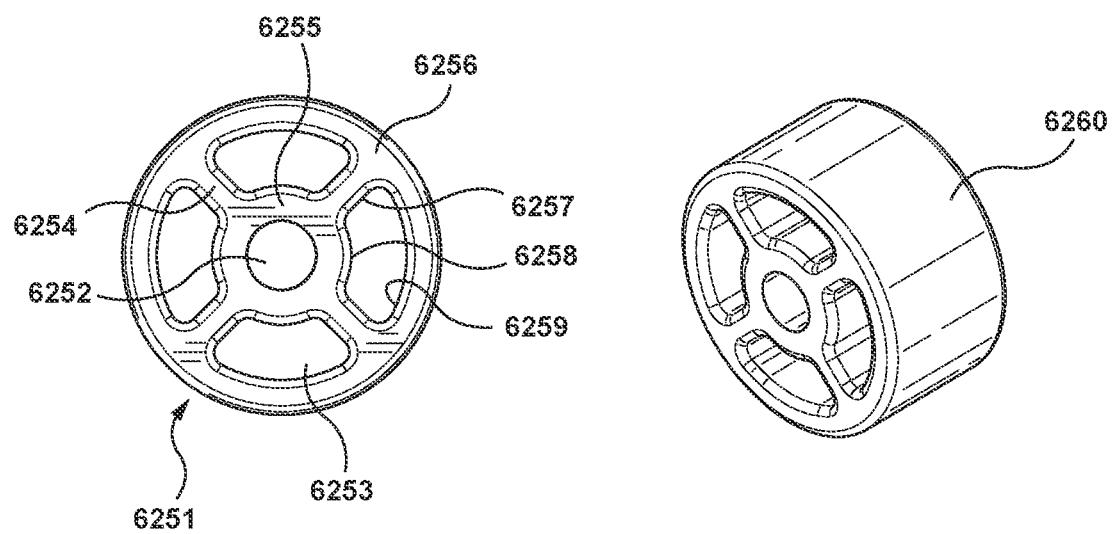
FIGS. 62A-B illustrate flow through retention bumpers consistent with embodiments hereof.

FIGS. 62A-62B illustrate a retention bumper 6251. The retention bumper 6251 is circular in profile and includes a central hub 6255 surrounding a central hollow 6252. Extending from the central hub 6255 are one or more radial spokes 6254 supporting a perimeter ring 6256. Between each pair of radial spokes 6254 is a hub face 6258. The central hollow 6252 is sized to accommodate disposition over an inner shaft of a balloon catheter, as discussed herein. The exterior surface 6260 of the perimeter ring 6256 defines an outer circumference of the retention bumper 6251. Between each pair of radial spokes 6254 on the interior of the perimeter ring 6256 is an interior perimeter face 6259. The one or more radial spokes 6254 further include interior radial faces 6257 extending between the central hub 6255 and the perimeter ring 6256. The flow passages 6253, which are defined by the hub faces 6258, the interior radial faces 6257, and the interior perimeter faces 6259, are passages cut into the retention bumper 6251 between each pair of radial spokes 6254. The hub faces 6258, the interior radial faces 6257, and the interior perimeter faces 6259 are each surfaces substantially parallel to the central axis of the retention bumper 6201. Accordingly, the flow passages 6203 run substantially parallel to the central axis of the retention bumper 6201. The cross-sectional dimensions of the flow passages 6253 are substantially constant through the entire length of the retention bumper 6251. By substantially constant it is meant that the cross-sectional dimensions are maintained within appropriate manufacturing tolerances, e.g., within 5%, 3%, and/or within 1% of constant. The flow passages 6253 may shaped as arc-sections of an annulus, as shown in FIG. 62A. In further embodiments, the flow passages 6253 may be defined by other shapes.

The exterior surface 6260 of the retention bumper 6251, defining the effective diameter, may have a diameter between 0.25 inches and 0.35 inches, between 0.27 and 0.33 inches, between 0.29 and 0.31 inches, or approximately 0.3 inches. The effective diameter of the retention bumpers 6251 may be larger than a balloon opening configured for being secured to an outer shaft and/or a distal tip. Accordingly, assembly of the retention bumpers 6251 to the inner shaft of a balloon catheter may occur while the balloon is undergoing processing. For example, the balloon catheter assembly methods discussed with respect to FIGS. 32A-32F, wherein a neck or opening of a balloon is processed to a smaller size after insertion of the retention bumpers, may be used with the retention bumpers 6251.

In embodiments, the retention bumper 6251 may be configured to be substantially non-compressible. The retention bumper may be 6251 formed from a suitable rigid material, including suitable plastics or polymers, including high density polyethylene (HDPE), TPE, Pebax® and any other suitable rigid material. In embodiments, the material of the retention bumper 6251 may be selected so as to be substantially non-compressible during conditions expected to accompany manufacture, assembly, or use. As used herein, substantially non-compressible during conditions expected to accompany manufacture, assembly, or use means that the retention bumper 6251 shows less than 5%, less than 3%, and/or less than 1% strain when subject to forces or stresses common during manufacture, assembly, and/or use. For example, a suitable durometer may be in excess of 60D, in excess of 65D, in excess of 70D, or in excess of 75D.

In embodiments, the retention bumper 6251 may be further configured to promote substantially longitudinal flow of inflation fluid and suppress, minimize, or eliminate radial flow of inflation fluid. As discussed above, the flow passages 6253 in the retention bumper 6251 have a substantially constant cross-section throughout the retention bumper 6251 length. Accordingly, the flow of inflation fluid through the flow passages 6253 may pass in substantially longitudinal streamlines with minimal or no radial flow.

FIGS. 63A-63C and FIGS. 64A-64C illustrate retention bumpers configured for incompressibility and longitudinal flow promotion. The retention bumpers 6301 and 6401, as illustrated in FIGS. 63A-63C and FIGS. 64A-64C are configured for use together as a proximal retention bumper (6301) and a distal retention bumper (6401) in a balloon catheter, as illustrated in FIGS. 65A-65C.

In the following discussion of the retention bumpers 6301 and 6401, the terms "proximal" and "distal" are used to conveniently describe elements of the retention bumpers 6301 and 6401. Such usage is non-limiting. The proximal and distal aspects of the retention bumpers 6301 and 6401 in the following description refer to one possible configuration in a balloon catheter, as described with respect to FIGS. 65A-65C. Other configurations are contemplated and the retention bumpers 6301 and 6401 may be employed or used in any appropriate manner, including those that reverse the position of these retention bumpers 6301 and 6401 to position the "proximal" features distally of "distal" features.

Figures 63A, 63B, 63C:
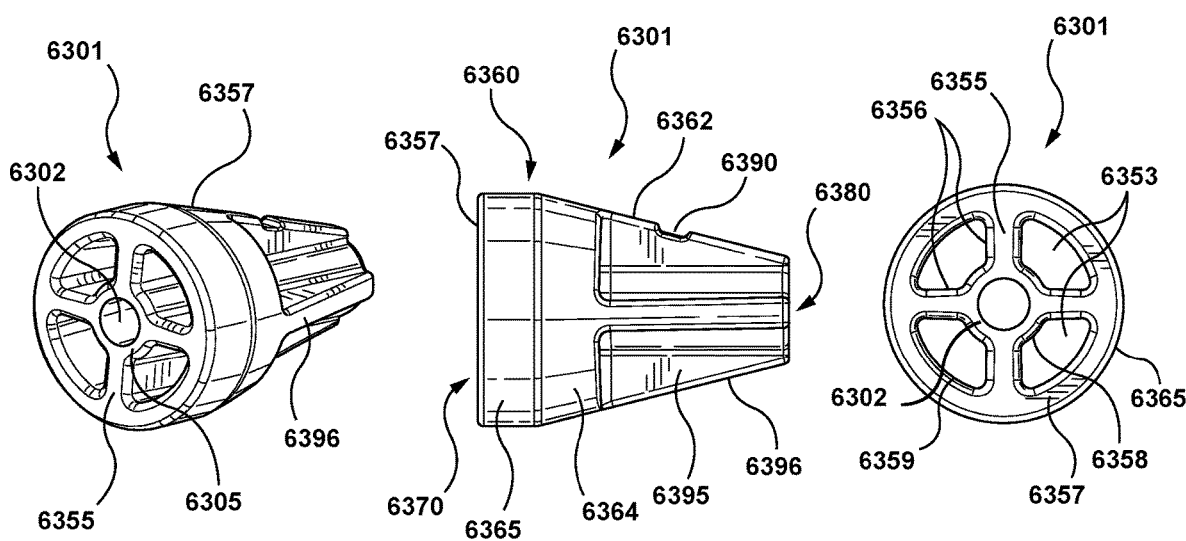
FIGS. 63A-63C illustrate spoked hub and taper retention bumpers consistent with embodiments hereof.

FIGS. 63A-63C illustrate the retention bumper 6301 having a spoked hub and extended tapered configuration. The retention bumper 6301 includes a central hub 6305 extending the length of the retention bumper 6301 and surrounding a central hollow 6302. The central hollow 6302 is approximately circular and extends the length of the central hub 6305 along a longitudinal axis of the retention bumper 6301. The central hollow 6302 is sized to accommodate disposition over an inner shaft of a balloon catheter, as discussed herein.

The central hub 6305 supports two portions of the retention bumper 6301. At a base end 6370 of the retention bumper 6301, the central hub 6305 supports a spoked ring portion 6360. Adjacent the spoked ring portion 6360, the central hub 6305 supports a tapered spoke portion 6362 extending towards an end 6380 of the retention bumper 6301.

The spoked ring portion 6360 is formed from one or more radial spokes 6355 extending from the central hub 6305 to a perimeter ring 6357 supported by the radial spokes 6355. The perimeter ring 6357 includes a first exterior face 6365 and a second exterior face 6364. The first exterior face 6365 of the perimeter ring 6357 is approximately cylindrical parallel to a central longitudinal axis of the retention bumper 6301. The first exterior face 6365 defines the outer circumference of the retention bumper 6301. The second exterior face 6364 is tapered from a diameter equivalent to the outer circumference of the retention bumper 6301 to a smaller diameter.

Between each pair of radial spokes 6355 on an exterior of the central hub 6302 is a hub face 6358. Between each pair of radial spokes 6355 on the interior of the perimeter ring 6357 is an interior perimeter face 6359. The one or more radial spokes 6355 further include interior radial faces 6356 extending between the central hub 6305 and the perimeter ring 6357. Flow passages 6353 are defined by the hub faces 6358, the interior radial faces 6356, and the interior perimeter faces 6359. The flow passages 6353 extend the length of the perimeter ring 6357, that is, the lengths of the first exterior face 6365 and the second exterior face 6364.

The flow passages 6353 are passages in the retention bumper 6301 between each pair of radial spokes 6355. The hub faces 6358, the interior radial faces 6356, and the interior perimeter faces 6359 exhibit a slight draft for manufacturing purposes. Accordingly, the proximal or distal sides of the flow passages 6353 may be slightly larger in cross-section than the opposing sides. The draft may be selected for manufacturing purposes and may result in a slightly larger cross-section at either end of the flow passages 6353. The slight draft in these faces assists during a manufacturing process, as discussed in greater detail below. The draft angle may be less than 2%, less than 1%, and/or less than 0.5%. The slight draft angle of the interior perimeter faces 6359 of the perimeter ring 6357 does not correspond to the larger taper exhibited by the second exterior face 6364 of the spoked ring portion 6360. Accordingly, the cross-sectional dimensions of the flow passages 6353 may vary slightly across the length of the spoked ring portion 6360. Variance of the cross section may be less than 5%, less than 3%, and/or less than 1%. The flow passages 6353 may shaped as arc-sections of an annulus, as shown in FIG. 63C. In further embodiments, the flow passages 6353 may be defined by other shapes. In yet further embodiments, the hub faces 6358, the interior radial faces 6356, and the interior perimeter faces 6359 are manufactured so as to be substantially parallel to one another, exhibiting no draft angles.

The tapered spoke portion 6362 extends from the spoked ring portion 6360 to the end 6380 of the retention bumper 6301. The tapered spoke portion 6362 includes one or more tapered spokes 6395 extending longitudinally from the second exterior face 6364 of the perimeter ring 6357 to the end 6380 of the retention bumper 6301. The tapered spokes 6395 each include an exterior face 6396 facing radially outwards relative to the central longitudinal axis of the retention bumper 6301. The one or more tapered spokes 6395 each correspond to the one or more radial spokes 6355. At a distal end adjacent to the spoked ring portion 6360, the tapered spokes 6395 extend radially such that the exterior face 6396 provides a contiguous surface with the second exterior face 6364 of the spoked ring portion 6360. At the end 6380 of the retention bumper 6301, the tapered spokes 6395 taper towards the central hub 6305 such that the tapered spokes 6395 extend radially a smaller distance than at their distal end. In embodiments, the tapered spokes 6395 taper towards the central hub 6305 such that they do not extend inwardly of the exterior diameter of the central hub 6305, e.g., the hub face 6358.

In embodiments, e.g., as shown in FIG. 63B, the taper angle of the second exterior face 6364 and the exterior face 6396 may be approximately the same, resulting in substantially straight taper profile. In other embodiments, the taper angle of the second exterior face 6364 and the exterior face 6396 may be different, resulting in a transition angle where the exterior face 6396 and the second exterior face 6364 meet. The taper angle of the second exterior face 6364 and the exterior face 6396 may be defined as the angle between a line parallel to the face and the central longitudinal axis of the retention bumper 6301. In embodiments, the taper angle of the second exterior face 6364 may range between 12 and 18 degrees. In embodiments, the taper angle of the exterior face 6396 may range between 12 and 18 degrees. The taper angles of the exterior faces 6396 of each tapered spoke 6395 may be approximately equal to one another.

The first exterior face 6365 of the spoked ring portion 6360 of the retention bumper 6301 defines the effective diameter of the retention bumper 6301, and may have a diameter between approximately 0.265 and 0.294 inches. In such embodiments, the retention bumper 6301 is sized and configured for entry into an opening or neck of a balloon of a balloon catheter after the balloon has been fully formed, as discussed in greater detail below with respect to FIGS. 65A-65C.

In embodiments, the retention bumper 6301 may include a recess 6390 on one of the exterior faces 6396 of the tapered spokes 6395. The recess 6390 facilitates manufacturing by providing space for an injection molding gate. Affording space for an injection molding gate may reduce the likelihood of damage to other components of the balloon catheter 6500, e.g., the balloon 6510. The recess 6390 and its illustrated placement is optional and may vary according to manufacturing requirements.

In embodiments, the retention bumper 6301 may be manufactured with chamfered and/or beveled edges. As illustrated in FIGS. 63A-63C, the edges and transitions between various faces may be chamfered, beveled, or otherwise smoothed. Such chamfers and bevels may facilitate manufacturing, for example, by easing mold release. Such chamfers and bevels may also facilitate balloon catheter assembly, by providing fewer edges to catch on other components. In embodiments, some or all of the edges and transitions may not be chamfered or beveled and may exhibit substantially square corners and edges.

The retention bumper 6301 is configured to be substantially non-compressible. The retention bumper is 6301 formed from a suitable rigid material, including suitable plastics or polymers, including high density polyethylene (HDPE), TPE, Pebax® and any other suitable rigid material. In embodiments, the material of the retention bumper includes a radiopaque filler, such as a barium sulfate. The addition of a radiopaque filler assists with imaging processes such as fluoroscopy during prosthetic implant delivery and deployment. In embodiments, the material of the retention bumper 6301 is selected so as to be substantially non-compressible during conditions expected to accompany manufacture, assembly, or use. As used herein, substantially non-compressible during conditions expected to accompany manufacture, assembly, or use means that the retention bumper 6301 shows less than 5%, less than 3%, and/or less than 1% strain when subject to forces or stresses common during manufacture, assembly, and/or use. For example, a suitable durometer may be in excess of 55D, in excess of 60D, in excess of 65D, in excess of 70D, or in excess of 75D.

The retention bumper 6301 is further configured to promote substantially longitudinal flow of inflation fluid and suppress, minimize, or eliminate radial flow of inflation fluid. Despite the draft angle of the hub faces 6358, the interior radial faces 6356, and the interior perimeter faces 6359, the cross-section of the flow passages 6353 does not vary significantly throughout the retention bumper 6301 length. Accordingly, the flow of inflation fluid through the flow passages 6301 may pass in substantially longitudinal streamlines with minimal or no radial flow.

In some embodiments, the first exterior face 6365 of the spoked ring portion 6360 of the retention bumper 6301 may have a diameter between 0.25 inches and 0.35 inches, between 0.27 and 0.33 inches, or between 0.26 and 0.30 inches. The effective diameter of the retention bumper 6301 may be larger than a balloon opening configured for being secured to the outer shaft and/or a distal tip. Accordingly, assembly of the retention bumper 6301 to the inner shaft of a balloon catheter may occur while the balloon is undergoing processing. For example, the balloon catheter assembly methods discussed with respect to FIGS. 32A-32F, wherein a neck or opening of a balloon is processed to a smaller size after insertion of the retention bumpers, may be used with the retention bumper 6301.

Figure 64A:
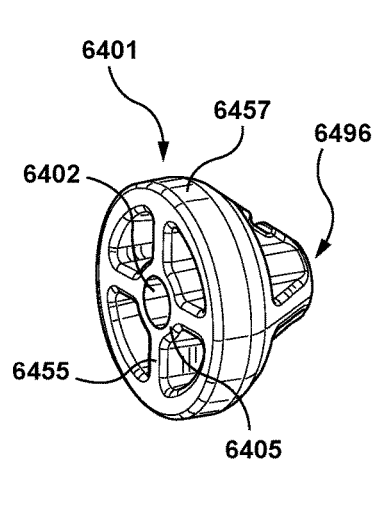
FIGS. 64A-64C illustrate spoked hub and taper retention bumpers consistent with embodiments hereof.
Figure 64B:
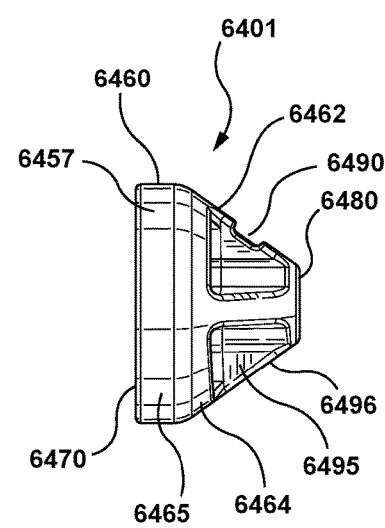
Figure 64C:
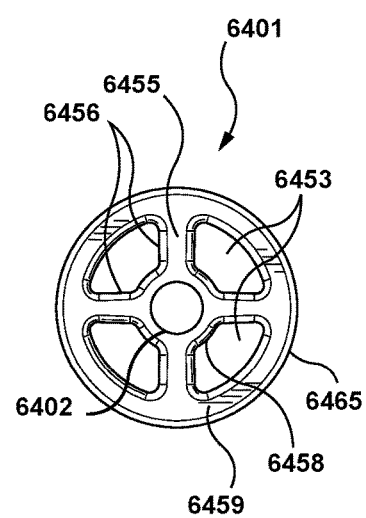
Figure 65A:
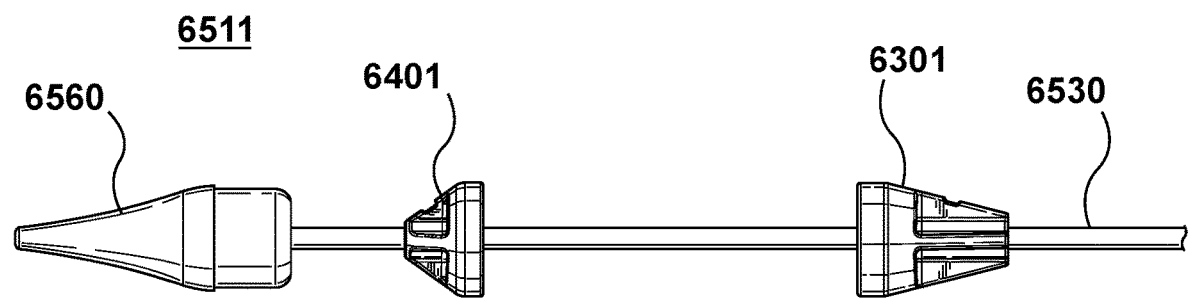
FIGS. 65A-65C illustrate a balloon catheter assembly including spoked hub and taper retention bumpers consistent with embodiments hereof.
Figure 65B:
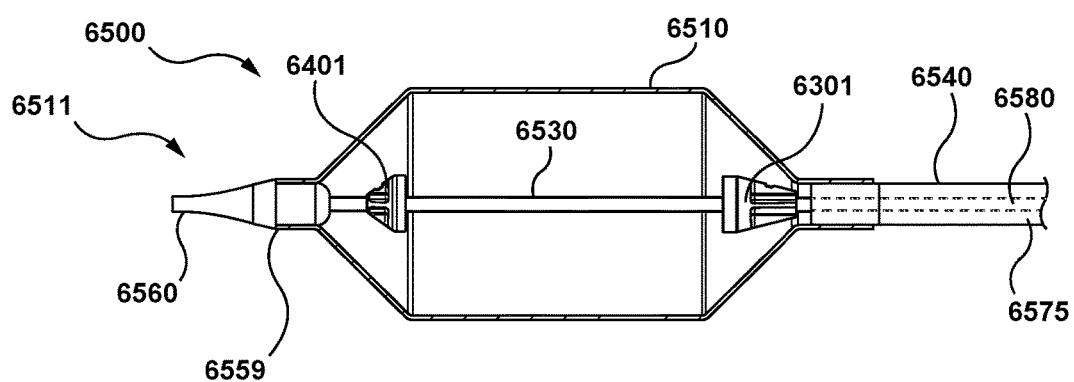
Figure 65C:
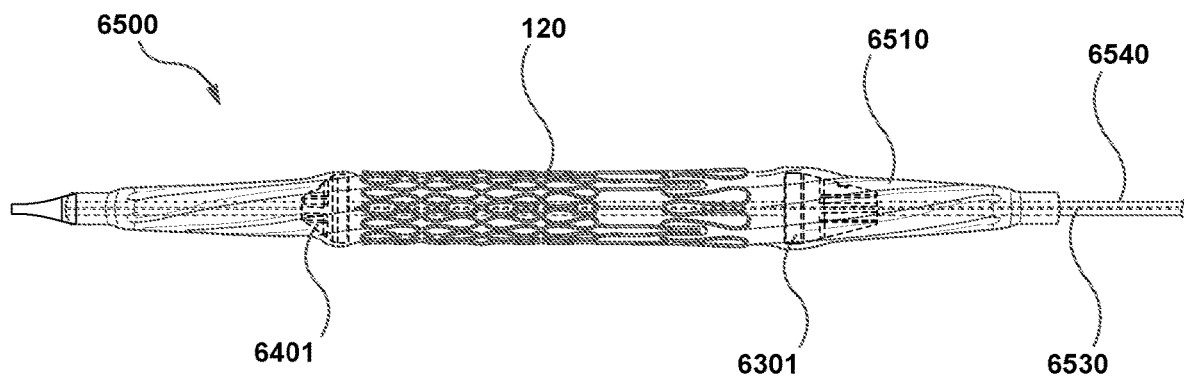

FIGS. 64A-64C illustrate the retention bumper 6401, designed for use in conjunction with the retention bumper 6301. In embodiments, the retention bumper 6401 may be configured for use as a distal retention bumper, as explained in greater detail with respect to FIGS. 65A-65C. The retention bumper 6401 may include all of the same features and components of the retention bumper 6301 and may differ chiefly in the axial length of some components, the angle of taper, and the overall length of the retention bumper. Differences between the retention bumper 6401 and the retention bumper 6301 are discussed in greater detail below.

FIGS. 64A-64C illustrate the retention bumper 6401 having a spoked hub and taper configuration. The retention bumper 6401 includes a central hub 6405 extending the length of the retention bumper 6401 and surrounding a central hollow 6402. The central hollow 6402 is approximately circular and extends the length of the central hub 6405 along a central longitudinal axis of the retention bumper 6401. The central hollow 6402 is sized to accommodate disposition over an inner shaft of a balloon catheter, as discussed herein.

The central hub 6405 supports two portions of the retention bumper 6401. At a base end 6470 of the retention bumper 6401, the central hub 6405 supports a spoked ring portion 6460. Adjacent the spoked ring portion 6460, the central hub 6405 supports a tapered spoke portion 6462 extending towards an apex end 6480 of the retention bumper 6401.

The spoked ring portion 6460 is formed from one or more radial spokes 6455 extending from the central hub 6405 to a perimeter ring 6457 supported by the radial spokes 6455. The perimeter ring 6457 includes a first exterior face 6465 and a second exterior face 6464. The first exterior face 6465 of the perimeter ring 6457 is approximately cylindrical parallel to the central longitudinal axis of the retention bumper 6401. The first exterior face 6465 defines the outer circumference of the retention bumper 6401. The second exterior face 6464 is tapered from a diameter equivalent to the outer circumference of the retention bumper 6401 to a smaller diameter.

Between each pair of radial spokes 6455 on an exterior of the central hub 6402 is a hub face 6458. Between each pair of radial spokes 6455 on the interior of the perimeter ring 6457 is an interior perimeter face 6459. The one or more radial spokes 6455 further include interior radial faces 6456 extending between the central hub 6405 and the perimeter ring 6457. Flow passages 6453 are defined by the hub faces 6458, the interior radial faces 6456, and the interior perimeter faces 6459. The flow passages 6453 extend the length of the perimeter ring 6457, that is, the lengths of the first exterior face 6465 and the second exterior face 6464

The flow passages 6453 are passages in the retention bumper 6401 between each pair of radial spokes 6455. The hub faces 6458, the interior radial faces 6456, and the interior perimeter faces 6459 exhibit a slight draft for manufacturing purposes. Accordingly, the distal sides or the proximal sides of the flow passages 6453 may be slightly larger in cross-section than the opposing sides. The draft may be selected for manufacturing purposes and may result in a slightly larger cross-section at either end of the flow passages 6453. The slight draft in these faces assists during a manufacturing process, as discussed in greater detail below. The draft angle may be less than 2%, less than 1%, and/or less than 0.5%. The slight draft angle of the interior perimeter faces 6459 of the perimeter ring 6457 does not correspond to the larger taper exhibited by the second exterior face 6464 of the spoked ring portion 6460. Accordingly, the cross-sectional dimensions of the flow passages 6453 may vary slightly across the length of the spoked portion 6460. Variance of the cross section may be less than 5%, less than 3%, and/or less than 1%. The flow passages 6453 may be shaped as arc-sections of an annulus, as shown in FIG. 64C. In further embodiments, the flow passages 6453 may be defined by other shapes. In yet further embodiments, the hub faces 6458, the interior radial faces 6456, and the interior perimeter faces 6459 are manufactured so as to be substantially parallel to one another, exhibiting no draft angles.

The tapered spoke portion 6462 extends longitudinally from the spoked ring portion 6460 to the apex end 6480 of the retention bumper 6401. The tapered spoke portion 6462 includes one or more tapered spokes 6495 extending longitudinally from the second exterior face 6464 of the perimeter ring 6457 to the apex end 6480 of the retention bumper 6401. The tapered spokes 6495 each include an exterior face 6496 facing radially outwards relative to the central longitudinal axis of the retention bumper 6401. The one or more tapered spokes 6495 each correspond to the one or more radial spokes 6455. At an end of the tapered spoke portion 6462 adjacent to the spoked ring portion 6460, the tapered spokes 6495 extend radially such that the exterior face 6496 provides a contiguous surface with the second exterior face 6464 of the spoked ring portion 6460. At the apex end 6480 of the retention bumper 6401, the tapered spokes 6495 taper towards the central hub 6405 such that the tapered spokes 6495 extend radially a smaller distance than at their distal end. In embodiments, the tapered spokes 6495 taper towards the central hub 6405 such that they do not extend inwardly of the exterior diameter of the central hub 6405, e.g., the hub face 6458.

In embodiments, e.g., as shown in FIG. 64B, the taper angle of the second exterior face 6464 and the exterior face 6496 may be approximately the same, resulting in a substantially straight taper profile. In other embodiments, the taper angle of the second exterior face 6464 and the exterior face 6496 may be different, resulting in a transition angle where the exterior face 6496 and the second exterior face

6464 meet. The taper angle of the second exterior face 6464 and the exterior face 6496 may be defined as the angle between a line parallel to the face and the central longitudinal axis of the retention bumper 6401. In embodiments, the taper angle of the second exterior face 6464 may range between 25 and 65 degrees, between 30 and 60 degrees, between 35 and 55 degrees, or between 40 and 50 degrees. In embodiments, the taper angle of the second exterior face 6464 may be approximately 36.5 degrees. In embodiments, the taper angle of the exterior face 6496 may range between 25 and 65 degrees, between 30 and 60 degrees, or between 35 and 55 degrees. In embodiments, the taper angle of the exterior face 6496 may be approximately 45 degrees. The taper angles of the exterior faces 6496 of each tapered spoke 6495 may be approximately equal to one another.

The taper angles of the second exterior face 6464 and the exterior face 6496 of the retention bumper 6401 are greater than the corresponding taper angles of the retention bumper 6301. Greater taper angles result in a longitudinally shorter tapered spoke portion 6462 in the retention bumper 6401 relative to the tapered spoke portion 6362 in the retention bumper 6301. Additionally, the spoked ring portion 6460 of the retention bumper 6401 may be longitudinally shorter than the spoked ring portion 6360 of the retention bumper 6301. Combined, these differences may provide for an overall length of the retention bumper 6401 that is less than 70%, less than 60%, less than 50%, and/or less than 40% of the length of the retention bumper 6301.

The first exterior face 6465 of the spoked portion 6460 of the retention bumper 6401 defines the effective diameter of the retention bumper 6401, and may have a diameter between approximately 0.265 and 0.294 inches. In such embodiments, the retention bumper 6401 is sized and configured for entry into an opening or neck of a balloon of a balloon catheter after the balloon has been fully formed, as discussed in greater detail below with respect to FIGS. 65A-65C.

In embodiments, the retention bumper 6401 may include a recess 6490 on the exterior face 6496 of one of the tapered spokes 6495. The recess 6490 facilitates manufacturing by providing space for an injection molding gate. The recess 6490 and its illustrated placement is optional and may vary according to manufacturing requirements.

In embodiments, the retention bumper 6401 may be manufactured with chamfered and/or beveled edges. As illustrated in FIGS. 64A-64C, the edges and transitions between various faces may be chamfered, beveled, or otherwise smoothed. Such chamfers and bevels may facilitate manufacturing, for example, by easing mold release. Such chamfers and bevels may also facilitate balloon catheter assembly, by providing fewer edges to catch on other components. In embodiments, some or all of the edges and transitions may not be chamfered or beveled and may exhibit substantially square corners and edges.

The retention bumper 6401 is configured to be substantially non-compressible. The retention bumper is 6401 formed from a suitable rigid material, including suitable plastics or polymers, including high density polyethylene (HDPE), TPE, Pebax® and any other suitable rigid material. In embodiments, the material of the retention bumper includes a radiopaque filler, such as a barium sulfate. The addition of a radiopaque filler assists with imaging processes such as fluoroscopy during prosthetic implant delivery and deployment. In embodiments, the material of the retention bumper 6401 is selected so as to be substantially non-compressible during conditions expected to accompany manufacture, assembly, or use. As used herein, substantially non-compressible during conditions expected to accompany manufacture, assembly, or use means that the retention bumper 6401 shows less than 5%, less than 3%, and/or less than 1% strain when subject to forces or stresses common during manufacture, assembly, and/or use. For example, a suitable durometer may be in excess of 60D, may be in excess of 55D, in excess of 60D, in excess of 65D, in excess of 70D, or in excess of 75D.

The retention bumper 6401 is further configured to promote substantially longitudinal flow of inflation fluid and suppress, minimize, or eliminate radial flow of inflation fluid. Despite the draft angle of the hub faces 6458, the interior radial faces 6456, and the interior perimeter faces 6459, the cross-section of the flow passages 6453 does not vary significantly throughout the retention bumper 6401 length. Accordingly, the flow of inflation fluid through the flow passages 6453 may pass in substantially longitudinal streamlines with minimal or no radial flow.

In some embodiments, the first exterior face 6465 of the spoked portion 6460 of the retention bumper 6401 may have a diameter between 0.25 inches and 0.35 inches, between 0.27 and 0.33 inches, or between 0.26 and 0.30 inches. The effective diameter of the retention bumpers 6401 may be larger than a balloon opening configured for being secured to the outer shaft and/or a distal tip. Accordingly, assembly of the retention bumpers 6401 to the inner shaft of a balloon catheter may occur while the balloon is undergoing processing. For example, the balloon catheter assembly methods discussed with respect to FIGS. 32A-32F, wherein a neck or opening of a balloon is processed to a smaller size after insertion of the retention bumpers, may be used with the retention bumpers 6251.

FIGS. 65A-65C illustrate states of an assembly process for a balloon catheter employing the retention bumpers 6301 and 6401. FIGS. 65A-65C illustrate an assembly process employing the retention bumpers 6301 and 6401 for example purposes only. The assembly process of FIGS. 65A-65C may be suitable for the retention bumpers 6301 and 6401 and other retention bumpers discussed herein. The assembly process of FIGS. 65A-65C is by way of example only, and balloon catheters including retention bumpers may be assembled using different steps in a different order without departing from the scope of the present disclosure.

FIG. 65A illustrates an inner assembly 6511 prepared for balloon catheter assembly. The inner assembly 6511 includes the inner shaft 6530, the retention bumper 6301 located proximally, the retention bumper 6401 located distally, and a distal tip 6560. The distal tip 6560 is secured to the inner shaft 6530. Over molding of the distal tip may be selected to provide a sure connection throughout usage of the balloon catheter and to facilitate manufacturing. In further embodiments, the distal tip 6560 may be secured via other techniques, such as by bonding and/or adhesive.

In the inner assembly 6511, retention bumpers 6301 and 6401 are secured to the inner shaft 6530. overholding of the retention bumpers 6301 and 6401 may be selected to provide a sure connection throughout usage of the balloon catheter, facilitate manufacturing, and ensure accurate placement of the retention bumpers 6301 and 6401 on the inner shaft 5930. The shorter length of the retention bumper 6401, located distally, may facilitate manufacturing by providing additional space between the retention bumper 6401 and the distal tip 6560. The additional space facilitates the placement of the inner assembly 6511 in a mold for injection molding. A longer retention bumper positioned at the distal end may cause interference between a mold and the already molded distal tip 6560. In further embodiments, the retention bumpers 6301 and 6401 may be secured via other techniques, such as by bonding and/or adhesive.

The retention bumper 6301 and the retention bumper 6401 may be positioned on the inner shaft 6530 such that the flow passages 6353 and 6453 (not shown) of each line up. As can be seen from FIGS. 63C and 64C, the cross-sections of the retention bumpers 6301 and 6401 may match and/or may be substantially the same. By "line up," it is meant that the retention bumpers 6301 and 6401 are oriented such that corresponding aspects of the cross sections of the retention bumpers 6301 and 6401 are aligned when viewed from an axial perspective. Accordingly, the radial spokes 6355 and 6455 of each may also line up. By lining up the flow passages 6353 and 6453, substantially longitudinal flowlines in the completed balloon catheter are promoted, because there is no need for flowlines to move in a rotational fashion between the bumpers to pass through the both sets of flow passages 6353 and 6453.

FIG. 65B illustrates the inner assembly 6511 combined with an outer shaft 6540 and a balloon 6510 to complete the distal end of the balloon catheter 6500. A proximal end of the balloon 6510 is bonded (e.g., laser bonded) to the outer shaft 6540 prior to insertion of the inner assembly 6511 into the balloon 6510 and insertion of the inner shaft 6530 into the outer shaft 6540. Bonding the balloon 6510 prior to insertion of the inner shaft 6530 into the outer shaft 6540 may facilitate the bonding process, because it alleviates a requirement for additional tooling, e.g., a hypotube, to protect the inner shaft 6530 during such bonding. As discussed above, due to the sizing of the retention bumpers 6301 and 6401, the inner assembly 6511 is configured to slide into the balloon opening 6559 of the balloon 6510 without compression.

The inner assembly 6511 is inserted into the distal balloon opening 6559 and then into the distal opening of the outer shaft 6540. After positioning of the inner shaft 6530 inside the outer shaft 6540, the inner shaft 6530 and the outer shaft 6540 define an inflation lumen 6575, through which inflation fluid may be passed to inflate the balloon 6510 during operation of the balloon catheter 6500. Further, the inner shaft 6530 defines a guidewire lumen 6580, through which a guidewire may be passed during operation of the balloon catheter 6500.

In further embodiments, the balloon 6510 may be bonded to the outer shaft 6540 after insertion of the inner assembly 6511 into the balloon 6510. Delaying bonding until after insertion may permit the inner assembly 6511 to be inserted into the balloon 6510 from either end. Delaying bonding may also permit the distal tip 6560 to be bonded to the balloon 6510 prior to bonding the balloon 6510 to the outer shaft 6540.

FIG. 65C illustrates completion of the assembly of the balloon catheter 6500 by pleating and/or folding the balloon 6510 so that it may be closely wrapped to the inner shaft 6530 to permit the crimping of a prosthetic heart valve 120 in the space between the proximal retention bumper 6301 and the distal retention bumper 6401.

The retention bumpers 6301 and 6401 may provide distinct advantages to the balloon catheter 6500 during operation and assembly. As discussed throughout with respect to other retention bumpers described herein, the retention bumpers 6301 and 6401 may serve to maintain an axial position of the prosthetic valve 120 when the prosthetic valve 120 is subject to lateral axial forces. Such lateral axial forces may be generated during delivery of the prosthetic valve 120 to a treatment site. For example, the lateral axial forces may be generated by an introducer sheath through which the balloon catheter 6500 is tracked to a deployment site. When the prosthetic valve 120 is subject to axial forces that may otherwise cause it to move axially, the sections of the balloon 6510 enlarged by the retention bumpers 6301 and 6401 provide a physical barrier to prevent axial movement. Further, the retention bumpers 6301 and 6401 may serve to expand an expandable introducer sheath and thereby cause it to provide less force on the prosthetic valve 120.

Additionally, during delivery through an expandable introducer sheath, the taper of the leading edge of the retention bumper 6401 may serve to facilitate passage of the balloon catheter 6500 through the introducer sheath. As the balloon catheter 6500 advances, the tapered edge of the retention bumper 6401 serves to expand the introducer sheath. Because the leading edge of the retention bumper 6401 is tapered, rather than flat, the enlarged section of the balloon catheter 6500 more gradually expands the introducer sheath, permitting an easier passage. Similarly, after deployment of the prosthetic valve, when the balloon catheter 6500 is withdrawn back into the introducer sheath for recovery, the elongated taper of the retention bumper 6301 may serve to facilitate reentry of the retention bumper 6301 into the introducer sheath.

In a further advantage, the elongated taper shape of both the retention bumper 6301 and the retention bumper 6401 serves to fill more space and provide a smoother transition underneath the balloon 6510 at either end of the prosthetic heart valve 120. The taper of the retention bumpers 6301 and 6401 permits the wrapped balloon 6510 to gradually transition from the widest portion over the retention bumpers 6301 and 6401 to the narrower portions proximal and distal of the retention bumpers 6301 and 6401. The taper prevents an abrupt transition that may hinder a deployment operation.

The difference between the tapers of the retention bumper 6301 and the retention bumper 6401 may also provide an advantage. As discussed above, the elongated and gradual taper of the retention bumper 6301 may serve to facilitate reentry into the introducer sheath. The shorter taper of the retention bumper 6401 may provide at least two advantages. First, the shorter taper may facilitate manufacturing. Manufacturing (e.g., over molding) of the retention bumper 6401 may be more challenging if the distance between the retention bumper 6401 and the distal tip 6560 is too small. The shorter taper on the retention bumper 6401 serves to increase the distance between the retention bumper 6401 and the distal tip 6560.

The shorter taper on the retention bumper 6401 may also permit smoother bending in the balloon catheter 6500 during a delivery operation. During delivery, the balloon catheter 6500 is tracked through an introducer sheath which has bends and curves according to a patient's vasculature. The prosthetic valve 120 is relatively stiffer than the inner shaft 6530, creating a stiffer portion of the balloon catheter 6500 where the prosthetic valve 120 is crimped. Because the retention bumper 6401 is also relatively stiffer than the inner shaft, a greater length of the retention bumper 6401 can create an extended portion of the balloon catheter 6500 that is relatively inflexible. Accordingly, by reducing the length of the relatively inflexible retention bumper 6401, a longer section of the balloon catheter 6500 distal of the retention bumper 6401 is created. Thus, the balloon catheter 6500 has greater flexibility at the delivery end and may pass through vascular curves more easily.

Figure 66:
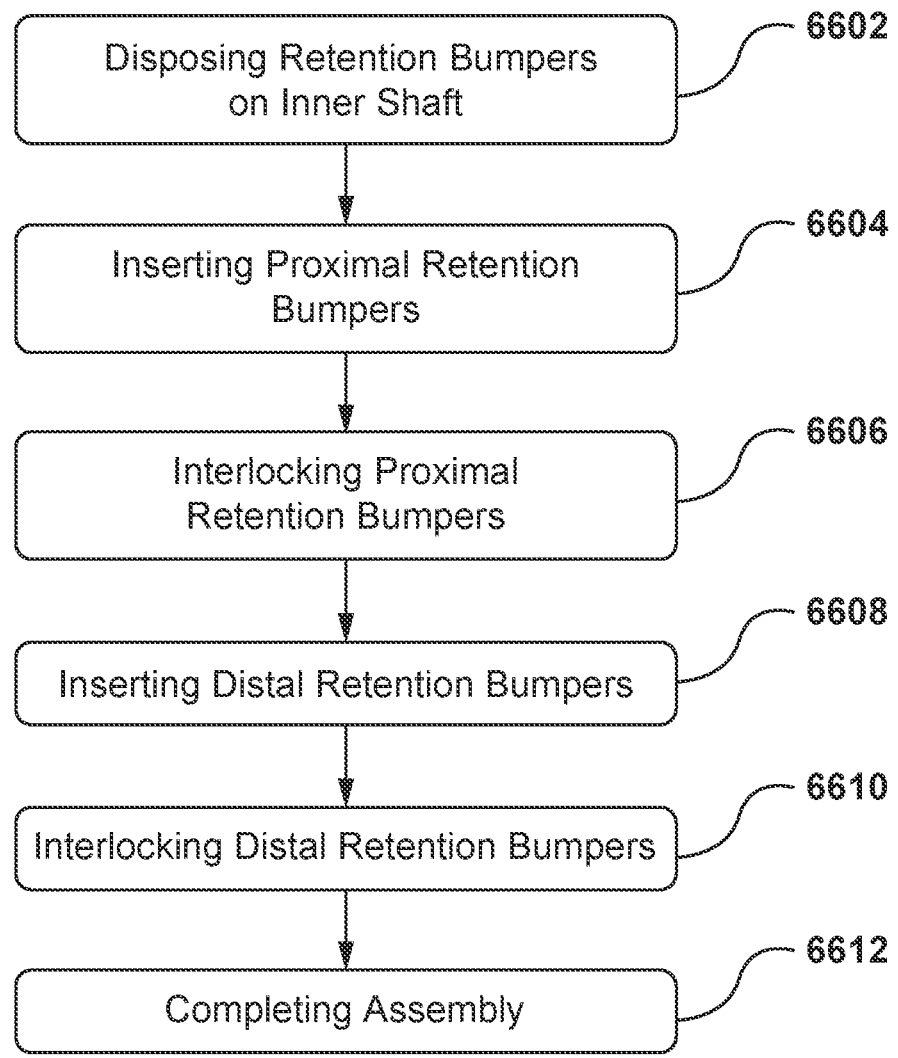
FIG. 66 is a flow chart of a balloon catheter assembly for a balloon enabled prosthetic heart valve delivery and deployment system employing multipart retention bumpers consistent with embodiments described herein.

FIG. 66 is a flow chart of a balloon catheter assembly process 6600 for assembly of a balloon catheter involving multipart retention bumpers. The devices and structures described herein reduce or prevent prosthetic heart valve migration during valve delivery. Methods of assembling a balloon catheter described below are consistent with any multipart retention bumpers described herein. In particular, the process 6600 is compatible with embodiments that employ multipart retention bumpers, for example, those embodiments associated with FIGS. 24A-29F and FIG. 57A-FIG. 59F, and with any combination of the embodiments described herein. It is not necessary that the following operations of process 6600 occur in the order in which they are described.

In an operation 6602 of balloon catheter assembly process 6600, the multipart retention bumpers are disposed on the inner shaft of a balloon catheter to form a partial assembly. In embodiments, the outer bumper portions of the multipart retention bumpers may be secured to the inner shaft, e.g., via over molding, while the inner wedge portions of the multipart retention bumpers are permitted freely slide on the inner shaft. In further embodiments, as discussed herein, different combinations of inner wedges and outer bumpers may be initially secured to the inner shaft and the assembly order altered accordingly. In embodiments, a distal tip may also be secured to the partial assembly at this time.

In an operation 6604, the distal multipart retention bumpers, including the inner wedges and the outer bumpers are inserted into a balloon of the balloon catheter. Prior to insertion, the balloon is bonded to the outer shaft of the balloon catheter. During insertion, the distal multipart retention bumpers are maintained at a first radially unexpanded size. In embodiments, maintaining the retention bumpers at a first radially unexpanded size may involve maintaining the inner wedges and outer bumpers in a non-interlocked configuration. In further embodiments, maintaining the multipart retention bumpers at a first radially unexpanded size may involve maintaining the inner wedges and outer bumpers in a partially-interlocked configuration that does not result in expansion of the outer bumper.

In an operation 6606, the proximal multipart retention bumpers are interlocked and expanded from the first radially unexpanded size to the second radially expanded size. The free moving proximal inner wedges are pressed into the secure outer bumpers to cause interlock and expansion of the multipart retention bumpers. The inner wedges and the outer bumpers may be snap fit to one another to complete the interlock and secure the inner wedges to the outer bumpers. To cause interlock, a tool may be inserted into the opening of the balloon of the balloon catheter to press the inner wedge into the outer bumper. In some embodiments, the inner wedge and the outer bumper may be manually manipulated through the material of the balloon.

In an operation 6608, the distal multipart retention bumpers, including the inner wedges and the outer bumpers, are inserted into the balloon of the balloon catheter. During insertion, the distal multipart retention bumpers are maintained at a first radially unexpanded size. In embodiments, maintaining the multipart retention bumpers at a first radially unexpanded size may involve maintaining the inner wedges and outer bumpers in a non-interlocked configuration. In further embodiments, maintaining the retention bumpers at a first radially unexpanded size may involve maintaining the inner wedges and outer bumpers in a partially-interlocked configuration that does not result in expansion of the outer bumper.

In an operation 6610, the distal multipart retention bumpers are interlocked and expanded from the first radially unexpanded size to the second radially expanded size. The free moving distal inner wedge is pressed or pulled into the secure outer bumper to cause interlock and expansion of the multipart retention bumper. The distal inner wedge and the distal outer bumper may be snap fit to one another to complete the interlock and secure the inner wedge to the outer bumper. To cause interlock, a tool may be inserted into the opening of the balloon of the balloon catheter to pull the distal inner wedge into the distal outer bumper. In some embodiments, the distal inner wedge and the distal outer bumper may be manually manipulated through the material of the balloon.

In an operation 6612, assembly of the balloon catheter is completed. In operation 6612, the balloon is bonded, e.g., via heat bonding, to the distal tip of the catheter. Completing balloon catheter assembly may further involve steps such as folding the balloon, attaching the inner shaft and the outer shaft to a proximal handle, crimping a prosthetic heart valve over the balloon, and any other step required to complete assembly of the balloon catheter.

As discussed above, e.g., with respect to FIGS. 59A-59F, the assembly process 6600 may include several variations without departing from the scope of this disclosure. For example, different portions of the multipart retention bumpers may be secured prior to assembly. In further embodiments, expansion of the multipart retention bumpers inside the balloon may be completed prior to or subsequent to securing the distal tip to the inner shaft, securing the outer shaft to the balloon, and/or securing the balloon to the distal tip. Suitable ordering of these processes may be selected to accommodate the expansion of the multipart retention bumpers.

Figure 67A:
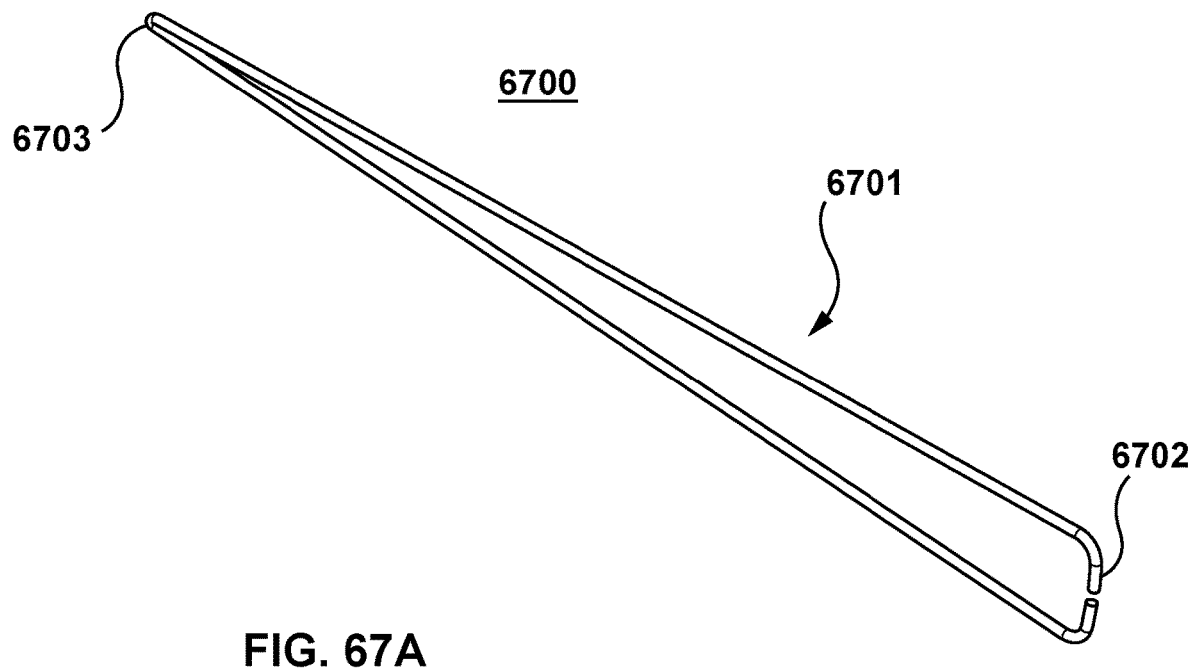
FIGS. 67A-B illustrate tools configured to facilitate the interlocking of multipart bumpers according to embodiments described herein.
Figure 67B:
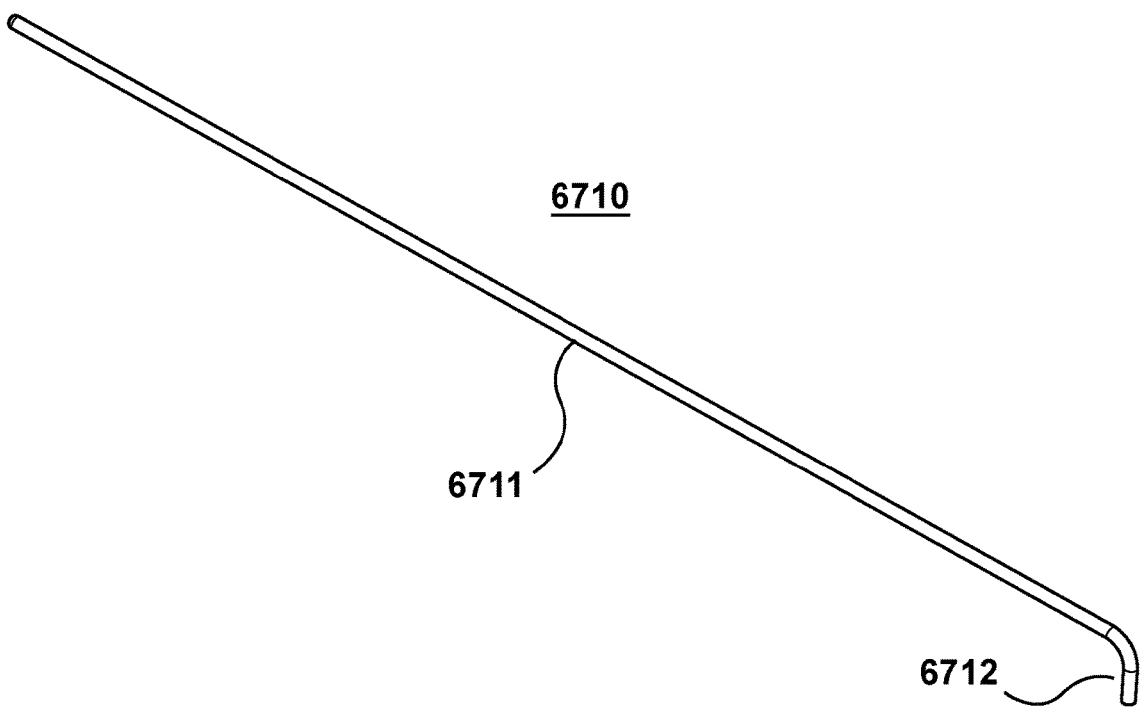

FIGS. 67A and 67B illustrate examples of tools configured for facilitating the assembly of the inner bumpers and outer bumpers inside of a balloon, described herein. FIG. 67A illustrates a double pronged bumper assembly tool 6700. The double pronged assembly tool 6700 includes two shafts 6701 having hooks 6702 disposed on one end thereof. At the end of the shafts 6701 opposite the hooks 6702, the shafts 6701 are joined at the hinge 6703. Each shaft 6701 is an elongated structure such as a tube or mandrel and may have a cylindrical, square, or other profile. The hooks 6702 project from the shafts 6701 at an angle configured to facilitate grasping or pulling of outer or inner bumpers. In embodiments, the hooks 6702 may extend from the shafts 6701 at an angle between 30° and 120°. The hinge 6703 may be a living hinge and/or a mechanical hinge. The double pronged assembly tool 6700 is adapted in size to be inserted into the neck or opening of a balloon. After insertion into the balloon, the hooks 6702 may be used to grasp or catch the outer bumpers and provide the pulling force necessary to pull the outer bumpers over the inner wedges or bumpers. Alternatively, the double pronged assembly tool 6700 may be employed to push the outer bumpers over the inner bumpers. In embodiments, the double pronged assembly tool 6700 may be used to push and/or pull the inner bumpers or wedges into an interlocking configuration with the outer bumpers. FIG. 67B illustrates a singled pronged bumper assembly tool 6710. The single pronged assembly tool 6710 includes a shaft 6711 having a hook 6712 disposed on one end thereof. The shaft 6711 is an elongated structure such as a tube or mandrel and may have a cylindrical, square, or other profile. The hook 6712 projects from the shafts 6711 at an angle configured to facilitate grasping or pulling of the outer bumpers. In embodiments, the hook 6712 may extend from the shaft 6711 at an angle between 30° and 120°. The single pronged assembly tool 6710 is adapted in size to be inserted into the neck or opening of a balloon. After insertion into the balloon, the hook 6712 may be used to grasp or catch the outer bumpers and provide the pulling force necessary to pull the outer bumpers over the inner bumpers or wedges. Alternatively, the single pronged assembly tool 6710 may be employed to push the outer bumpers over the inner bumpers or wedges. In embodiments, the single pronged assembly tool 6710 may be used to push and/or pull the inner bumpers or wedges into an interlocking configuration with the outer bumpers. In embodiments, multiple single pronged assembly tools 6710 may be used to facilitate bumper assembly. In further embodiments, any combination of multiple single pronged assembly tools 6710 and/or multiple double pronged assembly tools 6700 may be employed to facilitate bumper assembly.

The foregoing description has been presented for purposes of illustration and enablement and is not intended to be exhaustive or to limit the invention to the precise form disclosed. Other modifications and variations are possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:

1. A balloon catheter for deploying a prosthetic heart valve through balloon inflation, comprising:
    an inner shaft defining a guidewire lumen;
    an outer shaft surrounding the inner shaft defining an inflation lumen between the outer shaft and the inner shaft;
    a distal portion at a distal end of the outer shaft;
    a balloon disposed at the distal portion such that fluid delivered to the balloon via the inflation lumen causes the balloon to inflate; and
    a distal first retention bumper secured to the inner shaft, the distal first retention bumper including a spoked first portion including a first hub and first spokes extending directly radially outward from the first hub and defining first flow passages therebetween and a first tapered portion including first tapered spokes aligning with the first spokes.

2. The balloon catheter of claim 1, further comprising a proximal second retention bumper secured to the inner shaft, the proximal second retention bumper including a second spoked portion including a second hub and second spokes extending directly radially outward from the second hub and defining second flow passages therebetween and a second tapered portion including second tapered spokes aligning with the second spokes.

3. The balloon catheter of claim 2, wherein the first flow passages of the distal first retention bumper are radially aligned with the second flow passages of the proximal second retention bumper.

4. The balloon catheter of claim 3, wherein the first flow passages and the second flow passages permit longitudinal inflation fluid flow and limit radial inflation fluid flow.

5. The balloon catheter of claim 2, wherein the first tapered portion of the distal first retention bumper is shorter than the second tapered portion of the proximal second retention bumper.

6. The balloon catheter of claim 2, wherein the proximal first retention bumper and the distal second retention bumper are secured to the inner shaft by an over molding process.

7. The balloon catheter of claim 1, wherein the distal first retention bumper is adapted to maintain an axial position of the prosthetic heart valve when the prosthetic heart valve is subject to axial force.

8. The balloon catheter of claim 1, wherein the distal first retention bumper is substantially incompressible.

9. A balloon catheter for deploying a prosthetic heart valve through balloon inflation, comprising:
    an inner shaft defining a guidewire lumen;
    an outer shaft surrounding the inner shaft defining an inflation lumen between the outer shaft and the inner shaft;
    a distal portion at a distal end of the outer shaft;
    a balloon disposed at the distal portion such that fluid delivered to the balloon via the inflation lumen causes the balloon to inflate; and
    a first retention bumper secured to the inner shaft, the first retention bumper including a spoked first portion including a first hub having a first hub inner surface defining a first central hollow configured to receive the inner shaft, first spokes extending from a first hub outer surface of the first hub to a first exterior wall, and first flow passages defined between the first hub outer surface, a first exterior wall inner surface of the first exterior wall, and the first spokes, and a first tapered portion including first tapered spokes aligning with the first spokes.

10. The balloon catheter of claim 9, further comprising a second retention bumper secured to the inner shaft, the second retention bumper including a spoked second portion including a second hub having a second hub inner surface defining a second central hollow configured to receive the inner shaft, second spokes extending from a second hub outer surface of the second hub to a second exterior wall, and second flow passages defined between the second hub outer surface, a second exterior wall inner surface of the second exterior wall, and the second spokes, and a second tapered portion including second tapered spokes aligning with the second spokes.

11. The balloon catheter of claim 10, wherein the first flow passages of the first retention bumper are radially aligned with the second flow passages of the second retention bumper.

12. The balloon catheter of claim 10, wherein the first tapered portion of the first retention bumper is shorter than the second tapered portion of the second retention bumper.

13. The balloon catheter of claim 10,
    wherein the first hub extends from a proximal end to a distal end of the first retention bumper such that first spokes extend radially outward from the first hub outer surface and the first tapered spokes extend radially outward from the first hub outer surface, and
    wherein the second hub extends from a proximal end to a distal end of the second retention bumper such that second spokes extend radially outward from the second hub outer surface and the second tapered spokes extend radially outward from the second hub outer surface.

14. The balloon catheter of claim 9, wherein the first retention bumper is substantially incompressible.

15. The balloon catheter of claim 9, wherein the first hub extends from a proximal end to a distal end of the first retention bumper such that first spokes extend radially outward from the first hub outer surface and the first tapered spokes extend radially outward from the first hub outer surface.

16. A balloon catheter for deploying a prosthetic heart valve through balloon inflation, comprising:
    an inner shaft defining a guidewire lumen;
    an outer shaft surrounding the inner shaft defining an inflation lumen between the outer shaft and the inner shaft;

a distal portion at a distal end of the outer shaft;

a balloon disposed at the distal portion such that fluid delivered to the balloon via the inflation lumen causes the balloon to inflate; and a first retention bumper secured to the inner shaft, the first retention bumper including a first spoked portion including a first hub and first spokes defining first flow passages therebetween and a first tapered portion including first tapered spokes aligning with the first spokes, wherein the first retention bumper is coupled to the inner shaft adjacent a terminal distal end of the outer shaft such that a smaller diameter end of the first tapered spokes is disposed adjacent the terminal distal end of the outer shaft, a larger diameter end of the first tapered spokes is disposed distal of the smaller diameter end, and the first spokes are disposed distal of the tapered spokes.

17. The balloon catheter of claim 16, further comprising a second retention bumper secured to the inner shaft distal of the first retention bumper, the second retention bumper including a second spoked portion including a second hub and second spokes defining second flow passages therebetween and a second tapered portion including second tapered spokes aligning with the second spokes.

18. The balloon catheter of claim 17, wherein the first flow passages of the first retention bumper are radially aligned with the second flow passages of the second retention bumper.

19. The balloon catheter of claim 17, wherein the first tapered portion of the first retention bumper is shorter than the second tapered portion of the second retention bumper.

20. The balloon catheter of claim 17,
wherein the first hub extends from a proximal end to a distal end of the first retention bumper such that first spokes extend radially outward from a first hub outer surface and the first tapered spokes extend radially outward from the first hub outer surface, and
wherein the second hub extends from a proximal end to a distal end of the second retention bumper such that second spokes extend radially outward from a second hub outer surface and the second tapered spokes extend radially outward from the second hub outer surface.

21. The balloon catheter of claim 16, wherein the first retention bumper is substantially incompressible.

22. The balloon catheter of claim 16, wherein the first hub extends from a proximal end to a distal end of the first retention bumper such that first spokes extend radially outward from a first hub outer surface and the first tapered spokes extend radially outward from the first hub outer surface.

* * * * *